US011555073B2

(12) United States Patent
Chen et al.

(10) Patent No.: US 11,555,073 B2
(45) Date of Patent: Jan. 17, 2023

(54) ANTI-CD96 ANTIBODIES AND METHODS OF USE THEREOF

(71) Applicant: 23andMe, Inc., Sunnyvale, CA (US)

(72) Inventors: Yu Chen, Foster City, CA (US); Chingwei Vivian Lee, Foster City, CA (US); Germaine Fuh-Kelly, Pacifica, CA (US); Zuoan Yi, Mountain View, CA (US); Yao-ming Huang, San Mateo, CA (US); Valentine Yeung, Belmont, CA (US); Krista Maureen McCutcheon, Burlingame, CA (US); Samuel Nalle, Pacifica, CA (US); Augusta Eleanor Broughton, Fresno, CA (US); Louise Scharf, Redwood City, CA (US); Navneet Singh, San Francisco, CA (US); Tina Thai, San Mateo, CA (US); Shouhua Xiao, Foster City, CA (US)

(73) Assignee: 23andMe, Inc., Sunnyvale, GA (US)

( * ) Notice: Subject to any disclaimer, the term of this patent is extended or adjusted under 35 U.S.C. 154(b) by 114 days.

(21) Appl. No.: 16/719,108

(22) Filed: Dec. 18, 2019

(65) Prior Publication Data
US 2020/0199227 A1    Jun. 25, 2020

Related U.S. Application Data

(60) Provisional application No. 62/783,118, filed on Dec. 20, 2018.

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *C07K 16/2896* (2013.01); *A61K 2039/505* (2013.01); *C07K 2317/24* (2013.01); *C07K 2317/31* (2013.01); *C07K 2317/33* (2013.01); *C07K 2317/55* (2013.01); *C07K 2317/92* (2013.01)

(58) Field of Classification Search
None
See application file for complete search history.

(56) References Cited

U.S. PATENT DOCUMENTS

| 6,737,056 | B1 | 5/2004 | Presta |
| 7,332,581 | B2 | 2/2008 | Presta |
| 7,658,921 | B2 | 2/2010 | Dall'Acqua |
| 7,767,410 | B2 | 8/2010 | Weissman |
| 8,232,071 | B2 | 7/2012 | Weissman |
| 8,333,953 | B2 | 12/2012 | Lu |
| 8,673,321 | B2 | 3/2014 | Brodsky |
| 9,182,385 | B2 | 11/2015 | Fantl |
| 2004/0005559 | A1 | 1/2004 | Loring |
| 2004/0121370 | A1 | 6/2004 | Baldwin |
| 2004/0170982 | A1 | 9/2004 | Morris |
| 2006/0013822 | A1 | 1/2006 | Tittle |
| 2007/0048301 | A1 | 3/2007 | Clark |
| 2007/0134657 | A1 | 6/2007 | Poznansky |
| 2010/0291112 | A1 | 11/2010 | Kellner |
| 2011/0117578 | A1 | 5/2011 | Acres |
| 2011/0183924 | A1 | 7/2011 | Mintz |
| 2012/0070450 | A1 | 3/2012 | Ohara |
| 2012/0142001 | A1 | 6/2012 | Skog |
| 2013/0251720 | A1 | 9/2013 | Eaton |
| 2014/0010861 | A1 | 1/2014 | Bancel |
| 2014/0056890 | A1 | 2/2014 | Gurney |
| 2014/0186380 | A1 | 7/2014 | Gurney |
| 2014/0242077 | A1 | 8/2014 | Choi |
| 2014/0369924 | A1 | 12/2014 | Weissman |
| 2015/0153356 | A1 | 6/2015 | Meng |
| 2015/0216970 | A1 | 8/2015 | Grogan |
| 2015/0241427 | A1 | 8/2015 | Cesano |
| 2015/0252431 | A1 | 9/2015 | Streicher |
| 2015/0361396 | A1 | 12/2015 | Regev |
| 2016/0007893 | A1 | 1/2016 | Roberts |
| 2016/0200800 | A1 | 7/2016 | Wrammert |
| 2016/0200814 | A1 | 7/2016 | Smyth |
| 2017/0029504 | A1 | 2/2017 | White |
| 2017/0088607 | A1 | 3/2017 | White |

FOREIGN PATENT DOCUMENTS

| CN | 102240901 A | 11/2011 |
| WO | 2008073316 A2 | 6/2008 |
| WO | 2008077546 A1 | 7/2008 |
| WO | 2015024042 A1 | 2/2015 |
| WO | 2015024060 A1 | 2/2015 |
| WO | 2015066640 A1 | 5/2015 |
| WO | 2015121454 A1 | 8/2015 |
| WO | 2015138600 A2 | 9/2015 |
| WO | 2015170108 A1 | 11/2015 |
| WO | 2016005548 A1 | 1/2016 |
| WO | 2019030377 A1 | 2/2019 |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*

(Continued)

*Primary Examiner* — Nelson B Moseley, II
(74) *Attorney, Agent, or Firm* — FisherBroyles LLP; Adam Whiting

(57) ABSTRACT

The present disclosure provides binding proteins, such as antibodies and antigen-binding fragments, which specifically bind to human CD96 receptor protein (hu-CD96) and are capable of decreasing, inhibiting, and/or fully-blocking immune regulatory effects mediated by hu-CD96. The present disclosure also provides methods of using the antibodies (and compositions thereof) to treat diseases and conditions responsive to decreasing, inhibiting and/or blocking immune regulatory function or activity mediated by CD96 binding to CD155, including effects arising from CD96 interactions with CD226 and/or TIGIT.

28 Claims, 12 Drawing Sheets

Specification includes a Sequence Listing.

(56) References Cited

OTHER PUBLICATIONS

The International Search Report and The Written Opinion of the International Search Authority in PCT Application PCT/US2019/067123 (dated Apr. 21, 2020).
Barth,et al., Targeted indocyanine-green-loaded calcium phosphosilicate nanoparticles for In Vivo photodynamic therapy of leukemia, ACS nano.org, 2011, 5(7):15325-5337.
Bellora, et al., The interaction of human natural killer cells with either unpolarized or polarized macrophages results in different functional outcomes, PNAS, 2010, 107(50):121659-21664.
Bernhardt, Gunter, Tactile becomes tangible: CD96 discloses its inhibitory peculiarities, Nat. Immunol., 2014, 15(5):406-408.
Blake, et al., Molecular Pathways: Targeting CD96 and TIGIT for Cancer Immunotherapy, Clin. Cancer Res., 2016, 22:5183-5188.
Blake, et al., Suppression of Metastases Using a New Lymphocyte Checkpoint Target for Cancer Immunotherapy, Cancer Discovery, 2016, 6(4):446-459.
Bottino, et al., Identification of PVR (CD155) and Nectin-2 (CD112) as cell surface ligands for the Human DNAM-1 (CD226) activating molecule, J. Exp. Med., 2003, 198(4):557-567.
Brenner, et al., Encoded combinatorial chemistry, Proc. Natl. Acad. Sci. USA, 1992, 89:5381-5583.
Bryceson, et al., Synergy among receptors on resting NK cells for the activation of natural cytotoxicity and cytokine secretion, Blood, 2005, 107(1):159-166.
Carsten, et al., DNAX accessory molecule-1 mediated recognition of freshly isolated ovarian carcinoma by resting natural killer cells, Cancer Res., 2007, 67(3):1317-1325.
Chan, et al., The receptors CD96 and CD226 oppose each other in the regulation of natural killer cell functions, Nat. Immunol., 2014, 15(5):431-438.
Chan, et al., Receptors that interact with nectin and nectin-like proteins in the immunosurveillance and immunotherapy of cancer, Current Opinion in Immunology, 2012, 24:246-251.
Chan, et al., Molecular mechanisms of natural killer cell activation in response to cellular stress, Cell Death and Differentiation, 2014, 21:5-14.
Chan, et al., DNAM-1/CD155 Interactions Promote Cytokine and NK Cell-Mediated Suppression of Poorly Immunogenic Melanoma Metastases, J. Immunol., 2009, 184:902-911.
Chan, Christopher James, Ph.D. Thesis, Monash University, (Advisors Andrews & Smyth), Mechanisms of NK cell-mediated regulation of inflammation and cancer, Ph.D. Thesis, 2012, 1-304.
Chen, et al., Molecular mechanisms of T cell co-stimulation and co-inhibition, Nature Reviews Immunology, 2013, 13:227-242.
Diken, et al., CIMT 2014: Next waves in cancer immunotherapy—Report on the 12th annual meeting of the Association for Cancer Immunotherapy, Human Vaccines & Immunotherapeutics, 2014, 10(10:3090-3100.
Dougall, et al., TIGIT and CD96: new checkpoint receptor targets for cancer immunotherapy, Immunological Reviews, 2017, 276:112-120.
El-Sherbiny, et al., The requirement for DNAM-1, NKG2D, and NKp46 in the natural killer cell-mediated killing of Myeloma cells, Can. Res., 2007, 67(18):8444-8449.
Eriksson, et al., Differential Expression of CD96 Surface Molecule Represents CD8+ T Cells with Dissimilar Effector Function during HIV-1 Infection, PLOS One, 2012, 7:e51696.
Ferrari De Andrade, et al., DNAM-1 control of natural killer cells functions through nectin and nectin-like proteins, Immunol. and Cell Biol., 2013, 92:237-244.
Fuchs, et al., Cutting edge: CD96 (tactile) promotes NK cell-target cell adhesion by interacting with the poliovirus receptor (CD155), J. Immunol., 2004, 172:3994-3998.
Fuchs, et al., The role of NK cell recognition of nectin and nectin-like proteins in tumor immunosurveillance, Seminars in Cancer Biology, 2006, 16:359-366.

Gilfillan, et al., DNAM-1 promotes activation of cytotoxic lymphocytes by nonprofessional antigen-presenting cells and tumors, J. Exp. Med., 2008, 205:2965-2973.
Gong, et al., Establishment of an enzyme-linked immunosorbent assay system for determining soluble CD96 and its application in the measurement of sCD96 in patients with viral hepatitis B and hepatic cirrhosis, Clin. Exp. Immunol., 2008, 155:207-215.
Gramatzki, et al., Antibodies TC-12 (unique) and TH-111 (CD96) characterize T-cell acute lymphoblastic leukemia and subgroup of acute myeloid leukemia, Exp. Hematol., 1998, 26:209-1214.
Gramatzki, et al.,Abstract #274, "CD96 Antibody TH-111 Eradicates AML-LSC from Autografts and the Fc-Engineered Variant MSH-TH111e May be Used In Vivo", Biol Blood Marrow Transplant, 2016, 22:S200.
Guillerey, et al., Targeting natural killer cells in cancer immunotherapy, Nat. Immunol., 2016, 17(9):1025-1036.
Harjunpaa, et al., Abstract #3258, "The effects of targeting both PD-1 and CD96 on tumour immunity, autoimmunity and immune homeostasis" ,Eur. J. Immunol., 2016, 46(Suppl. 1):37.
Hosen, et al., CD96 is a leukemic stem cell-specific marker in human acute myeloid leukemia, Proc Natl Acad Sci, 2017, 104(26):11008-11013.
Hotzel, et al., A strategy for risk mitigation of antibodies with fast clearance, MABS, 2012, 4(6):753-760.
Iguchi-Manaka, et al., Accelerated tumor growth in mice deficient in DNAM-1 receptor, J. Exp. Med., 2008, 205 (13):2959-2964.
Koenig, et al., Deep Sequencing-guided Design of a High Affinity Dual Specificity Antibody to Target Two Angiogenic Factors in Neovascular Age-related Macular Degeneration., J Biol Chem., 2015, 290:(36)21773-21786.
Krasnova, et al., Bench to bedside: NK cells and control of metastasis, Clin. Immunol., 2015, 1-10, http://dx.doi.org/10.1016/j.clim.2015.10.001.
Kunkel, et al., Rapid and efficient site-specific mutagenesis without phenotypic selection, Methods Enzymol., 1987, 154:367-382.
Lakshmikanth, et al., NCRs and DNAM-1 mediate NK cell recognition and lysis of human and mouse melanoma cell lines in vitro and in vivo, J. Clin. Invest., 2009, 119(5):1251-1263.
Larsen, et al., Nonviral transfection of leukemic primary cells and cells lines by siRNA—a direct comparison between Nucleofection and Accell delivery ,Exp. Hematol., 2011, 39:1081-1089.
Lozano, et al., The TIGIT/CD226 axis regulates human T cell function, J. Immunol., 2012, 188:3869-3875.
Mahoney, et al., Combination cancer immunotherapy and new immunomodulatory targets, Nature Reviews Drug Discovery, 2015, 14:561-584.
Maier, et al., The adhesion receptor CD155 determines the magnitude of humoral immune responses against orally ingested antigens, Eur. J. Immunol., 2007, 37:2214-2225.
Majeti, R., Monoclonal antibody therapy directed against human acute myeloid leukemia stem cells, Oncogene, 2010, 30:1009-1019.
Martinet, et al., DNAM-1 Expression Marks an Alternative Program of NK Cell Maturation, Cell Reports, 2015, 11:85-97.
Martinet, et al., Balancing natural killer cell activation through paired receptors, Nature Reviews Immunology, 2015, 15:243-254.
Martinet, et al., Regulation of Immune Cell Functions through Nectin and Nectin-like Receptors, Encyclopedia of Immunobiology, 2016, 2:404-414.
Melero, et al., Evolving synergistic combinations of targeted immunotherapies to combat cancer, Nature Reviews Cancer, 2015, 15:457-472.
Meyer, et al., CD96 interaction with CD155 via its first Ig-like domain is modulated by alternative splicing or mutations in distal Ig-like domains, J. of Biol. Chem., 2008, 284(4):2235-2244.
Morimoto, et al., Interaction of cancer cells with platelets mediated by Necl-5/poliovirus receptor enhances cancer cell metastasis to the lungs, Oncogene, 2007, 27:264-273.
Nodehi, Sahar Mohseni, Improved antibody-dependent cell-mediated cytotoxicity (ADCC) of affinity maturated and Fc-Engineered antibodies directed against the AML stem cell antigen CD96, Dissertation in Fulfillment of the Requirements for a Degree

(56) References Cited

OTHER PUBLICATIONS of Doctor of Philosophy—Submitted to the Faculty of Mathematics and Natural Sciences—Christian Albrechts University of Kiel, 2010, 138 pages.
Nodehi, et al., Enhanced ADCC activity of affinity maturated and Fc-Engineered Mini-Antibodies directed against the AML stem cell antigen CD96, PLOS One, 2012, 7:e42426.
Seth, et al., The murine pan T cell marker CD96 is an adhesion receptor for CD155 and nectin-1,Biochem. and Biophys. Res. Communications, 2007, 364:959-965.
Shibuya, et al., CD226 (DNAM-1) is involved in lymphocyte function-associated antigen 1 costimulatory signal for naive T cell differentiation and proliferation, J. Exp. Med., 2003, 198(12):1829-1839.
Shields, et al., High resolution mapping of the binding site on human IgG1 for Fc gamma RI, Fc gamma RII, Fc gamma RIII, and FcRn and design of IgG1 variants with improved binding to the Fc gamma R., J Biol Chem., 2001, 276(9):6591-604.
Smyth, Mark J., NK cells in carcinogenesis and metastasis, Abstract, (Heidelberg Germany Natural Killer Cell Symposium 2012), 2012, 5 pages.
Souza-Fonseca-Guimaraes, et al., Abstract #S-24, Checkpoints and interferons in tumor control , J. Cyto., 2014, 70:21-27.
Stanietsky, et al., Paired NK cell receptors controlling NK cytotoxicity, Febs Letters, 2010, 584:4895-4900.
Stanietsky, et al., Mouse TIGIT inhibits NK-cell cytotoxicity upon interaction with PVR ,Eur. J. Immunol., 2013, 43(8):2138-2150.
Stanietsky, et al., The interaction of TIGIT with PVR and PVRL2 inhibits human NK cell cytotoxicity, PNAS, 2009, 106(42):17858-17863.
Stengel, et al., Structure of TIGIT immunoreceptor bound to poliovirus receptor reveals a cell-cell adhesion and signaling mechanism that requires cis-trans receptor clustering, PNAS, 2012, 109(14):5399-5404.
Tahara-Hanaoka, et al., Functional characterization of DNAM-1 (CD226) interaction with its ligands PVR (CD155) and nectin-2 (PRR-2/CD112), Int. Immunol., 2004, 16(4):533-538.
Tahara-Hanaoka, et al., Tumor rejection by the poliovirus receptor family ligands of the DNAM-1 (CD226) receptor, Blood, 2006, 107:1491-1496.
Toutirais, et al., DNAX accessory molecule-1 (CD226) promotes human hepatocellular carcinoma cell lysis by Vγ9Vδ2 T cells, Eur. J. Immunol., 2009, 39:1361-1368.
Wang et al., Identification and molecular cloning of tactile. A novel human T cell activation antigen that is a member of the Ig gene superfamily, J. Immunol., 1992, 148:2600-2608.
Xu, et al., A novel interface consisting of homologous immunoglobulin superfamily members with multiple functions, Cellular & Molecular Immunol., 2010, 7:11-19.
Yu, et al., The surface protein TIGIT suppresses T cell activation by promoting the generation of mature immunoregulatory dendritic cells, Nature Reviews | Immunology, 2009, 10(1):48-57.
Zeng, et al., Human CD96 gene cloning, expression and identification, J. South Med. Univ., 2011, 31(7):1232-1235.
Zhu, et al., Identification of CD112R as a novel checkpoint for human T cells, JEM, 2016, 213(2):167-176.
Zhu, Shensheng, Expressions and Functions of Human CD96 Molecule, Ph.D. Dissertation, Fourth Military University, 2008 04, Classification No. R392, Abstract, 3 pages.

* cited by examiner

FIG. 1

Humanization of 12F8

VL domain sequence

```
12F8       1  DIVMTQSQKFMSTSVGDRVSVTCKASQNVGTAIVWYQKKPGQSPKTLIYSASTRYTGVPD  60
IGKV1-9*01 1  ..QL...PS.L.A......TI..R.....GISSYLA...Q...KA..L...A...LQS...S  60
mAb1       1  ..QL...PSSL.A......TI...........Q...KA..V............S  60

12F8       61 RFTGSGSGTDFTLTISNVQSEDLAEYFCQQYSSSP  95
IGKV1-9*01 61 ..S.......E......SL.P..F.T.Y...LN.Y.  95
mAb1       61 ..S..............SL.P..F.T.Y........  95
```

VH domain sequence

```
12F8        1  QVQLQQPGAELVTPGASVKLSCKASGFTFTNNWMHWVKQRPGQGLEWIGMIHPNSGITNI  60
IGHV1-46*01 1  ....V.S....VKK....V.....Y....SYY...R.A.....M.I.N.SG.S.SY  60
mAb1.v1     1  ....V.S....VKK....V..........R.A.........V.........  60
mAb1.v2     1  ....V.S....VKK....V..........R...........  60
mAb1.v3     1  ....V.S....VKK....V..........R.A.........V.........  60
mAb1.v4     1  ....V.S....VKK....V..........R.A..................  60
mAb1.v5     1  ....V.S....VKK....V..........R.A..................  60
mAb1.v7     1  E...V.S....VKK....V..........R.A..................  60

12F8        61 NEKFKNKATVTVDKSSSTVYIQLSSLTSEDSAVYYCRS              98
IGHV1-46*01 61 AQ..QGRV.M.R.T.T......ME....R....T.......AR        96
mAb1        61 ......RV.M.T.T.T..A.ME..R..R.D.T.......AR          96
mAb1.v1     61 ......R...........E..R....R......T.                98
mAb1.v2     61 ......RV.M........T......ME..R..R.D.T.             98
mAb1.v3     61 ......RV.M.T.T.T..A.ME..R..R.D.T.                  98
mAb1.v4     61 ......RV.M.T.T.T..A.ME..R..R.D.T.                  98
mAb1.v5     61 ......RV.M........T......ME..R..R.D.T.             98
mAb1.v7     61 ......RV.M.T.T.T..A.ME..R..R.D.T.......AR          96
                                                                    98
```

FIG. 2

Humanization of 10G1

VH domain sequence

```
IGHV7-4-1*02   1  QVQLVQSGSELKKPGASVKVSCKASGYTFTSYAMNWVRQAPGQGLEWMGWINTNTGNPTY  60
h10G1          1  EI..........................P..T.G.S...............DS.V...  60
10G1           1  .I.......P......ET..I.......P..T.G.S....K....K......DS.V...  60

IGHV7-4-1*02  61  AQGFTGRFVFSLDTSVSTAYLQISSLKAEDTAVYYCAR  98
h10G1         61  .DD.K............................F...  98
10G1          61  .DD.K...A...E..AN........N...N..A.T.F...  98
```

VL domain sequence

```
IGKV6D-21*02   1  EIVLTQSPDFQSVTPKEKVTITCRASQSIGSSLHWYQQKPDQSPKLLIKYASQSISGVPS  60
h10G1          1  ...M.........................D.YRN........T......H..D....I..  60
10G1           1  D.LM.....TTL....G.T.SLS......D.YRN........SQGT.R......H..D....I..  60

IGKV6D-21*02  61  RFSGSGSGTDFTLTINSLEAEDAAAYYCHQSSSLP  95
h10G1         61  ....................L.GY.M.  95
10G1          61  ..T.........S...VKP..EGI...L.GY.M.  95
```

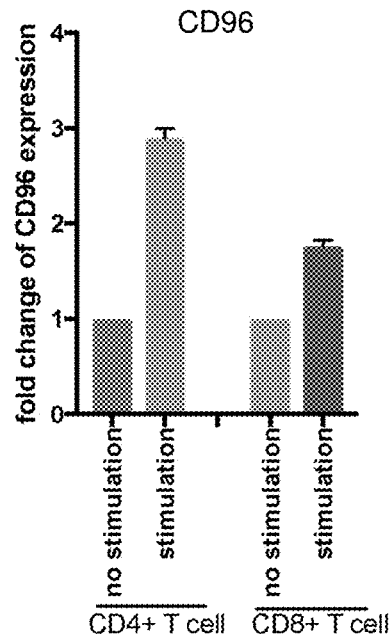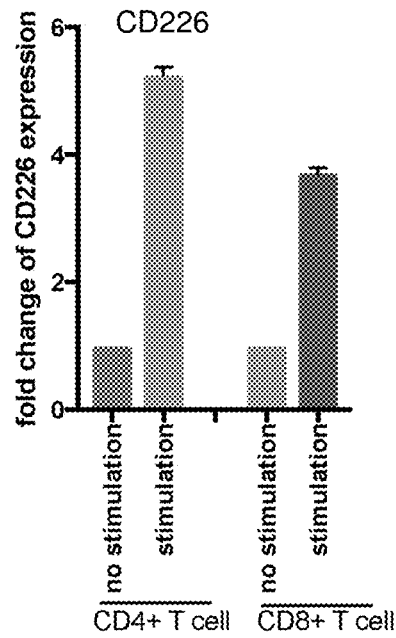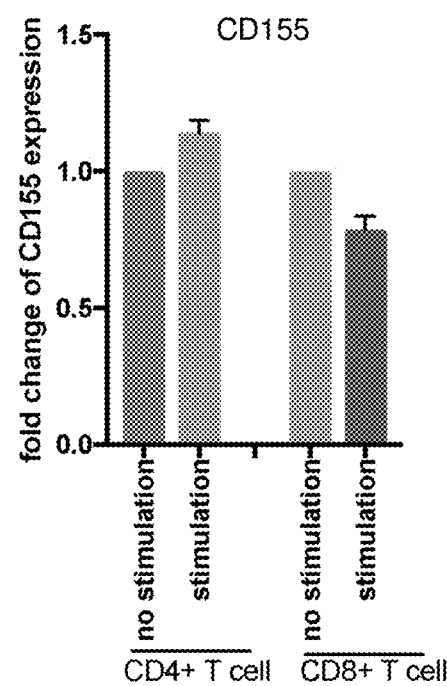

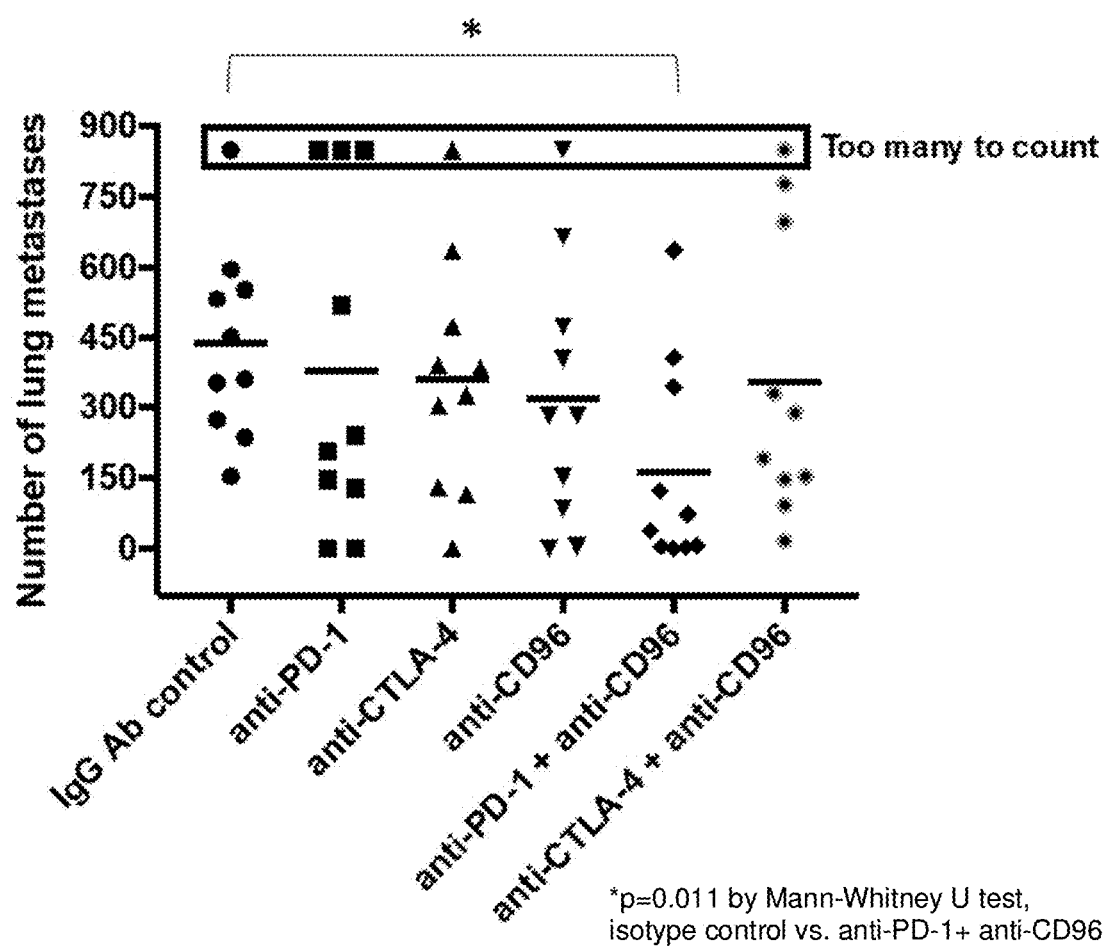

ANTI-CD96 ANTIBODIES AND METHODS OF USE THEREOF

CROSS REFERENCE TO RELATED APPLICATIONS

This application claims the benefit under 35 U.S.C. § 119(e) to U.S. Provisional Patent Application Ser. No. 62/783,118, filed on Dec. 20, 2018, the entireties of which are incorporated herein by reference.

FIELD OF THE INVENTION

The present disclosure relates generally to binding proteins, such as antibodies and antigen-binding fragments, which bind to the CD96 receptor protein and methods of using such binding proteins.

REFERENCE TO SEQUENCE LISTING

The official copy of the Sequence Listing is submitted concurrently with the specification as an ASCII formatted text file via EFS-Web, with a file name of "09402-003WO1_SeqList_ST25.txt", a creation date of Dec. 16, 2019, and a size of 398,046 bytes. The Sequence Listing filed via EFS-Web is part of the specification and is incorporated in its entirety by reference herein.

BACKGROUND OF THE INVENTION

CD96 (also known as "TACTILE") is a receptor expressed on the surface of T cells and natural killer (NK) cells. (See e.g., Blake S J, et al., (2016) "Molecular Pathways: Targeting CD96 and TIGIT for Cancer Immunotherapy," Clin Cancer Res 22(21): 5183-8.) CD96 is a member of the Ig superfamily and is further categorized as a member of the nectin/NECL family. CD96 has been found to be expressed in humans on the surface of T cells ($\alpha\beta$ and $\gamma\delta$), NK cells, a subpopulation of B cells, and in mice on T cells, NK cells and NKT cells. CD96 is known to function in concert with CD155, CD226 (also known as "DNAM"), and TIGIT, and is believed to play an important role in inhibiting immune function. The main ligand for CD96 is CD155 to which it binds with a stronger affinity than CD226 binding to CD155, but weaker than TIGIT binding to CD155. Human CD96 exists as two splice variants that exhibit different binding affinities to CD155. (See e.g., Meyer D, et al., (2009) "CD96 interaction with CD155 via its first Ig-like domain is modulated by alternative splicing or mutations in distal Ig-like domains," J Biol Chem 284: 2235-44.) It has been observed that Cd96 −/− mice exhibit a hypersensitive NK-cell response to stimulation by LPS, IL12, or IL18, as well as strong resistance to experimental lung metastases and MCA-induced fibrosarcomas. (See e.g., Chan C J, et al., (2014) "The receptors CD96 and CD226 oppose each other in regulation of natural killer cell functions," Nat Immunol 15:431-8.) Anti-CD96 mAbs have been shown to reduce the B16F10 and E0771 lung metastases in mouse models. (See e.g., Blake S J, et al., (2016) "Suppression of metastases using a new lymphocyte checkpoint target for cancer immunotherapy," Cancer Discover 6; 446-59.)

WO2015/024042A1 (published Feb. 26, 2015) suggests a method of reducing or relieving immune inhibition in a mammal that includes the step of at least partly inhibiting or reducing CD96 activity in one or more cells of the mammal. The suggested method includes a step of administering to the mammal a CD96 inhibitory agent, such as an anti-CD96 antibody, but no anti-CD96 antibodies are described in the disclosure.

WO2015/024060A1 (published Feb. 26, 2015) also suggests a method of reducing or relieving immune inhibition in a mammal that includes the step of at least partly inhibiting or reducing CD96 activity in one or more cells of the mammal. The disclosure suggests that a commercially available anti-human CD96 antibody "NK92.39" can be effective in increasing IFNγ production in human NK cells, but does not disclose any specific anti-CD96 antibodies that are capable of reducing CD96 activity or tumor growth.

SUMMARY OF THE INVENTION

The present disclosure provides antibodies that specifically bind human CD96 with high affinity. The antibodies are capable of decreasing, inhibiting, and/or fully-blocking immune regulatory effects mediated by CD96. Additionally, the antibodies are capable of decreasing, inhibiting, and/or fully-blocking immune regulatory function or activity mediated by CD96 binding to CD155. The present disclosure also provides compositions for and methods of treating diseases and conditions responsive to decreasing, inhibiting and/or blocking immune regulatory function or activity mediated by CD96, CD155, CD226, and/or TIGIT.

In some embodiments, the present disclosure provides an anti-CD96 antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:

(a) HVR-L1 comprises an amino acid sequence selected from KASQNVGTAIV (SEQ ID NO: 13), KSSQSLLDSDGKTYLN (SEQ ID NO: 17), RVSQDISFWLS (SEQ ID NO: 21), RASSNVKYMY (SEQ ID NO: 25), KASQSVTFADTGLMH (SEQ ID NO: 29), RSSTGAVTTSNYAN (SEQ ID NO: 33), RASQDIYRNLH (SEQ ID NO: 37), or RASQXIXXNXH (SEQ ID NO: 308), wherein X at position 5 is D, A, E, G, H, K, N, P, Q, S, or T; X at position 7 is Y, or F; X at position 8 is R, K, or Q; X at position 10 is L, I, M, or V;

(b) HVR-L2 comprises an amino acid sequence selected from SASTRYT (SEQ ID NO: 14), LVSKLDS (SEQ ID NO: 18), KASNLHT (SEQ ID NO: 22), YTSNLAS (SEQ ID NO: 26), RASNLEV (SEQ ID NO: 30), GTNNRAP (SEQ ID NO: 34), HASDSIS (SEQ ID NO: 38), or HAXXXXS (SEQ ID NO: 325), wherein X at position 3 is S, or E; X at position 4 is D, E, K, or Q; X at position 5 is S, H, L, R, or V; X at position 6 is I, or V;

(c) HVR-L3 comprises an amino acid sequence selected from QQYSSSPLT (SEQ ID NO: 15), LQATHSPQT (SEQ ID NO: 19), LQSQSYPYT (SEQ ID NO: 23), QQFTSSPLT (SEQ ID NO: 27), QQSREYPWT (SEQ ID NO: 31), SLWYGSHWV (SEQ ID NO: 35), LQGYSMPYT (SEQ ID NO: 39), or XQGYXMPXT (SEQ ID NO: 335), wherein X at position 1 is L, G, M, or Q; X at position 5 is S, A, E, Q, or V; X at position 8 is Y, or F;

(d) HVR-H1 comprises an amino acid sequence selected from TNNWMH (SEQ ID NO: 41), TGYGVT (SEQ ID NO: 45), TDYYIN (SEQ ID NO: 49), NDYYIN (SEQ ID NO: 53), SDYYMY (SEQ ID NO: 57), TNYGIH (SEQ ID NO: 61), TTYGMS (SEQ ID NO:

65), XNXXXH (SEQ ID NO: 72), wherein X at position 1 is T, A, D, E, G, H, K, N, Q, R, S, V, W, or Y; X at position 3 is N, A, F, G, H, M, R, S, V, or Y; X at position 4 is W, or F; X at position 5 is M, A, D, E, F, G, L, N, Q, R, S, T, V, or W, or XXXGXS (SEQ ID NO: 344), wherein X at position 1 is T, A, D, E, G, H, K, M, N, Q, R, or S; X at position 2 is T, D, E, G, H, N, Q, or S; X at position 3 is Y, F, M, or Q; X at position 5 is M, I, L, or V;
  (e) HVR-H2 comprises an amino acid sequence selected from MIHPNSGITNINE (SEQ ID NO: 42), EIYPGTVITYYNA (SEQ ID NO: 46), WIFPGTEGIYYNE (SEQ ID NO: 50), WIFPGRIITYYNE (SEQ ID NO: 54), AISDDGTYTYYPD (SEQ ID NO: 58), IIWAGGSTNYNS (SEQ ID NO: 62), WINTDSGVPTYAD (SEQ ID NO: 66), XXHXXXXXXXXXNX (SEQ ID NO: 107), wherein X at position 1 is M or F; X at position 2 is I, L, M, or V; X at position 4 is P, A, D, E, F, G, H, I, K, L, M, N, Q, R, S, T, V, or W; X at position 5 is N, A, D, E, F, G, H, I, K, L, M, Q, R, S, T, V, W, or Y; X at position 6 is S, A, G, T, or V; X at position 7 is G, A, or S; X at position 8 is I, A, or V; X at position 9 is T, A, D, E, G, H, I, K, L, M, N, Q, R, S, V, W, or Y; X at position 10 is N, A, M, or S; X at position 11 is I, F, G, H, K, L, M, N, Q, R, S, T, V, W, or Y; X at position 13 is E, A, D, G, H, K, L, M, N, P, Q, R, S, T, V, W, or Y, or WINTXXGVPTYAD (SEQ ID NO: 369), wherein X at position 5 is D, or E; X at position 6 is S, or T;
  (f) HVR-H3 comprises an amino acid sequence selected from RSDGTYEGYFDY (SEQ ID NO: 43), ARGLGRAMDY (SEQ ID NO: 47), AREGDYRYYSPLGY (SEQ ID NO: 51), ARGVGEGFDY (SEQ ID NO: 55), AKAGSYDYFDV (SEQ ID NO: 59), ARVSMMGFAY (SEQ ID NO: 63), ARNIYYGWGNFDY (SEQ ID NO: 67), RXDXXXXXYFDY (SEQ ID NO: 203), wherein X at position 2 is S, A, F, G, I, L, M, N, R, T, V, W, or Y; X at position 4 is G, or W; X at position 5 is T, D, E, F, H, I, K, L, M, N, Q, V, W, or Y; X at position 6 is Y, D, F, H, N, R, or W; X at position 7 is E, D, G, H, K, M, N, Q, R, V, or Y; X at position 8 is G, K, R, S, or T, or ARXIYYGWGXFDY (SEQ ID NO: 372), wherein X at position 3 is N, or M; X at position 10 is N, F, H, or Y.
  In some embodiments, the present disclosure provides an anti-CD96 antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:
  (a) HVR-L1 comprises the amino acid sequence of SEQ ID NO: 13;
  (b) HVR-L2 comprises the amino acid sequence of SEQ ID NO: 14;
  (c) HVR-L3 comprises the amino acid sequence of SEQ ID NO: 15;
  (d) HVR-H1 comprises an amino acid sequence selected from SEQ ID NOs: 41, 73-106;
  (e) HVR-H2 comprises an amino acid sequence selected from SEQ ID NOs: 42, 108-202;
  (f) HVR-H3 comprises an amino acid sequence selected from SEQ ID NOs: 43, 204-249.
  In some embodiments, the present disclosure provides an anti-CD96 antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:
  (a) HVR-L1 comprises the amino acid sequence of SEQ ID NO: 13;
  (b) HVR-L2 comprises the amino acid sequence of SEQ ID NO: 14;
  (c) HVR-L3 comprises the amino acid sequence of SEQ ID NO: 15;
  (d) HVR-H1 comprises an amino acid sequence selected from SEQ ID NOs: 41, 83, 91, 92, 94, 95, 102;
  (e) HVR-H2 comprises an amino acid sequence selected from SEQ ID NOs: 42, 108, 112, 113, 116, 118, 122, 125, 138, 178, 181, 190, 197;
  (f) HVR-H3 comprises an amino acid sequence selected from SEQ ID NOs: 43, 208, 219, 221, 223, 227.
  In some embodiments, the present disclosure provides an anti-CD96 antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:
  (a) HVR-L1 comprises an amino acid sequence selected from SEQ ID NOs: 37, 309-324;
  (b) HVR-L2 comprises an amino acid sequence selected from SEQ ID NOs: 38, 326-334;
  (c) HVR-L3 comprises an amino acid sequence selected from SEQ ID NOs: 39, 336-343;
  (d) HVR-H1 comprises an amino acid sequence selected from SEQ ID NOs: 65, 345-368;
  (e) HVR-H2 comprises an amino acid sequence selected from SEQ ID NOs: 66, 370-371;
  (f) HVR-H3 comprises an amino acid sequence selected from SEQ ID NOs: 67, 373-376.
  In some embodiments, the anti-CD96 antibody of the present disclosure comprises a light chain variable domain ($V_L$) amino acid sequence having at least 90% identity to a sequence selected from SEQ ID NO: 12, 16, 20, 24, 28, 32, or 36; and/or a heavy chain variable domain ($V_H$) amino acid sequence having at least 90% identity to a sequence selected from SEQ ID NO: 40, 44, 48, 52, 56, 60, or 64.
  In some embodiments, the present disclosure provides an anti-CD96 antibody wherein the antibody comprises a light chain variable domain ($V_L$) amino acid sequence having at least 90% identity to a sequence of SEQ ID NO: 68, and/or a heavy chain variable domain ($V_H$) amino acid sequence having at least 90% identity to a sequence selected from SEQ ID NOs: 69, 250, 251, 252, 253, 254, 255, 256, 257, 258, 259, 260, 261, 262, 263, 264, 265, 266, 267, 268, 269, 270, 271, 272, 273, 274, 275, 460, 461, 462, 463, or 464.
  In some embodiments, the present disclosure provides an anti-CD96 antibody wherein the antibody comprises a light chain variable domain ($V_L$) amino acid sequence having at least 90% identity to a sequence selected from SEQ ID NO: 70, and 377-409; and/or a heavy chain variable domain ($V_H$) amino acid sequence having at least 90% identity to a sequence selected from SEQ ID NO: 71, and 410-439.
  In some embodiments, the present disclosure provides an anti-CD96 antibody wherein the antibody comprises:
  (a) a light chain variable domain ($V_L$) amino acid sequence having at least 90% identity to SEQ ID NO: 12, and/or a heavy chain variable domain (V$_H$) amino acid sequence having at least 90% identity to SEQ ID NO: 40;

(b) a light chain variable domain (V$_L$) amino acid sequence having at least 90% identity to SEQ ID NO: 36, and/or a heavy chain variable domain (V$_H$) amino acid sequence having at least 90% identity to SEQ ID NO: 64;

(c) a light chain variable domain (V$_L$) amino acid sequence having at least 90% identity to SEQ ID NO: 68, and/or a heavy chain variable domain (V$_H$) amino acid sequence having at least 90% identity to a sequence selected from SEQ ID NOs: 69, 250, 251, 252, 253, 254, 255, 256, 257, 258, 259, 260, 261, 262, 263, 264, 265, 266, 267, 268, 269, 270, 271, 272, 273, 274, 275, 460, 461, 462, 463, or 464; or (d) a light chain variable domain (V$_L$) amino acid sequence having at least 90% identity to SEQ ID NO: 70, and/or a heavy chain variable domain (V$_H$) amino acid sequence having at least 90% identity to SEQ ID NO: 71.

In some embodiments, the present disclosure provides an anti-CD96 antibody wherein the antibody comprises:

(a) a light chain (LC) amino acid sequence having at least 90% identity to a sequence selected from SEQ ID NO: 440, 441, 442, 443, 444, 445, or 446; and/or a heavy chain (HC) amino acid sequence having at least 90% identity to a sequence selected from SEQ ID NO: 447, 448, 449, 450, 451, 452, 453, 484, 485, 486, 487, 488, 489, or 490;

(b) a light chain (LC) amino acid sequence having at least 90% identity to SEQ ID NO: 440; and/or a heavy chain (HC) amino acid sequence having at least 90% identity to SEQ ID NO: 447 or 484;

(c) a light chain (LC) amino acid sequence having at least 90% identity to SEQ ID NO: 446; and/or a heavy chain (HC) amino acid sequence having at least 90% identity to SEQ ID NO: 453 or 490;

(d) comprises a light chain (LC) amino acid sequence having at least 90% identity to SEQ ID NO: 454, and/or a heavy chain (HC) amino acid sequence having at least 90% identity to a sequence selected from SEQ ID NO: 455, 456, 457, 458, 459, 465, 466, 467, 468, 469, 491, 492, 493, 494, or 495; or (e) a light chain (LC) amino acid sequence having at least 90% identity to SEQ ID NO: 470; and/or a heavy chain (HC) amino acid sequence having at least 90% identity to SEQ ID NO: 471 or 501.

In some embodiments, the present disclosure provides an anti-CD96 antibody comprising:

(a) a first light chain hypervariable region (HVR-L1) of SEQ ID NO: 13, a second light chain hypervariable region (HVR-L2) of SEQ ID NO: 14, and a third light chain hypervariable region (HVR-L3) of SEQ ID NO: 15; and/or a first heavy chain hypervariable region (HVR-H1) of SEQ ID NO: 72, a second heavy chain hypervariable region (HVR-H2) of SEQ ID NO: 107, and a third heavy chain hypervariable region (HVR-H3) of SEQ ID NO: 203; or (b) a first light chain hypervariable region (HVR-L1) of SEQ ID NO: 308, a second light chain hypervariable region (HVR-L2) of SEQ ID NO: 325, a third light chain hypervariable region (HVR-L3) of SEQ ID NO: 335, and/or a first heavy chain hypervariable region (HVR-H1) of SEQ ID NO: 344, a second heavy chain hypervariable region (HVR-H2) of SEQ ID NO: 369, and a third heavy chain hypervariable region (HVR-H3) of SEQ ID NO: 372.

In some embodiments, the present disclosure provides an anti-CD96 antibody comprising:

(a) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 43;

(b) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 42, and a third heavy chain hypervariable region (HVR-H3) of SEQ ID NO: 43;

(c) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 108, and a third heavy chain hypervariable region (HVR-H3) of SEQ ID NO: 43;

(d) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 112, and a third heavy chain hypervariable region (HVR-H3) of SEQ ID NO: 43;

(e) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 190, and a third heavy chain hypervariable region (HVR-H3) of SEQ ID NO: 43;

(f) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 197, and a third heavy chain hypervariable region (HVR-H3) of SEQ ID NO: 43;

(g) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 221;

(h) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15;

and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 227;

(i) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 112, and a third heavy chain hypervariable region (HVR-H3) of SEQ ID NO: 221;

(j) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 112, and a third heavy chain hypervariable region (HVR-H3) of SEQ ID NO: 227;

(k) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 113, and a third heavy chain hypervariable region (HVR-H3) of SEQ ID NO: 221;

(l) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 113, and a third heavy chain hypervariable region (HVR-H3) of SEQ ID NO: 227; or (m) a first light chain hypervariable region (HVR-L1) of SEQ ID NO: 37, a second light chain hypervariable region (HVR-L2) of SEQ ID NO: 38, a third light chain hypervariable region (HVR-L3) of SEQ ID NO: 39; and/or a first heavy chain hypervariable region (HVR-H1) of SEQ ID NO: 65, a second heavy chain hypervariable region (HVR-H2) of SEQ ID NO: 66, and a third heavy chain hypervariable region (HVR-H3) of SEQ ID NO: 67.

In some embodiments, the present disclosure provides an anti-CD96 antibody comprising:

(a) a light chain variable domain ($V_L$) amino acid sequence of SEQ ID NO: 68; and/or a heavy chain variable domain ($V_H$) amino acid sequence of SEQ ID NO: 69;

(b) a light chain variable domain ($V_L$) amino acid sequence of SEQ ID NO: 68; and/or a heavy chain variable domain ($V_H$) amino acid sequence of SEQ ID NO: 250;

(c) a light chain variable domain ($V_L$) amino acid sequence of SEQ ID NO: 68; and/or a heavy chain variable domain ($V_H$) amino acid sequence of SEQ ID NO: 251;

(d) a light chain variable domain ($V_L$) amino acid sequence of SEQ ID NO: 68; and/or a heavy chain variable domain ($V_H$) amino acid sequence of SEQ ID NO: 252;

(e) a light chain variable domain ($V_L$) amino acid sequence of SEQ ID NO: 68; and/or a heavy chain variable domain ($V_H$) amino acid sequence of SEQ ID NO: 253;

(f) a light chain variable domain ($V_L$) amino acid sequence of SEQ ID NO: 68; and/or a heavy chain variable domain ($V_H$) amino acid sequence of SEQ ID NO: 254;

(g) a light chain variable domain ($V_L$) amino acid sequence of SEQ ID NO: 68; and/or a heavy chain variable domain ($V_H$) amino acid sequence of SEQ ID NO: 255;

(h) a light chain variable domain ($V_L$) amino acid sequence of SEQ ID NO: 68; and/or a heavy chain variable domain ($V_H$) amino acid sequence of SEQ ID NO: 256;

(i) a light chain variable domain ($V_L$) amino acid sequence of SEQ ID NO: 68; and/or a heavy chain variable domain ($V_H$) amino acid sequence of SEQ ID NO: 257;

(j) a light chain variable domain ($V_L$) amino acid sequence of SEQ ID NO: 68; and/or a heavy chain variable domain ($V_H$) amino acid sequence of SEQ ID NO: 258;

(k) a light chain variable domain ($V_L$) amino acid sequence of SEQ ID NO: 68; and/or a heavy chain variable domain ($V_H$) amino acid sequence of SEQ ID NO: 259;

(l) a light chain variable domain ($V_L$) amino acid sequence of SEQ ID NO: 68; and/or a heavy chain variable domain ($V_H$) amino acid sequence of SEQ ID NO: 260;

(m) a light chain variable domain ($V_L$) amino acid sequence of SEQ ID NO: 68; and/or a heavy chain variable domain ($V_H$) amino acid sequence of SEQ ID NO: 261;

(n) a light chain variable domain ($V_L$) amino acid sequence of SEQ ID NO: 68; and/or a heavy chain variable domain ($V_H$) amino acid sequence of SEQ ID NO: 262;

(o) a light chain variable domain ($V_L$) amino acid sequence of SEQ ID NO: 68; and/or a heavy chain variable domain ($V_H$) amino acid sequence of SEQ ID NO: 263;

(p) a light chain variable domain ($V_L$) amino acid sequence of SEQ ID NO: 68; and/or a heavy chain variable domain ($V_H$) amino acid sequence of SEQ ID NO: 264;

(q) a light chain variable domain ($V_L$) amino acid sequence of SEQ ID NO: 68; and/or a heavy chain variable domain ($V_H$) amino acid sequence of SEQ ID NO: 265;

(r) a light chain variable domain ($V_L$) amino acid sequence of SEQ ID NO: 68; and/or a heavy chain variable domain ($V_H$) amino acid sequence of SEQ ID NO: 266;

(s) a light chain variable domain ($V_L$) amino acid sequence of SEQ ID NO: 68; and/or a heavy chain variable domain ($V_H$) amino acid sequence of SEQ ID NO: 267;

(t) a light chain variable domain (V_L) amino acid sequence of SEQ ID NO: 68; and/or a heavy chain variable domain (V_H) amino acid sequence of SEQ ID NO: 268;
(u) a light chain variable domain (V_L) amino acid sequence of SEQ ID NO: 68; and/or a heavy chain variable domain (V_H) amino acid sequence of SEQ ID NO: 269;
(v) a light chain variable domain (V_L) amino acid sequence of SEQ ID NO: 68; and/or a heavy chain variable domain (V_H) amino acid sequence of SEQ ID NO: 270;
(w) a light chain variable domain (V_L) amino acid sequence of SEQ ID NO: 68; and/or a heavy chain variable domain (V_H) amino acid sequence of SEQ ID NO: 271;
(x) a light chain variable domain (V_L) amino acid sequence of SEQ ID NO: 68; and/or a heavy chain variable domain (V_H) amino acid sequence of SEQ ID NO: 272;
(y) a light chain variable domain (V_L) amino acid sequence of SEQ ID NO: 68; and/or a heavy chain variable domain (V_H) amino acid sequence of SEQ ID NO: 273;
(z) a light chain variable domain (V_L) amino acid sequence of SEQ ID NO: 68; and/or a heavy chain variable domain (V_H) amino acid sequence of SEQ ID NO: 274;
(aa) a light chain variable domain (V_L) amino acid sequence of SEQ ID NO: 68; and/or a heavy chain variable domain (V_H) amino acid sequence of SEQ ID NO: 275; or
(bb) a light chain variable domain (V_L) amino acid sequence of SEQ ID NO: 70; and/or a heavy chain variable domain (V_H) amino acid sequence of SEQ ID NO: 71.

In some embodiments, the present disclosure provides an anti-CD96 antibody wherein the antibody comprises:
(a) a light chain (LC) amino acid sequence of SEQ ID NO: 440, and a heavy chain (HC) amino acid sequence of SEQ ID NO: 447;
(b) a light chain (LC) amino acid sequence of SEQ ID NO: 441, and a heavy chain (HC) amino acid sequence of SEQ ID NO: 448;
(c) a light chain (LC) amino acid sequence of SEQ ID NO: 442, and a heavy chain (HC) amino acid sequence of SEQ ID NO: 449;
(d) a light chain (LC) amino acid sequence of SEQ ID NO: 443, and a heavy chain (HC) amino acid sequence of SEQ ID NO: 450;
(e) a light chain (LC) amino acid sequence of SEQ ID NO: 444, and a heavy chain (HC) amino acid sequence of SEQ ID NO: 451;
(f) a light chain (LC) amino acid sequence of SEQ ID NO: 445; and a heavy chain (HC) amino acid sequence of SEQ ID NO: 452;
(g) a light chain (LC) amino acid sequence of SEQ ID NO: 446, and a heavy chain (HC) amino acid sequence of SEQ ID NO: 453;
(h) a light chain (LC) amino acid sequence of SEQ ID NO: 454, and a heavy chain (HC) amino acid sequence of SEQ ID NO: 455;
(i) a light chain (LC) amino acid sequence of SEQ ID NO: 454, and a heavy chain (HC) amino acid sequence of SEQ ID NO: 456;
(j) a light chain (LC) amino acid sequence of SEQ ID NO: 454, and a heavy chain (HC) amino acid sequence of SEQ ID NO: 457;
(k) a light chain (LC) amino acid sequence of SEQ ID NO: 454, and a heavy chain (HC) amino acid sequence of SEQ ID NO: 458;
(l) a light chain (LC) amino acid sequence of SEQ ID NO: 454, and a heavy chain (HC) amino acid sequence of SEQ ID NO: 459;
(m) a light chain (LC) amino acid sequence of SEQ ID NO: 470, and a heavy chain (HC) amino acid sequence of SEQ ID NO: 471;
(n) a light chain (LC) amino acid sequence of SEQ ID NO: 440, and a heavy chain (HC) amino acid sequence of SEQ ID NO: 484;
(o) a light chain (LC) amino acid sequence of SEQ ID NO: 441, and a heavy chain (HC) amino acid sequence of SEQ ID NO: 485;
(p) a light chain (LC) amino acid sequence of SEQ ID NO: 442, and a heavy chain (HC) amino acid sequence of SEQ ID NO: 486;
(q) a light chain (LC) amino acid sequence of SEQ ID NO: 443, and a heavy chain (HC) amino acid sequence of SEQ ID NO: 487;
(r) a light chain (LC) amino acid sequence of SEQ ID NO: 444, and a heavy chain (HC) amino acid sequence of SEQ ID NO: 488;
(s) a light chain (LC) amino acid sequence of SEQ ID NO: 445; and a heavy chain (HC) amino acid sequence of SEQ ID NO: 489;
(t) a light chain (LC) amino acid sequence of SEQ ID NO: 446, and a heavy chain (HC) amino acid sequence of SEQ ID NO: 490;
(u) a light chain (LC) amino acid sequence of SEQ ID NO: 454, and a heavy chain (HC) amino acid sequence of SEQ ID NO: 491;
(v) a light chain (LC) amino acid sequence of SEQ ID NO: 454, and a heavy chain (HC) amino acid sequence of SEQ ID NO: 492;
(w) a light chain (LC) amino acid sequence of SEQ ID NO: 454, and a heavy chain (HC) amino acid sequence of SEQ ID NO: 493;
(x) a light chain (LC) amino acid sequence of SEQ ID NO: 454, and a heavy chain (HC) amino acid sequence of SEQ ID NO: 494;
(y) a light chain (LC) amino acid sequence of SEQ ID NO: 454, and a heavy chain (HC) amino acid sequence of SEQ ID NO: 495; or
(z) a light chain (LC) amino acid sequence of SEQ ID NO: 470, and a heavy chain (HC) amino acid sequence of SEQ ID NO: 501.

In various embodiments of the anti-CD96 antibody provided by the present disclosure, the antibody is characterized by one or more of the following properties:
(a) binds to human CD96 with a binding affinity of $1 \times 10^{-8}$ M or less, $1 \times 10^{-9}$ M or less, $1 \times 10^{-10}$ M or less, or $1 \times 10^{-11}$ M or less; optionally, wherein the binding affinity is measured by equilibrium dissociation constant ($K_D$) to a hu-CD96 polypeptide of SEQ ID NO: 4;
(b) binds to cynomolgus monkey CD96 with a binding affinity of $1 \times 10^{-8}$ M or less, $1 \times 10^{-9}$ M or less, $1 \times 10^{-10}$ M or less, or $1 \times 10^{-11}$ M or less; optionally, wherein the binding affinity is measured by equilibrium dissociation constant ($K_D$) to a cy-CD96 polypeptide of SEQ ID NO: 7;
(c) binds to human CD96 and to cynomolgus monkey CD96 with a binding affinity of $1 \times 10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a hu-CD96 polypeptide of SEQ ID NO: 4 and a cy-CD96 polypeptide of SEQ ID NO: 7;

(d) binds to human CD96 isoform 1 expressed on a cell with an antibody $EC_{50}$ concentration of 5 nM or less, 1 nM or less, or 0.1 nM or less; optionally, wherein the cell is a HEK293T cell;

(e) binds to human CD96 isoform 2 expressed on a cell with an antibody $EC_{50}$ concentration of 5 nM or less, 1 nM or less, or 0.1 nM or less; optionally, wherein the cell is a CHO cell;

(f) binds to human PBMCs with an antibody $EC_{50}$ concentration of 5 nM or less, 1 nM or less, or 0.1 nM or less;

(g) binds to cynomolgus monkey PBMCs with an antibody $EC_{50}$ concentration of 5 nM or less, 1 nM or less, or 0.1 nM or less;

(h) decreases binding of human CD155 to human CD96 expressed on CHO cells by at least 90%, at least 95%, at least 99%, or 100%; optionally, wherein at a human CD155 concentration of 10 nM the antibody has an $IC_{50}$ of 5 nM or less, 1 nM or less, or 0.1 nM or less;

(i) increases IFNγ secretion from human PBMCs by at least 1.8-fold, at least 1.9-fold, at least 2-fold, at least 2.1 fold, or at least 2.20-fold; optionally, wherein the antibody has an $EC_{50}$ concentration of 0.3 nM or less, 0.2 nM or less, or 0.1 nM or less;

(j) increases IL-2 secretion from human PBMCs by at least 1.8-fold, at least 1.9-fold, at least 2-fold, at least 2.1 fold, or at least 2.20-fold; optionally, wherein the antibody has an $EC_{50}$ concentration of 0.3 nM or less, 0.2 nM or less, or 0.1 nM or less;

(k) specifically binds to one or more amino acid residues within domain 1 of hu-CD96, wherein domain 1 comprises the amino acid sequence of SEQ ID NO: 5; optionally, wherein the one or more amino acid residues within domain 1 of hu-CD96 comprise residues T49 and V50 of SEQ ID NO:2, which correspond to residues T28 and V29 of SEQ ID NO: 5.

(l) does not bind to amino acid residues within domain 2 and/or domain 3 of human CD96;

(m) binds to human and/or cynomolgus monkey CD226 expressed on cells, optionally HEK293 cells, with an antibody $EC_{50}$ concentration of 500 nM or less, 300 nM or less, 250 nM or less, 200 nM or less, 150 nM or less, 100 nM or less, or 50 nM or less;

(n) binds to human CD226 with a binding affinity of 1 µM or less, 900 nM or less, 800 nM or less, 700 nM or less, from 1 µM to 50 nM, or from 800 nM to 200 nM; optionally, wherein the binding affinity is measured by equilibrium dissociation constant ($K_D$) to a huCD226 polypeptide of SEQ ID NO:482; and/or (o) binds to cynomolgus monkey CD226 with a binding affinity of 1 µM or less, 800 nM or less, 500 nM or less, 300 nM or less, 100 nM or less, from 1 µM to 50 nM, from 500 nM to 60 nM, or from 300 nM to 70 nM; optionally, wherein the binding affinity is measured by equilibrium dissociation constant ($K_D$) to a cyCD226 polypeptide of SEQ ID NO:483.

The present disclosure also provides embodiments of the anti-CD96 antibody, wherein: (i) the antibody is a monoclonal antibody; (ii) the antibody is a human, humanized, or chimeric antibody; (iii) the antibody is a full length antibody of class IgG, optionally, wherein the class IgG antibody has an isotype selected from IgG1, IgG2, IgG3, and IgG4; (iv) the antibody is an Fc region variant, optionally an Fc region variant that alters effector function (e.g., a variant resulting in an effectorless antibody), or an Fc region variant that alters antibody half-life, or an Fc region variant that alters both effector function and antibody half-life, including in all instances where the Fc region may or may not contain a c-terminal lysine; (v) the antibody is an antibody fragment, optionally selected from the group consisting of F(ab')$_2$, Fab', Fab, Fv, single domain antibody (VHH), and scFv; (vi) the antibody is an immunoconjugate, optionally, wherein the immunoconjugate comprises a therapeutic agent for treatment of a CD96-mediated disease or condition; (vii) the antibody is a multi-specific antibody, optionally a bispecific antibody; and (viii) the antibody is a synthetic antibody, wherein the HVRs are grafted onto a scaffold or framework other than an immunoglobulin scaffold or framework; optionally, a scaffold selected from an alternative protein scaffold and an artificial polymer scaffold.

In some embodiments, the present disclosure provides an anti-CD96 antibody wherein the antibody is a multispecific antibody, optionally a bispecific antibody. In some embodiments, the present disclosure provides an anti-CD96 antibody wherein the antibody is a bispecific antibody comprising a specificity for an antigen that is an immune checkpoint molecule; optionally, wherein the immune checkpoint molecule is selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA; optionally, wherein the antigen is selected from PD1, TIGIT, LAG3, PVRIG, KIR, TIM-3, and CRTAM.

In some embodiments, the present disclosure provides an anti-CD96 antibody that specifically binds CD96 and has a secondary affinity for CD226. In some embodiments, the present disclosure provides an anti-CD96 antibody that specifically binds human and/or cynomolgus monkey CD96 and has a secondary affinity for human and/or cynomolgus monkey CD226. Such secondary affinity may vary and may range from micromolar to nanomolar affinity and may be, e.g., a binding affinity of 1 µM or less, 900 nM or less, 800 nM or less, 700 nM or less, 600 nM or less, 500 nM or less, 400 nM or less, 300 nM or less, 200 nM or less, 100 nM or less, or 90 nM or less; optionally, wherein the binding affinity is measured by equilibrium dissociation constant ($K_D$) to a human CD226 polypeptide and/or a cynomolgus monkey CD226 polypeptide. In some embodiments, the secondary affinity of the anti-CD96 antibody for CD226 may be at least at least 50 nM, at least 60 nM, at least 70 nM, at least 80 nM, at least 90 nM, at least 100 nM, at least 200 nM, at least 300 nM, at least 400 nM, at least 500 nM, or at least 600 nM; optionally, wherein the binding affinity is measured by $K_D$ to a human CD226 polypeptide and/or a cynomolgus monkey CD226 polypeptide. In some embodiments, the secondary affinity of the anti-CD96 antibody for CD226 may range from 1 µM or less to 50 nM or more, 900 nM or less to 60 nM or more, 800 nM or less to 70 nM or more, or 700 nM or less to 80 nM or more; optionally, wherein the binding affinity is measured by $K_D$ to a human CD226 polypeptide and/or a cynomolgus monkey CD226 polypeptide. In some embodiments, the anti-CD96 antibody may bind CD226 with less than half the affinity with which the antibody binds CD96, including e.g., where the antibody binds CD96 with at least twice the affinity, at least 3× the affinity, at least 5× the affinity, or at least 10× the affinity, or at least 100× the affinity with which the antibody binds CD226.

In some embodiments, an anti-CD96 antibody of the present disclosure may bind to CD226 through a secondary affinity for CD226. In some embodiments, an anti-CD96 antibody of the present disclosure does not bind CD226 and is not characterized by having affinity for, e.g., a secondary affinity for, CD226. By "secondary affinity", as used herein, is meant an affinity for a secondary antigen that is substantially weaker than the affinity of the antibody for the primary antigen, i.e., CD96. By "substantially weaker", as used in this context, is generally meant that the primary affinity is at least twice the secondary affinity, at least 3× the secondary affinity, at least 5× the secondary affinity, at least 10× the secondary affinity, at least 100× the secondary affinity, etc. Accordingly, where the primary affinity, measured as $K_D$, may be in the nanomolar or subnanomolar range, the secondary affinity will generally be greater than 10 nM, including e.g., 25 nM or greater, 50 nM or greater, 75 nM or greater, 100 nM or greater, 250 nM or greater, 500 nM or greater, or 750 nM or greater.

Any binding due to secondary affinity may not result in a direct agonistic effect and/or a direct antagonistic effect on CD226 or any function thereof. By "not result in a direct agonistic effect on CD226", as used herein, is generally meant that administration of the active agent does not alone result in pharmacologically significant immune activation through CD226, such as immune cell proliferation and/or cytokine production, e.g., as compared to an appropriate control. By "not result in a direct antagonistic effect on CD226", as used herein, is generally meant that administration of the active agent does not alone result in pharmacologically significant inhibition of immune activation through CD226, such as inhibition of immune cell proliferation and/or cytokine production, e.g., as compared to an appropriate control. In some instances, direct binding to CD226 by an anti-CD96 antibody of the present disclosure may result in an enhancement of CD226-triggered cellular activity. In some instances, the anti-CD96 antibody is not an agonist and/or antagonist of CD226.

In other embodiments, the present disclosure provides isolated nucleic acids encoding the anti-CD96 antibodies disclosed herein.

In some embodiments, the present disclosure also provides a host cell comprising a nucleic acid encoding an anti-CD96 antibody as disclosed herein.

The disclosure also provides a method of producing an anti-CD96 antibody, wherein the method comprises culturing a host cell comprising a nucleic acid (or vector) encoding an anti-CD96 antibody so that an antibody is produced.

In some embodiments, the disclosure provides a pharmaceutical composition comprising an anti-CD96 antibody as disclosed herein and a pharmaceutically acceptable carrier. In some embodiments, the pharmaceutical composition further comprises a therapeutic agent for treatment of a CD96-mediated disease or condition. In some embodiments, the anti-CD96 antibody is the sole active agent of the pharmaceutical composition. In some embodiments, the pharmaceutical composition comprises the anti-CD96 antibody and an additional active agent, such as but not limited to e.g., a checkpoint inhibitor such as e.g., a second antibody comprising a specificity for an antigen that is an immune checkpoint molecule; optionally, wherein the immune checkpoint molecule is selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA; optionally, wherein the antigen is selected from PD1, TIGIT, LAG3, PVRIG, KIR, TIM-3, and CRTAM.

In some embodiments, the present disclosure provides a method of treating a CD96-mediated disease in a subject, comprising administering to the subject a therapeutically effective amount of an anti-CD96 antibody as disclosed herein, or a therapeutically effective amount of a pharmaceutical formulation of an anti-CD96 antibody as disclosed herein. In some embodiments, the anti-CD96 antibody is the sole active agent administered to the subject to treat the subject for the CD96-mediated condition. In some embodiments, the subject is administered more than one active agents, including e.g., 2 or more, 3 or more, 4 or more, or 5 or more active agents effective to treat the subject for the CD96-mediated condition, including e.g., where the more than one active agents include the anti-CD96 antibody and at least one additional active agent, such as but not limited to e.g., a checkpoint inhibitor such as e.g., one or more antibodies comprising a specificity for an antigen that is an immune checkpoint molecule.

In some embodiments, the present disclosure provides a method of treating a disease mediated by binding to CD155 expressed on cells in a subject, comprising administering to the subject a therapeutically effective amount of an anti-CD96 antibody as disclosed herein, or a therapeutically effective amount of a pharmaceutical formulation of an anti-CD96 antibody as disclosed herein. In some embodiments, the anti-CD96 antibody is the sole active agent administered to the subject to treat the subject for the disease mediated by binding to CD155 expressed on cells in the subject. In some embodiments, the subject is administered a plurality of active agents effective to treat the subject for the disease mediated by binding to CD155 expressed on cells in the subject, including e.g., where the plurality of active agents include the anti-CD96 antibody and an additional active agent, such as but not limited to e.g., a checkpoint inhibitor such as e.g., a second antibody comprising a specificity for an antigen that is an immune checkpoint molecule.

In some embodiments, the present disclosure provides a method of treating a disease mediated by CD226 and/or TIGIT in a subject, comprising administering to the subject a therapeutically effective amount of an anti-CD96 antibody as disclosed herein, or a therapeutically effective amount of a pharmaceutical formulation of an anti-CD96 antibody as disclosed herein. In some embodiments, the anti-CD96 antibody is the sole active agent administered to the subject to treat the subject for the disease mediated by CD226 and/or TIGIT in the subject. In some embodiments, the subject is administered a plurality of active agents effective to treat the subject for the disease mediated by CD226 and/or TIGIT in the subject, including e.g., where the plurality of active agents include the anti-CD96 antibody and an additional active agent, such as but not limited to e.g., a checkpoint inhibitor such as e.g., a second antibody comprising a specificity for an antigen that is an immune checkpoint molecule.

In some embodiments of the uses and methods of treatment disclosed herein, the CD96-mediated diseases and conditions, or the diseases mediated by CD155, CD226, and/or TIGIT, that can be treated with the anti-CD96 antibodies of the present disclosure, or pharmaceutical compositions thereof, include cancer and viral infections. In some embodiments, the cancer is selected from adrenal gland cancer, bladder cancer, brain cancer, breast cancer, cervical cancer, colorectal cancer, EGJ adenocarcinoma, esophageal cancer, gall bladder cancer, gastric cancer, head and neck cancer, heart cancer, hepatocellular carcinoma, kidney cancer, liver cancer, melanoma, mesothelioma, non-small cell lung cancer, ovarian cancer, pancreatic cancer, prostate cancer, spleen cancer, small cell lung cancer, testicular cancer, thyroid cancer, and uterine cancer. In some embodiments, the cancer is selected from lung cancer, skin cancer (e.g., melanoma), pancreatic cancer, endometrial cancer, prostate cancer, colorectal cancer, ovarian cancer, and bladder cancer. In some embodiments, the viral infection is selected from Cytomegalovirus (CMV), Epstein Barr Virus (EBV), Herpes Simplex Virus (HSV), Human Immunodeficiency Virus (HIV), Human Papilloma Virus (HPV), and Varicella Zoster Virus (VSV).

BRIEF DESCRIPTION OF THE FIGURES

FIG. 1 depicts the amino acid sequence alignment of the closest human germline kappa light chain $V_L$ region (Gene ID—V gene: IGKV1-9*01, J gene: IGKJ2*01) and heavy chain $V_H$ region (Gene ID—V gene: IGHV1-46*01, J gene: IGHJ4*03) against the $V_L$ and $V_H$ regions of the hybridoma-derived murine anti-hu-CD96 antibody, 12F8, and the humanized version of this antibody, mAb1, as well as six $V_H$ region variants mAb1.v1, mAb1.v2, mAb1.v3, mAb1.v4, mAb1.v5, and mAb1.v7.

FIG. 2 depicts the amino acid sequence alignment of the closest human germline kappa light chain $V_L$ region (Gene ID—V gene: IGKV6D-21*02, J gene: IGKJ4*02) and heavy chain $V_H$ region (Gene ID—V gene: IGHV7-4-1*02, J gene: IGHJ4*03) against the $V_L$ and $V_H$ regions of the hybridoma-derived murine anti-hu-CD96 antibody, 10G1, and the humanized version of this antibody, h10G1.

FIG. 4A shows upregulation of surface expression levels of CD96; CD226, and CD155 in response to FHA and IL-2 treatment; FIG. 4B shows IL-2 secretion levels in response to incubation with anti-CD-96 antibodies in comparison to control ("IgG1 iso").

FIG. 5A, FIG. 5B, and FIG. 5C depict plots of the effect of the anti-CD96 antibodies in primary human peripheral blood mononuclear cells (PBMCs) upon anti-CD3 and anti-CD28 treatment as described in Example 7. FIG. 5A shows surface expression levels of CD96; FIG. 5B shows surface expression levels of CD226; FIG. 5C shows surface expression levels of CD155.

FIG. 9 depicts distributions of the number of metastases counted 14 days after implantation in B16F10 lung metastasis model mice following treatment with an anti-CD96 antibody, an anti-PD1 antibody, an anti-CTLA-4 antibody, each alone, as well as, the anti-CD96 in combination with each of the anti-PD1 antibody, and the anti-CTLA-4 antibody.

FIG. 10A depicts changes in IL-2 levels and FIG. 10B depicts changes in IFNγ levels.

FIG. 11A depicts changes in IFNγ levels and FIG. 11B depicts changes in IL-2 levels.

FIG. 12A depicts binding to purified human CD226 ectodomain protein and FIG. 12B depicts binding to expressed purified cynomolgus monkey CD226 ectodomain protein.

DETAILED DESCRIPTION

Figure 3:
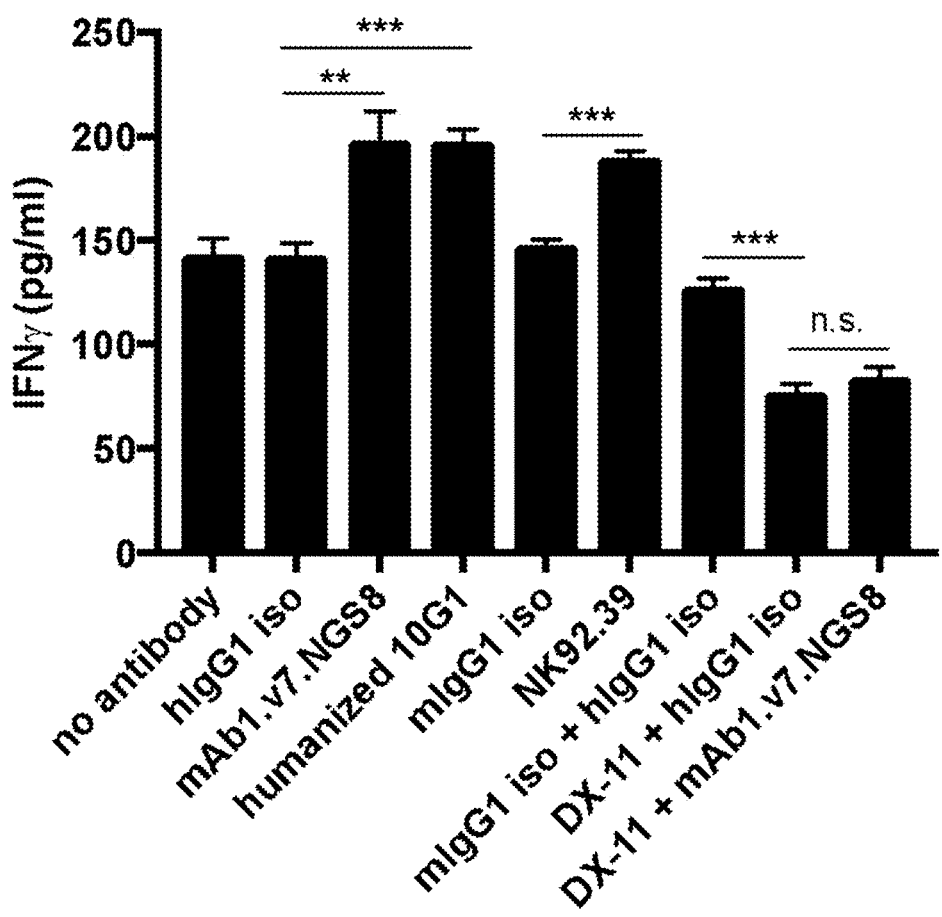
FIG. 3 depicts plots of IFNγ secretion triggered by the anti-CD96 antibodies mAb1.v7.NGS8 (or "NGS8"), humanized 10G1 ("h10G1"), NK92.39, and the control antibodies humanized IgG1+N297G mutation ("hIgG1 N297G iso", indicated as "hIgG iso" in the figure), mouse IgG1 ("mIgG1 iso"), alone, and also triggered by NGS8 or the control antibodies in the presence of the anti-CD226 antibody DX-11. Each condition was tested in 5 biological replicates. Student T-test was used to compare indicated groups. , p<0.005; *, p<0.001; NS, not significant.

The present disclosure provides antibodies, including humanized antibodies, that specifically bind CD96 with high affinity and thereby inhibit, decrease, and/or fully block the function of CD96 as a cell surface receptor involved in immune regulation, particularly the function of CD96 as an inhibitor of lymphocyte (e.g., T cell and NK cell) activation. Accordingly, it is contemplated that any of the compositions or formulations comprising an anti-CD96 antibody of the present disclosure can be used as therapeutics for treatment of diseases mediated by the function of CD96 or its target antigen, CD155, such as cancers and viral infections. Further, it is contemplated that the anti-CD96 antibody of the present disclosure can be used as a therapeutic in combination with other therapeutics, such as antibodies that target immune checkpoint molecules including, but not limited to, PD1, TIGIT, LAG3, PVRIG, KIR, TIM-3, and CRTAM. Among the therapeutics contemplated by the present disclosure is a bispecific antibody comprising the anti-CD96 binding specificity of an antibody of the present disclosure and another binding specificity of an antibody to an immune checkpoint molecule such as PD1, TIGIT, LAG3, PVRIG, KIR, TIM-3, and CRTAM.

Overview of Terminology and Techniques

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., *Molecular Cloning-A Laboratory Manual* (2nd Ed.), Vols. 1-3, Cold Spring Harbor Laboratory, Cold Spring Harbor, N.Y., 1989 (hereinafter "Sambrook"); *Current Protocols in Molecular Biology*, F. M. Ausubel et al., eds., Current Protocols, a joint venture between Greene Publishing Associates, Inc. and John Wiley & Sons, Inc. (supplemented through 2011) (hereinafter "Ausubel"); *Antibody Engineering*, Vols. 1 and 2, R. Kontermann and S. Dubel, eds., Springer-Verlag, Berlin and Heidelberg (2010); *Monoclonal Antibodies: Methods and Protocols*, V. Ossipow and N. Fischer, eds., 2nd Ed., Humana Press (2014); *Therapeutic Antibodies: From Bench to Clinic*, Z. An, ed., J. Wiley & Sons, Hoboken, N.J. (2009); and *Phage Display*, Tim Clackson and Henry B. Lowman, eds., Oxford University Press, United Kingdom (2004).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for the purpose of describing particular embodiments only and is not intended to be limiting. For purposes of interpreting this disclosure, the following description of terms will apply and, where appropriate, a term used in the singular form will also include the plural form and vice versa.

"CD96," as used herein, refers to a transmembrane glycoprotein of the Ig superfamily that that is encoded by the cluster of differentiation 96 gene in humans, however "CD96" as used herein encompasses the CD96 proteins of human, cynomolgus monkey, rhesus monkey, and their various isoforms. CD96 is expressed on the surface of T cells and NK cells and is also commonly referred to in the art as "TACTILE." Amino acid sequences of various exemplary CD96 proteins are known in the art and are provided in Table 1 below and the attached Sequence Listing.

"CD96 mediated condition" or "CD96 mediated disease," as used herein, encompasses any medical condition associated with the specific binding of CD96 to an antigen (e.g., CD155). For example, specific binding of CD96 to the cell surface receptor CD155 can affect the binding of CD155 to the immune regulatory molecules CD226 and/or TIGIT, which alters activation of lymphocytes (e.g., T cells and NK cells). Accordingly, CD96 mediated diseases can include, but are not limited to, any disease or condition mediated by and/or responsive to antagonists or inhibitors of CD155, CD226, and/or TIGIT, and/or any disease or condition responsive to inhibition of immune checkpoint inhibitors, including but not limited to cancers and viral infections. Specific exemplary cancers and viral infections are provided elsewhere herein.

"CD226," as used herein, refers to a transmembrane glycoprotein of the Ig superfamily that that is encoded by the cluster of differentiation 226 gene in humans, however "CD226" as used herein encompasses the CD226 proteins of human, cynomolgus monkey, rhesus monkey, mouse, and their various isoforms. CD226 is expressed on the surface of NK cells, platelets, monocytes, and a subset of T cells, and is also commonly referred to in the art as "DNAM-1." Amino acid sequences of exemplary CD226 proteins are known in the art and provided elsewhere herein.

"CD155," as used herein, refers to a transmembrane glycoprotein of the Ig superfamily that is encoded by the cluster of differentiation 155 gene in humans, however "CD155" as used herein encompasses the CD155 proteins of human, cynomolgus monkey, rhesus monkey, mouse, and their various isoforms that may exist. CD155 is expressed on the surface of many cancer cell lines and primary tumors and is also commonly referred to as "PVR" or "Necl5." Amino acid sequences of exemplary CD155 proteins are known in the art and are provided in Table 1 below and the attached Sequence Listing.

"TIGIT," as used herein, refers to a transmembrane glycoprotein of the Ig superfamily that that is expressed on the surface of T cells and NK cells. TIGIT is also referred to in the art as "T cell immunoreceptor with Ig and ITIM domains." Amino acid sequences of exemplary TIGIT proteins are known in the art.

"Immune checkpoint molecule," as used herein, refers to a molecule that functions to regulate an immune system pathway and thereby prevent it from attacking cells unnecessarily. Many immune checkpoint molecules, both inhibitory and co-stimulatory, are targets for immunotherapy (e.g., with blocking antibodies to block immune inhibition or with agonists to promote immune stimulation) in the treatment of cancer and viral infections. Exemplary immune checkpoint molecules targeted for cancer immunotherapy include, but are not limited to, PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA.

"Antibody," as used herein, refers to a molecule comprising one or more polypeptide chains that specifically binds to, or is immunologically reactive with, a particular antigen. Exemplary antibodies of the present disclosure include monoclonal antibodies, polyclonal antibodies, chimeric antibodies, humanized antibodies, human antibodies, multispecific (or heteroconjugate) antibodies (e.g., bispecific antibodies), monovalent antibodies (e.g., single-arm antibodies), multivalent antibodies, antigen-binding fragments (e.g., Fab', F(ab')$_2$, Fab, Fv, rIgG, and scFv fragments), antibody fusions, and synthetic antibodies (or antibody mimetics).

"Anti-CD96 antibody" or "antibody that binds CD96" refers to an antibody that binds CD96 with sufficient affinity such that the antibody is useful as a diagnostic and/or therapeutic agent in targeting CD96. In some embodiments, the extent of binding of an anti-CD96 specific antibody to an unrelated, non-CD96 antigen is less than about 20%, less than about 15%, less than about 10%, or less than about 5% of the binding of the antibody to CD96 as measured, e.g., by a radioimmunoassay (RIA) or surface plasmon resonance (SPR). In some embodiments, an antibody that binds to CD96 has a dissociation constant ($K_D$) of <1 μM, <100 nM, <10 nM, <1 nM, <0.1 nM, <0.01 nM, or <1 pM (e.g., $10^{-8}$ M or less, e.g., from $10^{-8}$ M to $10^{-13}$ M, e.g., from $10^{-9}$ M to $10^{-13}$ M).

"Full-length antibody," "intact antibody," or "whole antibody" are used herein interchangeably to refer to an antibody having a structure substantially similar to a native antibody structure or having heavy chains that contain an Fc region as defined herein.

"Antibody fragment" refers to a portion of a full-length antibody which is capable of binding the same antigen as the full-length antibody. Examples of antibody fragments include, but are not limited to, Fv, Fab, Fab', Fab'-SH, F(ab')$_2$; diabodies; linear antibodies; monovalent, or single-armed antibodies; single-chain antibody molecules (e.g., scFv); and multispecific antibodies formed from antibody fragments.

"Class" of an antibody refers to the type of constant domain or constant region possessed by its heavy chain. There are five major classes of antibodies: IgA, IgD, IgE, IgG, and IgM, and several of these are further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

"Variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs) (see, e.g., Kindt et al., Kuby Immunology, 6$^{th}$ ed., W.H. Freeman and Co., page 91). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (see, e.g., Portolano et al., J. Immunol. 150: 880-887 (1993); Clarkson et al., Nature 352:624-628 (1991)).

"Hypervariable region" or "HVR," as used herein, refers to each of the regions of an antibody variable domain which are hypervariable in sequence and/or form structurally defined loops ("hypervariable loops"). Generally, native antibodies comprise four chains with six HVRs; three in the heavy chain variable domain, $V_H$ (HVR-H1, HVR-H2, HVR-H3), and three in the light chain variable domain, $V_L$ (HVR-L1, HVR-L2, HVR-L3). The HVRs generally comprise amino acid residues from the hypervariable loops and/or from the "complementarity determining regions" (CDRs). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted in the table below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B[1] | H26-H35B[1] | H26-H32[1] | H30-H35B[1] |
|    | H31-H35[2]  | H26-H35[2]  | H26-H32[2] | H30-H35[2] |
| H2 | H50-H65 | H50-H58 | H53-H55 | H47-H58 |
| H3 | H95-H102 | H95-H102 | H96-H101 | H93-H101 |

[1]Kabat numbering
[2]Chothia numbering

Unless otherwise indicated, HVR residues and other residues in the variable domain (e.g., FR residues) are numbered herein according to Kabat et al., supra.

Hypervariable regions, as used herein, may include extended or alternative hypervariable regions as follows: 24-36 or 24-34 (L1), 46-56 or 50-56 (L2) and 89-97 or 89-96 (L3) in the $V_L$ domain and 26-35 or 30-35 (H1), 50-61, 50-65 or 49-65 (H2) and 93-102, 94-102, or 95-102 (H3) in the $V_H$ domain. The variable domain residues are numbered according to Kabat et al., supra, for each of these definitions.

"Complementarity determining region," or "CDR," as used herein, refers to the regions within the HVRs of the variable domain which have the highest sequence variability and/or are involved in antigen recognition. Generally, native antibodies comprise four chains with six CDRs; three in the heavy chain variable domains, $V_H$ (H1, H2, H3), and three in the light chain variable domains, $V_L$ (L1, L2, L3). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35 of H1, 50-61 of H2, and 95-102 of H3. (Numbering according to Kabat et al., supra).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in $V_H$ (or $V_L$): FR1-H1(L1)-FR2-H2(L2)-FR3-H3(L3)-FR4.

"Native antibody" refers to a naturally occurring immunoglobulin molecule. For example, native IgG antibodies are heterotetrameric glycoproteins of about 150,000 Daltons, composed of two identical light chains and two identical heavy chains that are disulfide-bonded. From N- to C-terminus, each heavy chain has a variable region ($V_H$), also called a variable heavy domain or a heavy chain variable domain, followed by three constant domains (CH1, CH2, and CH3). Similarly, from N- to C-terminus, each light chain has a variable region ($V_L$), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human HVRs and amino acid sequences from human FRs. In certain embodiments, a humanized antibody will comprise substantially all of at least one, and typically two, variable domains, in which all or substantially all of the HVRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Human antibody" refers to an antibody which possesses an amino acid sequence corresponding to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the $V_L$, the subgroup is subgroup kappa I as in Kabat et al., supra. In one embodiment, for the $V_H$, the subgroup is subgroup III as in Kabat et al., supra.

"Acceptor human framework" as used herein is a framework comprising the amino acid sequence of a light chain variable domain ($V_L$) framework or a heavy chain variable domain ($V_H$) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Fc region," refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain may vary, the human IgG heavy chain Fc sequence is usually defined to stretch from an amino acid residue at about position Cys226, or from about position Pro230, to the carboxyl-terminus of the Fc sequence. However, the C-terminal lysine (Lys447) of the Fc sequence may or may not be present. The Fc sequence of an immunoglobulin generally comprises two constant domains, a CH2 domain and a CH3 domain, and optionally comprises a CH4 domain.

"Fc receptor" or "FcR," refers to a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Daeron, Annu. Rev. Immunol. 15:203-234 (1997)). FcR, as used herein, also includes the neonatal receptor, FcRn, which is responsible for the transfer of maternal IgGs to the fetus (Guyer et al, J. Immunol. 1 17:587 (1976) and Kim et al, J. Immunol. 24:249 (1994)) and regulation of homeostasis of immunoglobulins. FcRs are reviewed, for example, in Ravetch and Kinet, Annu. Rev. Immunol 9:457-92 (1991); Capel et al, Immunomethods 4:25-34 (1994); and de Haas et al, J. Lab. Clin. Med. 126:330-41 (1995).

"Multivalent antibody," as used herein, is an antibody comprising three or more antigen binding sites. The multivalent antibody is preferably engineered to have the three or more antigen binding sites and is generally not a native sequence IgM or IgA antibody.

"Multispecific antibody" is an antibody having at least two different binding sites, each site with a different binding specificity. A multispecific antibody can be a full length antibody or an antibody fragment, and the different binding sites may bind each to a different antigen or the different binding sites may bind to two different epitopes of the same antigen.

"Fv fragment" refers to an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the $V_H$-$V_L$ dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

"Fab fragment' refers to an antibody fragment that contains a variable and constant domain of the light chain and a variable domain and the first constant domain (CH1) of the heavy chain. "F(ab')$_2$ fragments" comprise a pair of Fab fragments which are generally covalently linked near their carboxy termini by hinge cysteines between them. Other chemical couplings of antibody fragments also are known in the art.

"Antigen binding arm," as used herein, refers to a component of an antibody that has an ability to specifically bind a target molecule of interest. Typically the antigen binding arm is a complex of immunoglobulin polypeptide sequences, e.g., HVR and/or variable domain sequences of an immunoglobulin light and heavy chain.

"Single-chain Fv" or "scFv" refer to antibody fragments comprising the $V_H$ and $V_L$ domains of an antibody, wherein these domains are present in a single polypeptide chain.

Generally, an Fv polypeptide further comprises a polypeptide linker between the $V_H$ and $V_L$ domains which enables the scFv to form the desired antigen binding structure.

"Diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites.

"Linear antibodies" refers to the antibodies described in Zapata et al., Protein Eng., 8(10): 1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

"Naked antibody" refers to an antibody that is not conjugated to a heterologous moiety (e.g., a cytotoxic moiety) or radiolabel.

"Affinity" refers to the strength of the sum total of noncovalent interactions between a single binding site of a molecule (e.g., an antibody) and its binding partner (e.g., an antigen). "Binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured by common methods known in the art, including those described herein. Specific illustrative and exemplary embodiments for measuring binding affinity are described in the following.

"Binds specifically" or "specific binding" refers to binding of an antibody to an antigen with an affinity value of no more than about $1\times10^{-7}$ M. In some embodiments, an antibody may have a secondary affinity for an antigen other than the antigen to which it binds specifically, where "secondary affinity" will generally refer to binding of an antibody to a secondary antigen with an affinity value of more than about 10 nM as described elsewhere herein. Where an antibody may have a secondary affinity for a secondary antigen, such an antibody will nevertheless bind specifically to the primary antigen.

"Affinity matured" antibody refers to an antibody with one or more alterations in one or more HVRs, compared to a parent antibody which does not possess such alterations, such alterations resulting in an improvement in the affinity of the antibody for antigen.

"Functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen.

"Isolated antibody" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic methods (e.g., ion exchange or reverse phase HPLC). For review of methods for assessment of antibody purity, see, e.g., Flatman et al., J. Chromatogr. B 848:79-87.

"Substantially similar" or "substantially the same," as used herein, refers to a sufficiently high degree of similarity between two numeric values (for example, one associated with a test antibody and the other associated with a reference antibody), such that one of skill in the art would consider the difference between the two values to be of little or no biological and/or statistical significance within the context of the biological characteristic measured by said values (e.g., $K_D$ values).

"Substantially different," as used herein, refers to a sufficiently high degree of difference between two numeric values (generally one associated with a molecule and the other associated with a reference molecule) such that one of skill in the art would consider the difference between the two values to be of statistical significance within the context of the biological characteristic measured by said values (e.g., $K_D$ values).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

"Immunoconjugate" refers to an antibody conjugated to one or more heterologous molecule(s), including but not limited to a cytotoxic agent.

"Treatment," "treat" or "treating" refers to clinical intervention in an attempt to alter the natural course of a disorder in the individual being treated, and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of pharmaceutical formulation comprising an anti-CD96 antibody to a subject to delay development or slow progression of a disease or condition mediated by CD96 or disease or condition in which CD96 may play a role in the pathogenesis and/or progression.

"Pharmaceutical formulation" refers to a preparation in a form that allows the biological activity of the active ingredient(s) to be effective, and which contain no additional components which are toxic to the subjects to which the formulation is administered. A pharmaceutical formulation may include one or more active agents. For example, a pharmaceutical formulation may include an anti-CD96 antibody as the sole active agent of the formulation or may include an anti-CD96 antibody and one or more additional active agents, such as e.g., an immune checkpoint inhibitor.

By "sole active agent", as used herein, is meant that the agent referred to is the only agent present in the formulation, or used in the therapy, that provides, or would be expected to provide, the relevant pharmacological effect to treat the subject for the condition, consistent with the description of "treatment" as provided herein. A pharmaceutical formulation comprising a sole active agent does not exclude the presence of one or more non-active agents, such as e.g., a pharmaceutically acceptable carrier, in the formulation. A "non-active agent" is an agent that would not be expected to provide, or otherwise significantly contribute to, the relevant pharmacological effect intended to treat the subject for the condition.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Therapeutically effective amount" refers to the amount of an active ingredient or agent (e.g., a pharmaceutical formulation) to achieve a desired therapeutic or prophylactic result, e.g., to treat or prevent a disease, disorder, or condition in a subject. In the case of a CD96 mediated disease or condition, the therapeutically effective amount of the therapeutic agent is an amount that reduces, prevents, inhibits, and/or relieves to some extent one or more of the symptoms associated with the disease, disorder, or condition. For cancer therapy, efficacy in vivo can, for example, be measured by assessing the growth of a primary tumor, occurrence and/or growth of secondary tumor(s), occurrence and/or number of metastases, duration, severity, and/or recurrence of symptoms, the response rate (RR), duration of response, and/or quality of life.

"Concurrently," as used herein, refers to administration of two or more therapeutic agents, where at least part of the administration overlaps in time. Accordingly, concurrent administration includes a dosing regimen when the administration of one or more agent(s) continues after discontinuing the administration of one or more other agent(s).

"Individual" or "subject" refers to a mammal, including but not limited to, domesticated animals (e.g., cows, sheep, cats, dogs, and horses), primates (e.g., humans and non-human primates such as monkeys), rabbits, and rodents (e.g., mice and rats).

DETAILED DESCRIPTION OF VARIOUS EMBODIMENTS

I. CD96

CD96 is a transmembrane glycoprotein of the Ig superfamily that is expressed on the surface of cells, notable T cells and NK cells. The sequence and annotation of human CD96 (also referred to herein as "hu-CD96") can be found at UniProt entry P40200. The sequence of the full-length 585 amino acid hu-CD96 precursor protein (UniProt P40200) is set forth herein as SEQ ID NO: 1. A shorter isoform of hu-CD96, referred to as "isoform 2," is believed to be the predominant in vivo form of hu-CD96 (Meyer et al., (2009)). The sequence of the 569 amino acid isoform 2 of hu-CD96 precursor protein (UniProt P40200-2) is set forth herein as SEQ ID NO: 2. The 16-amino acid sequence at positions 183-198 of the full-length hu-CD96 isoform 1 (SEQ ID NO: 1) is missing in isoform 2 (SEQ ID NO: 2). An exemplary 1710 nucleotide sequence encoding isoform 2 hu-CD96 (GenBank M88282.1) is set forth herein as SEQ ID NO: 3.

The amino acid sequence of hu-CD96 comprises in consecutive order a signal peptide, extracellular domain, transmembrane domain, and cytoplasmic domain. The signal sequence of hu-CD96 comprises amino acids 1-21, the extracellular domain comprises amino acids 22-519, the transmembrane domain comprises amino acid 520-540, and the cytoplasmic domain comprises amino acids 541-585 (position numbering based on SEQ ID NO: 1). The extracellular domain of hu-CD96 further comprises three distinct Ig-like domains: "D1" comprises amino acids 38-125; "D2" comprises amino acids 156-238; and "D3" comprises amino acids 269-375 (position numbering based on SEQ ID NO: 1).

Recombinant polypeptide constructs corresponding to the extracellular portions of the isoform 2 hu-CD96 protein can be used as antigens to elicit anti-CD96 antibodies capable of binding the CD96 target antigen with high affinity, and preventing binding of CD96 to CD155. Polypeptide constructs corresponding to the extracellular portions of isoform 2, hu-CD96 protein useful as antigens include the polypeptides of amino acid sequences of SEQ ID NO: 4, 5, and 6. These polypeptides comprise the extracellular domain of isoform 2, hu-CD96 (positions V22-K516) (SEQ ID NO: 4), the D1 extracellular domain (positions V22-Q137) (SEQ ID NO: 5), and the combined domains D1, D2, and D3 (or "D1 D3") (positions V22-T375) (SEQ ID NO: 6). Additionally, recombinant polypeptide constructs corresponding to the complete extracellular domain and D1 D3 domains of the cynomolgus monkey CD96 protein ("cy-CD96") (SEQ ID NO: 7 and 8), and the D1 D3 domains of the rhesus monkey CD96 protein (rh-CD96) (SEQ ID NO: 9) are useful in as antigens in generating anti-CD96 antibodies capable of cross reacting with human CD96 and these primate species CD96 proteins. Recombinant polypeptide constructs corresponding to the extracellular portions of the CD96 target antigen human CD155 protein (SEQ ID NO: 10), and the corresponding mouse CD155 protein (SEQ ID NO: 11), are useful in developing the anti-CD96 antibodies with high affinity and cross-reactivity.

Recombinant polypeptide constructs corresponding to the extracellular portions of the human CD226 protein (SEQ ID NO: 482), and the corresponding cynomolgus CD226 protein (SEQ ID NO: 483), are useful in determining secondary binding properties of the anti-CD96 antibodies with CD226.

Table 1 below provides a summary description of the sequences of the various CD96 proteins, and the recombinant CD96, CD155, and CD226 polypeptide constructs of the present disclosure, and their sequence identifiers. The sequences also are included in the accompanying Sequence Listing.

TABLE 1

| CD96 and CD155 Sequences | | |
|---|---|---|
| Name | Sequence | SEQ ID NO: |
| hu-CD96 isoform 1 (UniProt 40200) | MEKKWKYCAVYYIIQIHFVKGVWEKTVNTEENVYATLGSDVNLTCQTQTVGFFV QMQWSKVTNKIDLIAVYHPQYGFYCAYGRPCESLVTFTETPENGSKWTLHLRNM SCSVSGRYECMLVLYPEGIQTKIYNLLIQTHVTADEWNSNHTIEIEINQTLEIP CFQNSSSKISSEFTYAWSVENSSTDSWVLLSKGIKEDNGTQETLISQNHLISNS TLLKDRVKLGTDYRLHLSPVQIFDDGRKFSCHIRVGPNKILRSSTTVKVFAKPE IPVIVENNSTDVLVERRFTCLLKNVFPKANITWFIDGSFLHDEKEGIYITNEER KGKDGFLELKSVLTRVHSNKPAQSDNLTIWCMALSPVPGNKVWNISSEKITFLL GSEISSTDPPLSVTESTLDTQPSPASSVSPARYPATSSVTLVDVSALRPNTTPQ PSNSSMTTRGFNYPWTSSGTDTKKSVSRIPSETYSSSPSGAGSTLHDNVFTSTA RAFSEVPTTANGSTKTNHVHITGIVVNKPKDGMSWPVIVAALLFCCMILFGLGV RKWCQYQKEIMERPPPFKPPPPPIKYTCIQEPNESDLPYHEMETL | 1 |
| hu-CD96 isoform 2 (UniProt 40200-2) | MEKKWKYCAVYYIIQIHFVKGVWEKTVNTEENVYATLGSDVNLTCQTQTVGFFV QMQWSKVTNKIDLIAVYHPQYGFYCAYGRPCESLVTFTETPENGSKWTLHLRNM SCSVSGRYECMLVLYPEGIQTKIYNLLIQTHVTADEWNSNHTIEIEINQTLEIP CFQNSSSKISSEFTYAWSVEDNGTQETLISQNHLISNSTLLKDRVKLGTDYRLH LSPVQIFDDGRKFSCHIRVGPNKILRSSTTVKVFAKPEIPVIVENNSTDVLVER RFTCLLKNVFPKANITWFIDGSFLHDEKEGIYITNEERKGKDGFLELKSVLTRV HSNKPAQSDNLTIWCMALSPVPGNKVWNISSEKITFLLGSEISSTDPPLSVTES TLDTQPSPASSVSPARYPATSSVTLVDVSALRPNTTPQPSNSSMTTRGFNYPWT SSGTDTKKSVSRIPSETYSSSPSGAGSTLHDNVFTSTARAFSEVPTTANGSTKT NHVHITGIVVNKPKDGMSWPVIVAALLFCCMILFGLGVRKWCQYQKEIMERPPP FKPPPPPIKYTCIQEPNESDLPYHEMETL | 2 |
| hu-CD96 isoform 2 (GenBank M88282.1) | ATGGAGAAAAAATGGAAATACTGTGCTGTCTATTACATCATCCAGATACATTTTG TCAAGGGAGTTTGGGAAAAAACAGTCAACACAGAAGAAAATGTTTATGCTACACT TGGCTCTGATGTCAACCTGACCTGCCAAACACAGACAGTAGGCTTCTTCGTGCAG ATGCAATGGTCCAAGGTCACCAATAAGATAGACCTGATTGCTGTCTATCATCCCC AATACGGCTTCTACTGTGCCTATGGGAGACCCTGTGAGTCACTTGTGACTTTCAC AGAAACTCCTGAGAATGGGTCAAAATGGACTCTGCACTTAAGGAATATGTCTTGT TCAGTCAGTGGAAGGTACGAGTGTATGCTTGTTCTGTATCCAGAGGGCATTCAGA CTAAAATCTACAACCTTCTCATTCAGACACACGTTACAGCAGATGAATGGAACAG CAACCATACGATAGAAATAGAGATAAATCAGACTCTGGAAATACCATGCTTTCAA AATAGCTCCTCAAAAATTTCATCTGAGTTCACCTATGCATGGTCGGTGGAGGATA ATGGAACTCAGGAAACACTTATCTCCCAAAATCACCTCATCAGCAATTCCACATT ACTTAAAGATAGAGTCAAGCTTGGTACAGACTACAGACTCCACCTCTCTCCAGTC CAAATCTTCGATGATGGGCGGAAGTTCTCTTGCCACATTAGAGTCGGTCCTAACA AAATCTTGAGGAGCTCCACCACAGTCAAGGTTTTTGCTAAACCAGAAATCCCTGT GATTGTGGAAAATAACTCCACGGATGTCTTGGTAGAGAGAAGATTTACCTGCTTA CTAAAGAATGTATTTCCCAAAGCAAATATCACATGGTTTATAGATGGAAGTTTTC TTCATGATGAAAAAGAAGGAATATATATTACTAATGAAGAGAGAAAAGGCAAAGA TGGATTTTTGGAACTGAAGTCTGTTTTAACAAGGGTACATAGTAATAAACCAGCC CAATCAGACAACTTGACCATTTGGTGTATGGCTCTGTCTCCAGTCCCAGGAAATA AAGTGTGGAACATCTCATCAGAAAAGATCACTTTTCTCTTAGGTTCTGAAATTTC CTCAACAGACCCTCCACTGAGTGTTACAGAATCTACCCTTGACACCCAACCTTCT CCAGCCAGCAGTGTATCTCCTGCAAGATATCCAGCTACATCTTCAGTGACCCTTG TAGATGTGAGTGCCTTGAGGCAAACACCACTCCTCAACCCAGCAATTCCAGTAT GACTACCCGAGGCTTCAACTATCCCTGGACCTCCAGTGGGACAGATACCAAAAAA TCAGTTTCACGGATACCTAGTGAAACATACAGTTCATCCCCCTCAGGTGCAGGCT CAACACTTCATGACAATGTCTTTACCAGCACAGCCAGAGCATTTTCAGAAGTCCC CACAACTGCCAATGGATCTACGAAAACTAATCACGTCCATATCACTGGTATTGTG GTCAATAAGCCCAAAGATGGAATGTCCTGGCCAGTGATTGTAGCAGCTTTACTCT TTTGCTGCATGATATTGTTTGGTCTTGGAGTGAGAAAATGGTGTCAGTACCAAAA AGAAATAATGGAAAGACCTCCACCTTTCAAGCCACCACCACCTCCCATCAAGTAC ACTTGCATTCAAGAGCCCAACGAAAGTGATCTGCCTTATCATGAGATGGAGACCC TCTAG | 3 |
| hu-CD96 isoform 2 extracellular domain V22 - K516 | VWEKTVNTEENVYATLGSDVNLTCQTQTVGFFVQMQWSKVTNKIDLIAVYHPQY GFYCAYGRPCESLVTFTETPENGSKWTLHLRNMSCSVSGRYECMLVLYPEGIQT KIYNLLIQTHVTADEWNSNHTIEIEINQTLEIPCFQNSSSKISSEFTYAWSVED NGTQETLISQNHLISNSTLLKDRVKLGTDYRLHLSPVQIFDDGRKFSCHIRVGP NKILRSSTTVKVFAKPEIPVIVENNSTDVLVERRFTCLLKNVFPKANITWFIDG SFLHDEKEGIYITNEERKGKDGFLELKSVLTRVHSNKPAQSDNLTIWCMALSPV | 4 |

TABLE 1-continued

CD96 and CD155 Sequences

| Name | Sequence | SEQ ID NO: |
|---|---|---|
|  | PGNKVWNISSEKITFLLGSEISSTDPPLSVTESTLDTQPSPASSVSPARYPATS SVTLVDVSALRPNTTPQPSNSSMTTRGFNYPWTSSGTDTKKSVSRIPSETYSSS PSGAGSTLHDNVFTSTARAFSEVPTTANGSTKTNHVHITGIVVNKPK |  |
| hu-CD96 isoform 2 domain D1 V22 - Q137 | VWEKTVNTEENVYATLGSDVNLTCQTQTVGFFVQMQWSKVTNKIDLIAVYHPQY GFYCAYGRPCESLVTFTETPENGSKWTLHLRNMSCSVSGRYECMLVLYPEGIQT KIYNLLIQ | 5 |
| hu-CD96 isoform 2 domains D1-D3 V22 - T375 | VWEKTVNTEENVYATLGSDVNLTCQTQTVGFFVQMQWSKVTNKIDLIAVYHPQY GFYCAYGRPCESLVTFTETPENGSKWTLHLRNMSCSVSGRYECMLVLYPEGIQT KIYNLLIQTHVTADEWNSNHTIEIEINQTLEIPCFQNSSSKISSEFTYAWSVED NGTQETLISQNHLISNSTLLKDRVKLGTDYRLHLSPVQIFDDGRKFSCHIRVGP NKILRSSTTVKVFAKPEIPIVIVENNSTDVLVERRFTCLLKNVFPKANITWFIDG SFLHDEKEGIYITNEERKGKDGFLELKSVLTRVHSNKPAQSDNLTIWCMALSPV PGNKVWNISSEKIT | 6 |
| cy-CD96 isoform 2 extracellular domains V22- K516 | VWGKPFNTEENIYATLGSDVNLTCQTQAKGFLVQMQWSKVTDKADLIALYHPQY GFHCAYGSPCESLVTFTQTPENGSKWTLHLRNMSSSVSGRYECMLTLYPEGMQT KIYNLLIQTHVTPDEWKSNHTIEIEINQTLEIPCFQNSSSEISSEFTYAWLVED NGTQQTLISQDHLISSSTLLKDRVKVGIDYRLHLSPVQIFDDGRKFSCHIRVGP DKILRSSTTIKVFAKPEIPMIVENNSTDVLVERTFTCLLKNVFPKANIIWFIDG SFLHDEKEGIYITNEERKGKDGFLELKSVLTRVHSDKPAQSDNLTIWCMALSPV PGNKVWNISSEKITFLLGSEMSTTDLPPSVTESTLDTQPSPASSVSPTRYPATS SVTLADVSALRPNTTPQSSSSSVTTQDFNYPWTSSGTDAKKSFSQIPSETYSSS PSGAGSTLHDNVFTSTTRALSEVPTTANGSTKTNHVHITGIVVSKPK | 7 |
| cy-CD96 domains D1D3 V22-T375 | VWGKPFNTEENIYATLGSDVNLTCQTQAKGFLVQMQWSKVTDKADLIALYHPQY GFHCAYGSPCESLVTFTQTPENGSKWTLHLRNMSSSVSGRYECMLTLYPEGMQT KIYNLLIQTHVTPDEWKSNHTIEIEINQTLEIPCFQNSSSEISSEFTYAWLVED NGTQQTLISQDHLISSSTLLKDRVKVGIDYRLHLSPVQIFDDGRKFSCHIRVGP DKILRSSTTIKVFAKPEIPMIVENNSTDVLVERTFTCLLKNVFPKANIIWFIDG SFLHDEKEGIYITNEERKGKDGFLELKSVLTRVHSDKPAQSDNLTIWCMALSPV PGNKVWNISSEKIT | 8 |
| rh-CD96 domains D1D3 V22-T375 | VWGKPLNTEENIYATLGSDVNLTCQTQAKGFLVQMQWSKVTDKADLIALYHPQY GFHCAYGSPCESLVTFTQTPENGSKWTLHLRNMSSSVSGRYECMLTLYPEGMQT KIYNLLIQTHVTPDEWKSNHTIEIEINQTLEIPCFQNSSSEISSEFTYAWLVED NGTQQTLISQDHLISSSTLLKDRVKVGTDYRLHLSPVQIFDDGRKFSCHIRVGP DKILRSSTTIKVFAKPEIPMIVENNSTDVLVERIFTCLLTNVFPKANIIWFIDG SFLHDEKEGIYITNEERKGKDGFLELKSVLTRVHSDKPAQSDNLTIWCMALSPV PGNKVWNISSEKIT | 9 |
| hu-CD155 extracellular domains W20-N343 | WPPPGTGDVVVQAPTQVPGFLGDSVTLPCYLQVPNMEVTHVSQLTWARHGESGS MAVFHQTQGPSYSESKRLEFVAARLGAELRNASLRMFGLRVEDEGNYTCLFVTF PQGSRSVDIWLRVLAKPQNTAEVQKVQLTGEPVPMARCVSTGGRPPAQITWHSD LGGMPNTSQVPGFLSGTVTVTSLWILVPSSQVDGKNVTCKVEHESFEKPQLLTV NLTVYYPPEVSISGYDNNWYLGQNEATLTCDARSNPEPTGYNWSTTMGPLPPFA VAQGAQLLIRPVDKPINTTLICNVTNALGARQAELTVQVKEGPPSEHSGMSRN | 10 |
| mo-CD155-extracellular domains D29-R345 | DIRVLVPYNSTGVLGGSTTLHCSLTSNENVTITQITWMKKDSGGSHALVAVFHP KKGPNIKEPERVKFLAAQQDLRNASLAISNLSVEDEGIYECQIATFPRGSRSTN AWLKVQARPKNTAEALEPSPTLILQDVAKCISANGHPPGRISWPSNVNGSHREM KEPGSQPGTTTVTSYLSMVPSRQADGKNITCTVEHESLQELDQLLVTLSQPYPP ENVSISGYDGNWYVGLTNLTLTCEAHSKPAPDMAGYNWSTTTGDFPNSVKRQGN MLLISTVEDGLNNTVIVCEVTNALGSGQGQVHIIVKEKPENMQQNTR | 11 |
| hu-CD226 | MDYPTLLLALLHVYRALCEEVLWHTSVPFAENMSLECVYPSMGILTQVEWFKIG TQQDSIAIFSPTHGMVIRKPYAERVYFLNSTMASNNMTLFFRNASEDDVGYYSC SLYTYPQGTWQKVIQVVQSDSFEAAVPSNSHIVSEPGKNVTLTCQPQMTWPVQA VRWEKIQPRQIDLLTYCNLVHGRNFTSKFPRQIVSNCSHGRWSVIVIPDVTVSD SGLYRCYLQASAGENETFVMRLTVAEGKTDNQYTLFVAGGTVLLLLFVISITTI IVIFLNRRRRRERRDLFTESWDTQKAPNNYRSPISTSQPTNQSMDDTREDIYVN YPTFSRRPKTRVDYKDDDDK | 482 |
| cy-CD226 | MDYPTLLLALLHVYRALCEEVLWHTSVPFAENMSLECVYPSVGILTQVEWFKIG TEKDSIAIFSPTHGMVIRKPYAERVYFLNSTMASNNMTLFFRNASEDDVGYYSC SLYTYPQGTWQKVIQVVQSDGFEAAVPPNSHIVSEPGKNITLTCQPQMTWPVQE VRWEKVQPHQIDLLTYCDLVHGRNFTSKFPRQIVSNCSHGSWSFIVVPDVTASD SGLYRCHLQASAGENETFVMRLTVAEGQTDNQYTRFVTGGTVLLLLFVISITTI IVIFLNRRRRRERNDLYTESWDTQKAPKNYRSPISANQPTNQSMDDTREDIYVN YPTFSRRPKTRVDYKDDDDK | 483 |

II. Anti-CD96 Antibodies

In some embodiments, the present disclosure provides structures of anti-CD96 antibodies in terms of the amino acid and encoding nucleotide sequences of the various well-known immunoglobulin features (e.g., HVRs, FRs, $V_H$, $V_L$ domains, and full-length heavy and light chains). Table 2 below provides a summary description of anti-CD96 antibody sequences of the present disclosure, and their sequence identifiers. The sequences are included in the accompanying Sequence Listing.

TABLE 2

Anti-CD96 antibody sequences

| Description | Sequence | SEQ ID NO: |
|---|---|---|
| 12F8 (mAb1) - VL | DIVMTQSQKFMSTSVGDRVSVTC<u>KASQNVGTAIV</u>WYQKKPGQSPKTLIY<u>S<br>ASTRYT</u>GVPDRFTGSGSGTDFTLTISNVQSEDLAEYFC<u>QQYSESPLT</u>FGS<br>GTKLEIK | 12 |
| 12F8 - HVR-L1<br>(VL positions 24-34) | KASQNVGTAIV | 13 |
| 12F8 - HVR-L2<br>(VL positions 50-56) | SASTRYT | 14 |
| 12F8 - HVR-L3<br>(VL positions 89-97) | QQYSSSPLT | 15 |
| 10H5 - VL | DVVMTQTPLTLSVTLGHPASISC<u>KSSQSLLDSDGKTYLN</u>WLLQRPGESPK<br>LLIY<u>LVSKLDS</u>GVPDRFTGSGSGTDFTLKISRVEAEDLGVYYC<u>LQATHSP<br>QT</u>FGGGTKLEIK | 16 |
| 10H5 - HVR-L1<br>(VL positions 24-34) | KSSQSLLDSDGKTYLN | 17 |
| 10H5 - HVR-L2<br>(VL positions 50-56) | LVSKLDS | 18 |
| 10H5 - HVR-L3<br>(VL positions 89-97) | LQATHSPQT | 19 |
| 1G8 - VL | DIQMNQSPSSLSASLGDTITITC<u>RVSQDISFWLS</u>WYQQKPGNIPKLLIY<u>K<br>ASNLHT</u>GVPPRFSGSGSGTDFTLTISSLQPEDIAAYYC<u>LQSQSYPYT</u>FGG<br>GTKLEIK | 20 |
| 1G8 - HVR-L1<br>(VL positions 24-34) | RVSQDISFWLS | 21 |
| 1G8 - HVR-L2<br>(VL positions 50-56) | KASNLHT | 22 |
| 1G8 - HVR-L3<br>(VL positions 89-97) | LQSQSYPYT | 23 |
| 16D9 - VL | ENVLTQSPAIMSATLGEKVTMNC<u>RASSNVKYMY</u>WYQQKSGVSPKLWIY<u>YT<br>SNLAS</u>GVPTRFSGSGSGTSYSLTISSVEAEDAATYYC<u>QQFTSSPLT</u>FGAG<br>TKLELK | 24 |
| 16D9 - HVR-L1<br>(VL positions 24-34) | RASSNVKYMY | 25 |
| 16D9 - HVR-L2<br>(VL positions 50-56) | YTSNLAS | 26 |
| 16D9 - HVR-L3<br>(VL positions 89-97) | QQFTSSPLT | 27 |
| 9H4 - VL | DIVLTQSPASLAVSLGQRAIISC<u>KASQSVTFADTGLMH</u>WYQQKPGQQPKL<br>LIY<u>RASNLEV</u>GVPTRFSGSGSGTDFTLNIHPVEEEDVATYYC<u>QQSREYPW<br>T</u>FGGGTKLEIK | 28 |
| 9H4 - HVR-L1<br>(VL positions 24-34) | KASQSVTFADTGLMH | 29 |
| 9H4 - HVR-L2<br>(VL positions 50-56) | RASNLEV | 30 |
| 9H4 - HVR-L3<br>(VL positions 89-97) | QQSREYPWT | 31 |

TABLE 2-continued

Anti-CD96 antibody sequences

| Description | Sequence | SEQ ID NO: |
|---|---|---|
| 7E5 - VL | QAVVTQESALTTSPGETVTLTC<u>RSSTGAVTTSNYAN</u>WVQEKPDHLFTGLI GG<u>TNNRAP</u>GVPARFSGSLIGDKAALTITGAQTEDEAIYFC<u>SLWYGSHWV</u>F GGGTKLTVL | 32 |
| 7E5 - HVR-L1 (VL positions 24-34) | RSSTGAVTTSNYAN | 33 |
| 7E5 - HVR-L2 (VL positions 50-56) | GTNNRAP | 34 |
| 7E5 - HVR-L3 (VL positions 89-97) | SLWYGSHWV | 35 |
| 10G1 - VL | DILMTQSPTTLSVTPGETVSLSC<u>RASQDIYRNLH</u>WYQQKSQGTPRLLIK<u>H ASDSIS</u>GIPSRFTGSGSGTDFTLSINSVKPEDEGIYYC<u>LQGYSMPYT</u>FGG GTKLEIK | 36 |
| 10G1 - HVR-L1 (VL positions 24-34) | RASQDIYRNLH | 37 |
| 10G1 - HVR-L2 (VL positions 50-56) | HASDSIS | 38 |
| 10G1 - HVR-L3 (VL positions 89-97) | LQGYSMPYT | 39 |
| 12F8 - VH | QVQLQQPGAELVTPGASVKLSCKASGFTF<u>TNNWMH</u>WVKQRPGQGLEWIG<u>M IHPNSGITNINE</u>KFKNKATVTVDKSSSTVYIQLSSLTSEDSAVYYC<u>RSDG TYEGYFDY</u>WGQGTPLTVSS | 40 |
| 12F8 - HVR-H1 (VH positions 30-35) | TNNWMH | 41 |
| 12F8 - HVR-H2 (VH positions 50-61) | MIHPNSGITNINE | 42 |
| 12F8 - HVR-H3 (VH positions 93-102) | RSDGTYEGYFDY | 43 |
| 10H5 - VH | QVQLQQSGADLARPGASIKLSCKASGYTF<u>TGYGVT</u>WVKQSTGQGLDWIG<u>E IYPGTVITYYNA</u>KFKGKATLTADKSSSTAYMELRSLTSEDSAVYFC<u>ARGL GRAMDY</u>WGQGTSVTVSS | 44 |
| 10H5 - HVR-H1 (VH positions 30-35) | TGYGVT | 45 |
| 10H5 - HVR-H2 (VH positions 50-61) | EIYPGTVITYYNA | 46 |
| 10H5 - HVR-H3 (VH positions 93-102) | ARGLGRAMDY | 47 |
| 1G8 -VH | QVQLQQSGPELLKPGASVKISCKASGYTF<u>TDYYIN</u>WVKQRPGQGLEWIG<u>W IFPGTEGIYYNE</u>KFKGKATLTVDKSSTTAYMLLSSLTSEDSAVYFC<u>AREG DYRYYSPLGY</u>WGQGTLVTVSA | 48 |
| 1G8 - HVR-H1 (VH positions 30-35) | TDYYIN | 49 |
| 1G8 - HVR-H2 (VH positions 50-61) | WIFPGTEGIYYNE | 50 |
| 1G8 - HVR-H3 (VH positions 93-102) | AREGDYRYYSPLGY | 51 |
| 16D9 - VH | QVQLQQSGPELVKPGASVKISCKASGYNF<u>NDYYIN</u>WVNQRPGQGLEWIG<u>W IFPGRIITYYNE</u>KFKGKATLTVDTSSNTAYMLLSSLTSEDSAVYFC<u>ARGV GEGFDY</u>WGQGTTLTVSS | 52 |
| 16D9 - HVR-H1 (VH positions 30-35) | NDYYIN | 53 |
| 16D9 - HVR-H2 (VH positions 50-61) | WIFPGRIITYYNE | 54 |

TABLE 2-continued

Anti-CD96 antibody sequences

| Description | Sequence | SEQ ID NO: |
|---|---|---|
| 16D9 - HVR-H3 (VH positions 93-102) | ARGVGEGFDY | 55 |
| 9H4 - VH | EVQLLETGGGLVKSGGSLKLSCAASGFTFSDYYMYWVRQTPEKRLEWVAAISDDGTYTYYPDSVKGRFTISRDNANNYLYLQMSSLKSEDTAIYYCAKAGSYDYFDVWGAGTTVTVSS | 56 |
| 9H4 - HVR-H1 (VH positions 30-35) | SDYYMY | 57 |
| 9H4 - HVR-H2 (VH positions 50-61) | AISDDGTYTYYPD | 58 |
| 9H4 - HVR-H3 (VH positions 93-102) | AKAGSYDYFDV | 59 |
| 7E5 - VH | QVQLKESGPGLVAPSQSLSIICTVSGFSLTNYGIHWIRQPPGKGLEWLGIIWAGGSTNYNSALMSRLTISKDNSKSQVFLKMNSLQTNDTAIYYCARVSMMGFAYWGQGTLVTVSA | 60 |
| 7E5 - HVR-H1 (VH positions 30-35) | TNYGIH | 61 |
| 7E5 - HVR-H2 (VH positions 50-61) | IIWAGGSTNYNS | 62 |
| 7E5 - HVR-H3 (VH positions 93-102) | ARVSMMGFAY | 63 |
| 10G1 - VH | QIQLVQSGPELKKPGETVKISCKASGYPFTTYGMSWVKQAPGKGLKWMGWINTDSGVPTYADDFKGRFAFSLETSANTAYLQINSLKNEDAATYFCARNIYYGWGNFDYWGQGTILTVSS | 64 |
| 10G1 - HVR-H1 (VH positions 30-35) | TTYGMS | 65 |
| 10G1 - HVR-H2 (VH positions 50-61) | WINTDSGVPTYAD | 66 |
| 10G1 - HVR-H3 (VH positions 93-102) | ARNIYYGWGNFDY | 67 |
| mAb1v7 - VL (humanized 12F8) | DIQLTQSPSSLSASVGDRVTITCKASQNVGTAIVWYQQKPGKAPKVLIYSASTRYTGVPSRFSGSGSGTDFTLTISSLQPEDFATYYCQQYSSSPLTFGQGTKVEIK | 68 |
| mAb1v7 - VH (humanized 12F8) | EVQLVQSGAEVKKPGASVKVSCKASGFTFTNNWMHWVRQAPGQGLEWIGMIHPNSGITNINEKFKNRVTMTTDTSTSTAYMELRSLRSEDTAVYYCRSDGTYEGYFDYWGQGTLVTVSS | 69 |
| h10G1 - VL (humanized 10G1) | EIVMTQSPDFQSVTPKEKVTITCRASQDIYRNLHWYQQKPDQTPKLLIKHASDSISGIPSRFSGSGSGTDFTLTINSLEAEDAAAYYCLQGYSMPYTFGGGTKVEIK | 70 |
| h10G1 - VH (humanized 10G1) | EIQLVQSGSELKKPGASVKVSCKASGYPFTTYGMSWVRQAPGQGLEWMGWINTDSGVPTYADDFKGRFVFSLDTSVSTAYLQISSLKAEDTAVYFCARNIYYGWGNFDYWGQGTLVTVSS | 71 |
| mAb1v7 - HVR-H1 - generic formula | XNXXXH<br>X at position 1 is T, A, D, E, G, H, K, N, Q, R, S, V, W, or Y; X at position 3 is N, A, F, G, H, M, R, S, V, or Y; X at position 4 is W, or F; X at position 5 is M, A, D, E, F, G, L, N, Q, R, S, T, V, or W | 72 |
| mAb1v7 - HVR-H1 - T30A | ANNWMH | 73 |
| mAb1v7 - HVR-H1 - T30D | DNNWMH | 74 |
| mAb1v7 - HVR-H1 - T30E | ENNWMH | 75 |

TABLE 2-continued

Anti-CD96 antibody sequences

| Description | Sequence | SEQ ID NO: |
|---|---|---|
| mAb1v7 - HVR-H1 - T30G | GNNWMH | 76 |
| mAb1v7 - HVR-H1 - T30H | HNNWMH | 77 |
| mAb1v7 - HVR-H1 - T30K | KNNWMH | 78 |
| mAb1v7 - HVR-H1 - T30N | NNNWMH | 79 |
| mAb1v7 - HVR-H1 - T30Q | QNNWMH | 80 |
| mAb1v7 - HVR-H1 - T30R | RNNWMH | 81 |
| mAb1v7 - HVR-H1 - T30S | SNNWMH | 82 |
| mAb1v7 - HVR-H1 - T30V | VNNWMH | 83 |
| mAb1v7 - HVR-H1 - T30W | WNNWMH | 84 |
| mAb1v7 - HVR-H1 - T30Y | YNNWMH | 85 |
| mAb1v7 - HVR-H1 - N32A | TNAWMH | 86 |
| mAb1v7 - HVR-H1 - N32F | TNFWMH | 87 |
| mAb1v7 - HVR-H1 - N32G | TNGWMH | 88 |
| mAb1v7 - HVR-H1 - N32H | TNHWMH | 89 |
| mAb1v7 - HVR-H1 - N32M | TNMWMH | 90 |
| mAb1v7 - HVR-H1 - N32R | TNRWMH | 91 |
| mAb1v7 - HVR-H1 - N32S | TNSWMH | 92 |
| mAb1v7 - HVR-H1 - N32V | TNVWMH | 93 |
| mAb1v7 - HVR-H1 - N32Y | TNYWMH | 94 |
| mAb1v7 - HVR-H1 - W33F | TNNFMH | 95 |
| mAb1v7 - HVR-H1 - M34A | TNNWAH | 96 |
| mAb1v7 - HVR-H1 - M34D | TNNWDH | 472 |
| mAb1v7 - HVR-H1 - M34E | TNNWEH | 97 |
| mAb1v7 - HVR-H1 - M34F | TNNWFH | 98 |
| mAb1v7 - HVR-H1 - M34G | TNNWGH | 473 |

TABLE 2-continued

Anti-CD96 antibody sequences

| Description | Sequence | SEQ ID NO: |
|---|---|---|
| mAb1v7 - HVR-H1 - M34L | TNNWLH | 99 |
| mAb1v7 - HVR-H1 - M34N | TNNWNH | 100 |
| mAb1v7 - HVR-H1 - M34Q | TNNWQH | 101 |
| mAb1v7 - HVR-H1 - M34R | TNNWRH | 102 |
| mAb1v7 - HVR-H1 - M34S | TNNWSH | 103 |
| mAb1v7 - HVR-H1 - M34T | TNNWTH | 104 |
| mAb1v7 - HVR-H1 - M34V | TNNWVH | 105 |
| mAb1v7 - HVR-H1 - M34W | TNNWWH | 106 |
| mAb1v7 - HVR-H2 - generic formula | XXHXXXXXXXXNX X at position 1 is M or F; X at position 2 is I, L, M, or V; X at position 4 is P, A, D, E, F, G, H, I, K, L, M, N, Q, R, S, T, V, or W; X at position 5 is N, A, D, E, F, G, H, I, K, L, M, Q, R, S, T, V, W, or Y; X at position 6 is S, A, G, T, or V; X at position 7 is G, A, or S; X at position 8 is I, A, or V; X at position 9 is T, A, D, E, G, H, I, K, L, M, N, Q, R, S, V, W, or Y; X at position 10 is N, A, M, or S; X at position 11 is I, F, G, H, K, L, M, N, Q, R, S, T, V, W, or Y; X at position 13 is E, A, D, G, H, K, L, M, N, P, Q, R, S, T, V, W, or Y | 107 |
| mAb1v7 - HVR-H2 - M50F | FIHPNSGITNINE | 108 |
| mAb1v7 - HVR-H2 - I51L | MLHPNSGITNINE | 109 |
| mAb1v7 - HVR-H2 - I51M | MMHPNSGITNINE | 110 |
| mAb1v7 - HVR-H2 - I51V | MVHPNSGITNINE | 111 |
| mAb1v7 - HVR-H2 - P52aA | MIHANSGITNINE | 112 |
| mAb1v7 - HVR-H2 - M50F/P52aA | FIHANSGITNINE | 113 |
| mAb1v7 - HVR-H2 - P52aD | MIHDNSGITNINE | 114 |
| mAb1v7 - HVR-H2 - P52aE | MIHENSGITNINE | 115 |
| mAb1v7 - HVR-H2 - P52aF | MIHFNSGITNINE | 116 |
| mAb1v7 - HVR-H2 - P52aG | MIHGNSGITNINE | 117 |
| mAb1v7 - HVR-H2 - P52aH | MIHHNSGITNINE | 118 |
| mAb1v7 - HVR-H2 - P52aI | MIHINSGITNINE | 119 |

TABLE 2-continued

Anti-CD96 antibody sequences

| Description | Sequence | SEQ ID NO: |
|---|---|---|
| mAb1v7 - HVR-H2 - P52aK | MIHKNSGITNINE | 120 |
| mAb1v7 - HVR-H2 - P52aL | MIHLNSGITNINE | 121 |
| mAb1v7 - HVR-H2 - P52aM | MIHMNSGITNINE | 122 |
| mAb1v7 - HVR-H2 - P52aN | MIHNNSGITNINE | 123 |
| mAb1v7 - HVR-H2 - P52aQ | MIHQNSGITNINE | 124 |
| mAb1v7 - HVR-H2 - P52aR | MIHRNSGITNINE | 125 |
| mAb1v7 - HVR-H2 - P52aS | MIHSNSGITNINE | 126 |
| mAb1v7 - HVR-H2 - P52aT | MIHTNSGITNINE | 127 |
| mAb1v7 - HVR-H2 - P52aV | MIHVNSGITNINE | 128 |
| mAb1v7 - HVR-H2 - P52aW | MIHWNSGITNINE | 129 |
| mAb1v7 - HVR-H2 - N53A | MIHPASGITNINE | 130 |
| mAb1v7 - HVR-H2 - N53D | MIHPDSGITNINE | 131 |
| mAb1v7 - HVR-H2 - N53E | MIHPESGITNINE | 132 |
| mAb1v7 - HVR-H2 - N53F | MIHPFSGITNINE | 133 |
| mAb1v7 - HVR-H2 - N53G | MIHPGSGITNINE | 134 |
| mAb1v7 - HVR-H2 - N53H | MIHPHSGITNINE | 135 |
| mAb1v7 - HVR-H2 - N53I | MIHPISGITNINE | 136 |
| mAb1v7 - HVR-H2 - N53K | MIHPKSGITNINE | 137 |
| mAb1v7 - HVR-H2 - N53L | MIHPLSGITNINE | 138 |
| mAb1v7 - HVR-H2 - N53M | MIHPMSGITNINE | 139 |
| mAb1v7 - HVR-H2 - N53Q | MIHPQSGITNINE | 140 |
| mAb1v7 - HVR-H2 - N53R | MIHPRSGITNINE | 141 |
| mAb1v7 - HVR-H2 - N53S | MIHPSSGITNINE | 142 |
| mAb1v7 - HVR-H2 - N53T | MIHPTSGITNINE | 143 |
| mAb1v7 - HVR-H2 - N53V | MIHPVSGITNINE | 144 |

TABLE 2-continued

Anti-CD96 antibody sequences

| Description | Sequence | SEQ ID NO: |
|---|---|---|
| mAb1v7 - HVR-H2 - N53W | MIHPWSGITNINE | 145 |
| mAb1v7 - HVR-H2 - N53Y | MIHPYSGITNINE | 146 |
| mAb1v7 - HVR-H2 - S54A | MIHPNAGITNINE | 147 |
| mAb1v7 - HVR-H2 - S54G | MIHPNGGITNINE | 148 |
| mAb1v7 - HVR-H2 - S54T | MIHPNTGITNINE | 149 |
| mAb1v7 - HVR-H2 - S54V | MIHPNVGITNINE | 150 |
| mAb1v7 - HVR-H2 - G55A | MIHPNSAITNINE | 151 |
| mAb1v7 - HVR-H2 - G55S | MIHPNSSITNINE | 152 |
| mAb1v7 - HVR-H2 - I56A | MIHPNSGATNINE | 153 |
| mAb1v7 - HVR-H2 - I56V | MIHPNSGVTNINE | 154 |
| mAb1v7 - HVR-H2 - T57A | MIHPNSGIANINE | 155 |
| mAb1v7 - HVR-H2 - T57D | MIHPNSGIDNINE | 156 |
| mAb1v7 - HVR-H2 - T57E | MIHPNSGIENINE | 157 |
| mAb1v7 - HVR-H2 - T57G | MIHPNSGIGNINE | 158 |
| mAb1v7 - HVR-H2 - T57H | MIHPNSGIHNINE | 159 |
| mAb1v7 - HVR-H2 - T57I | MIHPNSGIININE | 160 |
| mAb1v7 - HVR-H2 - T57K | MIHPNSGIKNINE | 161 |
| mAb1v7 - HVR-H2 - T57L | MIHPNSGILNINE | 162 |
| mAb1v7 - HVR-H2 - T57M | MIHPNSGIMNINE | 163 |
| mAb1v7 - HVR-H2 - T57N | MIHPNSGINNINE | 164 |
| mAb1v7 - HVR-H2 - T57Q | MIHPNSGIQNINE | 165 |
| mAb1v7 - HVR-H2 - T57R | MIHPNSGIRNINE | 166 |
| mAb1v7 - HVR-H2 - T57S | MIHPNSGISNINE | 167 |
| mAb1v7 - HVR-H2 - T57V | MIHPNSGIVNINE | 168 |
| mAb1v7 - HVR-H2 - T57W | MIHPNSGIWNINE | 169 |

TABLE 2-continued

Anti-CD96 antibody sequences

| Description | Sequence | SEQ ID NO: |
|---|---|---|
| mAb1v7 - HVR-H2 - T57Y | MIHPNSGIYNINE | 170 |
| mAb1v7 - HVR-H2 - N58A | MIHPNSGITAINE | 474 |
| mAb1v7 - HVR-H2 - N58M | MIHPNSGITMINE | 171 |
| mAb1v7 - HVR-H2 - N58S | MIHPNSGITSINE | 172 |
| mAb1v7 - HVR-H2 - I59F | MIHPNSGITNFNE | 173 |
| mAb1v7 - HVR-H2 - I59G | MIHPNSGITNGNE | 174 |
| mAb1v7 - HVR-H2 - I59H | MIHPNSGITNHNE | 175 |
| mAb1v7 - HVR-H2 - I59K | MIHPNSGITNKNE | 176 |
| mAb1v7 - HVR-H2 - I59L | MIHPNSGITNLNE | 177 |
| mAb1v7 - HVR-H2 - I59M | MIHPNSGITNMNE | 178 |
| mAb1v7 - HVR-H2 - I59N | MIHPNSGITNNNE | 179 |
| mAb1v7 - HVR-H2 - I59Q | MIHPNSGITNQNE | 180 |
| mAb1v7 - HVR-H2 - I59R | MIHPNSGITNRNE | 181 |
| mAb1v7 - HVR-H2 - I59S | MIHPNSGITNSNE | 182 |
| mAb1v7 - HVR-H2 - I59T | MIHPNSGITNTNE | 183 |
| mAb1v7 - HVR-H2 - I59V | MIHPNSGITNVNE | 184 |
| mAb1v7 - HVR-H2 - I59W | MIHPNSGITNWNE | 185 |
| mAb1v7 - HVR-H2 - I59Y | MIHPNSGITNYNE | 186 |
| mAb1v7 - HVR-H2 - E61A | MIHPNSGITNINA | 187 |
| mAb1v7 - HVR-H2 - E61D | MIHPNSGITNIND | 188 |
| mAb1v7 - HVR-H2 - E61G | MIHPNSGITNING | 189 |
| mAb1v7 - HVR-H2 - E61H | MIHPNSGITNINH | 190 |
| mAb1v7 - HVR-H2 - E61K | MIHPNSGITNINK | 191 |
| mAb1v7 - HVR-H2 - E61L | MIHPNSGITNINL | 192 |
| mAb1v7 - HVR-H2 - E61M | MIHPNSGITNINM | 193 |

TABLE 2-continued

Anti-CD96 antibody sequences

| Description | Sequence | SEQ ID NO: |
|---|---|---|
| mAb1v7 - HVR-H2 - E61N | MIHPNSGITNINN | 194 |
| mAb1v7 - HVR-H2 - E61P | MIHPNSGITNINP | 195 |
| mAb1v7 - HVR-H2 - E61Q | MIHPNSGITNINQ | 196 |
| mAb1v7 - HVR-H2 - E61R | MIHPNSGITNINR | 197 |
| mAb1v7 - HVR-H2 - E61S | MIHPNSGITNINS | 198 |
| mAb1v7 - HVR-H2 - E61T | MIHPNSGITNINT | 199 |
| mAb1v7 - HVR-H2 - E61V | MIHPNSGITNINV | 200 |
| mAb1v7 - HVR-H2 - E61W | MIHPNSGITNINW | 201 |
| mAb1v7 - HVR-H2 - E61Y | MIHPNSGITNINY | 202 |
| mAb1v7 - HVR-H3 - generic formula | RXDXXXXXYFDY X at position 2 is S, A, F, G, I, L, M, N, R, T, V, W, or Y; X at position 4 is G, or W; X at position 5 is T, D, E, F, H, I, K, L, M, N, Q, V, W, or Y; X at position 6 is Y, D, F, H, N, R, or W; X at position 7 is E, D, G, H, K, M, N, Q, R, V, or Y; X at position 8 is G, K, R, S, or T | 203 |
| MAb1V7 - HVR-H3 - S94A | RADGTYEGYFDY | 204 |
| mAb1v7 - HVR-H3 - S94F | RFDGTYEGYFDY | 205 |
| mAb1v7 - HVR-H3 - S94G | RGDGTYEGYFDY | 206 |
| mAb1v7 - HVR-H3 - S94I | RIDGTYEGYFDY | 207 |
| mAb1v7 - HVR-H3 - S94L | RLDGTYEGYFDY | 208 |
| mAb1v7 - HVR-H3 - S94M | RMDGTYEGYFDY | 209 |
| mAb1v7 - HVR-H3 - S94N | RNDGTYEGYFDY | 210 |
| mAb1v7 - HVR-H3 - S94R | RRDGTYEGYFDY | 211 |
| mAb1v7 - HVR-H3 - S94T | RTDGTYEGYFDY | 212 |
| mAb1v7 - HVR-H3 - S94V | RVDGTYEGYFDY | 213 |
| mAb1v7 - HVR-H3 - S94W | RWDGTYEGYFDY | 214 |
| mAb1v7 - HVR-H3 - S94Y | RYDGTYEGYFDY | 215 |
| mAb1v7 - HVR-H3 - G96W | RSDWTYEGYFDY | 216 |

TABLE 2-continued

Anti-CD96 antibody sequences

| Description | Sequence | SEQ ID NO: |
|---|---|---|
| mAb1v7 - HVR-H3 - T97D | RSDGDYEGYFDY | 217 |
| mAb1v7 - HVR-H3 - T97E | RSDGEYEGYFDY | 218 |
| mAb1v7 - HVR-H3 - T97F | RSDGFYEGYFDY | 219 |
| mAb1v7 - HVR-H3 - T97H | RSDGHYEGYFDY | 220 |
| mAb1v7 - HVR-H3 - T97I | RSDGIYEGYFDY | 221 |
| mAb1v7 - HVR-H3 - T97K | RSDGKYEGYFDY | 222 |
| mAb1v7 - HVR-H3 - T97L | RSDGLYEGYFDY | 223 |
| mAb1v7 - HVR-H3 - T97M | RSDGMYEGYFDY | 224 |
| mAb1v7 - HVR-H3 - T97N | RSDGNYEGYFDY | 225 |
| mAb1v7 - HVR-H3 - T97Q | RSDGQYEGYFDY | 226 |
| mAb1v7 - HVR-H3 - T97V | RSDGVYEGYFDY | 227 |
| mAb1v7 - HVR-H3 - T97W | RSDGWYEGYFDY | 228 |
| mAb1v7 - HVR-H3 - T97Y | RSDGYYEGYFDY | 229 |
| mAb1v7 - HVR-H3 - Y98D | RSDGTDEGYFDY | 230 |
| mAb1v7 - HVR-H3 - Y98F | RSDGTFEGYFDY | 231 |
| mAb1v7 - HVR-H3 - Y98H | RSDGTHEGYFDY | 232 |
| mAb1v7 - HVR-H3 - Y98N | RSDGTNEGYFDY | 233 |
| mAb1v7 - HVR-H3 - Y98R | RSDGTREGYFDY | 234 |
| mAb1v7 - HVR-H3 - Y98W | RSDGTWEGYFDY | 235 |
| mAb1v7 - HVR-H3 - E99D | RSDGTYDGYFDY | 236 |
| mAb1v7 - HVR-H3 - E99G | RSDGTYGGYFDY | 237 |
| mAb1v7 - HVR-H3 - E99H | RSDGTYHGYFDY | 238 |
| mAb1v7 - HVR-H3 - E99K | RSDGTYKGYFDY | 239 |
| mAb1v7 - HVR-H3 - E99M | RSDGTYMGYFDY | 240 |
| mAb1v7 - HVR-H3 - E99N | RSDGTYNGYFDY | 241 |

TABLE 2-continued

Anti-CD96 antibody sequences

| Description | Sequence | SEQ ID NO: |
|---|---|---|
| mAb1v7 - HVR-H3 - E99Q | RSDGTYQGYFDY | 242 |
| mAb1v7 - HVR-H3 - E99R | RSDGTYRGYFDY | 243 |
| mAb1v7 - HVR-H3 - E99V | RSDGTYVGYFDY | 244 |
| mAb1v7 - HVR-H3 - E99Y | RSDGTYYGYFDY | 245 |
| mAb1v7 - HVR-H3 - G100K | RSDGTYEKYFDY | 246 |
| mAb1v7 - HVR-H3 - G100R | RSDGTYERYFDY | 247 |
| mAb1v7 - HVR-H3 - G100S | RSDGTYESYFDY | 248 |
| mAb1v7 - HVR-H3 - G100T | RSDGTYETYFDY | 249 |
| mAb1v7 - VH - M34R/P52aF/T97V (mAb1v7.2) | EVQLVQSGAEVKKPGASVKVSCKASGFTF<u>TNNWRH</u>WVRQAPGQGLEWIGM IHFNSGITNINEKFKNRVTMTTDTSTSTAYMELRSLRSEDTAVYYC<u>RSDG VYEGYFDY</u>WGQGTLVTVSS | 250 |
| mAb1v7 - VH - N32R/P52aV/T97L (mAb1v7.6) | EVQLVQSGAEVKKPGASVKVSCKASGFTF<u>TNRWMH</u>WVRQAPGQGLEWIGM IHVNSGITNINEKFKNRVTMTTDTSTSTAYMELRSLRSEDTAVYYC<u>RSDG LYEGYFDY</u>WGQGTLVTVSS | 251 |
| mAb1v7 - VH - M34D/N53L/T97V (mAb1v7.8) | EVQLVQSGAEVKKPGASVKVSCKASGFTF<u>TNNWDH</u>WVRQAPGQGLEWIGM IHPLSGITNINEKFKNRVTMTTDTSTSTAYMELRSLRSEDTAVYYC<u>RSDG VYEGYFDY</u>WGQGTLVTVSS | 252 |
| mAb1v7 - VH - M34R/P52aM/T97V (mAb1v7.9) | EVQLVQSGAEVKKPGASVKVSCKASGFTF<u>TNNWRH</u>WVRQAPGQGLEWIGM IHMNSGITNINEKFKNRVTMTTDTSTSTAYMELRSLRSEDTAVYYC<u>RSDG VYEGYFDY</u>WGQGTLVTVSS | 253 |
| mAb1v7 - VH - M34R/N53L/T97V (mAb1v7.10) | EVQLVQSGAEVKKPGASVKVSCKASGFTF<u>TNNWRH</u>WVRQAPGQGLEWIGM IHPLSGITNINEKFKNRVTMTTDTSTSTAYMELRSLRSEDTAVYYC<u>RSDG VYEGYFDY</u>WGQGTLVTVSS | 254 |
| mAb1v7 - VH - T30V/I59T/T97I (mAb1v7.14) | EVQLVQSGAEVKKPGASVKVSCKASGFTF<u>VNNWMH</u>WVRQAPGQGLEWIGM IHPNSGITNTNEKFKNRVTMTTDTSTSTAYMELRSLRSEDTAVYYC<u>RSDG IYEGYFDY</u>WGQGTLVTVSS | 255 |
| mAb1v7 - VH - M34D/N53M/T97F (mAb1v7.15) | EVQLVQSGAEVKKPGASVKVSCKASGFTF<u>TNNWDH</u>WVRQAPGQGLEWIGM IHPMSGITNINEKFKNRVTMTTDTSTSTAYMELRSLRSEDTAVYYC<u>RSDG FYEGYFDY</u>WGQGTLVTVSS | 256 |
| mAb1v7 - VH - M34R/T97V (mAb1v7.16) | EVQLVQSGAEVKKPGASVKVSCKASGFTF<u>TNNWRH</u>WVRQAPGQGLEWIGM IHPNSGITNINEKFKNRVTMTTDTSTSTAYMELRSLRSEDTAVYYC<u>RSDG VYEGYFDY</u>WGQGTLVTVSS | 257 |
| mAb1v7 - VH - N32S/I59R/T97I (mAb1v7.19) | EVQLVQSGAEVKKPGASVKVSCKASGFTF<u>TNSWMH</u>WVRQAPGQGLEWIGM IHPNSGITNRNEKFKNRVTMTTDTSTSTAYMELRSLRSEDTAVYYC<u>RSDG IYEGYFDY</u>WGQGTLVTVSS | 258 |
| mAb1v7 - VH - N32Y/I59M/T97V (mAb1v7.21) | EVQLVQSGAEVKKPGASVKVSCKASGFTF<u>TNYWMH</u>WVRQAPGQGLEWIGM IHPNSGITNMNEKFKNRVTMTTDTSTSTAYMELRSLRSEDTAVYYC<u>RSDG VYEGYFDY</u>WGQGTLVTVSS | 259 |
| mAb1v7 - VH - M34G/P52aR/T97I (mAb1v7.24) | EVQLVQSGAEVKKPGASVKVSCKASGFTF<u>TNNWGH</u>WVRQAPGQGLEWIGM IHRNSGITNINEKFKNRVTMTTDTSTSTAYMELRSLRSEDTAVYYC<u>RSDG IYEGYFDY</u>WGQGTLVTVSS | 260 |
| mAb1v7 - VH - N32R/P52aH/T97V (mAb1v7.48) | EVQLVQSGAEVKKPGASVKVSCKASGFTF<u>TNRWMH</u>WVRQAPGQGLEWIGM IHHNSGITNINEKFKNRVTMTTDTSTSTAYMELRSLRSEDTAVYYC<u>RSDG VYEGYFDY</u>WGQGTLVTVSS | 261 |

TABLE 2-continued

Anti-CD96 antibody sequences

| Description | Sequence | SEQ ID NO: |
|---|---|---|
| mAb1v7 - VH - M34S/P52aR/T97V (mAb1v7.50) | EVQLVQSGAEVKKPGASVKVSCKASGFTF<u>TNNWSH</u>WVRQAPGQGLEWIG<u>M</u><br><u>IHRNSGITNINE</u>KFKNRVTMTTDTSTSTAYMELRSLRSEDTAVYYC<u>RSDG</u><br><u>VYEGYFDY</u>WGQGTLVTVSS | 262 |
| mAb1v7 - VH - M34N//N58A/S94L (mAb1v7.59) | EVQLVQSGAEVKKPGASVKVSCKASGFTF<u>TNNWNH</u>WVRQAPGQGLEWIG<u>M</u><br><u>IHPNSGITAINE</u>KFKNRVTMTTDTSTSTAYMELRSLRSEDTAVYYC<u>RLDG</u><br><u>TYEGYFDY</u>WGQGTLVTVSS | 263 |
| mAb1v7 - VH - N32R/P52aA/T97V (mAb1v7.70) | EVQLVQSGAEVKKPGASVKVSCKASGFTF<u>TNRWMH</u>WVRQAPGQGLEWIG<u>M</u><br><u>IHANSGITNINE</u>KFKNRVTMTTDTSTSTAYMELRSLRSEDTAVYYC<u>RSDG</u><br><u>VYEGYFDY</u>WGQGTLVTVSS | 264 |
| mAb1v7 - VH - W33F (mAb1v7.NGS1) | EVQLVQSGAEVKKPGASVKVSCKASGFTF<u>TNNFMH</u>WVRQAPGQGLEWIG<u>M</u><br><u>IHPNSGITNINE</u>KFKNRVTMTTDTSTSTAYMELRSLRSEDTAVYYC<u>RSDG</u><br><u>TYEGYFDY</u>WGQGTLVTVSS | 265 |
| mAb1v7 - VH - M50F (mAb1v7.NGS2) | EVQLVQSGAEVKKPGASVKVSCKASGFTF<u>TNNWMH</u>WVRQAPGQGLEWIG<u>F</u><br><u>IHPNSGITNINE</u>KFKNRVTMTTDTSTSTAYMELRSLRSEDTAVYYC<u>RSDG</u><br><u>TYEGYFDY</u>WGQGTLVTVSS | 266 |
| mAb1v7 - VH - P52aA (mAb1v7.NGS3) | EVQLVQSGAEVKKPGASVKVSCKASGFTF<u>TNNWMH</u>WVRQAPGQGLEWIG<u>M</u><br><u>IHANSGITNINE</u>KFKNRVTMTTDTSTSTAYMELRSLRSEDTAVYYC<u>RSDG</u><br><u>TYEGYFDY</u>WGQGTLVTVSS | 267 |
| mAb1v7 - VH - E61H (mAb1v7.NGS4) | EVQLVQSGAEVKKPGASVKVSCKASGFTF<u>TNNWMH</u>WVRQAPGQGLEWIG<u>M</u><br><u>IHPNSGITNINH</u>KFKNRVTMTTDTSTSTAYMELRSLRSEDTAVYYC<u>RSDG</u><br><u>TYEGYFDY</u>WGQGTLVTVSS | 268 |
| mAb1v7 - VH - E61R (mAb1v7.NGS5) | EVQLVQSGAEVKKPGASVKVSCKASGFTF<u>TNNWMH</u>WVRQAPGQGLEWIG<u>M</u><br><u>IHPNSGITNINR</u>KFKNRVTMTTDTSTSTAYMELRSLRSEDTAVYYC<u>RSDG</u><br><u>TYEGYFDY</u>WGQGTLVTVSS | 269 |
| mAb1v7 - VH - T97I (mAb1v7.NGS6) | EVQLVQSGAEVKKPGASVKVSCKASGFTF<u>TNNWMH</u>WVRQAPGQGLEWIG<u>M</u><br><u>IHPNSGITNINE</u>KFKNRVTMTTDTSTSTAYMELRSLRSEDTAVYYC<u>RSDG</u><br><u>IYEGYFDY</u>WGQGTLVTVSS | 270 |
| mAb1v7 - VH - T97V (mAb1v7.NGS7) | EVQLVQSGAEVKKPGASVKVSCKASGFTF<u>TNNWMH</u>WVRQAPGQGLEWIG<u>M</u><br><u>IHPNSGITNINE</u>KFKNRVTMTTDTSTSTAYMELRSLRSEDTAVYYC<u>RSDG</u><br><u>VYEGYFDY</u>WGQGTLVTVSS | 271 |
| mAb1v7 - VH - W33F/P52aA/T97I (mAb1v7.NGS8) | EVQLVQSGAEVKKPGASVKVSCKASGFTF<u>TNNFMH</u>WVRQAPGQGLEWIG<u>M</u><br><u>IHANSGITNINE</u>KFKNRVTMTTDTSTSTAYMELRSLRSEDTAVYYC<u>RSDG</u><br><u>IYEGYFDY</u>WGQGTLVTVSS | 272 |
| mAb1v7 - VH - W33F/P52aA/T97V (mAb1v7.NGS9) | EVQLVQSGAEVKKPGASVKVSCKASGFTF<u>TNNFMH</u>WVRQAPGQGLEWIG<u>M</u><br><u>IHANSGITNINE</u>KFKNRVTMTTDTSTSTAYMELRSLRSEDTAVYYC<u>RSDG</u><br><u>VYEGYFDY</u>WGQGTLVTVSS | 273 |
| mAb1v7 - VH - W33F/M50F/P52aA/ T97I (mAb1v7.NGS10) | EVQLVQSGAEVKKPGASVKVSCKASGFTF<u>TNNFMH</u>WVRQAPGQGLEWIG<u>F</u><br><u>IHANSGITNINE</u>KFKNRVTMTTDTSTSTAYMELRSLRSEDTAVYYC<u>RSDG</u><br><u>IYEGYFDY</u>WGQGTLVTVSS | 274 |
| mAb1v7 - VH-W33F/M50F/P52aA/ T97V (mAb1v7.NGS11) | EVQLVQSGAEVKKPGASVKVSCKASGFTF<u>TNNFMH</u>WVRQAPGQGLEWIG<u>F</u><br><u>IHANSGITNINE</u>KFKNRVTMTTDTSTSTAYMELRSLRSEDTAVYYC<u>RSDG</u><br><u>VYEGYFDY</u>WGQGTLVTVSS | 275 |
| 12F8 - FR-L1 | DIVMTQSQKFMSTSVGDRVSVTC | 276 |
| 12F8 - FR-L2 | WYQKKPGQSPKTLIY | 277 |
| 12F8 - FR-L3 | GVPDRFTGSGSGTDFTLTISNVQSEDLAEYFC | 278 |
| 12F8 - FR-L4 | FGSGTKLEIK | 279 |
| mAb1v7 - FR-L1 | DIQLTQSPSSLSASVGDRVTITC | 280 |
| mAb1v7 - FR-L2 | WYQQKPGKAPKVLIY | 281 |
| mAb1v7- FR-L3 | GVPSRFSGSGSGTDFTLTISSLQPEDFATYYC | 282 |
| mAb1v7- FR-L4 | FGQGTKVEIK | 283 |

TABLE 2-continued

Anti-CD96 antibody sequences

| Description | Sequence | SEQ ID NO: |
|---|---|---|
| 10G1 - FR-L1 | DILMTQSPTTLSVTPGETVSLSC | 284 |
| 10G1 - FR-L2 | WYQQKSQGTPRLLIK | 285 |
| 10G1 - FR-L3 | GIPSRFTGSGSGTDFTLSINSVKPEDEGIYYC | 286 |
| 10G1 - FR-L4 | FGGGTKLEIK | 287 |
| h10G1 - FR-L1 | EIVMTQSPDFQSVTPKEKVTITC | 288 |
| h10G1 - FR-L2 | WYQQKPDQTPKLLIK | 289 |
| h10G1 - FR-L3 | GIPSRFSGSGSGTDFTLTINSLEAEDAAAYYC | 290 |
| h10G1 - FR-L4 | FGGGTKVEIK | 291 |
| 12F8 - FR-H1 | QVQLQQPGAELVTPGASVKLSCKASGFTF | 292 |
| 12F8 - FR-H2 | WVKQRPGQGLEWIG | 293 |
| 12F8 - FR-H3 | KFKNKATVTVDKSSSTVYIQLSSLTSEDSAVYYC | 294 |
| 12F8 - FR-H4 | WGQGTPLTVSS | 295 |
| 10G1 - FR-H1 | QIQLVQSGPELKKPGETVKISCKASGYPF | 296 |
| 10G1 - FR-H2 | WVKQAPGKGLKWMG | 297 |
| 10G1 - FR-H3 | DFKGRFAFSLETSANTAYLQINSLKNEDAATYFC | 298 |
| 10G1 - FR-H4 | WGQGTILTVSS | 299 |
| mAb1v7- FR-H1 | EVQLVQSGAEVKKPGASVKVSCKASGFTF | 300 |
| mAb1v7- FR-H2 | WVRQAPGQGLEWIG | 301 |
| mAb1v7- FR-H3 | KFKNRVTMTTDTSTSTAYMELRSLRSEDTAVYYC | 302 |
| mAb1v7- FR-H4 | WGQGTLVTVSS | 303 |
| h10G1 - FR-H1 | EIQLVQSGSELKKPGASVKVSCKASGYPF | 304 |
| h10G1 - FR-H2 | WVRQAPGQGLEWMG | 305 |
| h10G1 - FR-H3 | DFKGRFVFSLDTSVSTAYLQISSLKAEDTAVYFC | 306 |
| h10G1 - FR-H4 | WGQGTLVTVSS | 307 |
| h10G1 - HVR-L1 - generic formula | RASQXIXXNXH<br>X at position 5 is D, A, E, G, H, K, N, P, Q, S, or T; X at position 7 is Y, or F; X at position 8 is R, K, or Q; X at position 10 is L, I, M, or V. | 308 |
| h10G1 - HVR-L1 - D28A | RASQAIYRNLH | 309 |
| h10G1 - HVR-L1 - D28E | RASQEIYRNLH | 310 |
| h10G1 - HVR-L1 - D28G | RASQGIYRNLH | 311 |
| h10G1 - HVR-L1 - D28H | RASQHIYRNLH | 312 |
| h10G1 - HVR-L1 - D28K | RASQKIYRNLH | 313 |
| h10G1 - HVR-L1 - D28N | RASQNIYRNLH | 314 |
| h10G1 - HVR-L1 - D28P | RASQPIYRNLH | 315 |

TABLE 2-continued

Anti-CD96 antibody sequences

| Description | Sequence | SEQ ID NO: |
|---|---|---|
| h10G1 - HVR-L1 - D28Q | RASQQIYRNLH | 316 |
| h10G1 - HVR-L1 - D28S | RASQSIYRNLH | 317 |
| h10G1 - HVR-L1 - D28T | RASQTIYRNLH | 318 |
| h10G1 - HVR-L1 - Y30F | RASQDIFRNLH | 319 |
| h10G1 - HVR-L1 - R31K | RASQDIYKNLH | 320 |
| h10G1 - HVR-L1 - R31Q | RASQDIYQNLH | 321 |
| h10G1 - HVR-L1 - L33I | RASQDIYRNIH | 322 |
| h10G1 - HVR-L1 - L33M | RASQDIYRNMH | 323 |
| h10G1 - HVR-L1 - L33V | RASQDIYRNVH | 324 |
| h10G1 - HVR-L2 generic formula | HAXXXXS<br>X at position 3 is S, or E; X at position 4 is D, E, K, or Q; X at position 5 is S, H, L, R, or V; X at position 6 is I, or V. | 325 |
| h10G1 - HVR-L2 - S52E | HAEDSIS | 326 |
| h10G1 - HVR-L2 - D53E | HASESIS | 327 |
| h10G1 - HVR-L2 - D53K | HASKSIS | 328 |
| h10G1 - HVR-L2 - D53Q | HASQSIS | 329 |
| h10G1 - HVR-L2 - S54H | HASDHIS | 330 |
| h10G1 - HVR-L2 - S54L | HASDLIS | 331 |
| h10G1 - HVR-L2 - S54R | HASDRIS | 332 |
| h10G1 - HVR-L2 - S54V | HASDVIS | 333 |
| h10G1 - HVR-L2 - I55V | HASDSVS | 334 |
| h10G1 - HVR-L3 generic formula | XQGYXMPXT<br>X at position 1 is L, G, M, or Q; X at position 5 is S, A, E, Q, or V; X at position 8 is Y, or F. | 335 |
| h10G1 - HVR-L3 - L89G | GQGYSMPYT | 336 |
| h10G1 - HVR-L3 - L89M | MQGYSMPYT | 337 |
| h10G1 - HVR-L3 - L89Q | QQGYSMPYT | 338 |
| h10G1 - HVR-L3 - S93A | LQGYAMPYT | 339 |

TABLE 2-continued

Anti-CD96 antibody sequences

| Description | Sequence | SEQ ID NO: |
|---|---|---|
| h10G1 - HVR-L3 - S93E | LQGYEMPYT | 340 |
| h10G1 - HVR-L3 - S93Q | LQGYQMPYT | 341 |
| h10G1 - HVR-L3 - S93V | LQGYVMPYT | 342 |
| h10G1 - HVR-L3 - Y96F | LQGYSMPFT | 343 |
| h10G1 - HVR-H1 - generic formula | XXXGXS<br>X at position 1 is T, A, D, E, G, K, M, N, Q, R, or S; X at position 2 is T, D, H, E, G, H, N, Q, or S; X at position 3 is Y, F, M, or Q; X at position 5 is M, I, L, or V. | 344 |
| h10G1 - HVR-H1 - T30A | ATYGMS | 345 |
| h10G1 - HVR-H1 - T30D | DTYGMS | 346 |
| h10G1 - HVR-H1 - T30E | ETYGMS | 347 |
| h10G1 - HVR-H1 - T30G | GTYGMS | 348 |
| h10G1 - HVR-H1 - T30H | HTYGMS | 349 |
| h10G1 - HVR-H1 - T30K | KTYGMS | 350 |
| h10G1 - HVR-H1 - T30M | MTYGMS | 351 |
| h10G1 - HVR-H1 - T30N | NTYGMS | 352 |
| h10G1 - HVR-H1 - T30Q | QTYGMS | 353 |
| h10G1 - HVR-H1 - T30R | RTYGMS | 354 |
| h10G1 - HVR-H1 - T30S | STYGMS | 355 |
| h10G1 - HVR-H1 - T31D | TDYGMS | 356 |
| h10G1 - HVR-H1 - T31E | TEYGMS | 357 |
| h10G1 - HVR-H1 - T31G | TGYGMS | 358 |
| h10G1 - HVR-H1 - T31H | THYGMS | 359 |
| h10G1 - HVR-H1 - T31N | TNYGMS | 360 |
| h10G1 - HVR-H1 - T31Q | TQYGMS | 361 |
| h10G1 - HVR-H1 - T31S | TSYGMS | 362 |
| h10G1 - HVR-H1 - Y32F | TTFGMS | 363 |

TABLE 2-continued

Anti-CD96 antibody sequences

| Description | Sequence | SEQ ID NO: |
|---|---|---|
| h10G1 - HVR-H1 - Y32M | TTMGMS | 364 |
| h10G1 - HVR-H1 - Y32Q | TTQGMS | 365 |
| h10G1 - HVR-H1 - M34I | TTYGIS | 366 |
| h10G1 - HVR-H1 - M34L | TTYGLS | 367 |
| h10G1 - HVR-H1 - M34V | TTYGVS | 368 |
| h10G1 - HVR-H2 - generic formula | WINTXXGVPTYAD<br>X at position 5 is D, or E; X at position 6 is S, or T. | 369 |
| h10G1 - HVR-H2 - D53E | WINTESGVPTYAD | 370 |
| h10G1 - HVR-H2 - S54T | WINTDTGVPTYAD | 371 |
| h10G1 - HVR-H3 - generic formula | ARXIYYGWGXFDY<br>X at position 3 is N, or M; X at position 10 is N, F, H, or Y. | 372 |
| h10G1 - HVR-H3 - N95M | ARMIYYGWGNFDY | 373 |
| h10G1 - HVR-H3 - N100bF | ARNIYYGWGFFDY | 374 |
| h10G1 - HVR-H3 - N100bH | ARNIYYGWGHFDY | 375 |
| h10G1 - HVR-H3 - N100bY | ARNIYYGWGYFDY | 376 |
| h10G1 - VL - D28A | EIVMTQSPDFQSVTPKEKVTITCRASQAIYRNLHWYQQKPDQTPKLLIKH ASDSISGIPSRFSGSGSGTDFTLTINSLEAEDAAAYYCLQGYSMPYTFGG GTKVEIK | 377 |
| h10G1 - VL - D28E | EIVMTQSPDFQSVTPKEKVTITCRASQEIYRNLHWYQQKPDQTPKLLIKH ASDSISGIPSRFSGSGSGTDFTLTINSLEAEDAAAYYCLQGYSMPYTFGG GTKVEIK | 378 |
| h10G1 - VL - D28G | EIVMTQSPDFQSVTPKEKVTITCRASQGIYRNLHWYQQKPDQTPKLLIKH ASDSISGIPSRFSGSGSGTDFTLTINSLEAEDAAAYYCLQGYSMPYTFGG GTKVEIK | 379 |
| h10G1 - VL - D28H | EIVMTQSPDFQSVTPKEKVTITCRASQHIYRNLHWYQQKPDQTPKLLIKH ASDSISGIPSRFSGSGSGTDFTLTINSLEAEDAAAYYCLQGYSMPYTFGG GTKVEIK | 380 |
| h10G1 - VL - D28K | EIVMTQSPDFQSVTPKEKVTITCRASQKIYRNLHWYQQKPDQTPKLLIKH ASDSISGIPSRFSGSGSGTDFTLTINSLEAEDAAAYYCLQGYSMPYTFGG GTKVEIK | 381 |
| h10G1 - VL - D28N | EIVMTQSPDFQSVTPKEKVTITCRASQNIYRNLHWYQQKPDQTPKLLIKH ASDSISGIPSRFSGSGSGTDFTLTINSLEAEDAAAYYCLQGYSMPYTFGG GTKVEIK | 382 |
| h10G1 - VL - D28P | EIVMTQSPDFQSVTPKEKVTITCRASQPIYRNLHWYQQKPDQTPKLLIKH ASDSISGIPSRFSGSGSGTDFTLTINSLEAEDAAAYYCLQGYSMPYTFGG GTKVEIK | 383 |
| h10G1 - VL - D28Q | EIVMTQSPDFQSVTPKEKVTITCRASQQIYRNLHWYQQKPDQTPKLLIKH ASDSISGIPSRFSGSGSGTDFTLTINSLEAEDAAAYYCLQGYSMPYTFGG GTKVEIK | 384 |

TABLE 2-continued

Anti-CD96 antibody sequences

| Description | Sequence | SEQ ID NO: |
|---|---|---|
| h10G1 - VL - D28S | EIVMTQSPDFQSVTPKEKVTITC<u>RASQSIYRNLH</u>WYQQKPDQTPKLLIK<u>H<br>ASDSIS</u>GIPSRFSGSGSGTDFTLTINSLEAEDAAAYYC<u>LQGYSMPYT</u>FGG<br>GTKVEIK | 385 |
| h10G1 - VL - D28T | EIVMTQSPDFQSVTPKEKVTITC<u>RASQTIYRNLH</u>WYQQKPDQTPKLLIK<u>H<br>ASDSIS</u>GIPSRFSGSGSGTDFTLTINSLEAEDAAAYYC<u>LQGYSMPYT</u>FGG<br>GTKVEIK | 386 |
| h10G1 - VL - Y30F | EIVMTQSPDFQSVTPKEKVTITC<u>RASQDIFRNLH</u>WYQQKPDQTPKLLIK<u>H<br>ASDSIS</u>GIPSRFSGSGSGTDFTLTINSLEAEDAAAYYC<u>LQGYSMPYT</u>FGG<br>GTKVEIK | 387 |
| h10G1 - VL - R31K | EIVMTQSPDFQSVTPKEKVTITC<u>RASQDIYKNLH</u>WYQQKPDQTPKLLIK<u>H<br>ASDSIS</u>GIPSRFSGSGSGTDFTLTINSLEAEDAAAYYC<u>LQGYSMPYT</u>FGG<br>GTKVEIK | 388 |
| h10G1 - VL - R31Q | EIVMTQSPDFQSVTPKEKVTITC<u>RASQDIYQNLH</u>WYQQKPDQTPKLLIK<u>H<br>ASDSIS</u>GIPSRFSGSGSGTDFTLTINSLEAEDAAAYYC<u>LQGYSMPYT</u>FGG<br>GTKVEIK | 389 |
| h10G1 - VL - L33I | EIVMTQSPDFQSVTPKEKVTITC<u>RASQDIYRNIH</u>WYQQKPDQTPKLLIK<u>H<br>ASDSIS</u>GIPSRFSGSGSGTDFTLTINSLEAEDAAAYYC<u>LQGYSMPYT</u>FGG<br>GTKVEIK | 390 |
| h10G1 - VL - L33M | EIVMTQSPDFQSVTPKEKVTITC<u>RASQDIYRNMH</u>WYQQKPDQTPKLLIK<u>H<br>ASDSIS</u>GIPSRFSGSGSGTDFTLTINSLEAEDAAAYYC<u>LQGYSMPYT</u>FGG<br>GTKVEIK | 391 |
| h10G1 - VL - L33V | EIVMTQSPDFQSVTPKEKVTITC<u>RASQDIYRNVH</u>WYQQKPDQTPKLLIK<u>H<br>ASDSIS</u>GIPSRFSGSGSGTDFTLTINSLEAEDAAAYYC<u>LQGYSMPYT</u>FGG<br>GTKVEIK | 392 |
| h10G1 - VL - S52E | EIVMTQSPDFQSVTPKEKVTITC<u>RASQDIYRNLH</u>WYQQKPDQTPKLLIK<u>H<br>AEDSIS</u>GIPSRFSGSGSGTDFTLTINSLEAEDAAAYYC<u>LQGYSMPYT</u>FGG<br>GTKVEIK | 393 |
| h10G1 - VL - D53E | EIVMTQSPDFQSVTPKEKVTITC<u>RASQDIYRNLH</u>WYQQKPDQTPKLLIK<u>H<br>ASESIS</u>GIPSRFSGSGSGTDFTLTINSLEAEDAAAYYC<u>LQGYSMPYT</u>FGG<br>GTKVEIK | 394 |
| h10G1 - VL - D53K | EIVMTQSPDFQSVTPKEKVTITC<u>RASQDIYRNLH</u>WYQQKPDQTPKLLIK<u>H<br>ASKSIS</u>GIPSRFSGSGSGTDFTLTINSLEAEDAAAYYC<u>LQGYSMPYT</u>FGG<br>GTKVEIK | 395 |
| h10G1 - VL - D53Q | EIVMTQSPDFQSVTPKEKVTITC<u>RASQDIYRNLH</u>WYQQKPDQTPKLLIK<u>H<br>ASQSIS</u>GIPSRFSGSGSGTDFTLTINSLEAEDAAAYYC<u>LQGYSMPYT</u>FGG<br>GTKVEIK | 396 |
| h10G1 - VL - S54H | EIVMTQSPDFQSVTPKEKVTITC<u>RASQDIYRNLH</u>WYQQKPDQTPKLLIK<u>H<br>ASDHIS</u>GIPSRFSGSGSGTDFTLTINSLEAEDAAAYYC<u>LQGYSMPYT</u>FGG<br>GTKVEIK | 397 |
| h10G1 - VL - S54L | EIVMTQSPDFQSVTPKEKVTITC<u>RASQDIYRNLH</u>WYQQKPDQTPKLLIK<u>H<br>ASDLIS</u>GIPSRFSGSGSGTDFTLTINSLEAEDAAAYYC<u>LQGYSMPYT</u>FGG<br>GTKVEIK | 398 |
| h10G1 - VL - S54R | EIVMTQSPDFQSVTPKEKVTITC<u>RASQDIYRNLH</u>WYQQKPDQTPKLLIK<u>H<br>ASDRIS</u>GIPSRFSGSGSGTDFTLTINSLEAEDAAAYYC<u>LQGYSMPYT</u>FGG<br>GTKVEIK | 399 |
| h10G1 - VL - S54V | EIVMTQSPDFQSVTPKEKVTITC<u>RASQDIYRNLH</u>WYQQKPDQTPKLLIK<u>H<br>ASDVIS</u>GIPSRFSGSGSGTDFTLTINSLEAEDAAAYYC<u>LQGYSMPYT</u>FGG<br>GTKVEIK | 400 |
| h10G1 - VL - I55V | EIVMTQSPDFQSVTPKEKVTITC<u>RASQDIYRNLH</u>WYQQKPDQTPKLLIK<u>H<br>ASDSVS</u>GIPSRFSGSGSGTDFTLTINSLEAEDAAAYYC<u>LQGYSMPYT</u>FGG<br>GTKVEIK | 401 |
| h10G1 - VL - L89G | EIVMTQSPDFQSVTPKEKVTITC<u>RASQDIYRNLH</u>WYQQKPDQTPKLLIK<u>H<br>ASDSIS</u>GIPSRFSGSGSGTDFTLTINSLEAEDAAAYYC<u>GQGYSMPYT</u>FGG<br>GTKVEIK | 402 |

TABLE 2-continued

Anti-CD96 antibody sequences

| Description | Sequence | SEQ ID NO: |
|---|---|---|
| h10G1 - VL - L89M | EIVMTQSPDFQSVTPKEKVTITCRASQDIYRNLHWYQQKPDQTPKLLIKHASDSISGIPSRFSGSGSGTDFTLTINSLEAEDAAAYYCMQGYSMPYTFGGGTKVEIK | 403 |
| h10G1 - VL - L89Q | EIVMTQSPDFQSVTPKEKVTITCRASQDIYRNLHWYQQKPDQTPKLLIKHASDSISGIPSRFSGSGSGTDFTLTINSLEAEDAAAYYCQQGYSMPYTFGGGTKVEIK | 404 |
| h10G1 - VL - S93A | EIVMTQSPDFQSVTPKEKVTITCRASQDIYRNLHWYQQKPDQTPKLLIKHASDSISGIPSRFSGSGSGTDFTLTINSLEAEDAAAYYCLQGYAMPYTFGGGTKVEIK | 405 |
| h10G1 - VL - S93E | EIVMTQSPDFQSVTPKEKVTITCRASQDIYRNLHWYQQKPDQTPKLLIKHASDSISGIPSRFSGSGSGTDFTLTINSLEAEDAAAYYCLQGYEMPYTFGGGTKVEIK | 406 |
| h10G1 - VL - S93Q | EIVMTQSPDFQSVTPKEKVTITCRASQDIYRNLHWYQQKPDQTPKLLIKHASDSISGIPSRFSGSGSGTDFTLTINSLEAEDAAAYYCLQGYQMPYTFGGGTKVEIK | 407 |
| h10G1 - VL - S93V | EIVMTQSPDFQSVTPKEKVTITCRASQDIYRNLHWYQQKPDQTPKLLIKHASDSISGIPSRFSGSGSGTDFTLTINSLEAEDAAAYYCLQGYVMPYTFGGGTKVEIK | 408 |
| h10G1 - VL - Y96F | EIVMTQSPDFQSVTPKEKVTITCRASQDIYRNLHWYQQKPDQTPKLLIKHASDSISGIPSRFSGSGSGTDFTLTINSLEAEDAAAYYCLQGYSMPFTFGGGTKVEIK | 409 |
| h10G1 - VH - T30A | EIQLVQSGSELKKPGASVKVSCKASGYPFATYGMSWVRQAPGQGLEWMGWINTDSGVPTYADDFKGRFVFSLDTSVSTAYLQISSLKAEDTAVYFCARNIYYGWGNFDYWGQGTLVTVSS | 410 |
| h10G1 - VH - T30D | EIQLVQSGSELKKPGASVKVSCKASGYPFDTYGMSWVRQAPGQGLEWMGWINTDSGVPTYADDFKGRFVFSLDTSVSTAYLQISSLKAEDTAVYFCARNIYYGWGNFDYWGQGTLVTVSS | 411 |
| h10G1 - VH - T30E | EIQLVQSGSELKKPGASVKVSCKASGYPFETYGMSWVRQAPGQGLEWMGWINTDSGVPTYADDFKGRFVFSLDTSVSTAYLQISSLKAEDTAVYFCARNIYYGWGNFDYWGQGTLVTVSS | 412 |
| h10G1 - VH - T30G | EIQLVQSGSELKKPGASVKVSCKASGYPFGTYGMSWVRQAPGQGLEWMGWINTDSGVPTYADDFKGRFVFSLDTSVSTAYLQISSLKAEDTAVYFCARNIYYGWGNFDYWGQGTLVTVSS | 413 |
| h10G1 - VH - T30H | EIQLVQSGSELKKPGASVKVSCKASGYPFHTYGMSWVRQAPGQGLEWMGWINTDSGVPTYADDFKGRFVFSLDTSVSTAYLQISSLKAEDTAVYFCARNIYYGWGNFDYWGQGTLVTVSS | 414 |
| h10G1 - VH - T30K | EIQLVQSGSELKKPGASVKVSCKASGYPFKTYGMSWVRQAPGQGLEWMGWINTDSGVPTYADDFKGRFVFSLDTSVSTAYLQISSLKAEDTAVYFCARNIYYGWGNFDYWGQGTLVTVSS | 415 |
| h10G1 - VH - T30M | EIQLVQSGSELKKPGASVKVSCKASGYPFMTYGMSWVRQAPGQGLEWMGWINTDSGVPTYADDFKGRFVFSLDTSVSTAYLQISSLKAEDTAVYFCARNIYYGWGNFDYWGQGTLVTVSS | 416 |
| h10G1 - VH - T30N | EIQLVQSGSELKKPGASVKVSCKASGYPFNTYGMSWVRQAPGQGLEWMGWINTDSGVPTYADDFKGRFVFSLDTSVSTAYLQISSLKAEDTAVYFCARNIYYGWGNFDYWGQGTLVTVSS | 417 |
| h10G1 - VH - T30Q | EIQLVQSGSELKKPGASVKVSCKASGYPFQTYGMSWVRQAPGQGLEWMGWINTDSGVPTYADDFKGRFVFSLDTSVSTAYLQISSLKAEDTAVYFCARNIYYGWGNFDYWGQGTLVTVSS | 418 |
| h10G1 - VH - T30R | EIQLVQSGSELKKPGASVKVSCKASGYPFRTYGMSWVRQAPGQGLEWMGWINTDSGVPTYADDFKGRFVFSLDTSVSTAYLQISSLKAEDTAVYFCARNIYYGWGNFDYWGQGTLVTVSS | 419 |
| h10G1 - VH - T30S | EIQLVQSGSELKKPGASVKVSCKASGYPFSTYGMSWVRQAPGQGLEWMGWINTDSGVPTYADDFKGRFVFSLDTSVSTAYLQISSLKAEDTAVYFCARNIYYGWGNFDYWGQGTLVTVSS | 420 |

TABLE 2-continued

Anti-CD96 antibody sequences

| Description | Sequence | SEQ ID NO: |
|---|---|---|
| h10G1 - VH - T31D | EIQLVQSGSELKKPGASVKVSCKASGYPFTDYGMSWVRQAPGQGLEWMGW INTDSGVPTYADDFKGRFVFSLDTSVSTAYLQISSLKAEDTAVYFCARNI YYGWGNFDYWGQGTLVTVSS | 421 |
| h10G1 - VH - T31E | EIQLVQSGSELKKPGASVKVSCKASGYPFTEYGMSWVRQAPGQGLEWMGW INTDSGVPTYADDFKGRFVFSLDTSVSTAYLQISSLKAEDTAVYFCARNI YYGWGNFDYWGQGTLVTVSS | 422 |
| h10G1 - VH - T31G | EIQLVQSGSELKKPGASVKVSCKASGYPFTGYGMSWVRQAPGQGLEWMGW INTDSGVPTYADDFKGRFVFSLDTSVSTAYLQISSLKAEDTAVYFCARNI YYGWGNFDYWGQGTLVTVSS | 423 |
| h10G1 - VH - T31H | EIQLVQSGSELKKPGASVKVSCKASGYPFTHYGMSWVRQAPGQGLEWMGW INTDSGVPTYADDFKGRFVFSLDTSVSTAYLQISSLKAEDTAVYFCARNI YYGWGNFDYWGQGTLVTVSS | 424 |
| h10G1 - VH - T31N | EIQLVQSGSELKKPGASVKVSCKASGYPFTNYGMSWVRQAPGQGLEWMGW INTDSGVPTYADDFKGRFVFSLDTSVSTAYLQISSLKAEDTAVYFCARNI YYGWGNFDYWGQGTLVTVSS | 425 |
| h10G1 - VH - T31Q | EIQLVQSGSELKKPGASVKVSCKASGYPFTQYGMSWVRQAPGQGLEWMGW INTDSGVPTYADDFKGRFVFSLDTSVSTAYLQISSLKAEDTAVYFCARNI YYGWGNFDYWGQGTLVTVSS | 426 |
| h10G1 - VH - T31S | EIQLVQSGSELKKPGASVKVSCKASGYPFTSYGMSWVRQAPGQGLEWMGW INTDSGVPTYADDFKGRFVFSLDTSVSTAYLQISSLKAEDTAVYFCARNI YYGWGNFDYWGQGTLVTVSS | 427 |
| h10G1 - VH - Y32F | EIQLVQSGSELKKPGASVKVSCKASGYPFTTFGMSWVRQAPGQGLEWMGW INTDSGVPTYADDFKGRFVFSLDTSVSTAYLQISSLKAEDTAVYFCARNI YYGWGNFDYWGQGTLVTVSS | 428 |
| h10G1 - VH - Y32M | EIQLVQSGSELKKPGASVKVSCKASGYPFTTMGMSWVRQAPGQGLEWMGW INTDSGVPTYADDFKGRFVFSLDTSVSTAYLQISSLKAEDTAVYFCARNI YYGWGNFDYWGQGTLVTVSS | 429 |
| h10G1 - VH - Y32Q | EIQLVQSGSELKKPGASVKVSCKASGYPFTTQGMSWVRQAPGQGLEWMGW INTDSGVPTYADDFKGRFVFSLDTSVSTAYLQISSLKAEDTAVYFCARNI YYGWGNFDYWGQGTLVTVSS | 430 |
| h10G1 - VH - M34I | EIQLVQSGSELKKPGASVKVSCKASGYPFTTYGISWVRQAPGQGLEWMGW INTDSGVPTYADDFKGRFVFSLDTSVSTAYLQISSLKAEDTAVYFCARNI YYGWGNFDYWGQGTLVTVSS | 431 |
| h10G1 - VH - M34L | EIQLVQSGSELKKPGASVKVSCKASGYPFTTYGLSWVRQAPGQGLEWMGW INTDSGVPTYADDFKGRFVFSLDTSVSTAYLQISSLKAEDTAVYFCARNI YYGWGNFDYWGQGTLVTVSS | 432 |
| h10G1 - VH - M34V | EIQLVQSGSELKKPGASVKVSCKASGYPFTTYGVSWVRQAPGQGLEWMGW INTDSGVPTYADDFKGRFVFSLDTSVSTAYLQISSLKAEDTAVYFCARNI YYGWGNFDYWGQGTLVTVSS | 433 |
| h10G1 - VH - D53E | EIQLVQSGSELKKPGASVKVSCKASGYPFTTYGMSWVRQAPGQGLEWMGW INTESGVPTYADDFKGRFVFSLDTSVSTAYLQISSLKAEDTAVYFCARNI YYGWGNFDYWGQGTLVTVSS | 434 |
| h10G1 - VH - S54T | EIQLVQSGSELKKPGASVKVSCKASGYPFTTYGMSWVRQAPGQGLEWMGW INTDTGVPTYADDFKGRFVFSLDTSVSTAYLQISSLKAEDTAVYFCARNI YYGWGNFDYWGQGTLVTVSS | 435 |
| h10G1 - VH - N95M | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARMI YYGWGNFDYWGQGTLVTVSS | 436 |
| h10G1 - VH - N100bF | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARNI YYGWGFFDYWGQGTLVTVSS | 437 |
| h10G1 - VH - N100bH | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARNI YYGWGHFDYWGQGTLVTVSS | 438 |

TABLE 2-continued

Anti-CD96 antibody sequences

| Description | Sequence | SEQ ID NO: |
|---|---|---|
| h10G1 - VH - N100bY | EIQLVQSGSELKKPGASVKVSCKASGYPF<u>TTYGMS</u>WVRQAPGQGLEWMG<u>W INTDSGVPTYA</u>DDFKGRFVFSLDTSVSTAYLQISSLKAEDTAVYFC<u>ARNI YYGWGYFDY</u>WGQGTLVTVSS | 439 |
| 12F8 - LC Full length | DIVMTQSQKFMSTSVGDRVSVTC<u>KASQNVGTAIV</u>WYQKKPGQSPKTLIY<u>S ASTRYT</u>GVPDRFTGSGSGTDFTLTISNVQSEDLAEYFC<u>QQYSSSPLT</u>FGS GTKLEIKGQPKAAPSVTLFPPSSEELQANKATLVCLISDFYPGAVTVAWK ADSSPVKAGVETTTPSKQSNNKYAASSYLSLTPEQWKSHKSYSCQVTHEG STVEKTVAPTECS | 440 |
| 10H5 - LC Full length | DVVMTQTPLTLSVTLGHPASISC<u>KSSQSLLDSDGKTYLN</u>WLLQRPGESPK LLIY<u>LVSKLDS</u>GVPDRFTGSGSGTDFTLKISRVEAEDLGVYYC<u>LQATHSP QT</u>FGGGTKLEIKGQPKAAPSVTLFPPSSEELQANKATLVCLISDFYPGAV TVAWKADSSPVKAGVETTTPSKQSNNKYAASSYLSLTPEQWKSHKSYSCQ VTHEGSTVEKTVAPTECS | 441 |
| 1G8 - LC Full length | DIQMNQSPSSLSASLGDTITITC<u>RVSQDISFWLS</u>WYQQKPGNIPKLLIY<u>K ASNLHT</u>GVPPRFSGSGSGTDFTLTISSLQPEDIAAYYC<u>LQSQSYPYT</u>FGG GTKLEIKGQPKAAPSVTLFPPSSEELQANKATLVCLISDFYPGAVTVAWK ADSSPVKAGVETTTPSKQSNNKYAASSYLSLTPEQWKSHKSYSCQVTHEG STVEKTVAPTECS | 442 |
| 16D9 - LC Full length | ENVLTQSPAIMSATLGEKVTMNC<u>RASSNVKYMY</u>WYQQKSGVSPKLWIYY<u>T SNLAS</u>GVPTRFSGSGSGTSYSLTISSVEAEDAATYYC<u>QQFTSSPLT</u>FGAG TKLELKGQPKAAPSVTLFPPSSEELQANKATLVCLISDFYPGAVTVAWKA DSSPVKAGVETTTPSKQSNNKYAASSYLSLTPEQWKSHKSYSCQVTHEGS TVEKTVAPTECS | 443 |
| 9H4 - LC Full length | DIVLTQSPASLAVSLGQRAIISC<u>KASQSVTFADTGLMH</u>WYQQKPGQQPKL LIY<u>RASNLEV</u>GVPTRFSGSGSGTDFTLNIHPVEEEDVATYYC<u>QQSREYPW T</u>FGGGTKLEIKGQPKAAPSVTLFPPSSEELQANKATLVCLISDFYPGAVT VAWKADSSPVKAGVETTTPSKQSNNKYAASSYLSLTPEQWKSHKSYSCQV THEGSTVEKTVAPTECS | 444 |
| 7E5 - LC Full length | QAVVTQESALTTSPGETVTLTC<u>RSSTGAVTTSNYAN</u>WVQEKPDHLFTGLI GGT<u>NNRAP</u>GVPARFSGSLIGDKAALTITGAQTEDEAIYFC<u>SLWYGSHWVF </u>GGGTKLTVLGQPKAAPSVTLFPPSSEELQANKATLVCLISDFYPGAVTVA WKADSSPVKAGVETTTPSKQSNNKYAASSYLSLTPEQWKSHKSYSCQVTH EGSTVEKTVAPTECS | 445 |
| 10G1 - LC Full length | DILMTQSPTTLSVTPGETVSLSC<u>RASQDIYRNLH</u>WYQQKSQGTPRLLIK<u>H ASDSIS</u>GIPSRFTGSGSGTDFTLSINSVKPEDEGIYYC<u>LQGYSMPYT</u>FGG GTKLEIKGQPKAAPSVTLFPPSSEELQANKATLVCLISDFYPGAVTVAWK ADSSPVKAGVETTTPSKQSNNKYAASSYLSLTPEQWKSHKSYSCQVTHEG STVEKTVAPTECS | 446 |
| 12F8 - HC Full length hIgG1.N297G | QVQLQQPGAELVTPGASVKLSCKASGFTF<u>TNNWMH</u>WVKQRPGQGLEWIG<u>M IHPNSGITNINEK</u>FKNKATVTVDKSSSTVYIQLSSLTSEDSAVYYC<u>ARSDG TYEGYFDY</u>WGQGTPLTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 447 |
| 10H5 - HC Full length hIgG1.N297G | QVQLQQSGADLARPGASIKLSCKASGYTF<u>TGYGVT</u>WVKQSTGQGLDWIG<u>E IYPGTVITYYNAK</u>FKGKATLTADKSSSTAYMELRSLTSEDSAVYFC<u>ARGL GRAMDY</u>WGQGTSVTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYGSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPG | 448 |
| 1G8 - HC Full length hIgG1.N297G | QVQLQQSGPELLKPGASVKISCKASGYTF<u>TDYYIN</u>WVKQRPGQGLEWIG<u>W IFPGTEGIYYNEK</u>FKGKATLTVDKSSTTAYMLLSSLTSEDSAVYFC<u>AREG DYRYYSPLGY</u>WGQGTLVTVSAASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREEQY GSTYRVVSVLTVLHQDWLNGKEYKCKVSNKALPAPIEKTISKAKGQPREP | 449 |

TABLE 2-continued

Anti-CD96 antibody sequences

| Description | Sequence | SEQ ID NO: |
|---|---|---|
| | QVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPG | |
| 16D9 - HC Full length hIgG1.N297G | QVQLQQSGPELVKPGASVKISCKASGYNF<u>NDYYIN</u>WVNQRPGQGLEWIG<u>W IFPGRIITYYNEK</u>FKGKATLTVDTSSNTAYMLLSSLTSEDSAVYFC<u>ARGV GEGFDY</u>WGQGTTLTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYGSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPG | 450 |
| 9H4 - HC Full length hIgG1.N297G | EVQLLETGGGLVKSGGSLKLSCAASGFTF<u>SDYYMY</u>WVRQTPEKRLEWVA<u>A ISDDGTYTYYPD</u>SVKGRFTISRDNANNYLYLQMSSLKSEDTAIYYC<u>AKAG SYDYFDV</u>WGAGTTVTVSSASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYGST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPG | 451 |
| 7E5 - HC Full length hIgG1.N297G | QVQLKESGPGLVAPSQSLSIICTVSGFSL<u>TNYGIH</u>WIRQPPGKGLEWLG<u>I IWAGGSTNYNS</u>ALMSRLTISKDNSKSQVFLKMNSLQTNDTAIYYC<u>ARVSM MGFAY</u>WGQGTLVTVSSASTKGPSVFPLAPSSKSTSGGTAALGCLVKDYFP EPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTL MISRTPEVTCVVVDVSHEDPEVKFNWYVDGVEVHNAKTKPREEQYGSTYR VVSVLTVLHQDWLNGKEYKCKVSNKALPAPIEKTISKAKGQPREPQVYTL PPSRDELTKNQVSLTCLVKGFYPSDIAVEWESNGQPENNYKTTPPVLDSD GSFFLYSKLTVDKSRWQQGNVFSCSVMHEALHNHYTQKSLSLSPG | 452 |
| 10G1 - HC Full length hIgG1.N297G | QIQLVQSGPELKKPGETVKISCKASGYPF<u>TTYGMS</u>WVKQAPGKGLKWMG<u>W INTDSGVPTYADD</u>FKGRFAFSLETSANTAYLQINSLKNEDAATYFC<u>ARNI YYGWGNFDY</u>WGQGTILTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYG STYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPG | 453 |
| mAb1v7 - LC Full length | DIQLTQSPSSLSASVGDRVTITC<u>KASQNVGTAIV</u>WYQQKPGKAPKVLTY<u>S ASTRYT</u>GVPSRFSGSGSGTDFTLTISSLQPEDFATYYC<u>QQYSSSPLT</u>FGQ GTKVEIKGQPKAAPSVTLFPPSSEELQANKATLVCLISDFYPGAVTVAWK ADSSPVKAGVETTTPSKQSNNKYAASSYLSLTPEQWKSHKSYSCQVTHEG STVEKTVAPTECS | 454 |
| mAb1v7 - HC Full length hIgG.N297G | EVQLVQSGAEVKKPGASVKVSCKASGFTF<u>TNNWMH</u>WVRQAPGQGLEWIG<u>M IHPNSGITNINEK</u>FKNRVTMTTDTSTSTAYMELRSLRSEDTAVYYC<u>RSDG TYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 455 |
| mAb1v7 - HC - W33F/P52aA/T97I (mAb1v7.NGS8) Full length hIgG1.N297G | EVQLVQSGAEVKKPGASVKVSCKASGFTF<u>TNNFMH</u>WVRQAPGQGLEWIG<u>M IHANSGITNINEK</u>FKNRVTMTTDTSTSTAYMELRSLRSEDTAVYYC<u>RSDG IYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 456 |
| mAb1v7 - HC - W33F/P52aA/T97V (mAb1v7.NGS9) Full length hIgG1.N297G | EVQLVQSGAEVKKPGASVKVSCKASGFTF<u>TNNFMH</u>WVRQAPGQGLEWIG<u>M IHANSGITNINEK</u>FKNRVTMTTDTSTSTAYMELRSLRSEDTAVYYC<u>RSDG VYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK | 457 |

TABLE 2-continued

Anti-CD96 antibody sequences

| Description | Sequence | SEQ ID NO: |
|---|---|---|
| | DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | |
| mAb1v7 - HC - W33F/M50F/P52aA/ T97I (mAb1v7.NGS10) Full length hIgG1.N297G | EVQLVQSGAEVKKPGASVKVSCKASGFTF<u>TNNFMH</u>WVRQAPGQGLEWIG<u>F IHANSGITNINE</u>KFKNRVTMTTDTSTSTAYMELRSLRSEDTAVYYC<u>RSDG IYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 458 |
| mAb1v7 - HC - W33F/M50F/P52aA/ T97V (11Ab1V7.NGS11) Full length hIgG1.N297G | EVQLVQSGAEVKKPGASVKVSCKASGFTF<u>TNNFMH</u>WVRQAPGQGLEWIG<u>F IHANSGITNINE</u>KFKNRVTMTTDTSTSTAYMELRSLRSEDTAVYYC<u>RSDG VYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 459 |
| mAb1.v1 - VH | QVQLVQSGAEVKKPGASVKVSCKASGFTF<u>TNNWMH</u>WVRQRPGQGLEWIG<u>M IHPNSGITNINE</u>KFKNRATVTVDKSSSTVYIELRSLRSEDTAVYYC<u>RSDG TYEGIFDY</u>WGQGTLVTVSS | 460 |
| mAb1.v2 - VH | QVQLVQSGAEVKKPGASVKVSCKASGFTF<u>TNNWMH</u>WVRQRPGQGLEWIG<u>M IHPNSGITNINE</u>KFKNRATVTVDKSSSTVYIELRSLRSEDTAVYYC<u>RSDG TYEGYFDY</u>WGQGTLVTVSS | 461 |
| mAb1.v3 - VH | QVQLVQSGAEVKKPGASVKVSCKASGFTF<u>TNNWMH</u>WVRQAPGQGLEWVG<u>M IHPNSGITNINE</u>KFKNRVTMTVDKSTSTVYMELRSLRSDDTAVYYC<u>RSDG TYEGYFDY</u>WGQGTLVTVSS | 462 |
| mAb1.v4 - VH | QVQLVQSGAEVKKPGASVKVSCKASGFTF<u>TNNWMH</u>WVRQAPGQGLEWIG<u>M IHPNSGITNINE</u>KFKNRVTMTTDTSTSTAYMELRSLRSDDTAVYYC<u>RSDG TYEGYFDY</u>WGQGTLVTVSS | 463 |
| mAb1.v5 - VH | QVQLVQSGAEVKKPGASVKVSQKASGFTF<u>TNNWMH</u>WVRQAPGQGLEWIG<u>M THPNSGITNINE</u>KFKNEVTMTVDKSTSTVYMELRSLRSDDTAVYYC<u>ARDG TYEGYFDY</u>WGQGTLVTVSS | 464 |
| mAb1.v1 - HC Full length hIgG1.N297G | QVQLVQSGAEVKKPGASVKVSCKASGFTF<u>TNNWMH</u>WVRQRPGQGLEWIG<u>M IHPNSGITNINE</u>KFKNRATVTVDKSSSTVYIELRSLRSEDTAVYYC<u>RSDG TYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 465 |
| mAb1.v2 - HC Full length hIgG1.N297G | QVQLVQSGAEVKKPGASVKVSCKASGFTF<u>TNNWMH</u>WVRQRPGQGLEWIG<u>M IHPNSGITNINE</u>KFKNRATVTVDKSSSTVYIELRSLRSEDTAVYYC<u>RSDG TYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 466 |
| mAb1.v3 - HC Full length hIgG1.N297G | QVQLVQSGAEVKKPGASVKVSCKASGFTF<u>TNNWMH</u>WVRQAPGQGLEWVG<u>M IHPNSGITNINE</u>KFKNRVTMTVDKSTSTVYMELRSLRSDDTAVYYC<u>RSDG TYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 467 |

TABLE 2-continued

Anti-CD96 antibody sequences

| Description | Sequence | SEQ ID NO: |
|---|---|---|
| mAb1.v4- HC Full length hIgG1.N297G | QVQLVQSGAEVKKPGASVKVSCKASGFTF<u>TNNWMH</u>WVRQAPGQGLEWIG<u>M IHPNSGITNINE</u>KFKNRVTMTTDTSTSTAYMELRSLRSDDTAVYYC<u>RSDG TYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSQDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRINQQGNVFSCSVMHEALHNHYTQKSLSLSPG | 468 |
| mAb1.v5- HC Full length hIgG1.N297G | QVQLVQSGAEVKKPGASVKVSCKASGFTF<u>TNNWMH</u>WVRQAPGQGLEWIG<u>M IHPNSGITNINE</u>KFKNRVTMTVDKSTSTVYMELRSLRSDDTAVYYC<u>ARDG TYEGYFDY</u>WGQGYLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 469 |
| h10G1 - LC Full length | EIVMTQSPDFQSVTPKEKVTITC<u>RASQDIYRNLH</u>WYQQKPDQTPKLLIK<u>H ASDSIS</u>GIPSRFSGSGSGTDFTLTINSLEAEDAAAYYC<u>LQGYSMPYT</u>FGG GTKVEIKGQPKAAPSVTLFPPSSEELQANKATLVCLISDFYPGAVTVAWK ADSSPVKAGVETTTPSKQSNNKYAASSYLSLTPEQWKSHKSYSCQVTHEG STVEKTVAPTECS | 470 |
| h10G1 - HC Full length hIgG1.N297G | EIQLVQSGSELKKPGASVKVSCKASGYPF<u>TTYGMS</u>WVRQAPGQGLEWMG<u>W INTDSGVPTYADD</u>FKGRFVFSLDTSVSTAYLQISSLKAEDTAVYFC<u>ARNI YYGWGNFDY</u>WGQGTLVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYG STYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPG | 471 |
| 12F8 - HC Full length hIgG1.N297G + C-term Lys | QVQLQQPGAELVTPGASVKLSCKASGFTF<u>TNNWMH</u>WVKQRPGQGLEWIG<u>M IHPNSGITNINE</u>KFKNKATVTVDKSSSTVYIQLSSLTSEDSAVYYC<u>RSDG TYEGYFDY</u>WGQGTPLTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 484 |
| 10H5 - HC Full length hIgG1.N297G + C-term Lys | QVQLQQSGADLARPGASIKLSCKASGYTF<u>TGYGVT</u>WVKQSTGQGLDWIG<u>E IYPGTVITYYNA</u>KFKGKATLTADKSSTAYMELRSLTSEDSAVYFC<u>ARGL GRAMDY</u>WGQGTSVTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYGSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGK | 485 |
| 1G8 - HC Full length hIgG1.N297G + C-term Lys | QVQLQQSGPELLKPGASVKISCKASGYTF<u>TDYYIN</u>WVKQRPGQGLEWIG<u>W IFPGTEGIYYNE</u>KFKGKATLTVDKSSTAYMLLSSLTSEDSAVYFC<u>AREG DYRYYSPLGY</u>WGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREEQY GSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPG K | 486 |
| 16D9 - HC Full length hIgG1.N297G + C-term Lys | QVQLQQSGPELVKPGASVKISCKASGYNF<u>NDYYIN</u>WVNQRPGQGLEWIG<u>W IFPGRIIITYYNE</u>KFKGKATLTVDTSSNTAYMLLSSLTSEDSAVYFC<u>ARGV GEGFDY</u>WGQGTTLTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYGSTY RVVSVLTVLHQDWLNGKEYKCKVSNKALPAPIEKTISKAKGQPREPQVYT | 487 |

TABLE 2-continued

Anti-CD96 antibody sequences

| Description | Sequence | SEQ ID NO: |
|---|---|---|
| | LPPSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPGK | |
| 9H4 - HC<br>Full length<br>hIgG1.N297G + C-<br>term Lys | EVQLLETGGGLVKSGGSLKLSCAASGFTF<u>SDYYMY</u>WVRQTPEKRLEWVA<u>A</u><br><u>ISDDGTYTYYPD</u>SVKGRFTISRDNANNYLYLQMSSLKSEDTAIYYC<u>AKAG</u><br><u>SYDYFDV</u>WGAGTTVTVSSASTKGPSVFPLAPSSKSTSGGTAALGCLVKDY<br>FPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYGST<br>YRVVSVLTVLHQDWLNGKEYKCKVSNKALPAPIEKTISKAKGQPREPQVY<br>TLPPSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPGK | 488 |
| 7E5 - HC<br>Full length<br>hIgG1.N297G + C-<br>term Lys | QVQLKESGPGLVAPSQSLSIICTVSGFSL<u>TNYGIH</u>WIRQPPGKGLEWLG<u>I</u><br><u>IWAGGSTNYNS</u>ALMSRLTISKDNSKSQVFLKMNSLQTNDTAIYYC<u>ARVSM</u><br><u>MGFAY</u>WGQGTLVTVSAASTKGPSVFPLAPSSKSTSGGTAALGCLVKDYFP<br>EPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQYGSTYR<br>VVSVLTVLHQDWLNGKEYKCKVSNKALPAPIEKTISKAKGQPREPQVYTL<br>PPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGK | 489 |
| 10G1 - HC<br>Full length<br>hIgG1.N297G + C-<br>term Lys | QIQLVQSGPELKKPGETVKISCKASGYPF<u>TTYGMS</u>WVKQAPGKGLKWMG<u>W</u><br><u>INTDSGVPTYADD</u>FKGRFAFSLETSANTAYLQINSLKNEDAATYFC<u>ARNI</u><br><u>YYGWGNFDY</u>WGQGTILTVSSASTKGPSVFPLAPSSKSTSGGTAALGCLVK<br>DYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYG<br>STYRVVSVLTVLHQDWLNGKEYKCKVSNKALPAPIEKTISKAKGQPREPQ<br>VYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPGK | 490 |
| mAb1v7 - HC<br>Full length<br>hIgG.N297G + C-term<br>Lys | EVQLVQSGAEVKKPGASVKVSCKASGFTF<u>TNNWMH</u>WVRQAPGQGLEWIG<u>M</u><br><u>IHPNSGITNINE</u>KFKNRVTMTTDTSTSTAYMELRSLRSEDTAVYYC<u>RSDG</u><br><u>TYEGYFDY</u>WGQGTLVTVSSASTKGPSVFPLAPSSKSTSGGTAALGCLVK<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 491 |
| MAb1V7 - HC -<br>W33F/P52aA/T97I<br>(mAb1v7.NGS8)<br>Full length<br>hIgG1.N297G + C-<br>term Lys | EVQLVQSGAEVKKPGASVKVSCKASGFTF<u>TNNFMH</u>WVRQAPGQGLEWIG<u>M</u><br><u>IHANSGITNINE</u>KFKNRVTMTTDTSTSTAYMELRSLRSEDTAVYYC<u>RSDG</u><br><u>IYEGYFDY</u>WGQGTLVTVSSASTKGPSVFPLAPSSKSTSGGTAALGCLVK<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 492 |
| MAb1 V7 - HC -<br>W33F/P52aA/T97V<br>(mAb1v7.NGS9)<br>Full length<br>hIgG1.N297G + C-<br>term Lys | EVQLVQSGAEVKKPGASVKVSCKASGFTF<u>TNNFMH</u>WVRQAPGQGLEWIG<u>M</u><br><u>IHANSGITNINE</u>KFKNRVTMTTDTSTSTAYMELRSLRSEDTAVYYC<u>RSDG</u><br><u>VYEGYFDY</u>WGQGTLVTVSSASTKGPSVFPLAPSSKSTSGGTAALGCLVK<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 493 |
| mAb1v7- HC -<br>W33F/M50F/P52aA/<br>T97I<br>(mAb1v7.NGS10)<br>Full length<br>hIgG1.N297G + C-<br>term Lys | EVQLVQSGAEVKKPGASVKVSCKASGFTF<u>TNNFMH</u>WVRQAPGQGLEWIG<u>F</u><br><u>IHANSGITNINE</u>KFKNRVTMTTDTSTSTAYMELRSLRSEDTAVYYC<u>RSDG</u><br><u>IYEGYFDY</u>WGQGTLVTVSSASTKGPSVFPLAPSSKSTSGGTAALGCLVK<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 494 |

TABLE 2-continued

Anti-CD96 antibody sequences

| Description | Sequence | SEQ ID NO: |
|---|---|---|
| mAb1v7- HC - W33F/M50F/P52aA/ T97V (mAb1v7.NGS11) Full length hIgG1.N297G + C-term Lys | EVQLVQSGAEVKKPGASVKVSCKASGFTF<u>TNNFMH</u>WVRQAPGQGLEWIG<u>F IHANSGITNINEK</u>FKNRVTMTTDTSTSTAYMELRSLRSEDTAVYYC<u>RSDG VYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 495 |
| mAb1.v1 - HC Full length hIgG1.N297G + C-term Lys | QVQLVQSGAEVKKPGASVKVSCKASGFTF<u>TNNWMH</u>WVRQRPGQGLEWIG<u>M IHPNSGITNINEK</u>FKNRATVTVDKSSSTVYIELRSLRSEDTAVYYC<u>RSDG TYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAYTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 496 |
| mAb1.v2 - HC Full length hIgG1.N297G-term Lys | QVQLVQSGAEVKKPGASVKVSCKASGFTF<u>TNNWMH</u>WVRQRPGQGLEWIG<u>M IHPNSGITNINEK</u>FKNRATVTVDKSSSTVYIELRSLRSEDTAVYYC<u>RSDG TYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 497 |
| mAb1.v3 - HC Full length hIgG1.N297G-term Lys | QVQLVQSGAEVKKPGASVKVSCKASGFTF<u>TNNWMH</u>WVRQAPGQGLEWVG<u>M IHPNSGITNINEK</u>FKNRVTMTVDKSTSTVYMELRSLRSDDTAVYYC<u>RSDG TYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 498 |
| mAb1.v4 - HC Full length hIgG1.N297G + C-term Lys | QVQLVQSGAEVKKPGASVKVSCKASGFTF<u>TNNWMH</u>WVRQAPGQGLEWIG<u>M IHPNSGITNINEK</u>FKNRVTMTTDTSTSTAYMELRSLRSDDTAVYYC<u>RSDG TYFGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 499 |
| mAb1.v5 - HC Full length hIgG1.N297G + C-term Lys | QVQLVQSGAEVKKPGASVKVSCKASGFTF<u>TNNWMH</u>WVRQAPGQGLEWIG<u>M IHPNSGITNINEK</u>FKNRVTMTVDKSTSTVYMELRSLRSDDTAVYYCARDG TYEGYFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 500 |
| h10G1 - HC Full length hIgG1.N297G + C-term Lys | EIQLVQSGSELKKPGASVKVSCKASGYPF<u>TTYGMS</u>WVRQAPGQGLEWMG<u>W INTDSGVPTYADD</u>FKGRFVFSLDTSVSTAYLQISSLKAEDTAVYFC<u>ARNI YYGWGNFDY</u>WGQGTLVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYG STYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK | 501 |

1. Binding Affinity and Cell-Signaling Inhibition of Anti-CD96 Antibodies

In some embodiments, the anti-CD96 antibodies provided herein have an equilibrium dissociation constant ($K_D$) for binding to CD96 of <100 nM, <10 nM, <1 nM, <0.1 nM, <0.01 nM, or <0.001 nM (e.g., $10^{-8}$ M or less, from $10^{-3}$ M to $10^{-13}$ M, e.g., from $10^{-9}$ M to $10^{-13}$ M).

It is contemplated that the various anti-CD96 antibodies generated as disclosed herein include antibodies capable of high-affinity binding to hu-CD96, cy-CD96, and both hu-CD96 and cy-CD96. More specifically, in some embodiments, the anti-CD96 antibodies of the present disclosure bind to hu-CD96 with a binding affinity of $1\times10^{-8}$ M or less, $1\times10^{-9}$ M or less, $1\times10^{-10}$ M or less, or $1\times10^{-11}$ M or less. In some embodiments, the binding affinity is measured as the equilibrium dissociation constant ($K_D$) for binding to the hu-CD96 polypeptide of SEQ ID NO: 4. In some embodiments, the anti-CD96 antibodies of the present disclosure bind to cy-CD96 with a binding affinity of $1\times10^{-8}$ M or less, $1\times10^{-9}$ M or less, $1\times10^{-10}$ M or less, or $1\times10^{-11}$ M or less. In some embodiments, the binding affinity is measured as the equilibrium dissociation constant ($K_D$) for binding to the cy-CD96 polypeptide of SEQ ID NO: 7. In some embodiments, the anti-CD96 antibodies of the present disclosure bind to both hu-CD96 and cy-CD96 with a binding affinity of $1\times10^{-8}$ M or less, $1\times10^{-9}$ M or less, $1\times10^{-10}$ M or less, or $1\times10^{-11}$ M or less. In some embodiments, the binding affinity is measured as the equilibrium dissociation constant ($K_D$) for binding to the hu-CD96 polypeptide of SEQ ID NO: 4 and the cy-CD96 polypeptide of SEQ ID NO: 7.

Generally, binding affinity of a ligand to its receptor can be determined using any of a variety of assays and expressed in terms of a variety of quantitative values. Specific CD96 binding assays useful in determining affinity of the antibodies are disclosed in the Examples herein. Additionally, antigen binding assays are known in the art and can be used herein including without limitation any direct or competitive binding assays using techniques such as western blots, radioimmunoassays, enzyme-linked immunoabsorbent assay (ELISA), "sandwich" immunoassays, surface plasmon resonance based assay (such as the BIAcore assay as described in WO2005/012359), immunoprecipitation assays, fluorescent immunoassays, protein A immunoassays, flow cytometric and fluorescence activated cell sorting (FACS) assays, and the like.

Accordingly, in some embodiments, the binding affinity is expressed as $K_D$ values and reflects intrinsic binding affinity (e.g., with minimized avidity effects). The anti-CD96 antibodies of the present disclosure exhibit strong binding affinities for the hu-CD96 polypeptide of SEQ ID NO: 4, for example, exhibiting $K_D$ values of between 10 nM and 1 µM. Accordingly, Anti-CD96 antibodies of the present disclosure may compete with antibodies having lower affinity for the same or overlapping epitopes of CD96, including epitopes within the D1 domain of hu-CD96 or the D1 domain of cy-CD96. For example, in some embodiments, antibodies of the present disclosure, having a $K_D$ for binding to hu-CD96 of 10 nM or less, compete with NK92.39 for binding of hu-CD96, including where such antibodies compete with NK92.39 for binding of the D1 domain of hu-CD96, including where such binding affinity is determined by surface plasmon resonance (SPR) measurement.

In some embodiments, the anti-CD96 antibodies provided herein decrease, inhibit, and/or fully-block CD96 binding to CD155, and immune regulation and/or immune signaling mediated by CD96 binding to CD155, including the activation of T cells and NK cells mediated by CD226. The ability of the antibodies to inhibit these immune regulatory and immune signaling pathways mediated by CD96 binding to CD155 can be assayed in vitro using known cell-based assays including the primary cell-based assays described in the Examples of the present disclosure.

Accordingly, in some embodiments, the CD96 antibodies of the present disclosure are characterized by one or more of following functional properties based on the ability to decrease, inhibit, and/or fully-block intracellular signaling by CD96-mediated pathways.

In some embodiments the anti-CD96 antibody binds to human CD96 isoform 1 expressed on a cell, such as an HEK293T cell, with an antibody $EC_{50}$ concentration of 5 nM or less, 1 nM or less, or 0.1 nM or less.

In some embodiments the anti-CD96 antibody binds to human CD96 isoform 2 expressed on a cell, such as a CHO cell, with an antibody $EC_{50}$ concentration of 5 nM or less, 1 nM or less, or 0.1 nM or less.

In some embodiments the anti-CD96 antibody binds to human PBMCs with an antibody $EC_{50}$ concentration of 5 nM or less, 1 nM or less, or 0.1 nM or less.

In some embodiments the anti-CD96 antibody binds to cynomolgus monkey PBMCs with an antibody $EC_{50}$ concentration of 5 nM or less, 1 nM or less, or 0.1 nM or less.

In some embodiments the anti-CD96 antibody decreases binding of human CD155 to human CD96 expressed on cells, such as CHO cells, by at least 90%, at least 95%, at least 99%, or 100%. In some embodiments, at a human CD155 concentration of 10 nM, the anti-CD96 anti body has an $IC_{50}$ value for decreasing CD155 binding of 5 nM or less, 1 nM or less, or 0.1 nM or less.

In some embodiments the anti-CD96 antibody increases IFNγ secretion and/or IL-2 secretion from human PBMCs (e.g., NK cells, T-cells) by at least 1.8-fold, at least 1.9-fold, at least 2-fold, at least 2.1-fold, or at least 2.2-fold; and in a further embodiment, this increase in IFNγ secretion is observed where the anti-CD96 has an $EC_{50}$ concentration of 0.3 nM or less, 0.2 nM or less, or 0.1 nM or less.

2. Antibody Fragments

In some embodiments, the anti-CD96 antibody of the present disclosure can be an antibody fragment. Antibody fragments useful with the binding determinants of the present disclosure include, but are not limited to, Fab, Fab', Fab'-SH, F(ab')$_2$, Fv, scFv fragments, monovalent, single domain antibody, one-armed or single-arm antibody, and other fragments described herein and known in the art. Accordingly, in some embodiments of the anti-CD96 antibodies of the present disclosure, the antibody is an antibody fragment selected from the group consisting of F(ab')$_2$, Fab', Fab, Fv, single domain antibody (VHH), single-arm antibody, and scFv.

For a review of various antibody fragments, see e.g., Hudson et al. Nat. Med. 9: 129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO93/16185; and U.S. Pat. Nos. 5,571,894 and 5,587,458. For a description of Fab and F(ab')$_2$ fragments comprising salvage receptor binding epitope residues and having increased in vive half-life, see U.S. Pat. No. 5,869,046. Other monovalent antibody forms are described in, e.g., WO2007/048037, WO2008/145137, WO2008/145138, and WO2007/059782. Monovalent, single-armed antibodies are described, e.g., in WO2005/063816. Diabodies are antibody fragments with two antigen-binding sites that may be bivalent or bispecific (see e.g., EP0404097; WO93/01161; Hudson et al., Nat. Med. 9: 129-134 (2003); and Hollinger et al., Proc. Natl. Acad. Sci. USA 90: 6444-6448 (1993)).

In some embodiments, the antibody fragments are single-domain antibodies which comprise all or a portion of the heavy chain variable domain or all or a portion of the light chain variable domain of an antibody. In some embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In some embodiments, the anti-CD96 antibody of the present disclosure can be a chimeric antibody. (See e.g., chimeric antibodies as described in U.S. Pat. No. 4,816,567; and Morrison et al., Proc. Natl. Acad. Sci. USA, 81:6851-6855 (1984)). In one embodiment, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched: antibody in which the class or subclass has been changed from that of the parent antibody. It is contemplated that chimeric antibodies can include antigen-binding fragments thereof.

In some embodiments, the anti-CD96 antibody of the present disclosure is a humanized antibody. Typically, a non-human antibody is humanized to reduce immunogenicity to humans, while retaining the specificity and affinity of the parental non-human antibody. Generally, a humanized antibody comprises one or more variable domains in which HVRs, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived) to restore or improve antibody specificity or affinity.

Humanized antibodies and methods of making them are reviewed, e.g., in Almagro and Fransson, Front. Biosci. 13: 1619-1633 (2008), and are further described, e.g., in Riechmann et al., Nature 332:323-329 (1988); Queen et al., Proc. Nat'l Acad. Sci. USA 86: 10029-10033 (1989); U.S. Pat. Nos. 5,821,337, 7,527,791, 6,982,321, and 7,087,409; Kashmiri et al, Methods 3625-34 (2005) (describing SDR (a-HVR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151: 2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol, 151: 2623 (1993)); human mature (somatically mutated) framework regions or human germline framework regions (see, e.g., Almagro and Fransson, Front. Biosci. 13: 1619-1633 (2008)); and framework regions derived from screening FR libraries (see, e.g., Baca et al., J. Biol. Chem. 272: 10678-10684 (1997) and Rosok et al., J. Biol. Chem. 271: 2261 1-22618 (1996)).

4. Human Antibodies

In some embodiments, the anti-CD96 antibody of the present disclosure can be a human antibody. Human antibodies can be produced using various techniques known in the art. Human antibodies are described generally in van Dijk and van de Winkel, Curr. Opin. Pharmacol. 5:368-74 (2001) and Lonberg, Curr. Opin. Immunol. 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., XENOMOUSE™ technology in U.S. Pat. Nos. 6,075,181 and 6,150,584; HUMAB® technology in U.S. Pat. No. 5,770,429; K-M MOUSE® technology in U.S. Pat. No. 7,041,870; and VELOCIMOUSE® technology in U.S. Pat. Appl. Pub. No. US 2007/0061900). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor J. Immunol, 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

In some embodiments, the anti-CD96 antibody of the present disclosure may be isolated by screening combinatorial libraries for antibodies with the desired activity or activities. For example, a variety of methods are known in the art for generating phage display libraries and screening such libraries for antibodies possessing the desired binding characteristics. The use of phage display for preparation of affinity matured variants of the humanized version of the anti-CD96 antibody of the present disclosure are described in the Examples disclosed herein. Other methods for producing such library-derived antibodies can be found in e.g., Hoogenboom et al., Methods in Molecular Biology 178: 1-37 (O'Brien et al., ed., Human Press, Totowa, N.J., 2001);

McCafferty et al., Nature 348:552-554; Clackson et al., Nature 352: 624-628 (1991); Marks et al., J. Mol. Biol. 222: 581-597 (1992); Marks and Bradbury, m Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 1 19-132 (2004).

6. Multispecific Antibodies

In some embodiments, the anti-CD96 antibody of the present disclosure is a multispecific antibody, e.g., a bispecific antibody. In some embodiments, the multispecific antibody is a monoclonal antibody having at least two different binding sites, each with a binding specificity for a different antigen, at least one of which specifically binds CD96.

In some embodiments, the multispecific antibody is a bispecific antibody comprising a specificity for CD96 and a specificity for another antigen that mediates immune regulation, immune signaling, and/or is expressed on a cancer or tumor cell. In some embodiments of the bispecific antibody, the other specificity is for an antigen that is an immune checkpoint molecule selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA. In some embodiments, the anti-CD96 bispecific antibody, the other antigen for which the antibody has specificity is selected from PD1, TIGIT, LAG3, PVRIG, KIR, TIM-3, and CRTAM.

In some embodiments, at least one of binding sites specifically binds a cytotoxic agent. In exemplary embodiments, an anti-CD96 antibody of the present disclosure is a bispecific antibody and can be used to localize a cytotoxic agent to cells which express CD96.

Techniques for making multispecific antibodies include, but are not limited to, recombinant co-expression of two immunoglobulin heavy chain-light chain pairs having different specificities (see e.g., Milstein and Cuello, Nature 305: 537 (1983), WO 93/08829, and Traunecker et al., EMBO J. 10: 3655 (1991)). "Knob-in-hole" engineering can also be used to generate bispecific antibodies useful with the anti-CD96 antibodies of the present disclosure. Techniques for knob-in-hole engineering are known in the art and described in e.g., U.S. Pat. No. 5,731,168.

Multispecific antibodies can also be made by engineering "electrostatic steering" effects that favor formation of Fc-heterodimeric antibody molecules rather than homodimers (WO 2009/089004A1); cross-linking two or more antibodies or fragments (see, e.g., U.S. Pat. No. 4,676,980, and Brennan et al., Science, 229: 81 (1985)); using leucine zippers to produce bispecific antibodies (see, e.g., Kostelny et al., J. Immunol, 148(5): 1547-1553 (1992)); using "diabody" technology for making bispecific antibody fragments (see, e.g., Hollinger et al., Proc. Natl. Acad. Sci. USA, 90:6444-6448 (1993)); using single-chain Fv (scFv) dimers (see, e.g. Gruber et al., J. Immunol, 152:5368 (1994)); or tri-specific antibodies (see e.g., Tutt et al., J. Immunol. 147: 60 (1991).

7. Antibody Variants

In some embodiments, variants of the anti-CD96 antibody of the present disclosure are also contemplated. For example, antibodies with improved binding affinity and/or other biological properties of the antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristic of CD96 antigen binding.

A. Substitution, Insertion, and Deletion Variants

In some embodiments, anti-CD96 antibody variants having one or more amino acid substitutions in addition to those described herein are provided. Sites for mutagenesis can include the HVRs and FRs. Typical "conservative" amino acid substitutions and/or substitutions based on common side-chain class or properties are well-known in the art and can be used in the embodiments of the present disclosure. The present disclosure also contemplates variants based on non-conservative amino acid substitutions in which a member of one of amino acid side chain class is exchanged for an amino acid from another class.

Amino acid side chains are typically grouped according to the following classes or common properties: (1) hydrophobic: Met, Ala, Val, Leu, lie, Norleucine; (2) neutral hydrophilic: Cys, Ser, Thr, Asn, Gin; (3) acidic: Asp, Glu; (4) basic: His, Lys, Arg; (5) chain orientation influencing: Gly, Pro; and (6) aromatic: Trp, Tyr, Phe.

Techniques are well-known in the art for amino acid substitution into an antibody and subsequent screening for desired function, e.g., retained/improved antigen binding, decreased immunogenicity, or improved ADCC or CDC.

Amino acid substitution variants can include substituting one or more hypervariable region residues of a parent antibody (e.g., a humanized or human antibody). Generally, the resulting variant(s) selected for further study will have modifications in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described in the Examples herein. Briefly, one or more HVR residues are mutated and the variant antibodies displayed on phage and screened for a particular biological activity (e.g., binding affinity).

A useful method for identifying residues or regions of an antibody that may be targeted for mutagenesis is "alanine scanning mutagenesis" (see e.g., Cunningham and Wells (1989) Science, 244: 1081-1085). In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be determined. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

Substitutions can be made in HVRs to improve antibody affinity. Such alterations may be made in "hotspots," i.e., residues encoded by codons that undergo mutation at high frequency during the somatic maturation process (see, e.g., Chowdhury, Methods Mol. Biol. 207:179-196 (2008)) with the resulting variant $V_H$ or $V_L$ being tested for binding affinity. In one embodiment, affinity maturation can be carried out by constructing and reselecting from secondary libraries (see e.g., in Hoogenboom et al., Methods in Molecular Biology 178:1-37 (O'Brien et al., ed., Human Press, Totowa, N.J., (2001).) Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots." In some embodiments of the variant $V_H$ and $V_L$ sequences provided above, each HVR either is unaltered, or contains no more than one, two or three amino acid substitutions.

B. Glycosylation Variants

In some embodiments, the anti-CD96 antibody of the present disclosure is altered to increase or decrease the extent to which the antibody is glycosylated. Addition or deletion of glycosylation sites to an antibody can be carried out by altering the amino acid sequence such that one or more glycosylation sites is created or removed.

In embodiments where the antibody comprises an Fc region, the carbohydrate attached to the Fc region can be altered. Typically, native antibodies produced by mammalian cells comprise a branched, biantennary oligosaccharide attached by an N-linkage to the asparagine at about position 297 ("N297") of the CH2 domain of the Fc region (see, e.g., Wright et al. TIBTECH 15:26-32 (1997)). The oligosaccharide may include various carbohydrates, such as mannose, N-acetyl glucosamine (GlcNAc), galactose, and sialic acid, as well as, a fucose attached to a GlcNAc in the "stem" of the bi-antennary oligosaccharide structure. In some embodiments, the modifications of the oligosaccharide of an Fc region of an antibody can create a variant with certain improved properties.

In some embodiments, the anti-CD96 antibody of the present disclosure can be a variant of a parent antibody, wherein the variant comprises a carbohydrate structure that lacks fucose attached (directly or indirectly) to an Fc region. For example, the amount of fucose in such antibody may be from about 1% to about 80%, from about 1% to about 65%, from about 5% to about 65%, or from about 20% to about 40%. The amount of fucose can be determined by calculating the average amount of fucose within the sugar chain at N297, relative to the sum of all glyco-structures attached to Asn 297 (e.g., complex, hybrid and high mannose structures) as measured by MALDI-TOF mass spectrometry (see e.g., WO 2008/077546). N297 refers to the asparagine residue located at about position 297 in the Fc region (Eu numbering of Fc region residues); however, N297 may also be located about ±3 amino acids upstream or downstream of position 297, i.e., between positions 294 and 300, due to minor sequence variations in antibodies.

In some embodiments, the fucosylation variants can have improved ADCC function. See, e.g., US Patent Publication Nos. US 2003/0157108, or US 2004/0093621. Examples of "defucosylated" or "fucose-deficient" antibodies and associated methods for preparing them are disclosed in e.g., US2003/0157108; US2003/0115614; US2002/0164328; US2004/0093621; US2004/0132140; US2004/0110704; US2004/0110282; US2004/0109865; WO2000/61739; WO2001/29246; WO2003/085119; WO2003/084570; WO2005/035586; WO2005/035778; WO2005/053742; WO2002/031140; Okazaki et al. J. Mol. Biol. 336:1239-1249 (2004); Yamane-Ohnuki et al. Biotech. Bioeng. 87: 614 (2004).

Cell lines useful for producing defucosylated antibodies include Led 3 CHO cells deficient in protein fucosylation (see e.g., Ripka et al. Arch. Biochem. Biophys. 249:533-545 (1986); US2003/0157108, and WO2004/056312), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

C. Fc Region Variants

In some embodiments, an anti-CD96 antibody of the present disclosure can comprise one or more amino acid modifications in the Fc region (i.e., an Fc region variant). The Fc region variant may comprise a human Fc region sequence (e.g., a human IgG1, IgG2, IgG3, or IgG4 Fc region) comprising an amino acid substitution at one or more amino acid residue positions. A wide range of Fc region variants known in the art that are useful with the anti-CD96 antibodies of the present disclosure are described below.

In some embodiments, the anti-CD96 antibody is an Fc region variant which has altered effector function. In some embodiments, the antibody with altered effector function possesses some (but not all of) the effector functions, decreased effector function, or none of the effector functions (e.g., effectorless) of the parent antibody. Effectorless Fc region variants are more desirable for certain applications where effector function (such as ADCC) is unnecessary or deleterious, and/or in vivo half-life of the antibody is important.

Fc region variant antibodies with reduced effector function, or which are effectorless, can include an amino acid substitution at one or more of the following Fc region positions: 238, 265, 269, 270, 297, 327 and 329. (see, e.g., U.S. Pat. No. 6,737,056). Such Fc region variants can include amino acid substitutions at two or more of positions 265, 269, 270, 297 and 327. Such Fc region variants can also include substitutions of both residues 265 and 297 to alanine (see e.g., U.S. Pat. No. 7,332,581). As disclosed in the Examples and elsewhere herein, in some embodiments, the anti-CD96 antibodies of the present disclosure are effectorless Fc region variants. In some embodiments, the effectorless Fc region variants of the anti-CD96 antibodies comprise the amino acid substitution N297G.

Fc region variants having improved or diminished binding to FcRs are disclosed in e.g., U.S. Pat. No. 6,737,056; WO 2004/056312; and Shields et al., J. Biol. Chem. 9(2): 6591-6604 (2001). Fc region variants having improved ADCC can comprise one or more amino acid substitutions at e.g., positions 298, 333, and/or 334 of the Fc region (based on EU numbering). Fc region variants having altered (i.e., either improved or diminished) C1q binding and/or Complement Dependent Cytotoxicity (CDC), as described in e.g., U.S. Pat. No. 6,194,551, WO99/51642, and Idusogie et al., J. Immunol. 164: 4178-4184 (2000). Fc region variants with increased half-lives and improved binding to the neonatal Fc receptor (FcRn) are disclosed in e.g., US2005/0014934A1 (Hinton et al.). Such Fc region variants comprise amino acid substitutions at one or more of positions: 238, 256, 265, 272, 286, 303, 305, 307, 311, 312, 317, 340, 356, 360, 362, 376, 378, 380, 382, 413, 424, and 434. Other Fc region variants with increased half-lives include the set of YTE mutations at positions 252, 254, and 256 (i.e., M252Y/S254T/T256E) described in e.g., U.S. Pat. No. 7,658,921B2 (Dall'Acqua et al.). Other examples of Fc region variants can be found in e.g., U.S. Pat. Nos. 5,648,260 and 5,624,821; and WO94/29351.

Generally, in vitro and/or in vivo cytotoxicity assays can be carried out to confirm the reduction/depletion of CDC and/or ADCC activities in an Fc region variant. For example, Fc receptor (FcR) binding assays can be conducted to ensure that the antibody lacks FcγR binding (hence likely lacking ADCC activity) but retains FcRn binding ability. The primary cells for mediating ADCC, NK cells express FcγRIII only, whereas monocytes express FcγRI, FcγRII, and FcγRIII. Non-limiting examples of in vitro assays to assess ADCC activity of a molecule of interest is described in U.S. Pat. No. 5,500,362 (see, e.g. Hellstrom, et al., Proc. Nat'l Acad. Sci. USA 83:7059-7063 (1986)) and Hellstrom, et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assay methods may be employed (see, for example, ACTI™ nonradioactive cytotoxicity assay for flow cytometry (CellTechnology, Inc. Mountain View, Calif.; and Cyto-Tox96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO2006/029879 and WO2005/100402. To assess complement activation, a CDC assay may be performed (see, e.g., Gazzano-Santoro et al., J. Immunol. Methods 202: 163 (1996); Cragg, M. S. et al., Blood 101:1045-1052 (2003); and Cragg, M. S. and M. J. Glennie, S W 103:2738-2743 (2004)). FcRn binding and in vivo clearance/half-life determinations can be performed using methods known in the art (see, e.g., Petkova, et al., Intl. Immunol. 18(12): 1759-1769 (2006)).

D. Cysteine Engineered Antibody Variants

In some embodiments, it is contemplated that the anti-CD96 antibody described herein can be substituted at specific non-HVR positions with cysteine residues so as to create reactive thiol groups. Such engineered "thioMAbs" can be used to conjugate the antibody to e.g., drug moieties or linker-drug moieties and thereby create immunoconjugates, as described elsewhere herein. Cysteine engineered antibodies can be generated as described in e.g., U.S. Pat. No. 7,521,541. In some embodiments, any one or more of the following antibody residues can be substituted with cysteine: V205 (Kabat numbering) of the light chain; A118 (EU numbering) of the heavy chain; and S400 (EU numbering) of the heavy chain Fc region.

E. Antibody Derivatives

In some embodiments, the anti-CD96 antibody of the present disclosure may be further modified (i.e., derivatized) with non-proteinaceous moieties. Non-proteinaceous moieties suitable for derivatization of the antibody include, but are not limited to, water soluble polymers, such as: polyethylene glycol (PEG), copolymers of ethylene glycol and propylene glycol, carboxy-methylcellulose, dextran, polyvinyl alcohol, polyvinyl pyrrolidone, poly-1, 3-dioxolane, poly-1, 3, 6-trioxane, ethylene/maleic anhydride copolymer, poly-amino acid homo-polymers or random co-polymers, and dextran or poly(n-vinyl pyrrolidone)polyethylene glycol, propropylene glycol homo-polymers, polypropylene oxide/ethylene oxide co-polymers, polyoxy-ethylated polyols (e.g., glycerol), polyvinyl alcohol, and mixtures thereof. In some embodiments, modification of the antibody can be carried out using methoxy-polyethylene glycol propionaldehyde. The polymers may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody, e.g., whether the antibody derivative will be used in a therapy under defined conditions.

8. Immunoconjugates

In some embodiments, the anti-CD96 antibody of the present disclosure can also be an immunoconjugate, wherein the immunoconjugate comprises an anti-CD96 antibody conjugated to one or more cytotoxic agents. Suitable cytotoxic agents contemplated by the present disclosure include chemotherapeutic agents, drugs, growth inhibitory agents, toxins (e.g., protein toxins, enzymatically active toxins of bacterial, fungal, plant, or animal origin, or fragments thereof), or radioactive isotopes.

In some embodiments, the immunoconjugate is an antibody-drug conjugate (ADC) in which an anti-CD96 antibody, as described herein, is conjugated to one or more drugs.

In some embodiments, an immunoconjugate of the present disclosure comprises an anti-CD96 antibody as described herein conjugated to a drug or therapeutic agent for the treatment of a CD96-mediated disease or condition.

In some embodiments, an anti-CD96 antibody as described herein can be conjugated to an enzymatically active toxin or a fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate of the present disclosure comprises an anti-CD96 antibody as described herein conjugated to a radioactive isotope (i.e., a radioconjugate). A variety of radioactive isotopes are available for the production of such radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb, and radioactive isotopes of Lu. In some embodiments, the immunoconjugate may comprise a radioisotope for scintigraphic detection, or a spin label for NMR detection or MRI. Suitable radioisotopes or spin labels can include, as $^{123}$I, $^{131}$I, $^{111}$In, $^{13}$C, $^{19}$F, $^{15}$N, $^{17}$O, various isotopes of Gd, Mn, and Fe.

Immunoconjugates of an anti-CD96 antibody and a cytotoxic agent, can be made using a variety of well-known bifunctional reagents and chemistries suitable for conjugating to proteins. Such reagents include but are not limited to: N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (e.g., dimethyl adipimidate HQ), active esters (e.g., disuccinimidyl suberate), aldehydes (e.g., glutaraldehyde), bis-azido compounds (e.g., bis-(p-azidobenzoyl)-hexanediamine), bis-diazonium derivatives (e.g., bis-(p-diazoniumbenzoyl)-ethylenediamine), diisocyanates (e.g., toluene-2,6-diisocyanate), and bis-active fluorine compounds (e.g., 1,5-difluoro-2,4-dinitrobenzene).

Reagents for preparing immunoconjugates of the present disclosure can also include commercially available "cross-linking" reagents such as: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) (see e.g., Pierce Biotechnology, Inc., Rockford, Ill., U.S.A).

9. Synthetic Antibodies

In some embodiments, the anti-CD96 antibody of the present disclosure can be a synthetic antibody comprising a set of CDRs or HVRs from an anti-CD96 immunoglobulin (e.g., HVR-L1, etc.) grafted onto a scaffold or framework other than an immunoglobulin scaffold or framework, such as an alternative protein scaffold, or an artificial polymer scaffold.

Exemplary alternative protein scaffolds contemplated for preparation of synthetic antibodies of the present disclosure can include, but are not limited to: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain Src homology domain 3, PDZ domains, TEM-1 beta-lactamase, thioredoxin, staphylococcal nuclease, PHD-finger domains, CL-2, BPTI, APPI, HPSTI, ecotin, LACI-D1, LDTI, MTI-II, scorpion toxins, insect defensin-A peptide, EETI-II, Min-23, CBD, PBP, cytochrome b-562, Ldl receptor domains, gamma-crystallin, ubiquitin, transferrin, and/or C-type lectin-like domains.

Exemplary artificial polymer (non-protein) scaffolds useful for synthetic antibodies are described in e.g., Fiedler et al., (2014) "Non-Antibody Scaffolds as Alternative Therapeutic Agents," in Handbook of Therapeutic Antibodies (eds S. Dübel and J. M. Reichert), Wiley-VCH Verlag GmbH & Co.; Gebauer et al., Curr. Opin. Chem. Biol, 13:245-255 (2009); Binz et al, Nat. Biotech., 23(10): 1257-1268 (2005).

IV. Recombinant Methods and Compositions

The anti-CD96 antibody of the present disclosure can be produced using recombinant methods and materials well-known in the art of antibody production. In some embodiments, the present disclosure provides an isolated nucleic acid encoding an anti-CD96 antibody. The nucleic acid can encode an amino acid sequence comprising the $V_L$ and/or an amino acid sequence comprising the $V_H$ of the antibody (e.g., the light and/or heavy chains of the antibody). In some embodiments, one or more vectors (e.g., expression vectors) comprising nucleic acid sequences encoding an anti-CD96 antibody of the present disclosure are provided. In some embodiments, a host cell comprising nucleic acid sequences encoding an anti-CD96 antibody of the present disclosure are provided. In one embodiment, the host cell has been transformed with a vector comprising a nucleic acid that encodes an amino acid sequence comprising the $V_L$ of the antibody and an amino acid sequence comprising the $V_H$ of the antibody. In another embodiment, the host cell has been transformed with a first vector comprising a nucleic acid that encodes an amino acid sequence comprising the $V_L$ of the antibody and a second vector comprising a nucleic acid that encodes an amino acid sequence comprising the $V_H$ of the antibody.

In some embodiments of the recombinant methods, the host cell used is a eukaryotic cell, such as a Chinese Hamster Ovary (CHO) cell, or a lymphoid cell (e.g., Y0, NS0, Sp20). In one embodiment, a method of making an anti-CD96 antibody is provided, wherein the method comprises culturing a host cell comprising a nucleic acid encoding the antibody, as provided above, under conditions suitable for expression of the antibody, and optionally recovering the antibody from the host cell (or host cell culture medium).

Briefly, recombinant production of an anti-CD96 antibody is carried out by isolating a nucleic acid encoding an antibody (e.g., as described herein) and inserting this nucleic acid into one or more vectors for further cloning and/or expression in a host cell. Such nucleic acids are readily isolated and sequenced using conventional procedures well-known in the art (e.g., by using oligonucleotide probes that are capable of binding specifically to genes encoding the heavy and light chains of the desired antibody). Suitable host cells and culturing methods for cloning or expressing the antibody-encoding vectors are well-known in the art and include prokaryotic or eukaryotic cells. Typically, after expression, the antibody may be isolated from cell paste in a soluble fraction and further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see e.g., Gerngross, Nat. Biotech. 22: 1409-1414 (2004), and Li et al., Nat. Biotech. 24:210-215 (2006)).

Suitable host cells for the expression of glycosylated anti-CD96 antibodies of the present disclosure can also be derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts (see, e.g., U.S. Pat. Nos. 5,959,177, 6,040,498, 6,420,548, and 7,125,978.

Examples of mammalian host cell lines useful for the production of the anti-CD96 antibodies of the present disclosure include Chinese hamster ovary (CHO) cells, including DHFR-CHO cells (see e.g., Urlaub et al., Proc. Natl. Acad. Sd. USA 77:4216 (1980)); myeloma cell lines such as Y0, NS0 and Sp2/0; monkey kidney CVI line transformed by SV40 (COS-7); human embryonic kidney line (293 or 293 cells as described, e.g., in Graham et al., J. Gen Virol. 36:59 (1977)): baby hamster kidney cells (BHK); mouse Sertoli cells (TM4 cells as described, e.g., in Mather, Biol. Reprod. 23:243-251 (1980)); monkey kidney cells (CVI); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells (see e.g., in Mather et al., Annals N Y. Acad. Sci. 383:44-68 (1982) and U.S. Pat. No. 6,235,498); Medical Research Council 5 (MRC 5) cells (such as e.g., those available from ATCC and also referred to as CCL-171); and Foreskin 4 (FS-4) cells (see e.g., in Vilcek et al. Ann. N. Y. Acad. Sci. 284:703-710 (1977), Gardner & Vilcek. J. Gen. Virol. 44:161-168 (1979), and Pang et al. Proc. Natl. Acad. Sci. U.S.A. 77:5341-5345 (1980)). For a general review of useful mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

V. Pharmaceutical Compositions and Formulations of Anti-CD96 Antibodies

The present disclosure also provides pharmaceutical compositions and pharmaceutical formulations comprising an anti-CD96 antibody. In some embodiments, the present disclosure provides a pharmaceutical formulation comprising an anti-CD96 antibody as described herein and a pharmaceutically acceptable carrier. In some embodiments, the anti-CD96 antibody is the sole active agent of the pharmaceutical composition. Such pharmaceutical formulations can be prepared by mixing an anti-CD96 antibody, having the desired degree of purity, with one or more pharmaceutically acceptable carriers. Typically, such antibody formulations can be prepared as an aqueous solution (see e.g., U.S. Pat. No. 6,171,586, and WO2006/044908) or as a lyophilized formulation (see e.g., U.S. Pat. No. 6,267,958).

Pharmaceutically acceptable carriers are generally non-toxic to recipients at the dosages and concentrations employed. A wide range of such pharmaceutically acceptable carriers are well-known in the art (see e.g., Remington's Pharmaceutical Sciences 16th edition, Osol, A. Ed. (1980)). Exemplary pharmaceutically acceptable carriers useful in the formulations of the present disclosure can include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Pharmaceutically acceptable carriers useful in the formulations of the present disclosure can also include interstitial drug dispersion agents, such as soluble neutral-active hyaluronidase glycoproteins (sHASEGP) (see e.g., US Pat. Publ. Nos. 2005/0260186 and 2006/0104968), such as human soluble PH-20 hyaluronidase glycoproteins (e.g., rHuPH20 or HYLENEX®, Baxter International, Inc.).

It is also contemplated that the formulations disclosed herein may contain active ingredients in addition to the anti-CD96, as necessary for the particular indication being treated in the subject to whom the formulation is administered. Preferably, any additional active ingredient has activity complementary to that of the anti-CD96 antibody activity and the activities do not adversely affect each other.

In some embodiments, the pharmaceutical composition comprises the anti-CD96 antibody and an additional active agent such as, but not limited to, a checkpoint inhibitor. Checkpoint inhibitors useful in such embodiments include, but are not limited to, a second antibody comprising a specificity for an antigen that is an immune checkpoint molecule. In some embodiments, the second antibody comprises a specificity for an immune checkpoint molecule selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA.

In at least one embodiment, the pharmaceutical composition comprises an anti-CD96 antibody and an additional active agent, wherein the additional active agent is an antibody comprising a specificity for an immune checkpoint molecule selected from PD1, TIGIT, LAG3, PVRIG, KIR, TIM-3, and CRTAM.

In at least one embodiment, the pharmaceutical composition comprising an anti-CD96 antibody and an additional active agent, wherein the additional active agent is an antibody comprising a specificity for the immune checkpoint molecule PD1. Exemplary antibodies comprising a specificity for PD1 that are useful in the pharmaceutical composition embodiments disclosed herein include, but are not limited to, dostarlimab, pembrolizumab, nivolumab, and pidilizumab.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, the formulation can be a sustained-release preparation of the antibody and/or other active ingredients. Suitable examples of sustained-release preparations include semipermeable matrices of solid hydrophobic polymers containing the antibody, which matrices are in the form of shaped articles, e.g. films, or microcapsules.

Typically, the formulations of the present disclosure to be administered to a subject are sterile. Sterile formulations may be readily prepared using well-known techniques, e.g., by filtration through sterile filtration membranes.

IV. Uses and Methods of Treatment

It is contemplated that any of the compositions or formulations comprising an anti-CD96 antibody of the present disclosure can be used for any methods or uses, such as in therapeutic methods that utilize their ability to specifically bind to CD96 and thereby inhibit, decrease, and/or fully block the function of CD96 as a cell surface receptor involved in immune regulation or signaling, particularly the function of CD96 in negatively regulating (or inhibiting) T cell or NK cell activation.

The cell surface receptor CD155 is the natural target antigen of CD96. Expression of CD155 on cells is understood to be induced by stress, and CD155 levels are affect the activation, by CD226, or the inhibition, by CD96 or TIGIT, of lymphocytes in mounting an immune response (e.g., activation of T cells and/or NK cells). Accordingly, it is contemplated that the anti-CD96 antibodies can be used in therapeutic methods that involve inhibiting, decreasing, and/or fully blocking the specific binding of CD96 to CD155.

CD226, another cell surface receptor in Ig superfamily which has a structure closely related to CD96, also binds CD155. CD226, however, functions to activate T cells or NK cells. Thus, without intending to be limited by any specific mechanism, the ability of the anti-CD96 antibodies of the present disclosure to block CD96 binding to CD155, may allow increased CD155 binding to CD226, which further results in increased CD226 activation of T cells and NK cells. In addition, without being bound by theory, a secondary affinity for CD226 of an anti-CD96 antibody may cause the antibody to act as an enhancer of CD226-triggered cellular activity, preventing CD226 from interacting with TIGIT, increase the effective local concentration of the antibody with respect to cells expressing both CD96 and CD226, or some combination thereof. Accordingly, it is further contemplated that the anti-CD96 antibodies of the present disclosure can be used in any therapeutic methods that utilize increased activation of T cells and NK cells.

There are a range of diseases, disorders, and conditions that can potentially be treated by inhibiting, decreasing, and/or fully blocking the immune regulatory and/or immune signaling activity of CD96, particularly, the immune inhibitory effect of CD96 on lymphocyte activation. The range of diseases, disorders, and conditions include, but are not limited to, cancers and viral infections.

For example, agents that block the immune inhibitory effects of certain proteins (e.g., PD1, TIGIT) are currently under development to treat a wide range of cancers including adrenal gland cancer, bladder cancer, brain cancer, breast cancer, cervical cancer, colorectal cancer, EGJ adenocarcinoma, esophageal cancer, gall bladder cancer, gastric cancer, head and neck cancer, heart cancer, hepatocellular carcinoma, kidney cancer, liver cancer, melanoma, mesothelioma, non-small cell lung cancer, ovarian cancer, pancreatic cancer, prostate cancer, spleen cancer, small cell lung cancer, testicular cancer, thyroid cancer, and uterine cancer. Accordingly, it is contemplated that any of the compositions or formulations comprising an anti-CD96 antibody of the present disclosure can be used for a method or use for the treatment of any of the above-listed cancers. In some embodiments, the cancer is selected from lung cancer, skin cancer (e.g., melanoma), pancreatic cancer, endometrial cancer, prostate cancer, colorectal cancer, ovarian cancer, and bladder cancer. In some embodiments, the present disclosure provides a method of treating cancer in a subject, the method comprising administering to the subject in need thereof a therapeutically effective amount of an anti-CD96 antibody of the present disclosure or administering to a subject a therapeutically effective amount of a pharmaceutical composition comprising an anti-CD96 antibody of the present disclosure and a pharmaceutically acceptable carrier.

Agents that block the immune inhibitory effects of certain proteins (e.g., PD1) have also been proposed for treatment of pathogenic infections (e.g., viral, bacterial, fungal infections). Accordingly, in some embodiments, the present disclosure provides a method of treating a pathogenic infection in a subject, the method comprising administering to the subject in need thereof a therapeutically effective amount of an anti-CD96 antibody of the present disclosure or administering to a subject a therapeutically effective amount of a pharmaceutical composition comprising an anti-CD96 antibody of the present disclosure and a pharmaceutically acceptable carrier. It is contemplated that any of the compositions or formulations comprising an anti-CD96 antibody of the present disclosure can be used for such a method for the treatment of a pathogenic infection, including, but not limited to an infection by one or more of the following clinically relevant pathogens: *Acinetobacter baumannii*, *Acinetobacter lwoffii*, *Acinetobacter* spp. (incl. MDR), *Actinomycetes*, Adenovirus, *Aeromonas* spp., *Alcaligenes faecalis*, *Alcaligenes* spp./*Achromobacter* spp., *Alcaligenes xylosoxidans* (incl. ESBL/MRGN), Arbovirus, *Aspergillus* spp., Astrovirus, *Bacillus anthracis*, *Bacillus cereus*, *Bacillus subtilis*, *Bacteroides fragilis*, *Bartonella quintana*, *Bordetella pertussis*, *Borrelia burgdorferi*, *Borrelia recurrentis*, *Brevundimonas diminuta*, *Brevundimonas vesicularis*, *Brucella* spp., *Burkholderia cepacia* (incl. MDR), *Burkholderia mallei*, *Burkholderia pseudomallei*, *Campylobacter jejuni/coli*, *Candida albicans*, *Candida krusei*, *Candida parapsilosis*. Chikungunya virus (CHIKV), *Chlamydia pneumoniae*, *Chlamydia psittaci*, *Chlamydia trachomatis*, *Citrobacter* spp., *Clostridium botulinum*, *Clostridium difficile*, *Clostridium perfringens*, *Clostridium tetani*. Coronavirus (incl. SARS- and MERS-CoV), *Corynebacterium diphtheriae*, *Corynebacterium pseudotuberculosis*, *Corynebacterium* spp., *Corynebacterium ulcerans*, *Coxiella burnetii*, Coxsackievirus, Crimean-Congo haemorrhagic fever virus, *Cryptococcus neoformans*, *Cryptosporidium hominis*, *Cryptosporidium parvum*, *Cyclospora cayetanensis*, Cytomegalovirus (CMV), Dengue virus, Ebola virus, Echovirus, *Entamoeba histolytica*, *Enterobacter aerogenes*, *Enterobacter cloacae* (incl. ESBL/MRGN), *Enterococcus faecalis* (incl. VRE), *Enterococcus faecium* (incl. VRE), *Enterococcus hirae*, *Epidermophyton* spp., Epstein-Barr virus (EBV), *Escherichia coli* (incl. EHEC, EPEC, ETEC, EIEC, EAEC, ESBUMRGN, DAEC), Foot-and-mouth disease virus (FMDV), *Francisella tularensis*, *Giardia lamblia*, *Haemophilus influenzae*, Hantavirus, *Helicobacter pylori*, Helminths (Worms), Hepatitis A virus (HAV), Hepatitis B virus (HBV), Hepatitis C virus (HCV), Hepatitis D virus, Hepatitis E virus, Herpes simplex virus (HSV), *Histoplasma capsulatum*, Human enterovirus 71, Human herpesvirus 6 (HHV-6), Human herpesvirus 7 (HHV-7), Human herpesvirus 8 (HHV-8), Human immunodeficiency virus (HIV), Human metapneumovirus, Human papillomavirus (HPV), Influenza virus, *Klebsiella granulomatis*, *Klebsiella oxytoca* (incl. ESBL/MRGN), *Klebsiella pneumoniae* MDR (incl. ESBL/MRGN), Lassa virus, *Leclercia adecarboxylata*, *Legionella pneumophila*. *Leishmania* spp., *Leptospira interrogans*, *Leuconostoc pseudomesenteroides*, *Listeria monocytogenes*, Marburg virus, Measles virus, *Micrococcus luteus*, *Microsporum* spp., Molluscipoxvirus, *Morganella* spp., Mumps virus, *Mycobacterium chimaera* Myco, *Mycobacterium leprae* Myco, *Mycobacterium tuberculosis* (incl. MDR), *Mycoplasma genitalium*, *Mycoplasma pneumoniae*, *Neisseria meningitidis*, *Neisseria gonorrhoeae*, Norovirus, *Orientia tsutsugamushi*, *Pantoea agglomerans*, Parainfluenza virus, Parvovirus, *Pediculus humanus capitis*, *Pediculus humanus corporis*, *Plasmodium* spp., *Pneumocystis jiroveci*, Poliovirus, Polyomavirus, *Proteus mirabilis* (incl. ESBL/MRGN), *Proteus vulgaris*, *Providencia rettgeri*, *Providencia stuartii*, *Pseudomonas aeruginosa*, *Pseudomonas* spp., Rabies virus, *Ralstonia* spp., Respiratory syncytial virus (RSV), Rhinovirus, *Rickettsia prowazekii*, *Rickettsia typhi*, *Roseomonas gilardii*, Rotavirus, Rubella virus, *Salmonella enteritidis*, *Salmonella paratyphi*, *Salmonella* spp., *Salmonella typhimurium*, *Sarcoptes scabiei* (Itch mite), Sapovirus, *Serratia marcescens* (incl. ESBL/MRGN), *Shigella sonnei*, *Sphingomonas species*, *Staphylococcus aureus* (incl. MRSA, VRSA), *Staphylococcus capitis*, *Staphylococcus epidermidis* (incl. MRSE), *Staphylococcus haemolyticus*, *Staphylococcus hominis*, *Staphylococcus lugdunensis*,

*Staphylococcus saprophyticus, Stenotrophomonas maltophilia, Streptococcus pneumoniae, Streptococcus pyogenes* (incl. PRSP), *Streptococcus* spp., TBE virus, *Toxoplasma gondii, Treponema pallidum, Trichinella spiralis, Trichomonas vaginalis, Trichophyton* spp., *Trichosporon* spp., *Trypanosoma brucei gambiense, Trypanosoma brucei rhodesiense, Trypanosoma cruzi*, Vaccinia virus, Varicella zoster virus (VSV), Variola virus, *Vibrio cholerae*, West Nile virus (WNV), Yellow fever virus, *Yersinia enterocolitica, Yersinia pestis, Yersinia pseudotuberculosis*, Zika virus, and the like.

In at least one embodiment, a composition or formulation comprising an anti-CD96 antibody of the present disclosure can be used for a method or use for the treatment of a viral infection, wherein the virus is selected from Adenovirus, Arbovirus, Astrovirus, Chikungunya virus (CHIKV), Coronavirus (incl. SARS- and MERS-CoV), Crimean-Congo haemorrhagic fever virus, Cytomegalovirus (CMV), Dengue virus, Ebola virus, Echovirus, Epstein-Barr virus (EBV), Foot-and-mouth disease virus (FMDV), Hantavirus, Hepatitis A virus (HAV), Hepatitis B virus (HBV), Hepatitis C virus (HCV), Hepatitis D virus, Hepatitis E virus, Herpes simplex virus (HSV), Human enterovirus 71, Human herpesvirus 6 (HHV-6), Human herpesvirus 7 (HHV-7), Human herpesvirus 8 (HHV-8), Human immunodeficiency virus (HIV), Human metapneumovirus, Human papillomavirus (HPV), Influenza virus, Marburg virus, Measles virus, Mumps virus, Norovirus, Parainfluenza virus, Parvovirus, Poliovirus, Polyomavirus, Rabies virus, Respiratory syncytial virus (RSV), Rhinovirus, Rotavirus, Rubella virus, Sapovirus, TBE virus, Vaccinia virus, Varicella zoster virus (VSV), Variola virus, West Nile virus (WNV), Yellow fever virus, and Zika virus.

As disclosed herein, including in the Examples below, the anti-CD96 antibodies of the present disclosure have the ability to decrease, inhibit, and/or block CD96 binding to CD155, and thereby alter CD155 interaction with the immune signaling pathways mediated by CD226 and TIGIT. Accordingly, in some embodiments, the present disclosure provides a method of treating a CD96-mediated disease or condition in a subject, the method comprising administering to the subject a therapeutically effective amount of an anti-CD96 antibody of the present disclosure or administering to a subject in need thereof a therapeutically effective amount of a pharmaceutical composition comprising an anti-CD96 antibody of the present disclosure and a pharmaceutically acceptable carrier. Similarly, in some embodiments, the present disclosure provides a method of treating a disease mediated by binding to CD155 expressed on cells in a subject, the method comprising administering to the subject, the method comprising administering to the subject a therapeutically effective amount of an anti-CD96 antibody of the present disclosure or administering to a subject in need thereof a therapeutically effective amount of a pharmaceutical composition comprising an anti-CD96 antibody of the present disclosure and a pharmaceutically acceptable carrier.

Administration of the anti-CD96 antibody, composition, or pharmaceutical formulation in accordance with the method of treatment provides an antibody-induced therapeutic effect that protects the subject from and/or treats the progression of a CD96-mediated disease in a subject. In some embodiments, the method of treatment can further comprise administration of one or more additional therapeutic agents or treatments known to those of skill in the art to prevent and/or treat the CD96-mediated disease or condition. Such methods comprising administration of one or more additional agents can encompass combined administration (where two or more therapeutic agents are included in the same or separate formulations), and separate administration, in which case, administration of the antibody composition or formulation can occur prior to, simultaneously, and/or following, administration of the additional therapeutic agent.

In some embodiments of the methods of treatment of the present disclosure, the anti-CD96 antibody or pharmaceutical formulation comprising an anti-CD96 antibody is administered to a subject by any mode of administration that delivers the agent systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion.

In some embodiments, a pharmaceutical formulation of the anti-CD96 antibody is formulated such that the antibody is protected from inactivation in the gut. Accordingly, the method of treatments can comprise oral administration of the formulation.

In some embodiments, use of the compositions or formulations comprising an anti-CD96 antibody of the present disclosure as a medicament are also provided. Additionally, in some embodiments, the present disclosure also provides for the use of a composition or a formulation comprising an anti-CD96 antibody in the manufacture or preparation of a medicament, particularly a medicament for treating, preventing or inhibiting a CD96-mediated disease. In a further embodiment, the medicament is for use in a method for treating, preventing or inhibiting a CD96-mediated disease comprising administering to an individual having a CD96-mediated disease an effective amount of the medicament. In certain embodiments, the medicament further comprises an effective amount of at least one additional therapeutic agent, or treatment. Exemplary additional therapeutic agents or treatments that can be used in such medicaments can include but are not limited to an antibody comprising a specificity for an immune checkpoint molecule such as PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA. In at least one embodiment, the additional therapeutic agent or treatment present in a medicament of the present disclosure is an antibody comprising a specificity for the immune checkpoint molecule PD1, including but not limited to an antibody selected from dostarlimab, pembrolizumab, nivolumab, and pidilizumab.

In a further embodiment, the medicament is for use in treating, inhibiting or preventing a CD96-mediated disease in a subject comprising administering to the subject an amount effective of the medicament to treat, inhibit or prevent the CD96-mediated disease.

For the prevention or treatment of a CD96-mediated disease or condition, the appropriate dosage of the anti- CD96 antibody contained in the compositions and formulations of the present disclosure (when used alone or in combination with one or more other additional therapeutic agents) will depend on the specific disease or condition being treated, the severity and course of the disease, whether the antibody is administered for preventive or therapeutic purposes, the previous therapy administered to the patient, the patient's clinical history and response to the antibody, and the discretion of the attending physician. The anti-CD96 antibody included in the compositions and formulations described herein, can be suitably administered to the patient at one time, or over a series of treatments. Various dosing schedules including but not limited to single or multiple administrations over various time-points, bolus administration, and pulse infusion are contemplated herein.

Depending on the type and severity of the disease, about 1 µg/kg to 15 mg/kg of anti-CD96 antibody in a formulation of the present disclosure is an initial candidate dosage for administration to a human subject, whether, for example, by one or more separate administrations, or by continuous infusion. Generally, the administered dosage of the antibody would be in the range from about 0.05 mg/kg to about 10 mg/kg. In some embodiments, one or more doses of about 0.5 mg/kg, 2.0 mg/kg, 4.0 mg/kg or 10 mg/kg (or any combination thereof) may be administered to a patient.

Dosage administration can be maintained over several days or longer, depending on the condition of the subject, for example, administration can continue until the CD96-mediated disease is sufficiently treated, as determined by methods known in the art. In some embodiments, an initial higher loading dose may be administered, followed by one or more lower doses. However, other dosage regimens may be useful. The progress of the therapeutic effect of dosage administration can be monitored by conventional techniques and assays.

Accordingly, in some embodiments of the methods of the present disclosure, the administration of the anti-CD96 antibody comprises a daily dosage from about 1 mg/kg to about 100 mg/kg. In some embodiments, the dosage of anti-CD96 antibody comprises a daily dosage of at least about 1 mg/kg, at least about 5 mg/kg, at least about 10 mg/kg, at least about 20 mg/kg, or at least about 30 mg/kg.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Generation of CD96 Polypeptides

This example illustrates the preparation of the various CD96 polypeptide constructs used as antigens in eliciting and screening the anti-CD96 antibodies of the present disclosure.

The extracellular domains of human (hu), cynomolgus monkey (cy) and rhesus monkey (rh) CD96 isoform 2 were produced recombinantly as full-length ECD or truncated (D1-D2-D3 Ig-like domains, referred to as D1D3, and D1-Ig-like domain only, referred to as D1) forms. The isoform 2 (short form) of CD96 was reported to be the predominant form in vivo (Meyer et al., (2009)). The extracellular domain of human CD155 was also produced recombinantly. The amino acid sequence boundaries of the expression constructs are provided in Table 1. All constructs had the following C-terminal TEV-Fc-FLAG tag sequence for purification and detection purposes: GGGGSEN-LYFQGGGGS-[human IgG1 Fc]-DYKDDDDK (SEQ ID NO: 475).

CD96-Fc fusion proteins were expressed in ExpiCHO cells (Thermo Fisher Scientific, Waltham, Mass., USA) according to the manufacturer's protocol. The CD155-Fc fusion protein was expressed in Expi293 cells (Thermo Fisher Scientific, Waltham, Mass., USA) according to the manufacturer's protocol. After harvest the clarified supernatant was applied to MabSelectSuRe protein A columns (GE Healthcare, Chicago, Ill., USA) equilibrated in TBS buffer (20 mM Tris pH 7.5, 150 mM NaCl, 0.02% NaN$_3$). Proteins were eluted with a 10 CV of elution buffer (20 mM Citrate pH 2.95, 150 mM NaCl). Protein containing fractions were pooled and loaded onto Superdex 200 Increase columns (GE Healthcare, Chicago, Ill., USA) equilibrated in HBS (25 mM HEPES pH 7.5, 150 mM NaCl). Peak fractions containing monodisperse protein were pooled and stored in HBS.

For some applications, the Fc tag was removed from the CD96 fusion proteins by cleavage with TEV protease (ATUM) according to the manufacturer's protocol. The cleavage products were applied to MabSelectSuRe protein A and HisTrap FF crude columns (GE Healthcare, Chicago, Ill., USA) equilibrated in TBS (20 mM Tris pH 7.5, 150 mM NaCl, 0.02% NaN3) to remove Fc and His-tagged TEV protease, respectively. The flow-through containing CD96 proteins was applied to Superdex 200 Increase columns equilibrated in HBS (25 mM HEPES pH 7.5, 150 mM NaCl). Peak fractions containing monodisperse protein were pooled and stored in HBS.

For some applications, recombinant hu-CD96 (M1-M503-polyHis) and CD155-Fc (M1-N343-hIgG1 Fc) were purchased from ThermoFisher Scientific (Waltham, Mass., USA).

Example 2: Generation of Anti-Hu-CD96 Antibodies Using Hybridoma Methods, Screening and Characterization This example illustrates the methods using mouse hybridoma technology to generate anti-hu-CD96 antibodies, and methods to screen and select antibodies for further characterization.

Immunizations and Fusions:

Balb/c, Swiss Webster, and C57BL/6 mice were immunized with recombinant extracellular domains of human, cynomolgus monkey, or rhesus monkey CD96 produced in-house or purchased commercially as described in Example 1. The adjuvant Magic Mouse (Creative Diagnostics, Shirley, N.Y.) was used for all immunizations. Titers were determined by ELISA as described below. Mice selected based on their titers were given a final pre-fusion boost without adjuvant. One day later, spleens were harvested and processed according to standard protocols. Splenocytes were fused with myeloma cells P3X63Ag8.653 cells (American Type Culture Collection CRL 1580) using PEG and following standard protocols and plated into 96-well plates at approximately 50,000 myeloma cells/well using standard techniques to maximize clonality of the resulting colonies. Parental hybridomas were selected using selection medium supplemented with AH (Azaserine+Hypoxanthine).

ELISA Assays:

After 12-14 days of culture, supernatants were collected and subjected to primary screening by ELISA with 96 well plates coated with human and sometimes cynomolgous monkey CD96 extracellular domain. 96-well MAXISORP® flat bottom plates (Thermo Fisher Scientific, Waltham, Mass.; catalogue number 439454) were coated overnight at 4° C. with 50 µl/well of protein at a concentration of 1 µg/mL or 0.5 µg/mL in coating buffer (0.05 M sodium bicarbonate buffer, pH 9.6 or phosphate buffered saline, PBS). After removing the coating solution, unspecific binding was blocked by addition of 200 µL of assay/blocking solution containing 1% bovine serum albumin (BSA) in phosphate buffered saline (PBS) pH 7.4 (ELISA diluent) and incubation at room temperature for one hour with agitation or overnight at 4° C. without agitation. Plates were then washed three times with 300 µL of PBS, 0.05% TWEEN®-20 (wash buffer). 100 µL of culture supernatant from individual hybridoma clones (or purified antibodies at the indicated concentration) was added to individual wells followed by incubation at room temperature for one hour with agitation. Plates were washed three times with wash buffer, then 50 µL/well of goat anti-mouse IgG Fc HRP (Bethyl Laboratories, Montgomery, Tex., USA; catalogue number A90-131P) at 1:3000 dilution or goat anti-mouse IgG (H+L) HRP (Jackson ImmunoResearch, Inc., West Grove Pa., USA; catalogue number 109-035-088) at 1:10000 dilution in ELISA diluent was added. The plate was incubated at room temperature for one hour with agitation, washed six times with wash buffer and developed for 3-10 minutes by addition of 50 µL/well of tetramethylbenzidine (TMB) microwell peroxidase substrate (Scytek Laboratories, Inc., Logan, Utah, USA; catalogue number TM1999). Enzymatic color development was stopped by acidification with 50 µL/well of 2N $H_2SO_4$ (Sigma-Aldrich Corporation, St. Louis, Mo., USA; catalogue number 258105). Plates were analyzed with a SpectraMax i3X plate reader (Molecular Devices LLC, San Jose, Calif., USA) at 450 nm.

The parental hybridoma hits identified from the primary screen were expanded to 24-well plates and a confirmatory ELISA was run following the primary screen protocol except that reduced coating antigen density of 0.1 µg/mL was sometimes used, to further confirm and screen for strong anti-hu/anti-cy CD96 binders.

Receptor Blocking Assay of Hybridoma Hits:

The supernatants of the hybridoma hits identified in the primary screen were also tested for their ability to block human CD155 and CD96 biochemical binding. 96-well MAXISORP® flat bottom plates (Thermo Fisher Scientific, Waltham, Mass.; Cat #439454) were coated overnight at 4° C. with 1 µg/mL goat anti-human Fc (Thermo Fisher Scientific, Waltham, Mass.; Cat #PA1-85606) in 50 µL/well in coating buffer (100 mM sodium bicarbonate, pH 9.4, in PBS). After removing the coating solution, unspecific binding was blocked by PBS containing 5% normal mouse serum (blocking buffer) and incubation at room temperature for one hour. Plates were then washed five times with 300 µL of PBS with 0.05% TWEEN®-20 (wash buffer) and added 500 ng/mL human CD155-hFc in 50 µg/well in PBS containing 1% BSA and 0.02% TWEEN®-20 (assay buffer) at room temperature for one hour. During blocking period, 50 ul/well of 100 nM or 50 nM hu-CD96-his and hybridoma supernatant of 50 ul/well in assay buffer were incubated at room temperature for one hour in Nunc F plate (Thermo Fisher Scientific, Waltham, Mass.; Cat #269620). Then antigen-antibody mix solution 80 ul/well was transferred into antigen coated wells at room temperature for one hour. Plates were washed five times with wash buffer, then 50 µL/well mouse anti-His-HRP (Thermo Fisher Scientific, Waltham, Mass.; Cat #A16090) in assay buffer was added at room temperature for one hour with agitation, washed five times with wash buffer and developed for 3-10 minutes with 50 µL/well of tetramethylbenzidine (TMB) microwell peroxidase substrate (VWR/Avantor, Radnor, Pa., USA; Cat #95059-156). Enzymatic color development was stopped with 50 µL/well of TMB stop solution (VWR/Avantor, Radnor, Pa., USA; Cat #95059-200). Plates were analyzed with a SpectraMax i3X plate reader (Molecular Devices LLC, San Jose, Calif., USA) at 450 nm. Parental hybridomas with the desired human and cy-CD96 binding as well as ability to block CD155 and CD96 binding were prioritized for subcloning and further characterization. Subcloning was carried out with limited dilution and visual inspection was performed to ensure clonality. Hybridoma subclones were screened with the same binding and blocking assays and selected positive hits were cryopreserved.

Purification of Hybridoma Antibodies:

Subclones were confirmed by primary screen antigen binding ELISA. Positive clones were scaled-up to 30 mL cultures in serum free medium and the antibodies were purified as follows. Supernatant media were clarified by centrifugation at 300 g for 10 min to remove cells and by filtration with 0.22 micron filter. Clarified supernatant media was mixed with POROS MabCapture A resin (Thermo Fisher Scientific, Waltham, Mass.) equilibrated with PBS buffer and incubated with gentle rotation for 1.5 h at room temperature. After incubation, the slurry was loaded into a column and the resin was washed with 20 column volumes of PBS buffer containing 0.5 M NaCl then eluted with 3 column volumes of 0.1 M acetic acid, 0.15 M NaCl. The eluent was quickly neutralized to pH5.2 with 1 M MOPS, pH7.0 and buffer exchanged to PBS buffer with PD-10 column (GE Healthcare, Chicago, Ill., USA).

CD96 Binding of Purified Hybridoma Antibodies:

The hu-CD96 and cy-CD96 antigen binding ELISA was performed on the purified hybridoma antibodies. Briefly, 96-well MAXISORP® flat bottom plates (Thermo Fisher Scientific, Waltham, Mass.; Cat #439454) were coated overnight at 4° C. with 0.5 µg/mL of hu-CD96D1D3-hFc and cynomolgus monkey CD96D1 D3-hFc in PBS. After removing the coating solution, unspecific binding was blocked by PBS containing 1% bovine serum albumin (blocking buffer) and incubation at room temperature for one hour. Plates were then washed three times with PBS and 0.05% TWEEN®-20 (wash buffer). Serial dilution of purified antibodies in PBS containing 0.5% BSA and 0.05% Tween 20 (ELISA buffer) was added to individual wells followed by incubation at room temperature for one hour with agitation. Plates were washed three times with wash buffer, then 100 µL/well of anti-mouse IgG-HRP (Thermo Fisher Scientific, Waltham, Mass.; Cat #626520) in ELISA buffer was added. The plate was incubated at room temperature for one hour with agitation, washed six times with wash buffer and developed for 3-10 minutes by addition of 50 µL/well of tetramethylbenzidine (TMB) microwell peroxidase substrate (VWR/Avantor, Radnor, Pa., USA; Cat #95059-156). Enzymatic color development was stopped with 50 µl./well of TMB stop solution (VWR/Avantor, Radnor, Pa., USA; Cat #95059-200). Plates were analyzed with a SpectraMax i3X plate reader (Molecular Devices LLC, San Jose, Calif., USA) at 450 nm. The CD96 binding $EC_{50}$ values are summarized in Table 3 (below).

TABLE 3

Antigen binding ELISA for anti-CD96 purified hybridoma antibodies

| Hybridoma | hu-CD96 Binding EC$_{50}$ (nM) | cy-CD96 Binding EC$_{50}$ (nM) |
|---|---|---|
| 12F8 | 0.25 | ~10 |
| 10H5 | 0.05 | >100 |
| 1G8 | 0.072 | No binding |
| 16D9 | 0.05 | No binding |
| 9H4 | 0.24 | No binding |
| 7E5 | 0.06 | 0.53 |
| 10G1 | 0.03 | 0.2 |
| NK92.39 | 0.98 | No binding |
| 14D3 | 0.2 | 0.6 |

CD155 Receptor Blocking of Purified Hybridoma Antibodies:

Human CD155 blocking ELISA was performed on purified hybridoma antibodies following the same protocol as described for CD96 (above), except that serial dilution of purified antibodies 50 µL/well (starting at 1 µM, 1:5 dilution) in assay buffer was added into the reaction. The blocking IC$_{50}$ value represents the antibody concentration that inhibited 50% of hu-CD96 binding to coated human CD155 and is summarized in Table 4 (below).

TABLE 4

Human CD155 Blocking ELISA for purified hybridoma antibodies

| Hybridoma | Blocking ELISA IC$_{50}$ (nM) |
|---|---|
| 12F8 | 0.95 |
| 10H5 | 0.958 |
| 1G8 | 0.883 |
| 16D9 | 1.063 |
| 9H4 | 2.23 |
| 7E5 | 2.15 |
| 10G1 | 2.59 |
| NK92.39 | 2.57 |
| 14D3 | No blocking |

As shown by the results in Tables 3 and 4 above, 14D3 is an antibody that binds hu-CD96 well but does not block the CD155 and CD96 interaction. Also, as is shown in Example 4 below, 14D3 does not bind the CD96 D1 domain. It is included herein as an example of CD96 binder, but non-blocker control antibody.

Sequencing of Purified Hybridoma Antibodies

Monoclonal anti-CD96 hybridoma hits were grown to a density of 1-3×10$^5$ in standard hybridoma medium (DMEM/F12, 10% FBS, 1% Glutamax, 1% pen/strep) for 7-10 days in a T75 flask with >80% viability. 1-3 million cells from cultures were pelleted in a 15 mL falcon tube at 300 g for 5 min. Pelleted cells were washed by resuspending cells in 5 mL ice cold PBS. PBS was removed and cells were resuspended in 1 mL of TRIZOL reagent (Life Technologies, Carlsbad, Calif., USA). The lysate was passed through a 1 mL syringe with a 20G1 gauge needle (BD 305175) 20 times to ensure lysis of the cells. TRIZOL/cell suspension was immediately frozen on dry ice and stored at −80° C. until processing. Total RNA was isolated from the lysate using Direct-zol RNA Miniprep Plus kit (Zymo Research, Irvine, Calif., USA) and 5 µg of total RNA was used to generate 5′-RACE-ready hybridoma cDNA using SMARTer RACE 5′ kit (Takara Bio, Japan).

To amplify heavy chain and light chain specific gene fragments from the cDNA, the following mouse variable region primers were used:

(i) V$_H$ region specific primers:

(SEQ ID NO: 476)
TCTTGTCCACCTTGGTGCTGCTGGCCGG,
and (SEQ ID NO: 477)
TTTGTCCACCGTGGTGCTGCTGGCTGGT;

(ii) V$_{kappa}$ region specific primer:

(SEQ ID NO: 478)
GATCAGTCCAACTGTTCAGGACGCC;
and (iii) V$_{lambda}$ region specific primers:

(SEQ ID NO: 479)
ACACTCAGCACGGGACAAACTCTTCTCCACAGT, (SEQ ID NO: 480)
ACACTCTGCAGGAGACAGACTCTTTTCCACAGT,
and (SEQ ID NO: 481)
ACACTCAGCACGGGACAAACTCTTCTCCACATG.

The region-specific primers were used in conjunction with universal primer provided in the kit in 5′-RACE PCR reactions. PCR products were purified and cloned into pRACE using an In-Fusion cloning kit (Takara Bio, Japan) and both strands were sequenced using Sanger sequencing with M13 forward and M13 reverse primers. The variable domain sequences of anti-CD96 hybridomas are summarized in Table 2 and provided in the attached Sequence Listing.

The variable sequences of the antibodies of clone 12F8.12B5 (also referred to herein as "12F8") and clone 10G1.3G8 (also referred to herein as "10G1") were used to recombinantly produce mouse human chimeric antibodies. Human IgG1 Fc with a N297G mutation was used to engineer these chimeric antibodies. The N297G mutation removes FcgR binding and the effector function of the antibody. Effector-less function of the anti-hu-CD96 antibodies can be critical for anti-tumor efficacy in binding to CD96 expressed on cytotoxic T cells and NK cells. The chimeric 12F8 and chimeric 10G1 antibodies were tested in CD96 ELISA binding assay and showed very similar properties as purified hybridoma antibodies, thereby further validating the HVR sequences.

Based on their superior properties in the above-described assays, the purified anti-hu-CD96 antibodies derived from hybridoma 12F8 and 10G1 were selected for humanization and further affinity maturation as described in the Examples below.

Example 3: Preparation of Humanized Versions of 12F8 and 10G1

This example illustrates the preparation of humanized versions of the murine anti-hu-CD96 derived from the hybridomas 12F8 and 10G1.

Humanization of Murine Anti-Hu-CD96 "mAb1"

As shown by the sequence alignments depicted in FIG. 1, the light chain variable region (V$_L$) and heavy chain variable region (V$_H$) sequences of murine antibody 12F8 were aligned against human germline antibody sequences, and the human germline kappa light chain (Gene ID—V gene: IGKV1-9*01, J gene: IGKJ2*01) and the human germline heavy chain (Gene ID—V gene: IGHV1-46*01, J gene: IGHJ4*03) were identified as the closest human frameworks.

HVRs of murine 12F8 light chain and heavy chain were grafted into the identified closest human frameworks respectively to generate the humanized antibody clone (also referred to herein as "mAb1"). In the process of humanization, six different versions of the mAb1 heavy chain were generated (versions mAb1.v1-mAb1.v5 and mAb1.v7), where different mouse framework residues were retained with the goal to minimize mouse residues while maintaining hu-CD96 binding. The variable domain amino acid sequences of the humanized antibodies, mAb1.v1-mAb1.v5 and mAb1.v7, are summarized in Table 2 and the attached Sequence Listing.

Humanization of Murine Anti-Hu-CD96 "10G1"

As shown by the sequence alignments depicted in FIG. 2, the light chain variable region ($V_L$) and heavy chain variable region ($V_H$) sequences of murine antibody from hybridoma 10G1 (also referred to as "10G1") were aligned against human germline antibody sequences, and the human germline kappa light chain (Gene ID—V gene: IGKV6D-21*02, J gene: IGKJ4*02) and the human germline heavy chain (Gene ID—V gene: IGHV7-4-1*02, J gene: IGHJ4*03) were identified as the closest human frameworks.

HVRs of murine 10G1 light chain and heavy chain were grafted into the identified closest human frameworks respectively to generate humanized antibody clone (also referred to as "h10G1"). In this process, positions 24-34, 50-56, and 89-97 of murine 10G1 $V_L$ were grafted to the human kappa light chain framework acceptor, and positions 31-35, 50-65, and 95-102 of murine 10G1 $V_H$ were grafted to the human heavy chain framework acceptor.

Position 4 in light chain framework region 1 (FW-L1), position 43 in light chain framework region 2 (FW-L2), position 58 in light chain framework region 3 (FW-L3), position 2 in heavy chain framework region 1 (FW-H1), position 28 in heavy chain framework region 1 (FW-H1) and position 91 in heavy chain framework region 3 (FW-H3) of murine 10G1 were also grafted into the human kappa light chain and heavy chain framework acceptors as those positions were found to be part of VH-VL interacting interface or the framework residues acting as "Vernier" zone, which may adjust HVR structure and fine-tune to fit to antigen (Foote et al., 1992).

The variable domain sequences of the humanized antibody, h10G1 is summarized in Table 2 and the attached Sequence Listing.

Generation of Recombinant IgG Versions of mAb1.v7 and h10G1

The heavy and light chain variable domain of mAb1.v7 and h10G1 were synthesized and cloned into pRK plasmid. The expression of recombinant mAb1.v7 and humanized 10G1 IgGs were performed using Expi293F expression system (Life Technologies, Carlsbad, Calif., USA) in accordance with the instruction provided. The ratio of the plasmids for the heavy chain and the light chain was kept at 1 to 1 for the transfection reaction and the transfected cells were cultured for 6 days before harvest.

Recombinant IgG molecules were purified with the following protocols. Supernatant media were clarified by centrifugation at 300 g for 10 min to remove cells and by filtration with 0.22 μm filter. Clarified supernatant media were mixed with POROS MabCapture A resin (Thermo Fisher Scientific, Waltham, Mass., USA) equilibrated with PBS buffer and incubated with gentle rotation for 1.5 h at room temperature. After incubation, the slurry was loaded into a column and the resin was washed with 20 column volumes of PBS buffer containing 0.5M NaCl then eluted with 3 column volumes of 0.1 M acetic acid, 0.15 M NaCl. The pH of the eluent was quickly adjusted to pH 5.2 with 1 M MOPS, pH 7.0 and buffer exchanged into to PBS buffer with PD-10 column (GE Healthcare).

Non-Specific Binding Assessment of mAb1.v7 and h10G1 IgG

Non-specific binding of mAb1.v7 and humanized 10G1 IgGs were assessed using baculovirus ELISA (see e.g., Hotzel et al., 2012). Briefly, baculovirus particles were coated on 96-well Maxisorp plates at a 2.5% suspension in 50 mM sodium carbonate buffer pH 9.6 at 4° C. for overnight. The plates were then blocked in PBS with 0.5% BSA (blocking buffer) at room temperature for one hour. Serial dilution of mAb1.v7 and h10G1 IgGs in PBS were added to the plates for an hour and plate was washed with PBS six times. Bound antibodies were detected with goat anti-human IgG conjugated to horseradish peroxidase (Jackson ImmunoResearch) in PBS. The plate was incubated at room temperature for one hour with agitation, washed six times with PBS and developed for 3-10 minutes by addition of 50 μL/well of tetramethylbenzidine (TMB) microwell peroxidase substrate (VWR, Cat #95059-156). Enzymatic color development was stopped with 50 μL/well of TMB stop solution (VWR, Cat #95059-200). Plates were analyzed with a SpectraMax i3X plate reader (Molecular Devices) at 450 nm and compared to reference antibodies. Both mAb1.v7 and h10G1 IgGs showed no detectable BV ELISA signal, indicating absence of non-specific binding to baculovirus particles.

Binding Affinities of Recombinant mAb1.v7 and h10G1

SPR measurement with a BIACORE™ 8K instrument was performed to determine the monovalent binding affinity of mAb1.v7 and h10G1 IgG to hu-CD96, cy-CD96, and mo-CD96. Briefly, antibodies were diluted at 0.5 μg/mL in HBS-P buffer (0.01 M HEPES pH 7.4, 0.15 M NaCl, 0.005% Surfactant P20) and applied to the Protein A chip at 30 μL/min flow rate for 60 s in flow cell 2 (FC2). Then 3-fold serial dilutions of hu-CD96, cy-CD96, or mo-CD96 in HBS-P buffer (0.01M HEPES pH 7.4, 0.15M NaCl, 0.005% surfactant P20) from (0.4 nM) to high (100 nM) were injected (flow rate: 30 μL/min) at 25° C. to both flow cell 1 (FC1) and flow cell 2 (FC2). The sensorgram was recorded and subject to reference and buffer subtraction before evaluating by BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) was calculated as the ratio of $k_{off}/k_{on}$ and summarized in Table 5.

TABLE 5

| | Binding affinity of mAb1.v7, h10G1 and NK92.39 to CD96 antigens | | |
|---|---|---|---|
| IgG | hu-CD96 $K_D$ (nM) | cy-CD96 $K_D$ (nM) | mo-CD96 $K_D$ (nM) |
| mAb1.v7 | 4.49 | ~1000 | ~386 |
| h10G1 | 1.17 | 0.74 | No binding |
| NK92.39[1] | 14.3 | No binding | No binding |

[1]NK92.39 is a commercially available antibody (Biolegend catalog # 338405) that was previously described (Fuchs et al., 2004).

Example 4: Epitope Mapping of mAb1.v7 and h10G1

Epitope Binning

The CD155-blocking anti-CD96 antibodies described here were determined by epitope binning to recognize 3 distinct epitopes on CD96. mAb1.v7 and h10G1 were determined to bind distinct but overlapping CD155-blocking epitopes on CD96. Antibodies 1G8, 10H5, 16D9 and NK92.39 share an epitope bin with 10G1, while 9H4 binds an epitope on CD96 that overlaps with that of h10G1 but not with that of mAb1.v7.

Epitope binning experiments were performed on a OctetRed96 by capturing antibody 1 on anti-Fc Octet sensors (ForteBio), binding CD96D1D3, and subsequently probing with antibody 2. If antibody 2 was capable of binding antibody 1-bound CD96D1 D3 then the two antibodies were assigned to different bins. If antibody 2 was unable to bind antibody 1-bound CD96D1 D3 then the two antibodies were assigned to the same epitope bin. Table 6 shows the epitope binning results.

TABLE 6

Epitope binning of anti-CD96 antibodies

| Antibody | mAb1.v7 | 9H4 | Nk92.39 | h10G1 | 1G8 | 7E5 | 14D3 | PBST |
|---|---|---|---|---|---|---|---|---|
| mAb1.v7 | − | + | − | − | − | + | + | − |
| 9H4 | + | − | − | − | − | + | + | − |
| Nk92.39 | − | − | − | − | − | + | + | − |
| h10G1 | − | − | − | − | − | + | + | − |
| 1G8 | − | − | − | − | − | + | + | − |
| 7E5 | + | + | + | + | + | − | + | − |
| 14D3 | + | + | + | + | + | + | − | − |

Domain Binding Site Mapping mAb1.v7 and h10G1 were determined to bind the D1 domain of CD96. Epitope mapping experiments were performed on an OctetRed96 by capturing the antibodies on anti-Fc Octet sensors (ForteBio) and testing their binding to recombinant huCD96D1-Fc and huCD96D1D3. Both mAb1.v7 and h10G1, but not antibody 14D3, bound to CD96D1 and CD96D1 D3 equally well, demonstrating that CD96D1 is sufficient for binding of these antibodies to full-length CD96.

Example 5: Affinity Maturation of Humanized Anti-CD96 Antibody mAb1.v7

This example illustrates phage library construction and panning techniques used for affinity maturation of the humanized anti-hu-CD96 antibody mAb1.v7 for improved binding to hu-CD96 and cy-CD96.

NNK Library Construction and Panning

To further improve the affinity of anti-CD96 antibody clone mAb1.v7, phage libraries were constructed from variant mAb1.v7 in Fab-amber format for monovalent Fab phage display with heavy chain HVR residues (i.e., HVR-H1, HVR-H2, and HVR-H3) randomized using the NNK degenerate codon that encodes for all 20 amino acids with 32 codons (see e.g., Brenner et al., 1992). Libraries were designed to allow one NNK mutation in each of the heavy chain HVRs. Synthesized mutagenesis oligonucleotides were then used to construct heavy chain libraries using Kunkel mutagenesis (see e.g., Kunkel et al., 1987). The resultant library DNA was electroporated into *E. coli* XL1 cells, yielding approximately $4 \times 10^9$ transformants. Phage libraries were incubated in SUPERBLOCK™ PBS buffer (Pierce) and 0.05% TWEEN® 20 for 30 min and then applied on hu-CD96 and cy-CD96 coated plates for first round panning. In the subsequent two to three rounds, phage libraries were incubated with decreasing concentration of biotinylated hu-CD96 or cy-CD96 antigen with 1000× non-biotinylated human or cy-CD96 as competitor in solution to increase the selection stringency. The eluted phage was infected with log-phase XL-1 and plated on LB carbenicillin plate at 37° C. overnight for further affinity screening Affinity Screening of mAb1.v7 Phage Variants Single spot phage competition ELISA was used to screen for phage affinity screening. 192 colonies from most stringent selections (biotinylated 0.1 nM of hu-CD96 or cy-CD96 with 1000× non-biotinylated human or cy-CD96) were grown in 400 μL 2YT with 4 μL helper phage M13KO7 overnight at 37° C. with shaking. After spinning down the pellet, the phage supernatant was diluted 1:1 with 2 nM hu-CD96, 20 nM cy-CD96 and ELISA buffer (0.5% BSA and 0.05% TWEEN®20 in PBS) in total 100 μL and incubated for two hours at room temperature with agitation. The 80 μL of mixture was transferred to hu-CD96 coated plate for 15 min to capture unbound phage. The plate was washed with wash buffer (0.05% TWEEN®20 in PBS), and HRP-conjugated anti-M13 antibody (Sino biological, Cat #11973-MM05-H-50) was added in ELISA buffer for 30 min. The plates were washed with wash buffer and developed tetramethylbenzidine (TMB) microwell peroxidase substrate (VWR, Cat #95059-156). Enzymatic color development was stopped using TMB stop solution (VWR, Cat #95059-200). Plates were analyzed with a SpectraMax i3X plate reader (Molecular Devices). The % inhibition was calculated by the $OD_{450}$ of wells with hu-CD96/cy-CD96 competitor divided by $OD_{450}$ of wells with buffer alone. The lower % inhibition indicated higher phage $IC_{50}$ against hu-CD96 or cy-CD96.

Selected top inhibition % phage variants from single spot competition were purified from culture supernatants. The optimal phage concentration was incubated with serially-diluted hu-CD96 or cy-CD96 in ELISA buffer in NUNC F plate for two hours. The 80 μL of the mixture was transferred to hu-CD96 coated wells for 15 min to capture unbound phage. The plate was washed with wash buffer (0.05% TWEEN®20 in PBS), and HRP-conjugated anti-M13 antibody (Sino biological, Cat #11973-MM05-H-50) was added in ELISA buffer for 30 min. The plates were washed and developed as described above. The absorbance at 450 nm was plotted as a function of antigen concentration in solution to determine phage $IC_{50}$. This was used as an affinity estimate for the Fab clone displayed on the surface of the phage. Phage plasmids (phagemids) were sequenced using $V_H$ specific primers and the variant sequences within the HVRs of 16 selected top mAb1.v7 phage variants are summarized in Table 7 (below).

TABLE 7

Variant HVR sequences of mAb1.v7 affinity improved phage variants

| Fab | HVR-H1 | | | | | | HVR-H2 | | | | | | | | | | | |
|---|---|---|---|---|---|---|---|---|---|---|---|---|---|---|---|---|---|---|
| | 30 | 31 | 32 | 33 | 34 | 35 | 50 | 51 | 52 | 52A | 53 | 54 | 55 | 56 | 57 | 58 | 59 | 60 | 61 |
| mAb1.v7 | T | N | N | W | M | H | M | I | H | P | N | S | G | I | T | N | I | N | E |
| mAb1.v7.2 | T | N | N | W | R | H | M | I | H | F | N | S | G | I | T | N | I | N | E |
| mAb1.v7.6 | T | N | R | W | M | H | M | I | H | V | N | S | G | I | T | N | I | N | E |
| mAb1.v7.8 | T | N | N | W | D | H | M | I | H | P | L | S | G | I | T | N | I | N | E |
| mAb1.v7.9 | T | N | N | W | R | H | M | I | H | M | N | S | G | I | T | N | I | N | E |
| mAb1.v7.10 | T | N | N | W | R | H | M | I | H | P | L | S | G | I | T | N | I | N | E |
| mAb1.v7.11 | T | N | N | F | M | H | M | I | H | P | N | S | G | G | T | N | I | N | E |
| mAb1.v7.14 | V | N | N | W | M | H | M | I | H | P | N | S | G | I | T | N | T | N | E |
| mAb1.v7.15 | T | N | N | W | D | H | M | I | H | P | M | S | G | I | T | N | I | N | E |
| mAb1.v7.16 | T | N | N | W | R | H | M | I | H | P | N | S | G | I | T | N | I | N | E |
| mAb1.v7.19 | T | N | S | W | M | H | M | I | H | P | N | S | G | I | T | N | R | N | E |
| mAb1.v7.21 | T | N | Y | W | M | H | M | I | H | P | N | S | G | I | T | N | M | N | E |
| mAb1.v7.24 | T | N | N | W | G | H | M | I | H | R | N | S | G | I | T | N | I | N | E |
| mAb1.v7.48 | T | N | R | W | M | H | M | I | H | H | N | S | G | I | T | N | I | N | E |
| mAb1.v7.50 | T | N | N | W | S | H | M | I | H | R | N | S | G | I | T | N | I | N | E |
| mAb1.v7.59 | T | N | N | W | N | H | M | I | H | P | N | S | G | I | T | A | I | N | E |
| mAb1.v7.70 | T | N | R | W | M | H | M | I | H | A | N | S | G | I | T | N | I | N | E |

| Fab | HVR-H3 | | | | | | | | | | | |
|---|---|---|---|---|---|---|---|---|---|---|---|---|
| | 93 | 94 | 95 | 96 | 97 | 98 | 99 | 100 | 100A | 100B | 101 | 102 |
| mAb1.v7 | R | S | D | G | T | Y | E | G | Y | F | D | Y |
| mAb1.v7.2 | R | S | D | G | V | Y | E | G | Y | F | D | Y |
| mAb1.v7.6 | R | S | D | G | L | Y | E | G | Y | F | D | Y |
| mAb1.v7.8 | R | S | D | G | V | Y | E | G | Y | F | D | Y |
| mAb1.v7.9 | R | S | D | G | V | Y | E | G | Y | F | D | Y |
| mAb1.v7.10 | R | S | D | G | V | Y | E | G | Y | F | D | Y |
| mAb1.v7.11 | R | S | D | E | T | Y | E | G | Y | F | D | Y |
| mAb1.v7.14 | R | S | D | G | I | Y | E | G | Y | F | D | Y |
| mAb1.v7.15 | R | S | D | G | F | Y | E | G | Y | F | D | Y |
| mAb1.v7.16 | R | S | D | G | V | Y | E | G | Y | F | D | Y |
| mAb1.v7.19 | R | S | D | G | I | Y | E | G | Y | F | D | Y |
| mAb1.v7.21 | R | S | D | G | V | Y | E | G | Y | F | D | Y |
| mAb1.v7.24 | R | S | D | G | I | Y | E | G | Y | F | D | Y |
| mAb1.v7.48 | R | S | D | G | V | Y | E | G | Y | F | D | Y |
| mAb1.v7.50 | R | S | D | G | V | Y | E | G | Y | F | D | Y |
| mAb1.v7.59 | R | L | D | G | T | Y | E | G | Y | F | D | Y |
| mAb1.v7.70 | R | S | D | G | V | Y | E | G | Y | F | D | Y |

The phage IC$_{50}$ values determined for the 16 selected Fab variants of Table 7 are summarized in Table 8 (below).

TABLE 8

Phage IC$_{50}$ values of mAb1.v7 affinity improved phage variants

| Clone | Phage IC50 (nM) | |
|---|---|---|
| | hCD96 | CyCD96 |
| mAb1.v7 | 0.5 | ~300 |
| mAb1.v7.2 | 0.08 | 1.8 |
| mAb1.v7.6 | 0.16 | 0.15 |
| mAb1.v7.8 | 0.17 | 0.45 |
| mAb1.v7.9 | 0.11 | 0.37 |
| mAb1.v7.10 | 0.19 | 0.76 |
| mAb1.v7.11 | 0.23 | 0.24 |
| mAb1.v7.14 | 0.1 | 1 |
| mAb1.v7.15 | 0.19 | 1.85 |
| mAb1.v7.16 | 0.1 | 1.6 |
| mAb1.v7.19 | 0.23 | 0.84 |
| mAb1.v7.21 | 0.15 | 0.91 |
| mAb1.v7.24 | 0.2 | 0.6 |
| mAb1.v7.48 | 0.1 | 0.3 |
| mAb1.v7.50 | 0.1 | 0.9 |
| mAb1.v7.59 | 0.1 | 1.6 |
| mAb1.v7.70 | 0.14 | 0.4 |

Generation of mAb1.v7 Affinity Improved Fab Variants

The 16 top phage variants of mAb1.v7 shown in Table 7 were synthesized for cloning into a mammalian Fab expression construct containing an 8×His tag to generate Fab proteins. Plasmids encoding the heavy or light chain were transfected into Expi293F cells (Thermo Fisher Scientific) for 20-30 mL expression using a 1:1 ratio of HC:LC. Fabs were purified with a HisPur Ni-NTA column by diluting supernatant 1.5× with 1× phosphate-buffered saline pH 7.2 ("PBS"), adding 10 mM imidazole, and binding to resin in batch mode for 2 hours. Resin was flowed over a column and washed with 20 CV PBS+20 mM imidazole and eluted with 5 CV PBS+250 mM imidazole. Samples were buffer exchanged to PBS using a PD10 column (GE Healthcare).

Affinity Measurement of mAb1.v7 Affinity Improved Fab Variants by BLI Analysis

The binding affinity of the generated Fab variants of mAb1.v7 for hu-CD96 and cy-CD96 was determined by OCTET (Pall ForteBio) Bio-Layer Interferometry (BLI) binding analysis. The biotinylated hu-CD96 or biotinylated cy-CD96 was diluted to a final concentration 10 μg/mL in experimental buffer (PBS buffer with 0.01% Tween-20) and immobilized on the Streptavidin Capture (SA) biosensors (Pall ForteBio). Three-fold serial dilutions of the mAb1.v7 Fab variants starting at 1 μM as analytes were diluted in the experimental buffer (PBS buffer with 0.01% Tween-20). The biosensors were equilibrated in experimental buffer at 30° C. for ten minutes prior to starting the experiment. The kinetics experiment was performed with the following steps, where the step name, solution and time are listed: Baseline (buffer—60 seconds), Loading (biotinylated antigen—200 seconds), Baseline 2 (buffer—minimum 120 seconds), Association (analyte—200-300 seconds) and Dissociation (buffer—1000 seconds). The resulting BLI signal from analyte association and dissociation from the immobilized antibody was analyzed using the Octet Data Analysis software (Pall ForteBio). First a reference subtraction was performed on all recorded traces using the reference well (biosensor that underwent same steps as experimental wells but no analyte for the Association step) and then all the traces were aligned to the beginning of the Association step. The entirety of the Association and Dissociation steps were used in a Global fit (minimum of four analyte concentration traces) in a 1:1 binding model to calculate the $K_D$ values for the 16 selected individual mAb1.v7 Fab variants as summarized in Table 9 (below).

TABLE 9

OCTET $K_D$ results for mAb1.v7 affinity improved phage variants

| Fab | Octet KD (nM) | |
|---|---|---|
| | hCD96 | CyCD96 |
| mAb1.v7 | 76 | >1000 |
| mAb1.v7.2 | 3.75 | 39.1 |
| mAb1.v7.6 | 28.4 | 284 |
| mAb1.v7.8 | 27 | 104 |
| mAb1.v7.9 | ~0.1 | 129 |
| mAb1.v7.10 | 2.71 | 117 |
| mAb1.v7.11 | 156 | 175 |
| mAb1.v7.14 | ~0.1 | 530 |
| mAb1.v7.15 | 3 | 160 |
| mAb1.v7.16 | 1.4 | 97.9 |
| mAb1.v7.19 | 0.63 | 261 |
| mAb1.v7.21 | 0.31 | 118 |
| mAb1.v7.24 | 0.31 | 118 |
| mAb1.v7.48 | ~0.1 | 68 |
| mAb1.v7.50 | 4.16 | 183 |
| mAb1.v7.59 | ~0.1 | 271 |
| mAb1.v7.70 | ~0.1 | 52.6 |

Affinity Measurement of mAb1.v7 Affinity Improved Fab Variants by BIACORE

To determine the binding kinetics of a subset of 5 selected affinity improved Fab variants of mAb1.v7 for binding to hu-CD96 and cy-CD96, SPR measurement with a BIACORE® 8K instrument was performed. Briefly, hu-CD96 Fc and cy-CD96 Fc were diluted at 10 μg/mL in HBS-P buffer (0.01 M HEPES pH 7.4, 0.15 M NaCl, 0.005% Surfactant P20) and applied to the Protein A chip at 30 μL/min flow rate for 60 s in flow cell 2 (FC2). Then flow 3-fold serial dilutions of mAb1.v7 Fab variants in HBS-P buffer (0.01 M HEPES pH 7.4, 0.15 M NaCl, 0.005% surfactant P20) from (0.4 nM) to high (1000 nM) were injected (flow rate: 30 μL/min) at 25° C. to both flow cell 1 (FC1) and flow cell 2 (FC2). The sensorgram was recorded and subject to reference and buffer subtraction before evaluating by BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) was calculated as the ratio of $k_{off}/k_{on}$, and the values determined for the mAb1.v7 and the 5 Fab variants are summarized in Table 10 (below).

TABLE 10

Binding affinity ($K_D$) and CD155 blocking IC$_{50}$ values for selected top mAb1.v7 Fab variants to hu-CD96 and cy-CD96

| | Biacore_hCD96 | | | Biacore_CyCD96 | | | CD155 blocking | |
|---|---|---|---|---|---|---|---|---|
| | Kon | Koff | KD | Kon | Koff | KD | IC50 (nM) | |
| Fab | (1/Ms) | (1/s) | (nM) | (1/Ms) | (1/s) | (nM) | hCD96 | CyCD96 |
| mAb1.v7 | 1.83E+04 | 8.17E−04 | 44.6 | 1.15E+03 | 2.57E−02 | ~1000 | 0.74 | ~300 |
| mAb1.v7.2 | 1.58E+04 | 1.06E−05 | 0.67 | 2.60E+04 | 2.40E−04 | 9.24 | 0.7 | 2.17 |
| mAb1.v7.9 | 1.39E+04 | 7.02E−05 | 5.05 | 3.64E+04 | 8.02E−04 | 22 | 0.42 | 3.18 |
| mAb1.v7.16 | 7.38E+03 | 2.81E−06 | 0.38 | 1.04E+04 | 9.72E−04 | 94 | 0.8 | 1.42 |
| mAb1.v7.48 | 1.59E+04 | 1.26E−05 | 0.795 | 3.66E+04 | 3.28E−04 | 8.9 | 0.42 | 4.8 |
| mAb1.v7.70 | 1.59E+04 | 2.74E−05 | 1.73 | 3.72E+04 | 1.89E−04 | 5 | 0.8 | 2 |

CD155 Receptor Blocking Activity of Affinity Improved Fab Variants of mAb1.v7

The selected 5 affinity matured Fab variants of mAb1.v7 Fab were assayed for blocking of human CD155 (hu-CD155) receptor by ELISA as follows. Briefly, 96-well MAXISORP® flat bottom plates (Thermofisher, Cat #439454) were coated overnight at 4° C. with 2 μg/mL goat anti-mouse Fc (Thermofisher, Cat #31168) in PBS. After removing the coating solution, unspecific binding was blocked with PBS containing 1% bovine serum albumin (BSA) and incubation at room temperature for one hour. Plates were then washed five times in PBS with 0.05% TWEEN®-20 (wash buffer) and added 1 μg/mL hu-CD155-mFc in PBS for 1 hour in room temperature. During blocking period, 50 μL/well of 4 nM biotinylated hu-CD96 or 40 nM biotinylated cy-CD96 with serial dilution of the Fab variants 50 μL/well (starting at 2 μM, 1:3 dilution) for two hours at room temperature with PBS containing 0.5% BSA and 0.05% Tween 20 (ELISA buffer) in NUNC F plate (Thermofisher, Cat #269620). Then transferred the antigen-antibody mix solution 80 μL/well into hu-CD155-mFc coated wells at room temperature for 15 min. Plates were then washed with wash buffer to which was added 50 μL/well Streptavidin poly-HRP (Thermofisher, Cat #21140) diluted 1:5000 in ELISA buffer at room temperature for one hour with agitation. The plates were washed with wash buffer and developed for 3-10 minutes by addition of 50 μL/well of tetramethylbenzidine (TMB) microwell peroxidase substrate (VWR, Cat #95059-156). Enzymatic color development was stopped with 50 μL/well of TMB stop solution (VWR, Cat #95059-200). Plates were analyzed with a SpectraMax i3X plate reader (Molecular Devices) at 450 nm. The blocking $IC_{50}$ represents the concentration of the Fab that inhibits 50% of biotinylated hu-CD96 or biotinylated cy-CD96 binding to the coated hu-CD155-mFc. The blocking $IC_{50}$ values for the mAbv1.7 and the 5 selected affinity matured Fab variants (mAb1.v7.2, mAb1.v7.9, mAb1.v7.16, mAb1.v7.48, mAb1.v7.70) are summarized in Table 10 (above).

Sequencing of mAb1.v7 Affinity Maturation Libraries

In order to further improve affinity and mitigate oxidation liability risks, next-generation sequencing (NGS) of the mAb1.v7 affinity maturation libraries was performed. Phagemid double stranded DNA was isolated from E. coli XL-1 cells carrying phagemids from the initial phage library (unsorted libraries) and from the second and third rounds of solution selection (sorted libraries). Purified DNA was used as the template to generate amplicons of $V_H$ regions using Illumina 16s library preparation protocol. Sequencing adapters and dual-index barcodes were added using Illumina Nextera XT Index Kit. In preparation for sequencing on Illumina MiSeq, adapter-ligated amplicons were subjected to standard Illumina library denaturing and sample loading protocol using MiSeq Reagent Kit v3 (600 cycles). Paired-end sequencing was performed to cover the entire length of the amplicon with insert size of 200 bp to 300 bp.

Paired-end sequencing data were first assembled using paired-end assembler PANDAseq (see e.g., Masella et al., 2012) to obtain complete amplicons. Quality control (QC) was then performed on identified amplicons, where each amplicon was checked for no insertion or deletion of sequences and no stop codons, each HVR sequence was allowed to carry only up to one NNK mutation and no non-NNK mutation. Position weight matrices were generated by calculating the frequency of all mutations of every randomized position. Enrichment ratios for each mutation were calculated by dividing the frequency of a given mutation at a given position in the sorted sample with the frequency of the very same mutation in the unsorted sample, as described previously (Koenig et al., 2015). The HVR-H region mutations identified by NGS as resulting in improved binding to hu-CD96 and cy-CD96 are summarized in Table 11.

TABLE 11 mAb1.v7 HVR-H mutations with high affinity binding to hu-CD96 and cy-CD96

HVR-H1

T30A, T30D, T30E, T30G, T30H, T30K, T30N, T30Q, T30R, T30S, T30V, T30W, T30Y
N32A, N32F, N32G, N32H, N32M, N32R, N32S, N32V, N32Y
W33F
M34A, M34E, M34F, M34L, M34N, M34Q, M34R, M34S, M34T, M34V, M34W
HVR-H2

M50F
I51L, I51M, I51V
P52aA, P52aD, P52aE, P52aF, P52aG, P52aH, P52aI, P52aK, P52aL, P52aM, P52aN, P52aQ, P52aR, P52aS, P52aT, P52aV, P52aW
N53A, N53D, N53E, N53F, N53G, N53H, N53I, N53K, N53L, N53M, N53Q, N53R, N53S, N53T, N53V, N53W, N53Y
S54A, S54G, S54T, S54V
G55A, G55S
I56A, I56V
T57A, T57D, T57E, T57G, T57H, T57I, T57K, T57L, T57M, T57N, T57Q, T57R, T57S, T57V, T57W, T57Y
N58M, N58S
I59F, I59G, I59H, I59K, I59L, I59M, I59N, I59Q, I59R,

TABLE 11-continued mAb1.v7 HVR-H mutations with high affinity binding to hu-CD96 and cy-CD96

I59S, I59T, I59V, I59W, I59Y
E61A, E61D, E61G, E61H, E61K, E61L, E61M, E61N, E61P, E61Q, E61R, E61S, E61T, E61V, E61W, E61Y
HVR-H3

S94A, S94F, S94G, S94I, S94L, S94M, S94N, S94R, S94T, S94V, S94W, S94Y
G96W
T97D, T97E, T97F, T97H, T97I, T97K, T97L, T97M, T97N, T97Q, T97V, T97W, T97Y
Y98D, Y98F, Y98H, Y98N, Y98R, Y98W
E99D, E99G, E99H, E99K, E99M, E99N, E99Q, E99R, E99V, E99Y
G100K, G100R, G100S, G100T

Generation of Affinity Improved Fab Variants of mAb1.v7

Nine of the mAb1.v7 Fab variant mutations identified by NGS analysis shown in Table 11 (above) were selected based on high enrichment ratio and/or presence of mutations that minimize oxidation liability (e.g. W33F, M50F) and synthesized for cloning into a mammalian Fab expression construct containing an 8×His tag to generate Fab proteins (hereinafter referred to as mAb1.v7.NGS1-mAb1.v7.NGS9).

Plasmids encoding the heavy or light chain were transfected into Expi293F cells (Thermo Fisher) for 20-30 mL expression using a 1:1 ratio of HC:LC. Fabs were purified with a HisPur Ni-NTA column by diluting supernatant 1.5× with 1× phosphate-buffered saline pH 7.2 ("PBS"), adding 10 mM imidazole, and binding to resin in batch mode for 2 hours. Resin was flowed over a column and washed with 20 CV PBS+20 mM imidazole and eluted with 5 CV PBS+250 mM imidazole. Samples were buffer exchanged to PBS using a PD10 column (GE Healthcare).

OCTET Binding Assay of Affinity Improved Fab Variants of mAb1.v7

The binding of affinity matured Fab variants of mAb1.v7 to hu-CD96 and cy-CD96 was measured by OCTET (Pall ForteBio) Bio-Layer Interferometry (BLI). Biotinylated hu-CD96 or biotinylated CyCD96 was diluted to a final concentration 10 μg/mL in experimental buffer (PBS buffer with 0.01% Tween-20) and immobilized on the Streptavidin (SA) capture biosensors (Pall ForteBio). Three-fold serial dilution of mAb1.v7 Fab variants starting at 1 μM as analytes were diluted in the experimental buffer (PBS buffer with 0.01% Tween-20). The biosensors were equilibrated in experimental buffer at 30° C. for 10 min prior to starting the experiment.

Kinetics experiments were performed with the following steps, where the step name, solution and time are listed: Baseline (buffer—60 seconds), Loading (biotinylated antigen—200 seconds), Baseline 2 (buffer—minimum 120 seconds), Association (analyte—200-300 seconds) and Dissociation (buffer—1000 seconds).

Resulting BLI signals from analyte association and dissociation from the immobilized antibody was analyzed using the OCTET Data Analysis software (Pall ForteBio). First a reference subtraction was performed on all recorded traces using the reference well (biosensor that underwent same steps as experimental wells but no analyte for the Association step) and then all the traces were aligned to the beginning of the Association step. The entirety of the Association and Dissociation steps were used in a Global fit (minimum of four analyte concentration traces) in a 1:1 binding model to calculate the $K_D$ for individual affinity matured Fab variants of mAb1.v7 summarized in Table 12.

TABLE 12

Variant HVR sequences and OCTET binding affinities of mAb1.v7 Fab variants mAb1.v7.NGS1-mAb1.v7.NGS9

| Fab | HVR-H1 | | | | | | HVR-H2 | | | | | | | | | | | |
|---|---|---|---|---|---|---|---|---|---|---|---|---|---|---|---|---|---|---|
| | 30 | 31 | 32 | 33 | 34 | 35 | 50 | 51 | 52 | 52A | 53 | 54 | 55 | 56 | 57 | 58 | 59 | 60 | 61 |
| mAb1.v7 | T | N | N | W | M | H | M | I | H | P | N | S | G | I | T | N | I | N | E |
| mAb1.v7.NGS1 | T | N | N | F | M | H | M | I | H | P | N | S | G | I | T | N | I | N | E |
| mAb1.v7.NGS2 | T | N | N | W | M | H | F | I | H | P | N | S | G | I | T | N | I | N | E |
| mAb1.v7.NGS3 | T | N | N | W | M | H | M | I | H | A | N | S | G | I | T | N | I | N | E |
| mAb1.v7.NGS4 | T | N | N | W | M | H | M | I | H | P | N | S | G | I | T | N | I | N | H |
| mAb1.v7.NGS5 | T | N | N | W | M | H | M | I | H | P | N | S | G | I | T | N | I | N | R |
| mAb1.v7.NGS6 | T | N | N | W | M | H | M | I | H | P | N | S | G | I | T | N | I | N | E |
| mAb1.v7.NGS7 | T | N | N | W | M | H | M | I | H | P | N | S | G | I | T | N | I | N | E |
| mAb1.v7.NGS8 | T | N | N | F | M | H | M | I | H | A | N | S | G | I | T | N | I | N | E |
| mAb1.v7.NGS9 | T | N | N | F | M | H | M | I | H | A | N | S | G | I | T | N | I | N | E |

| Fab | HVR-H3 | | | | | | | | | | | |
|---|---|---|---|---|---|---|---|---|---|---|---|---|
| | 93 | 94 | 95 | 96 | 97 | 98 | 99 | 100 | 100A | 100B | 101 | 102 |
| mAb1.v7 | R | S | D | G | T | Y | E | G | Y | F | D | Y |
| mAb1.v7.NGS1 | R | S | D | G | T | Y | E | G | Y | F | D | Y |
| mAb1.v7.NGS2 | R | S | D | G | T | Y | E | G | Y | F | D | Y |
| mAb1.v7.NGS3 | R | S | D | G | T | Y | E | G | Y | F | D | Y |
| mAb1.v7.NGS4 | R | S | D | G | T | Y | E | G | Y | F | D | Y |
| mAb1.v7.NGS5 | R | S | D | G | T | Y | E | G | Y | F | D | Y |
| mAb1.v7.NGS6 | R | S | D | G | I | Y | E | G | Y | F | D | Y |
| mAb1.v7.NGS7 | R | S | D | G | V | Y | E | G | Y | F | D | Y |
| mAb1.v7.NGS8 | R | S | D | G | I | Y | E | G | Y | F | D | Y |
| mAb1.v7.NGS9 | R | S | D | G | V | Y | E | G | Y | F | D | Y |

| Fab | Octet KD (nM) | |
|---|---|---|
| | hu-CD96 | cy-CD96 |
| mAb1.v7 | 76 | ~1000 |
| mAb1.v7.NGS1 | 49 | 271 |
| mAb1.v7.NGS2 | 63 | ~100 |
| mAb1.v7.NGS3 | 0.1 | ~1000 |
| mAb1.v7.NGS4 | 31.5 | 739 |
| mAb1.v7.NGS5 | 43.6 | 85 |
| mAb1.v7.NGS6 | 5.32 | 289 |
| mAb1.v7.NGS7 | 5.61 | 383 |
| mAb1.v7.NGS8 | 0.1 | 93 |
| mAb1.v7.NGS9 | 0.1 | 82 |

According to the OCTET binding analysis in Table 12, the mAb1.v7. NGS8 and mAb1.v7.NGS9 Fab variants showed the highest binding affinity to hu-CD96 and cy-CD96.

In order to mitigate the oxidation risk based on the presence of Met residue at position 50 of HVR-H2, further Fab variants, mAb1.v7.NGS10 and mAb1.v7.NGS11 were generated with an M50F substitution of mAb1.v7.NGS8 and mAb1.v7.NGS9, respectively, as shown by sequences in Table 13 (below).

TABLE 13

Variant HVR sequences of mAb1.v7 NGS8-NGS11

| Fab | HVR-H1 | | | | | | HVR-H2 | | | | | | | | | | | |
|---|---|---|---|---|---|---|---|---|---|---|---|---|---|---|---|---|---|---|
| | 30 | 31 | 32 | 33 | 34 | 35 | 50 | 51 | 52 | 52A | 53 | 54 | 55 | 56 | 57 | 58 | 59 | 60 | 61 |
| mAb1.v7 | T | N | N | W | M | H | M | I | H | P | N | S | G | I | T | N | I | N | E |
| mAb1.v7.NGS8 | T | N | N | F | M | H | M | I | H | A | N | S | G | I | T | N | I | N | E |
| mAb1.v7.NGS9 | T | N | N | F | M | H | M | I | H | A | N | S | G | I | T | N | I | N | E |
| mAb1.v7.NGS10 | T | N | N | F | M | H | F | I | H | A | N | S | G | I | T | N | I | N | E |
| mAb1.v7.NGS11 | T | N | N | F | M | H | F | I | H | A | N | S | G | I | T | N | I | N | E |

TABLE 13-continued

Variant HVR sequences of mAb1.v7 NGS8-NGS11

| Fab | HVR-H3 | | | | | | | | | | | |
|---|---|---|---|---|---|---|---|---|---|---|---|---|
| | 93 | 94 | 95 | 96 | 97 | 98 | 99 | 100 | 100A | 100B | 101 | 102 |
| mAb1.v7 | R | S | D | G | T | Y | E | G | Y | F | D | Y |
| mAb1.v7.NGS8 | R | S | D | G | I | Y | E | G | Y | F | D | Y |
| mAb1.v7.NGS9 | R | S | D | G | V | Y | E | G | Y | F | D | Y |
| mAb1.v7.NGS10 | R | S | D | G | I | Y | E | G | Y | F | D | Y |
| mAb1.v7.NGS11 | R | S | D | G | V | Y | E | G | Y | F | D | Y | hu-CD96 and cy-CD96 binding affinities and CD155 blocking activities of mAb1.v7 NGS8-NGS11 Fabs were determined and are summarized in Table 14 (below).

TABLE 14 hu-CD96 and cy-CD96 binding affinities and CD155 blocking activities of mAb1.v7 NGS8-NGS11 Fabs

| Fab | Biacore_hCD96 | | | Biacore_CyCD96 | | | CD155 blocking IC50 (nM) | |
|---|---|---|---|---|---|---|---|---|
| | Kon (1/Ms) | Koff (1/s) | KD (nM) | Kon (1/Ms) | Koff (1/s) | KD (nM) | hCD96 | CyCD96 |
| mAb1.v7 | 1.83E+04 | 8.17E−04 | 44.6 | 1.15E+03 | 2.57E−02 | >1000 | 0.74 | ~300 |
| mAb1.v7.NGS8 | 1.67E+04 | 2.53E−05 | 1.8 | 2.65E+04 | 3.83E−04 | 14.5 | 0.2 | 0.92 |
| mAb1.v7.NGS9 | 1.42E+04 | 8.32E−05 | 5.85 | 2.48E+04 | 4.14E−04 | 16.7 | 0.78 | 0.73 |
| mAb1.v7.NGS10 | 1.21E+04 | 2.60E−05 | 2.1 | 1.14E+04 | 3.43E−04 | 30 | 0.54 | 0.84 |
| mAb1.v7.NGS11 | 1.05E+04 | 2.75E−05 | 2.62 | 1.12E+04 | 2.15E−04 | 19.1 | 0.59 | 0.95 |

The four lead mAb1.v7 variants NGS8, NGS9, NGS10, and NGS11, were reformatted into pRK mammalian expression IgG vectors, and recombinant IgGs were expressed and purified as described in Example 2.

Example 6: Affinity Maturation of Humanized Anti-CD96 Antibody h10G1

This example illustrates phage library construction and panning techniques used for affinity maturation of the humanized anti-hu-CD96 antibody h10G1 for improved binding to hu-CD96 and cy-CD96.

NNK Library Construction and Panning

To further improve the affinity of anti-CD96 antibody clone h10G1, phage libraries were constructed from h10G1 in Fab-amber format for monovalent Fab phage display with light chain HVR residues (i.e., HVR-L1, HVR-L2 and HVR-L3) and heavy chain HVR residues (i.e., HVR-H1, HVR-H2, and HVR-H3) randomized using the NNK degenerate codon that encodes for all 20 amino acids with 32 codons (see e.g., Brenner et al., 1992). Libraries were designed to allow one NNK mutation in each of the six HVRs. Synthesized mutagenesis oligonucleotides were then used to construct phage libraries using Kunkel mutagenesis (see e.g., Kunkel et al., 1987). The resultant library DNA was electroporated into E. coli XL1 cells, yielding approximately $4 \times 10^9$ transformants. Phage libraries were incubated in SUPERBLOCK™ PBS buffer (Pierce) and 0.05% TWEEN® 20 for 30 min and then applied on hu-CD96 and cy-CD96 coated plates for first round panning. In the subsequent two to three rounds, phage libraries were incubated with decreasing concentration of biotinylated hu-CD96 or cy-CD96 antigen with 1000× non-biotinylated human or cy-CD96 as competitor in solution to increase the selection stringency. The eluted phage was infected with log-phase XL-1 and plated on LB carbenicillin plate at 37° C. overnight for further affinity screening Sequencing of h10G1 Affinity Maturation Libraries In order to further improve affinity and mitigate oxidation liability risks, next-generation sequencing (NGS) of the h10G1 affinity maturation libraries was performed. Phagemid double stranded DNA was isolated from E. coli XL-1 cells carrying phagemids from the initial phage library (unsorted libraries) and from the second and third rounds of solution selection (sorted libraries). Purified DNA was used as the template to generate amplicons of $V_L$ and $V_H$ regions using Illumina 16s library preparation protocol. Sequencing adapters and dual-index barcodes were added using Illumina Nextera XT Index Kit. In preparation for sequencing on Illumina MiSeq, adapter-ligated amplicons were subjected to standard Illumina library denaturing and sample loading protocol using MiSeq Reagent Kit v3 (600 cycles). Paired-end sequencing was performed to cover the entire length of the amplicon with insert size of 200 bp to 300 bp.

Paired-end sequencing data were first assembled using paired-end assembler PANDAseq (see e.g., Masella et al., 2012) to obtain complete amplicons. Quality control (QC) was then performed on identified amplicons, where each amplicon was checked for no insertion or deletion of sequences and no stop codons, each HVR sequence was allowed to carry only up to one NNK mutation and no non-NNK mutation. Position weight matrices were generated by calculating the frequency of all mutations of every randomized position. Enrichment ratios for each mutation were calculated by dividing the frequency of a given mutation at a given position in the sorted sample with the frequency of the very same mutation in the unsorted sample, as described previously (Koenig et al., 2015). The HVR-L and H region mutations of h10G1 identified by NGS as resulting in improved binding to hu-CD96 and cy-CD96 are summarized in Table 15 (below).

TABLE 15

HVR-L and HVR-H mutations of h10G1 with high
affinity binding to hu-CD96 and cy-CD96

HVR-L1

D28A, D28E, D28G, D28H, D28K, D28N, D28P, D28Q, D28S, D28T
Y30F
R31K, R31Q
L33I, L33M, L33V

HVR-L2

S52E
D53E, D53K, D53Q
S54H, S54L, S54R, S54V
I55V

CDR-L3

L89G, L89M, L89Q
S93A, S93E, S93Q, S93V
Y96F

HVR-H1

T30A, T30D, T30E, T30G, T30H, T30K, T30M, T30N, T30Q, T30R, T30S
T31D, T31E, T31G, T31H, T31N, T31Q, T31S
Y32F, Y32M, Y32Q,
M34I, M34L, M34V

HVR-H2

D53E
S54T

HVR-H3

N95M
N100bF, N100bH, N100bY

Example 7: In Vitro Assays of Anti-CD96 Antibodies

This example illustrates cell-based assays used to characterize the functional activity of the anti-CD96 antibodies described in the previous Examples.

Binding Affinity Determination

To determine the binding affinity to hu-CD96 and cy-CD96 at 37° C. of the recombinant anti-CD96 IgGs, SPR measurement with a BIACORE™ 8K instrument was performed. Briefly, a 1:4 dilution of Biotin CAPture Reagent (GE Healthcare) into HBS-EP buffer (0.01 M HEPES pH 7.4, 0.15 M NaCl, 3 mM EDTA, 0.005% Surfactant P20) was applied to the chip at 2 µL/min flow rate. For the kinetics measurements, 20 nM biotinylated hu-CD96-Fc and cy-CD96-Fc was captured at 10 µL/min to achieve ~50 response units in the second flow cell (FC2). FC1 was kept as a reference. Next, 4-fold serial dilutions of IgG in HBS-P buffer (0.01 M HEPES pH 7.4, 0.15 M NaCl, 0.005% surfactant P20) from low (3.125 nM) to high (200 nM) concentration were injected (flow rate: 10 µL/min) at 37° C. The sensorgram was recorded and subject to reference and buffer subtraction before evaluating by BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) value was calculated as the ratio of $k_{off}/k_{on}$. The BIACORE® determined binding affinity values are summarized in Table 16 (below).

TABLE 16

Binding affinity of anti-CD96 IgGs binding to hu-CD96 and cy-CD96

| Antibody | hu-CD96 @ 37° C. | | | cy-CD96 @ 37° C. | | |
|---|---|---|---|---|---|---|
| | On-rate $k_{on}$ (1/Ms) | Off-rate $k_{off}$ (1/s) | $K_D$ (nM) | On-rate $k_{on}$ (1/Ms) | Off-rate $k_{off}$ (1/s) | $K_D$ (nM) |
| mAb1.v7.NGS8 | $1.29 \times 10^5$ | $1.99 \times 10^{-5}$ | 0.15 | $4.15 \times 10^5$ | $6.06 \times 10^{-4}$ | 1.46 |
| mAb1.v7.NGS9 | $2.66 \times 10^5$ | $5.42 \times 10^{-5}$ | 0.2 | $2.55 \times 10^5$ | $7.34 \times 10^{-4}$ | 2.88 |
| mAb1.v7.NGS10 | $1.44 \times 10^5$ | $1.84 \times 10^{-6}$ | 0.01 | $7.67 \times 10^5$ | $3.74 \times 10^{-4}$ | 0.49 |
| mAb1.v7.NGS11 | $1.73 \times 10^5$ | $1.38 \times 10^{-5}$ | 0.08 | $3.38 \times 10^5$ | $5.13 \times 10^{-4}$ | 1.52 |
| h10G1 | $6.12 \times 10^5$ | $3.93 \times 10^{-4}$ | 0.64 | $6.99 \times 10^6$ | $7.89 \times 10^{-3}$ | 1.13 |
| NK92.39 | $8.44 \times 10^4$ | $1.2 \times 10^{-3}$ | 14.2 | no binding | no binding | no binding |

Binding to Hu-CD96 Isoforms 1 and 2 Expressed on Cells

Only isoform 2 of hu-CD96 was used in the above described in vitro binding affinity experiments. To examine binding of anti-CD96 antibodies to the two distinct isoforms of hu-CD96 expressed on cells, we used HEK293T or CHO cells transiently or stably expressing hu-CD96 and FACS analysis. Only isoform 2 of hu-CD96 was used in the above described in vitro binding affinity experiments. In this experiment, both isoform 1 and isoform 2 of hu-CD96 were tested.

Isoform 1 of hu-CD96 (Origene, catalog #RC213845) was transiently expressed in HEK293T cells following standard lipofectamine or Fugene transfection protocol. CD96-expressing 293 Ts were incubated with antibodies for 20 minutes at 4° C. Cells were washed, and binding was detected by incubation with anti-mouse IgG-FITC (Biolegend, catalog #406001) for 20 minutes at 4° C. Cell binding was analyzed by flow cytometry with a CytoFLEX (Beckman Coulter). Binding curves were calculated as a percentage of cells positive for bound antibody.

As shown by the results in Table 17 (below), the anti-CD96 antibodies, mAb1.v7, 10G1, 7E5, and 9H4 bind to HEK293T-CD96 (iso1) cells dose-dependently and potently. Control antibody muIgG1 did not show any binding above background.

TABLE 17

Anti-CD96 binding to HEK293T-CD96 (isoform 1) cell binding (% positive)

| Antibody (nM) | mAb1.v7 | 10G1 | 7E5 | 9H4 | muIgG1 |
|---|---|---|---|---|---|
| 50 | 61.0 | 56.1 | 52.1 | 57.8 | 0.75 |
| 10 | 48.8 | 53.4 | 47.4 | 48.4 | 0.48 |
| 2 | 27.3 | 48.1 | 37.1 | 28.5 | 0.49 |
| 0.4 | 12.2 | 34.6 | 20.4 | 13.9 | 0.49 |
| 0.08 | 0.8 | 16.5 | 8.5 | 1.5 | 0.41 |
| 0.016 | 0.5 | 4.4 | 1.0 | 0.5 | 0.41 |
| $EC_{50}$ (nM) | 2.6 | 0.24 | 0.71 | 2.1 | |

Isoform 2 of hu-CD96 (DNA construct: Origene, catalog #RC221005) was expressed on a single-cell-clone-derived CHO stable cell line. Binding of the anti-CD96 antibodies to the CHO cells were determined as described above with isoform 1 of hu-CD96.

As shown in Table 18 (below), the anti-CD96 antibodies mAb1.v7, 10G1, 7E5, 9H4, 14D3, and 1G8 bind to the isoform 2 of CD96 expressed on CHO cells dose-dependently and potently. By comparison, NK92.39 (Fuchs et al., 2004; Biolegend catalog #338405) bound the cells with slightly higher $EC_{50}$ and a lower maximal level of binding. The control antibody muIgG1 did not show any binding above background.

TABLE 18

CHO-CD96 (isoform 2) cell binding (% positive)

| Antibody (nM) | mAb1.v7 | 10G1 | 7E5 | 9H4 | 14D3 | 1G8 | NK92.39 | muIgG1 |
|---|---|---|---|---|---|---|---|---|
| 50 | 44.1 | 39.8 | 58.9 | 46.2 | 42.1 | 34.8 | 22.0 | 0.42 |
| 10 | 44.8 | 39.2 | 56.1 | 46.1 | 44.4 | 35.3 | 21.5 | 0.18 |
| 2 | 42.4 | 34.9 | 53.3 | 44.2 | 38.1 | 26.2 | 15.8 | 0.27 |
| 0.4 | 17.7 | 25.0 | 44.1 | 24.1 | 24.1 | 7.1 | 4.0 | 0.14 |
| 0.08 | 1.4 | 9.4 | 24.6 | 3.1 | 6.4 | 0.2 | 0.2 | 0.11 |
| 0.016 | 0.4 | 0.4 | 3.6 | 0.3 | 0.3 | 0.0 | 0.1 | 0.06 |
| 0.0032 | 0.5 | 0.1 | 0.1 | 0.3 | 0.1 | 0.1 | 0.1 | 0.03 |
| $EC_{50}$ (nM) | 0.52 | 0.23 | 0.11 | 0.38 | 0.33 | 1.04 | 1.15 | |

Binding to Human and Cynomolgus Monkey PBMCs

The ability of the anti-CD96 antibodies to bind primary immune cells from human and cynomolgus monkey with lower level of receptor expression was measured. Human PBMCs (StemCell Technologies, catalog #70025) and cynomolgus monkey PBMCs (Primate Biologicals, catalog #CM-MC) were incubated with human TruStain FcX (Biolegend, catalog #422302) for 10 minutes at 4° C., followed by incubation with an anti-CD96 antibody for 20 minutes at 4° C. Cells were washed and the anti-CD96 antibody binding was detected by incubation with anti-mouse IgG-PE (Thermo Fisher, catalog #M30204) or anti-human IgG (Fab')2-PE (Thermo Fisher, catalog #H10104) for 20 minutes at 4° C. Cells were washed, and immune subtypes were labeled with anti-CD3 (BD, catalog #557705), anti-CD4 (Biolegend, catalog #317424) and anti-CD8 (BD, catalog #557760) for 20 minutes at 4° C. Cell binding was analyzed by flow cytometry with a CytoFLEX (Beckman Coulter). Binding curves were calculated as a percentage of cells positive for bound antibody in the cell type of interest.

As shown in Table 19 (below), the anti-CD96 antibodies mAb1.v7.NGS8, mAb1.v7.NGS9, mAb1.v7.NGS10, mAb1.v7.NGS11, and h10G1 bound to primary human and cynomolgus monkey PBMC immune cells dose-dependently and potently. In comparison, the NK92.39 antibody (Fuchs et al., 2004; Biolegend catalog #338405) only bound to human PBMC but not to cynomolgus monkey PBMC. This is consistent with NK92.39's lack of binding to cy-CD96D1 D3 protein as shown in biochemical binding measurements. The negative control antibodies hu-IgG1 and mu-IgG1 did not show any binding above background.

TABLE 19

Human PBMC and Cynomolgus Monkey PBMC cell binding

| Antibody (nM) | mAb1.v7.NGS8 | mAb1.v7.NGS9 | mAb1.v7.NGS10 | mAb1.v7.NGS11 | h10G1 | NK92.39 | Hu-IgG1 | Mu-IgG1 |
|---|---|---|---|---|---|---|---|---|
| Human PBMC cell binding (% positive) | | | | | | | | |
| 80 | 97.8 | 97.8 | 97.7 | 97.2 | 88.7 | 91.9 | 3.10 | 2.34 |
| 16 | 96.2 | 97.1 | 97.1 | 96.7 | 81.4 | 94.3 | 4.61 | 2.05 |
| 3.2 | 92.3 | 95.1 | 93.8 | 94.2 | 64.4 | 76.7 | 4.67 | 1.42 |
| 0.64 | 89.3 | 90.8 | 88.8 | 89.7 | 53.5 | 27.4 | 4.04 | 1.50 |
| 0.128 | 64.2 | 64.7 | 66.7 | 61.1 | 39.1 | 2.0 | 3.98 | 1.09 |
| 0.0256 | 22.0 | 22.5 | 16.9 | 11.6 | 14.6 | 0.9 | 5.50 | 1.48 |
| 0.00512 | 8.6 | 8.2 | 6.1 | 5.4 | 5.4 | 1.3 | 5.29 | 0.98 |
| $EC_{50}$ (nM) | 0.072 | 0.071 | 0.069 | 0.083 | 0.28 | 1.22 | | |
| Cynomolgus Monkey PBMC cell binding (% positive) | | | | | | | | |
| 80 | 74.5 | 73.8 | 75.2 | 81.9 | 68.3 | 4.9 | 2.36 | 1.90 |
| 16 | 77.2 | 76.1 | 78.5 | 80.8 | 66.1 | 5.4 | 0.64 | 1.77 |
| 3.2 | 75.5 | 77.9 | 76.7 | 78.4 | 58.1 | 5.2 | 1.15 | 0.95 |
| 0.64 | 70.7 | 71.0 | 73.1 | 74.3 | 51.2 | 4.7 | 0.59 | 1.07 |
| 0.128 | 45.3 | 49.4 | 64.6 | 63.5 | 38.2 | 5.2 | 0.31 | 0.83 |
| 0.0256 | 11.6 | 19.7 | 37.2 | 41.0 | 16.8 | 5.0 | 0.57 | 1.00 |
| 0.00512 | 5.1 | 7.1 | 9.5 | 10.4 | 7.4 | 4.5 | 0.41 | 0.76 |
| $EC_{50}$ (nM) | 0.097 | 0.073 | 0.024 | 0.025 | 0.12 | 1.1 | | |

Binding to Hu-CD96-CHO Cells and Blocking of CD155-Fc Binding

CHO cells stably expressing isoform 2 of hu-CD96 (Origene, catalog #RC221005) were incubated with anti-CD96 antibodies for 20 minutes at 4° C. The cells were washed, and then incubated with 10 nM human CD155-Fc-FLAG for 30 minutes at 4° C. Cells were washed, and then human CD155-Fc-FLAG binding was detected by incubation with anti-FLAG-APC (Columbia Biosciences, catalog #D3-1718-1MG) for 20 minutes at 4° C. Cell binding was analyzed by flow cytometry with a CytoFLEX (Beckman Coulter). CD155 binding is represented as median fluorescence intensity (MedFI).

As shown in Table 20 (below), the anti-CD96 antibodies, mAb1.v7.NGS8, mAb1.v7.NGS9, mAb1.v7.NGS10, mAb1.v7.NGS11, and h10G1 inhibited soluble hu-CD155 binding to CD96-expressing CHO cells dose-dependently and potently. The antibody NK92.39 (Fuchs et al., 2004; Biolegend catalog #338405) inhibited receptor binding similarly. The negative control antibodies, hu-IgG1 and mu-IgG1 did not show any inhibition.

TABLE 20

Human CD155-Fc binding to CD96-CHOs (MedFI)

| Antibody (nM) | mAb1.v7.NGS8 | mAb1.v7.NGS9 | mAb1.v7.NGS10 | mAb1.v7.NGS11 | h10G1 | NK92.39 | Hu-IgG1 | Mu-IgG1 |
|---|---|---|---|---|---|---|---|---|
| 100 | 4181 | 4145 | 5113 | 4206 | 5120 | 5053 | 51722 | 75952 |
| 20 | 4287 | 4256 | 4936 | 4460 | 4857 | 5039 | 57317 | 71606 |
| 4 | 4958 | 6098 | 4936 | 4864 | 4857 | 5039 | 63058 | 71606 |
| 0.8 | 23616 | 32194 | 23615 | 23650 | 5871 | 40338 | 58268 | 66575 |
| 0.16 | 52891 | 54650 | 54073 | 51858 | 21243 | 62592 | 59441 | 64380 |
| 0.032 | 47801 | 53011 | 57740 | 57672 | 52051 | 69262 | 52821 | 65374 |
| 0.0064 | 49207 | 56593 | 55923 | 63569 | 65668 | 64104 | 47697 | 64347 |
| $IC_{50}$ (nM) | 0.76 | 0.91 | 0.57 | 0.46 | 0.06 | 0.91 | | |

Primary Human NK Cell Assay

Functional activity of the anti-CD96 antibodies was tested on primary human natural killer (NK) cells. Primary human peripheral blood NK cells (StemCell Technologies, catalog #70036) were incubated with antibodies in complete media containing 100 µg/mL recombinant human IL-12 (VWR, catalog #10773-012) and 50 ng/mL recombinant human IL-18 (VWR, catalog #75791-086) in round bottom plates coated with 0.25 µg per well of CD155-huFc for 5 hours at 37° C. IFNγ in the supernatant was determined by ELISA (Thermo Fisher, catalog #88-7316-86).

As shown in Table 21 (below), the anti-CD96 antibodies, mAb1.v7.NGS10 and h10G1 increased IFNγ secretion from NK cells dose-dependently and potently. NK92.39 (Fuchs et al., 2004; Biolegend catalog #338405) also enhanced IFNγ secretion but the effect was weaker and less potent (61% of maximal efficacy of h10G1).

TABLE 21

Human NK cell IFNγ secretion (fold over background, n = 5/condition)

| Antibody (nM) | mAb1.v7.NGS10 | h10G1 | hu-IgG1 | NK92.39 | mu-IgG1 |
|---|---|---|---|---|---|
| 250 | 1.87 | 1.87 | 1.12 | 1.62 | 1.05 |
| 50 | 2.05 | 2.21 | 1.04 | 1.68 | 0.96 |
| 10 | 1.94 | 2.19 | 1.03 | 1.39 | 0.91 |
| 2 | 2.12 | 2.08 | 1.07 | 1.27 | 1.14 |
| 0.4 | 1.81 | 1.96 | 1.23 | 0.69 | 1.00 |
| 0.08 | 1.36 | 1.38 | 1.51 | 1.38 | |
| 0.016 | 1.24 | 1.13 | 1.01 | | |
| 0.0032 | 1.00 | 1.00 | 1.33 | | |
| $EC_{50}$ (nM) | 0.084 | 0.112 | | 5.53 | |

Primary Human NK Cell Assay in the Presence of Anti-CD226

Functional activity of the anti-CD96 antibodies in triggering IFNγ secretion was also measured in the presence of the antagonistic anti-CD226 antibody DX-11 (Abcam catalog #ab33397). Primary human peripheral blood NK cells were incubated with indicated anti-CD96 antibodies, control isotype antibodies, or anti-CD226 antibody (DX-11) in complete media containing 100 μg/ml recombinant human IL-12 and 50 ng/ml recombinant human IL-18 in plates coated with 0.25 μg per well of CD155-Fc for 5 hours at 37° C. IFNγ concentration in the supernatant was determined by ELISA. Each condition was tested in 5 biological replicates. As shown in FIG. 3, the IFNγ secretion triggered by the anti-CD96 antibodies mAb1.v7.NGS8 and h10G1 was completely elimination by the presence of the antagonistic anti-CD226 antibody DX-11. The results of this experiment thus demonstrate that the effect of the IFNγ stimulatory effect of the anti-CD96 antibodies is CD226-dependent.

Primary Human CD4+ T Cell Assay

Figure 4A:
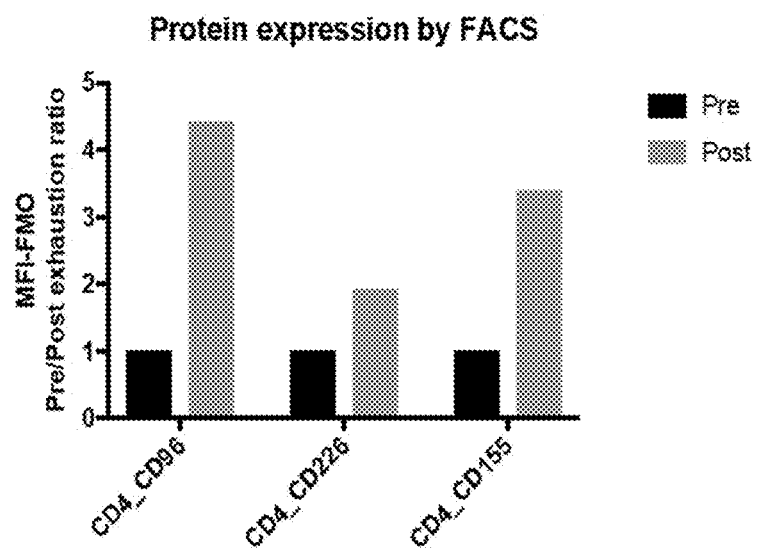
FIG. 4A and FIG. 4B depict plots of the activity of the anti-CD96 antibodies in primary human CD4+ T cells upon treatment with IL-2 and PHA as described in Example 7.
Figure 4B:
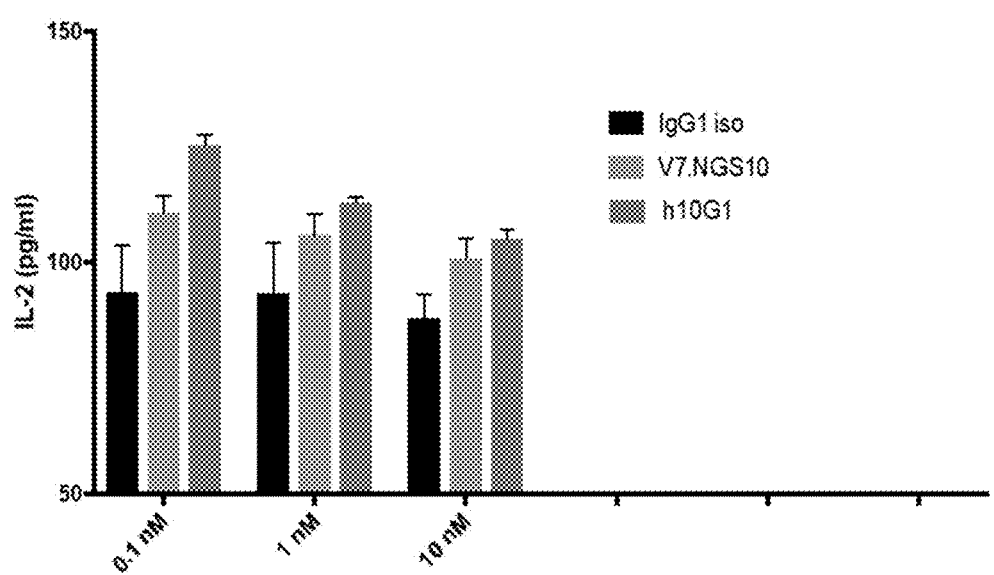

Functional activity of the anti-CD96 antibodies was also tested on primary human CD4+ T cells that were chronically stimulated in vitro for 7 days with 4 ng/ml IL-2 and 2 ug/ml PHA. (A) Treated cells were stained with fluorochrome-conjugated anti-CD96 (clone 6F9), anti-CD226 (clone 11A8), anti-CD155 (clone 2H7CD155), isotype control Abs and live/dead staining dye. Surface expression level were analyzed by flow cytometry with a CytoFLEX (Beckman Coulter). As shown in FIG. 4A, surface expression levels of CD96, CD226, and CD155 were upregulated with IL2 and PHA treatment. CD96 level was upregulated 4.4-fold. (B) These chronically stimulated CD4+ T cells were incubated with anti-CD96 antibodies in complete media for 5 hours at 37° C. in plates previously coated with 10 μg/ml of anti-CD3 (UCHT1) and g/ml of CD155-huFc. Secreted IL-2 in media was measured by ELISA (Invitrogen Cat #88-7025-88). As shown in FIG. 4B, IL2 secretion was increased by addition of anti-CD96 antibodies mAb1.v7.NGS10 and h10G1 at concentrations as low as 0.1 nM. This effect was seen in at least 3 different donors. Dose titration of mAb1.v7.NGS10 demonstrated an $EC_{50}$ of 53 μM for mAb1.v7.NGS10 (data not shown).

Primary Human PBMC Assay

Functional activity of the anti-CD96 antibodies was also tested on primary human peripheral blood mononuclear cells (PBMCs). $2\times10^5$/well human PBMCs were plated in 96-well round-bottom plate. 10 μg/ml mAb1.v7.NGS10 or h10G1 or huIgG1(E−) isotype control Abs were added for 30 min. The cells were then stimulated with 0.1 μg/ml anti-CD3 Ab and 1 μg/ml anti-CD28 Ab for three days. (A) Cells were stained with fluorochrome-conjugated anti-CD3 (OKT3), anti-CD4 (OKT4), anti-CD8 (SK1), anti-CD96 (6F9), anti-CD226 (11A8), anti-CD155 (2H7CD155), isotype control Abs (MOPC21) and live/dead staining dye. Surface expression levels were analyzed by flow cytometry with a CytoFLEX (Beckman Coulter). As shown in FIG. 5A and FIG. 5B surface expression levels of CD96 and CD226 were upregulated with anti-CD3 and anti-CD28 treatment. However, as shown in FIG. 5C, CD155 level was not dramatically changed.

Figure 6:
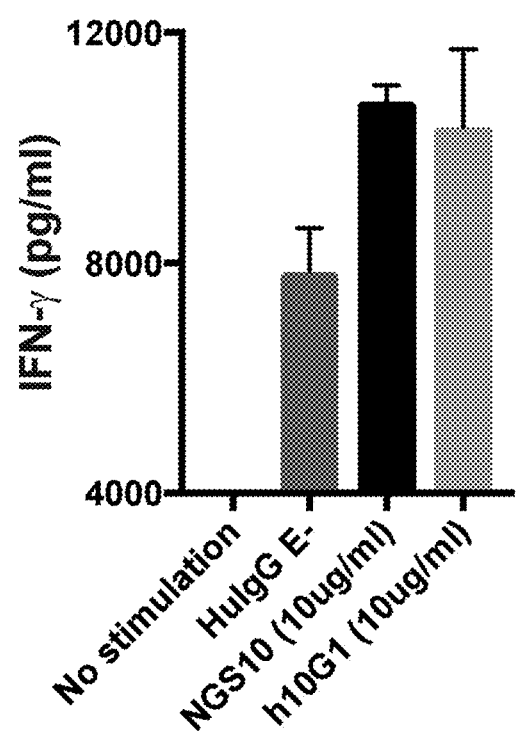
FIG. 6 depicts plots of IFNγ secretion from PBMCs upon addition of anti-CD96 antibodies mAb1.v7.NGS10 and h10G1 as described in Example 7.

IFNγ secretion into the supernatant also was analyzed by ELISA (Invitrogen Cat #88-7316-88). As shown in FIG. 6, IFNγ secretion was increased by addition of anti-CD96 antibodies mAb1.v7.NGS10 and h10G1, and this effect was seen in at least 3 different donors. Dose titration of h10G1 demonstrated an $EC_{50}$ of 23 μM (data not shown).

Example 8: In Vivo Tumor Models to Evaluate Activity of Anti-CD96 Antibodies

This example illustrates in vivo tumor model studies of the functional activity of a surrogate anti-mo-CD96 antibody 3.3.

A. Validation of Surrogate Anti-Mo-CD96 Antibody 3.3 (Antigen Binding, Blocking)

Purified anti-mo-CD96 from clone 3.3 (hereinafter "3.3 antibody") was obtained from BioLegend (Part #93137). IgG was coupled to amine-reactive OCTET sensors (ForteBio) at 20 mg/mL in sodium acetate pH 5.0 using EDC/NHS chemistry according to the manufacturer's protocol. Recombinant mo-CD96 ectodomain (M1-M536, ThermoFisher) was diluted into PBS containing 0.02% v/v Tween 20 and evaluated for binding to mAb2-coated sensors at concentrations of 200 nM, 50 nM, 12.5 nM, 3.125 nM and 0.78 nM. The resulting sensograms were fit with a 1:1 binding model to yield a $K_D$ of 0.75 nM.

The 3.3 antibody was also tested for its ability to bind mo-CD96 expressed on cells and block binding to soluble mouse CD155 protein. CHO cells stably expressing mo-CD96 (Origene, catalog #MR209314) were incubated with the 3.3 antibody for 20 minutes at 4° C. Cells were washed, and then incubated with 10 nM mouse CD155-huFc for 30 minutes at 4° C. Cells were washed, and then CD155-huFc binding was detected by incubation with anti-human IgG-APC (Biolegend, catalog #409306) for 20 minutes at 4° C. Cell binding was analyzed by flow cytometry with a CytoFLEX (Beckman Coulter). Antibody 3.3 inhibited mouse CD155 binding with an $IC_{50}$ of 4.8 nM.

The quality of all of the antibodies used for in vivo experiments were checked using HPLC-SEC, A280, and mass-spec (intact reduced, non-reduced). In addition, endotoxin level was determined and acceptable criteria is set at <0.5 EU/mg.

B. Subcutaneous Tumor Models—EMT6 and B16F10

A summary of the subcutaneous tumor model studies is shown in Table 22 (below).

TABLE 22

Summary of in vivo subcutaneous tumor study protocol

| Model | Strain (Vendor) | Cell number | Tumor Volume at randomization | Dosing |
|---|---|---|---|---|
| EMT6 | Balb/cAnHsd (Envigo) | $4 \times 10^5$ | 75-120 mm³ (on Day 11) | 10 mg/kg of each antibody on days 11, 14, 18, 21, 25, 28, 32 |

TABLE 22-continued

Summary of in vivo subcutaneous tumor study protocol

| Model | Strain (Vendor) | Cell number | Tumor Volume at randomization | Dosing |
|---|---|---|---|---|
| B16F10 | C57BL/6J (Jackson Labs) | $5 \times 10^4$ | 48-104 mm$^3$ (on Day 12) | 10 mg/kg of each antibody on days 12, 15, 19, 22, 26, 29, 33 |

Reagents:

InVivoPlus Rat IgG2a Isotype control (3.38 mg/ml, Clone: 2A3, Catalog #BP0089, Lot #627416N1) was obtained from BioXcell. ULTRA-LEAF™ Purified Rat IgG1 Isotype control (3.3 mg/ml, Clone: RTK2071, Lot #B252227) was obtained from BioLegend. InVivoPlus anti-mouse PD-1 (3.1 mg/ml, Clone: RMP1-14, Catalog #: BP0146, Lot #665417S1) was obtained from BioXcell. ULTRA-LEAF™ Purified anti-mo-CD96 (3.3 mg/ml, Clone: 3.3, Part #93137, Lot #B252222) was obtained from BioLegend.

Animals and Husbandry:

Female mice (7-9 weeks of age) were used in the studies. The animals were fed irradiated Harlan 2918.15 Rodent Diet and water ad libitum. Animals were ear tagged for identification purposes and shaved on the left dorsal flank area in preparation of cell implantation. Animals were housed in Innovive disposable ventilated caging with corn cob bedding at 60 complete air changes per hour. The environment was controlled to a temperature range of 70°±2° F. and a humidity range of 30-70%. All procedures carried out in this experiment were conducted by skilled personnel in compliance with all the laws, regulations and guidelines of the National Institutes of Health (NIH) and with the approval of Explora Bio Labs' Animal Care and Use Committee (San Diego, Calif.).

Cell Preparation and Implantation:

EMT6 and B16F10 cells were obtained from ATCC. EMT6 cells were cultured and expanded in Waymouth's MB 752/1 Medium with 2 mM L-glutamine, 15% fetal bovine serum (FBS), and 1% 100× Penicillin/Streptomycin (PS). B16F10 cells were cultured and expanded in Dulbecco's Modified Eagles Medium (DMEM) with 10% fetal bovine serum (FBS), and 1% 100× Penicillin/Streptomycin (PS). The growth environment was maintained in an incubator with a 5% $CO_2$ atmosphere at 37° C. When expansion was complete, the cells (passage 3) were trypsinized using a 0.25% trypsin-EDTA solution. The cells were then washed and counted. Pre-implantation cell viability was 92%-94%. The cells were placed in a 1:1 solution of Dulbecco's Phosphate Buffered Saline (DPBS) and Matrigel (BD Biosciences, Catalog #354234) Test animals were sterilized at the implantation site with an alcohol prep pad and were implanted subcutaneously on Day 0 in 0.1 mL using a 25-gauge needle and 1 mL syringe. $4 \times 10^5$ EMT6 cells were implanted in Balb/c mice.

Measurements and Antibody Treatment:

Tumors were allowed to grow and were then randomized into study groups. Equal distribution of tumor volumes was ensured by using the matched distribution method in StudyLog Study Director version 3.1.399.8. Mice were distributed to ensure that the mean body weights for all groups were within 10% of the overall mean tumor burden for the study population. Mice received twice weekly i.p. injections 10 mg/kg of each antibody treatment for 3 weeks and tumor volumes were monitored. Group 1 received IgG2a and IgG1 isotype control antibodies, group 2 received anti-PD1 and IgG1 isotype control antibodies, and group 3 received anti-PD1 and anti-CD96 antibodies.

Assessment of Side Effects:

All animals were observed for clinical signs of distress or toxicity at least once daily. Animals were weighed once per week. If an individual animal showed overt signs of distress or 15% body weight loss, the individual animal was weighed daily. Animals were euthanized if body weight loss was in excess of 20% or other clinical signs that warranted euthanasia. Individual animals were euthanized when their tumor volume reached or exceeded 2000 mm$^3$.

Results—Subcutaneous EMT6 and B16F10 Tumor Studies

Anti-tumor efficacy of anti-CD96 antibody 3.3 was evaluated in the EMT6 subcutaneous syngeneic mouse model. As shown in Table 23 (below), the combination treatment of an anti-PD1 and an anti-CD96 improved animal survival compared to single agent treatment with anti-PD1.

TABLE 23

EMT6 subcutaneous syngeneic mice with tumors <2000 mm$^3$

| Treatment group | Day 32 | Day 38 | Day 56 |
|---|---|---|---|
| Control (Rat IgG2a control + Rat IgG1 control) | 11/15 (73%) | 3/15 (20%) | 0/15 (0%) |
| Anti-PD1 single agent treatment (Rat anti-PD1 + Rat IgG1 control) | 10/15 (66%) | 6/15 (40%) | 1/15 (7%) |
| Anti-PD1 + anti-CD96 combination (Rat anti-PD1 + Rat anti-CD96) | 14/15 (93%) | 11/15 (73%) | 6/15 (40%) |

Figure 7:
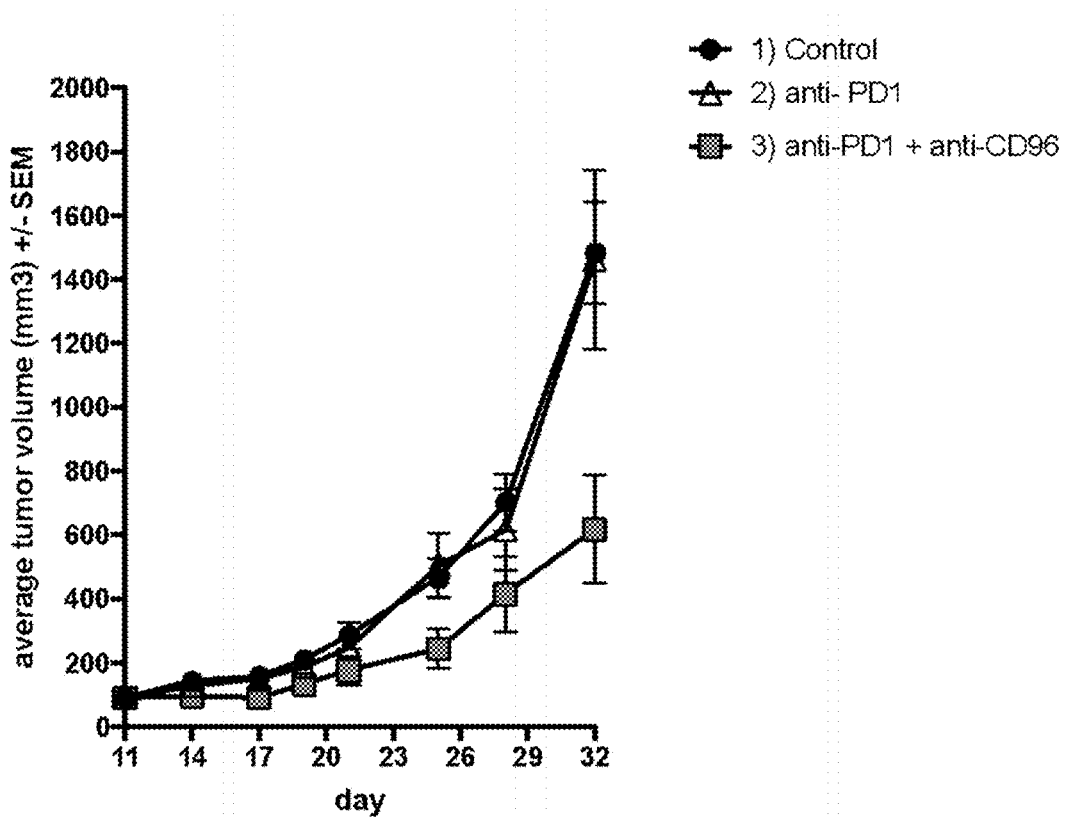
FIG. 7 depicts plots of average tumor volume of EMT6 syngeneic mouse model tumors in mice treated with control (IgG2a and IgG1 isotype control antibodies), anti-CD96 antibody 3.3 alone, or combination of anti-CD96 antibody 3.3 with anti-PD1 antibody RMP1-14.

Further, as shown in FIG. 7, the combination treatment with anti-PD1 and anti-CD96 decreased tumor volume in the EMT6 mouse model compared to single agent treatment with anti-PD1 or isotype control antibodies.

Anti-tumor efficacy of anti-CD96 antibody 3.3 also was evaluated in the B16F10 subcutaneous syngeneic mouse model. As shown in Table 24 (below) the combination treatment of anti-PD1 and anti-CD96 improved animal survival significantly compared to the single-agent treatment with anti-PD1 (p-0.02 for aPD1 v aPD1+aCD96 (Bonferroni adjusted)).

TABLE 24

B16F10 subcutaneous syngeneic mice with tumors <2000 mm$^3$

| Treatment group | Day 26 | Day 31 | Day 35 |
|---|---|---|---|
| Control (Rat IgG2a control + Rat IgG1 control) | 6/15 (40%) | 0/15 (0%) | 0/15 (0%) |
| Anti-PD1 (Rat anti-PD1 + Rat IgG1 control) | 12/15 (66%) | 2/15 (13%) | 0/15 (0%) |
| Anti-PD1 + anti-CD96 (Rat anti-PD1 + Rat anti-CD96) | 14/15 (93%) | 7/15 (46%) | 1/15 (7%) |

Figure 8:
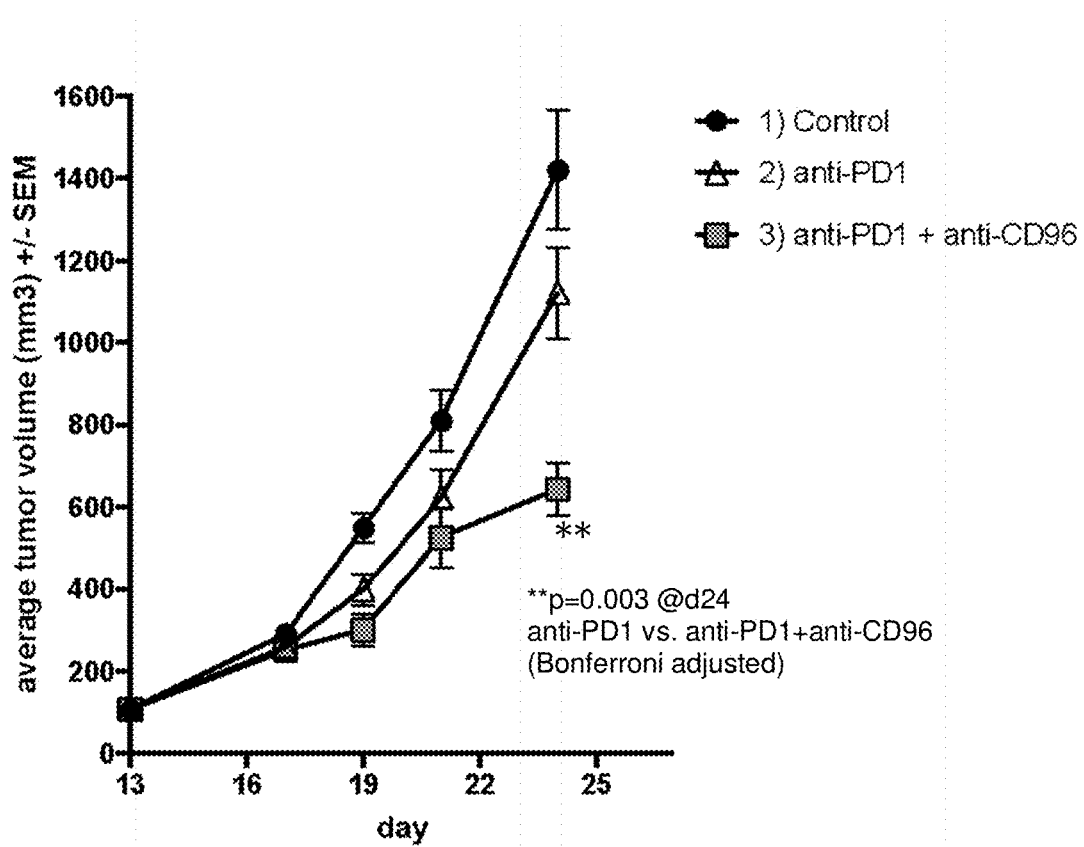
FIG. 8 depicts plots of average tumor volume of B16F10 syngeneic mouse model tumors in mice treated with control (IgG2a and IgG1 isotype control antibodies), anti-CD96 antibody 3.3 alone, or combination of anti-CD96 antibody 3.3 with anti-PD1 antibody RMP1-14.

Further, as shown in FIG. 8, the anti-PD1 and anti-CD96 combination treatment decreased tumor volume significantly in the B16F10 mouse model compared to the anti-PD1 single agent treatment or isotype control antibody treatment.

I.V. Luna Metastasis Model—B16F10

Anti-tumor efficacy of anti-CD96 antibody 3.3 was evaluated in the B16F10 i.v. lung metastasis model. Mice received 250 μg of each antibody via i.p. injection on Day 0 and Day 3 relative to implantation. Further materials and methods of the study are provided below.

Reagents:

InVivoPlus Rat IgG2a Isotype control (7.8 mg/ml, Clone: 2A3, Catalog #: BP0089, Lot #627416N1) was obtained from BioXcell. ULTRA-LEAF™ Purified Rat IgG1 Isotype control (1.11 mg/ml, Clone: RTK2071, Part #: 92233, Lot #B231146) was obtained from BioLegend. InVivoPlus anti-mouse PD-1 (6.66 mg/ml, Clone: RMP1-14, Catalog #: BP0146, Lot #61461601) was obtained from BioXcell. InVivoPlus anti-mouse CTLA-4 (6.45 mg/ml, Clone: 9D9, Catalog #: BP0164, Lot #619816S1) was obtained from BioXcell. ULTRA-LEAF™ Purified anti-mo-CD96 (2.66 mg/ml, Clone: 3.3, Part #: 93137, Lot #B231145) was obtained from BioLegend.

Animals and Husbandry:

Female Envigo C57BL/6 mice (C57BL/6NHsd) were used in this study. They were 6-7 weeks old on Day 1 of the experiment. The animals were fed irradiated Harlan 2918.15 Rodent Diet and water ad libitum. Animals were housed in Innovive disposable ventilated caging with corn cob bedding inside Biobubble® Clean Rooms that provide H.E.P.A filtered air into the bubble environment at 100 complete air changes per hour. All treatments and body weight determinations were carried out in the bubble environment. The environment was controlled to a temperature range of 70°±2° F. and a humidity range of 30-70%. All procedures carried out in this experiment were conducted in compliance with all the laws, regulations and guidelines of the National Institutes of Health (NIH) and with the approval of Molecular Imaging, Inc.'s Animal Care and Use Committee. Molecular Imaging, Inc. is an AAALAC accredited facility.

Cell Preparation and Implantation:

B16F10 cells were obtained from ATCC and grown in Dulbecco's Modified Eagle Medium (DMEM) which was supplemented with 10% non-heat-inactivated Fetal Bovine Serum (FBS) and 1% 100× Penicillin/Streptomycin/L-Glutamine (PSG). The growth environment was maintained in an incubator with a 5% CO2 atmosphere at 37° C. When expansion was complete, the cells (passage 10) were trypsinized using 0.25% trypsin-EDTA solution. The pre-implantation cell viability was 95%. Test animals were implanted intravenously, via the lateral tail vein on Day 0 with $2.0 \times 10^5$ cells in 0.2 mL using a 27-gauge needle and syringe.

Sampling and Lung Metastasis Counting:

Whole blood and lungs were sampled from all mice on Day 14 after implantation. All mice were euthanized via over exposure to carbon dioxide. Whole blood was collected via cardiac puncture. Following collection, 60% of the blood collected was added K2EDTA coated Microtainers® and inverted several times to ensure thorough mixing of the blood and EDTA. The same volume (1:1 ratio) of Streck Cell Preservative™ was added to the tube. Lungs were excised, placed in a Petri dish and laid flat. Lungs were photographed on both the dorsal and ventral surfaces and discarded. Lung metastases were counted using Image J software (see e.g., Rasband, W. S., ImageJ, U.S. National Institutes of Health, Bethesda, Md., USA; available at: imagej.nih.gov/ij/, 1997-2016). Both ventral and dorsal surfaces were counted. All metastases that were ranging from a light grey to black colors were counted. In case of merged nodules, the best effort was made to distinguish the metastases and count as accurately as possible. If there were too many nodules leading to black regions, the tissue was noted as "Too many to count" (TMTC). Raw counts were then summed (ventral+dorsal surfaces) by animal and averaged by group. All "TMTC" lungs and lung without any metastases to count (0) were excluded from the final average calculation.

Assessment of Side-Effects:

All animals were observed for clinical signs at least once daily. Animals were weighed on each day of treatment. Individual body weights were recorded 3 times weekly. Treatment-related weight loss in excess of 20% is generally considered unacceptably toxic. In this report, a dosage level is described as tolerated if treatment-related weight loss (during and two weeks after treatment) is <20%.

Results—B16F10 i.v. Lung Metastasis Model

As shown in FIG. 9, the anti-PD-1+anti-CD96 combination treatment decreased the number of lung metastases significantly compared to isotype control antibody treatment when evaluated 14 days after implantation (p-0.011 by Mann-Whitney U test, comparing isotype control vs. anti-PD-1+anti-CD96).

Example 9: Design of a Bispecific Anti-CD96 Antibody

A bispecific antibody targeting both CD96 and another antigen target on NK or T cells, such as PD-1, TIGIT, LAG3, PVRIG, or KIR could also be used as an anti-tumor treatment. It is contemplated that a bispecific antibody comprising an anti-CD96 binding component of the present disclosure and another anti-tumor target binding component can be prepared with a common-light-chain manufacturing-friendly approach.

Example 10: Anti-CD96 Antibody Increases IFNγ and IL-2 Secretion from Patient Derived PBMCs Cancer patient PBMC assay: Functional activity of the anti-CD96 antibodies was tested on primary cancer patient PBMCs. Primary cancer patient PBMCs (Discovery Life Sciences) were incubated with antibodies in complete media containing 0.1 μg/mL anti-CD3 Ab (commercially available from Thermo Fisher) and 1 μg/mL anti-CD28 Ab (commercially available from Thermo Fisher) in 384 well plates for 72 hours at 37° C. IFNγ and IL-2 levels in the supernatant were determined by ELISA (kit commercially available from Thermo Fisher).

Figure 10A:
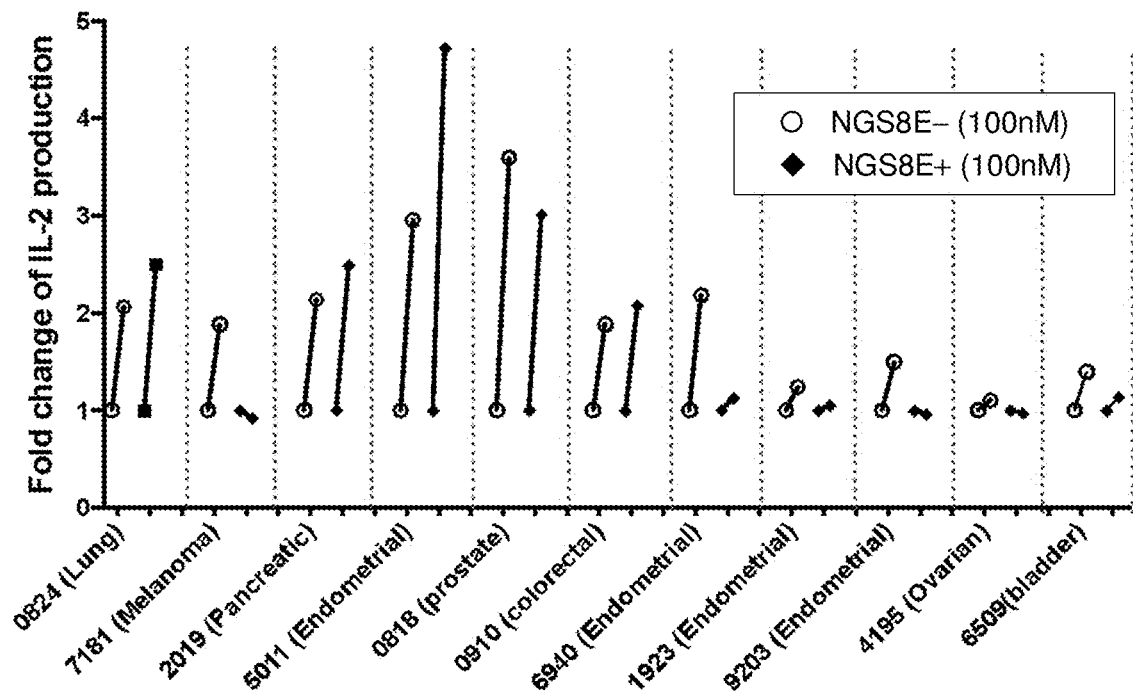
FIG. 10A and FIG. 10B depict the change in cytokine release after treatment of primary PBMC samples from patients with various cancers with anti-CD96 antibody, or an effectorless variant thereof.
Figure 10B:
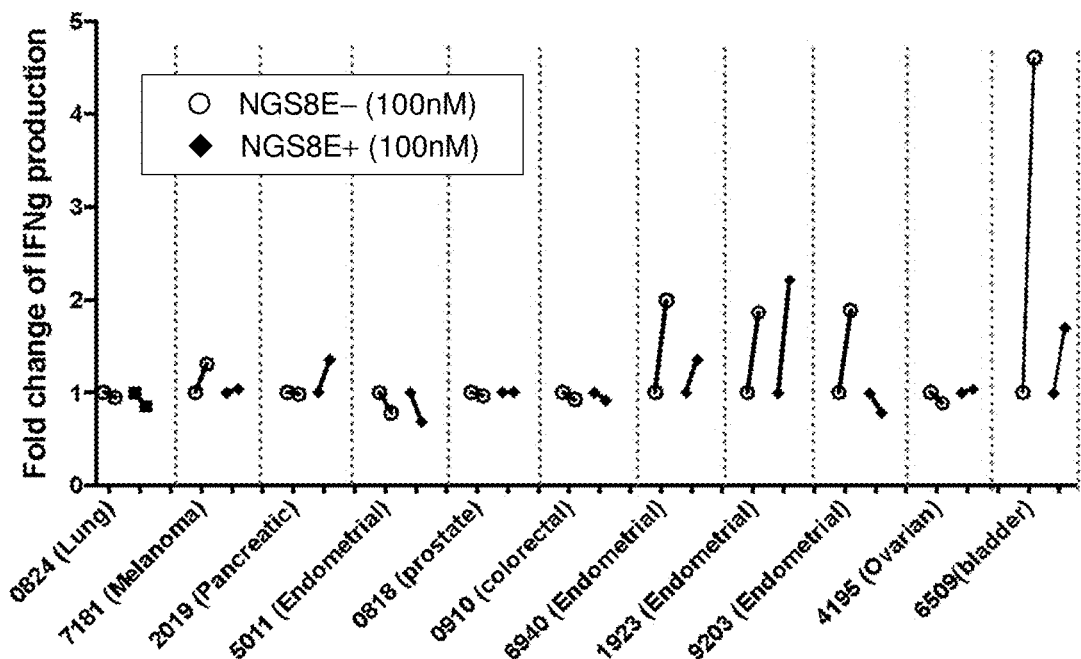

As shown in FIG. 10A, anti-CD96 antibody NGS8 increased PBMC secretion of IL-2 in samples derived from patients having various different cancer types. Specifically, FIG. 10A shows the fold change in IL-2 production, normalized to isotype control, in samples treated with 100 nM of either effector minus NGS8 ("NGS8E-"; human IgG1 with N297G mutation) or effector-containing NGS8 ("NGS8E+"; human IgG1 wildtype Fc). The first (left) marker of each data pair indicates the isotype control and the second (right) marker, linked by a line, indicates the fold-change from isotype control following treatment with the specified antibody. FIG. 10B shows the fold change in IFNγ production, normalized to isotype control, in samples in samples treated with 100 nM of either effector minus NGS8 (NGS8E-) or effector-containing NGS8 (NGS8E+) as assessed in the cancer patient PBMC assay. As above, the first (left) marker of each data pair indicates the isotype control and the second (right) marker, linked by a line, indicates the fold-change from isotype control following treatment with the specified antibody. NGS8E- antibody treatment significantly increased IFNγ production in four of eleven patient PBMC samples. Collectively, FIG. 10A and FIG. 10B demonstrate that treatment with the anti-CD96 antibody stimulates cytokine secretion, resulting in increases in IL-2 and/or IFNγ, in PBMC samples obtained from subjects with various different cancers.

Figure 11A:
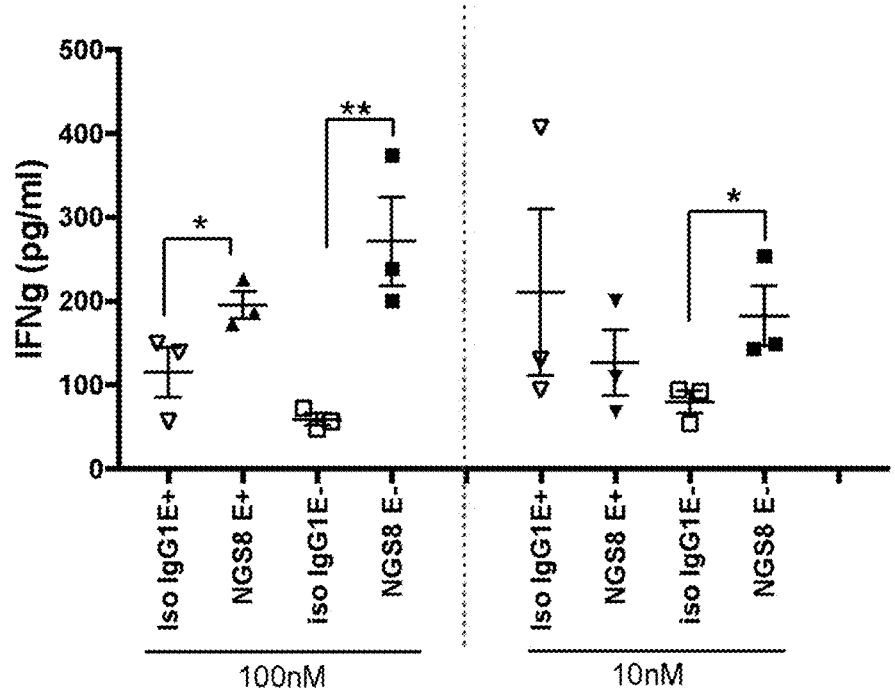
FIG. 11A and FIG. 11B depict the stimulation of cytokine secretion in primary PBMC samples collected from a bladder cancer patient and subsequently treated with anti-CD96 antibody, or an effectorless variant thereof.
Figure 11B:
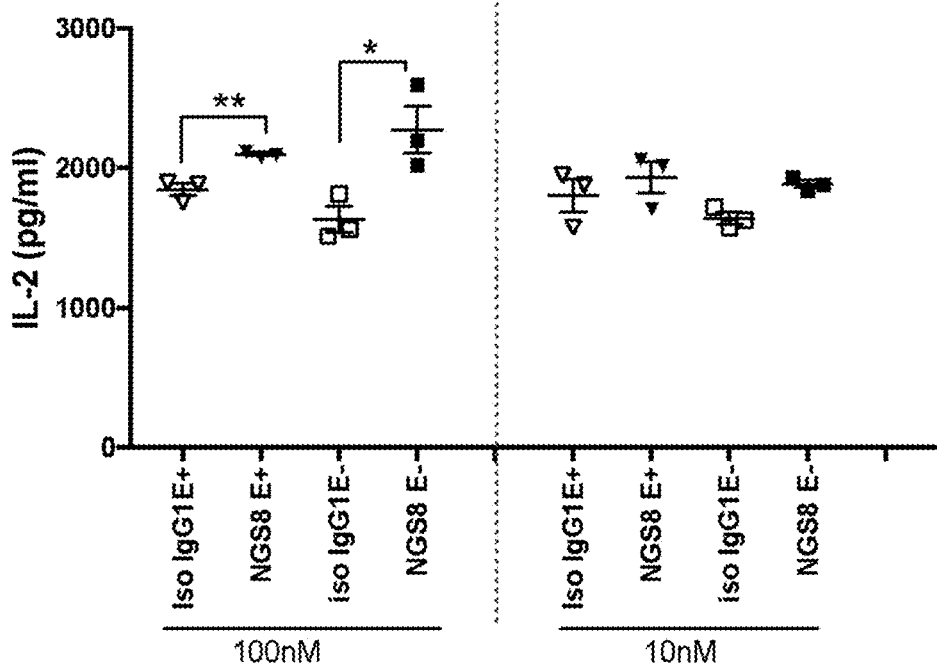

FIG. 11A and FIG. 11B further demonstrate stimulation of cytokine secretion in primary PBMCs collected from a bladder cancer (transitional cell carcinoma, NOS) patient. Specifically, the measured levels of IFNγ ("IFNg"; FIG. 11A) and IL-2 (FIG. 11B) are shown after treatment with 100 nM or 10 nM NGS8E+ or NGS8E−, relative to treatment with corresponding effector-containing (Iso IgG1E+) or effector-minus (Iso IgG1E−) isotype controls. Statistically significant increases (indicated with asterisks) in IFNγ were seen after 100 nM and 10 nM treatments and in IL-2 after the 100 nM treatment. These results further demonstrate the stimulation of cytokine secretion in cancer patient derived PBMCs following treatment with anti-CD96 antibodies described herein.

Example 11: Mapping of Anti-CD96 Antibody Binding Sites Via Site-Directed Mutagenesis Site-directed mutagenesis, mutating hCD96 residues to corresponding cyCD96 residues in the D1 domain, was performed to map the binding sites of anti-CD96 antibodies. The highly homologous human and cynomolgus monkey CD96 amino acid sequences were aligned and the human residues at the indicated positions (see Table 25) were mutated to the corresponding residue in the cyno protein to generate the "human-to-cyno" mutations. Binding to cells transfected to express human-to-cyno mutated forms of CD96 was assessed and the resulting effects on binding of the indicated antibody are shown in the following table.

TABLE 25

Effects on antibody binding of site-directed mutagenesis

| CD96 Residue Position(s) | Human Residue(s) | Cyno Residue(s) | Effect on binding of 9H4 | Effect on binding of mAb1 | Effect on binding of 16D9 or 1G8 |
| --- | --- | --- | --- | --- | --- |
| 49-50 | TV | AK | No effect | Lost binding | Lost binding |
| 53 | F | L | No effect | No effect | No effect |
| 63 | N | D | | No effect | No effect |
| 65 | I | A | | No effect | No effect |
| 70 | V | L | No effect | No effect | No effect |
| 78 | Y | H | Lost binding | No effect | No effect |
| 83 | R | S | | No effect | No effect |
| 93 | E | Q | No effect | No effect | No effect |
| 110 | C | S | | | |
| 121 | V | T | Increased binding | Slightly increased binding | Slightly increased binding |

Example 12: Secondary Binding of NGS8 and 10G1 Antibodies to CD226

In order to assess the generated antibodies for secondary binding to CD226, sequences encoding human CD226 ("hu-CD226") (SEQ ID NO: 482) and cyno CD226 ("cy-CD226") (SEQ ID NO: 483) (see Table 26 and Sequence Listing) were each cloned into pcDNA3.1 expression vector and Expi293 cells were separately transfected with plasmid containing either the hu-CD226 or cy-CD226 coding sequence. Starting concentrations of 1 μM and corresponding 3× serial dilutions of each antibody, NGS8, 10G1, and MABT398 (CD226 positive control, EMD Millipore, Burlington, Mass., USA), were prepared for staining. Secondary antibodies employed included goat anti-mouse F(ab)2-PE (Invitrogen, Carlsbad, Calif., USA) and goat anti-human F(ab)2-PE (Jackson ImmunoResearch, West Grove, Pa., USA).

TABLE 26

| encoded CD226 amino acid sequences used in assay: | |
| --- | --- |
| huCD226 (NP_006557.2) | MDYPTLLLALLHVYRALCEEVLWHTSVPFAENMSLECV YPSMGILTQVEWFKIGTQQDSIAIFSPTHGMVIRKPYA ERVYFLNSTMASNNMTLFFRNASEDDVGYYSCSLYTYP QGTWQKVIQVVQSDSFEAAVPSNSHIVSEPGKNVTLTC QPQMTWPVQAVRWEKIQPRQIDLLTYCNLVHGRNFTSK FPRQIVSNCSHGRWSVIVIPDVTVSDSGLYRCYLQASA GENETFVMRLTVAEGKTDNQYTLFVAGGTVLLLLFVIS ITTIIVIFLNRRRRRERRDLFTESWDTQKAPNNYRSPI STSQPTNQSMDDTREDIYVNYPTFSRRPKTRVDYKDDD DK(SEQ ID NO: 482; signal sequence underlined, flag tag in bold) |
| cyCD226 (XP_005586537.1) | MDYPTLLLALLHVYRALCEEVLWHTSVPFAENMSLECV YPSVGILTQVEWFKIGTEKDSIAIFSPTHGMVIRKPYA ERVYFLNSTMASNNMTLFFRNASEDDVGYYSCSLYTYP QGTWQKVIQVVQSDGFEAAVPPNSHIVSEPGKNITLTC QPQMTWPVQEVRWEKVQPHQIDLLTYCDLVHGRNFTSK FPRQIVSNCSHGSWSFIVVPDVTASDSGLYRCHLQASA GENETFVMRLTVAEGQTDNQYTRFVTGGTVLLLLFVIS ITTIIVIFLNRRRRRERNDLYTESWDTQKAPKNYRSPI SANQPTNQSMDDTREDIYVNYPTFSRRPKTRVDYKDDD DK(SEQ ID NO: 483; signal sequence underlined, flag tag in bold) |

Figure 12A:
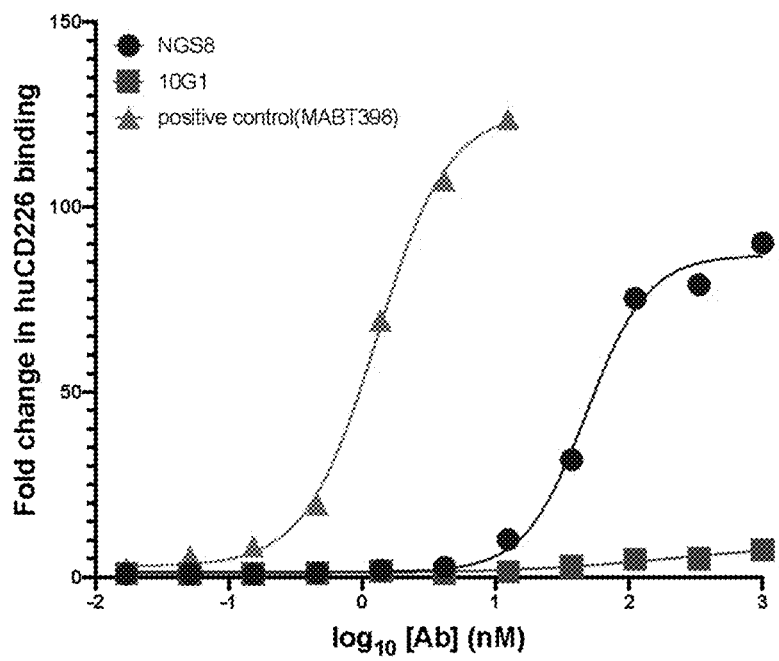
FIG. 12A and FIG. 12B depict the binding of anti-CD96 antibodies to CD226 expressed on cells transfected with CD226-encoding expression constructs.
Figure 12B:
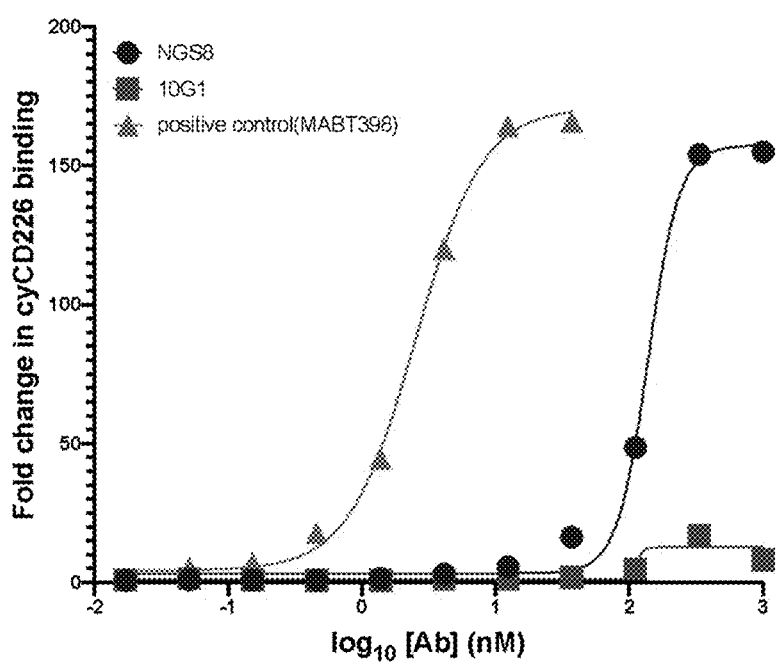

Samples, each containing one million transfected cells, were stained with primary antibody for 1 hr and secondary antibody for 30 min at 4° C. with agitation. Stained cells were washed in FACS buffer (1% BSA in PBS), fixed in 4% freshly prepared paraformaldehyde, and analyzed by flow cytometry. Ten thousand events were collected for each sample and curves, showing the fold change in CD226 binding, were separately plotted for hu-CD226 (FIG. 12A) and cy-CD226 (FIG. 12B) expressing cells. Calculated $EC_{50}$ values are provided in the following table.

TABLE 27

FACS binding of antibodies to hu-CD226 and cy-CD226

| mAb | hu-CD226 EC50(nM) | cy-CD226 EC50(nM) |
| --- | --- | --- |
| NGS8 | 48.13 | 143 |
| 10G1 | 232.1 | N.D. |
| MABT398 | 1.289 | 2.54 |

To determine the binding affinity to hu-CD226 and cy-CD226 of mAb1.v7.NGS8, h10G1, hCD155 and anti-hCD226 antibody DX11 (Abcam, cat #Ab33397), SPR measurement with a BIACORE™ 8K instrument was performed. Briefly, a 1:4 dilution of Biotin CAPture Reagent (GE Healthcare) into HBS-EP buffer (0.01 M HEPES pH 7.4, 0.15 M NaCl, 3 mM EDTA, 0.005% Surfactant P20) was applied to the chip at 2 μL/min flow rate. For the kinetics measurements, 5 μg/ml of biotinylated hu-CD226 His tag (Sino biological, cat #10565-H08H) and cy-CD226 His tag (Arco biosystems, cat #DN1-C52H9) was captured at 10 μL/min to achieve ~50 response units in the second flow cell (FC2). FC1 was kept as a reference. Next, 3-fold serial dilutions of IgG in HBS-P buffer (0.01 M HEPES pH 7.4, 0.15 M NaCl, 0.005% surfactant P20) from low (1.3 nM) to high (1000 nM) concentration were injected (flow rate: 30 μL/min) at 25° C. The sensorgram was recorded and subject to reference and buffer subtraction before evaluating by BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) value was calculated as the ratio of $k_{off}/k_{on}$. Steady state fitting analysis, using manufacturer's instrument settings (Biacore, Inc., Uppsala, Sweden), was used in some instances due to fast association/dissociation rate. The BIACORE® determined binding affinity values are summarized in Table 28.

TABLE 28

Binding affinity of IgGs or receptor binding to hu-CD226 and cy-CD226

| IgG | hu-CD226 KD (nM) | cy-CD226 $K_D$ (nM) |
|---|---|---|
| mAb1.v7.NGS8 | 631* | 84.8* |
| h10G1 | No binding | No binding |
| hCD155 | 161* | 67.5* |
| DX11 | 6.9 | 0.02 |

*steady state fitting

The above demonstrates that NGS8 binds to both hu-CD226 and cy-CD226, with SPR measured affinities in the 1 μM to 50 nM range. Thus, in addition to binding CD96 with at least nanomolar and even subnanomolar affinities, in some embodiments, anti-CD96 antibodies of the present disclosure also have demonstrated secondary affinity, e.g., of 700 nM or less, for CD226 which, like CD96, interacts with CD155 expressed on another cell.

Notwithstanding the appended claims, the disclosure set forth herein is also defined by the following clauses, which may be beneficial alone or in combination, with one or more other causes or embodiments. Without limiting the foregoing description, certain non-limiting clauses of the disclosure numbered as below are provided, wherein each of the individually numbered clauses may be used or combined with any of the preceding or following clauses. Thus, this is intended to provide support for all such combinations and is not necessarily limited to specific combinations explicitly provided below:

1. An anti-CD96 antibody comprising: (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3); wherein:

(a) HVR-L1 comprises an amino acid sequence selected from KASQNVGTAIV (SEQ ID NO: 13), KSSQSLLDSDGKTYLN (SEQ ID NO: 17), RVSQDISFWLS (SEQ ID NO: 21), RASSNVKYMY (SEQ ID NO: 25), KASQSVTFADTGLMH (SEQ ID NO: 29), RSSTGAVTTSNYAN (SEQ ID NO: 33), RASQDIYRNLH (SEQ ID NO: 37), or RASQXIXXNXH (SEQ ID NO: 308), wherein X at position 5 is D, A, E, G, H, K, N, P, Q, S, or T; X at position 7 is Y, or F; X at position 8 is R, K, or Q; X at position 10 is L, I, M, or V;

(b) HVR-L2 comprises an amino acid sequence selected from SASTRYT (SEQ ID NO: 14), LVSKLDS (SEQ ID NO: 18), KASNLHT (SEQ ID NO: 22), YTSNLAS (SEQ ID NO: 26), RASNLEV (SEQ ID NO: 30), GTNNRAP (SEQ ID NO: 34), HASDSIS (SEQ ID NO: 38), or HAXXXXS (SEQ ID NO: 325), wherein X at position 3 is S, or E; X at position 4 is D, E, K, or Q; X at position 5 is S, H, L, R, or V; X at position 6 is I, or V;

(c) HVR-L3 comprises an amino acid sequence selected from QQYSSSPLT (SEQ ID NO: 15), LQATHSPQT (SEQ ID NO: 19), LQSQSYPYT (SEQ ID NO: 23), QQFTSSPLT (SEQ ID NO: 27), QQSREYPWT (SEQ ID NO: 31), SLWYGSHWV (SEQ ID NO: 35), LQGYSMPYT (SEQ ID NO: 39), or XQGYXMPXT (SEQ ID NO: 335), wherein X at position 1 is L, G, M, or Q; X at position 5 is S, A, E, Q, or V; X at position 8 is Y, or F;

(d) HVR-H1 comprises an amino acid sequence selected from TNNWMH (SEQ ID NO: 41), GYGVT (SEQ ID NO: 45), TDYYIN (SEQ ID NO: 49), NDYYIN (SEQ ID NO: 53), SDYYMY (SEQ ID NO: 57), TNYGIH (SEQ ID NO: 61), TTYGMS (SEQ ID NO: 65), XNXXXH (SEQ ID NO: 72), wherein X at position 1 is T, A, D, E, G, H, K, N, Q, R, S, V, W, or Y; X at position 3 is N, A, F, G, H, M, R, S, V, or Y; X at position 4 is W, or F; X at position 5 is M, A, D, E, F, G, L, N, Q, R, S, T, V, or W, or XXXGXS (SEQ ID NO: 344), wherein X at position 1 is T, A, D, E, G, H, K, M, N, Q, R, or S; X at position 2 is T, D, E, G, H, N, Q, or S; X at position 3 is Y, F, M, or Q; X at position 5 is M, I, L, or V;

(e) HVR-H2 comprises an amino acid sequence selected from MIHPNSGITNINE (SEQ ID NO: 42), EIYPGTVITYYNA (SEQ ID NO: 46), WIFPGTEGIYYNE (SEQ ID NO: 50), WIFPGRIITYYNE (SEQ ID NO: 54), AISDDGTYTYYPD (SEQ ID NO: 58), IIWAGGSTNYNSA (SEQ ID NO: 62), WINTDSGVPTYAD (SEQ ID NO: 66), XXHXXXXXXXXNX (SEQ ID NO: 107), wherein X at position 1 is M or F; X at position 2 is I, L, M, or V; X at position 4 is P, A, D, E, F, G, H, I, K, L, M, N, Q, R, S, T, V, or W; X at position 5 is N, A, D, E, F, G, H, I, K, L, M, Q, R, S, T, V, W, or Y; X at position 6 is S, A, G, T, or V; X at position 7 is G, A, or S; X at position 8 is I, A, or V; X at position 9 is T, A, D, E, G, H, I, K, L, M, N, Q, R, S, V, W, or Y; X at position 10 is N, A, M, or S; X at position 11 is I, F, G, H, K, L, M, N, Q, R, S, T, V, W, or Y; X at position 13 is E, A, D, G, H, K, L, M, N, P, Q, R, S, T, V, W, or Y, or WINTXXGVPTYAD (SEQ ID NO: 369), wherein X at position 5 is D, or E; X at position 6 is S, or T;

(f) HVR-H3 comprises an amino acid sequence selected from RSDGTYEGYFDY (SEQ ID NO: 43), ARGLGRAMDY (SEQ ID NO: 47), AREGDYRYYSPLGY (SEQ ID NO: 51), ARGVGEGFDY (SEQ ID NO: 55), AKAGSYDYFDV (SEQ ID NO: 59), ARVSMMGFAY (SEQ ID NO: 63), ARNIYYGWGNFDY (SEQ ID NO: 67), RXDXXXXXY (SEQ ID NO: 203), wherein X at position 2 is S, A, F, G, I, L, M, N, R, T, V, W, or Y; X at position 4 is G, or W; X at position 5 is T, D, E, F, H, I, K, L, M, N, Q, V, W, or Y; X at position 6 is Y, D, F, H, N, R, or W; X at position 7 is E, D, G, H, K, M, N, Q, R, V, or Y; X at position 8 is G, K, R, S, or T, or ARXIYYGWGXFDY (SEQ ID NO: 372), wherein X at position 3 is N, or M; X at position 10 is N, F, H, or Y.

2. The antibody of clause 1, wherein: (a) HVR-L1 comprises the amino acid sequence of KASQNVGTAIV (SEQ ID NO: 13); (b) HVR-L2 comprises the amino acid sequence of SASTRYT (SEQ ID NO: 14); (c) HVR-L3 comprises the amino acid sequence of QQYSSSPLT (SEQ ID NO: 15).

3. The antibody of any one of clauses 1-2, wherein:

(a) HVR-H1 comprises the amino acid sequence of XNXXXH (SEQ ID NO: 72), wherein X at position 1 is T, A, D, E, G, H, K, N, Q, R, S, V, W, or Y; X at position 3 is N, A, F, G, H, M, R, S, V, or Y; X at position 4 is W, or F; X at position 5 is M, A, D, E, F, G, L, N, Q, R, S, T, V, or W;

(b) HVR-H2 comprises the amino acid sequence of XXHXXXXXXXXNX (SEQ ID NO: 107), wherein X at position 1 is M or F; X at position 2 is I, L, M, or V; X at position 4 is P, A, D, E, F, G, H, I, K, L, M, N, Q, R, S, T, V, or W; X at position 5 is N, A, D, E, F, G, H, I, K, L, M, Q, R, S, T, V, W, or Y; X at position 6 is S, A, G, T, or V; X at position 7 is G, A, or S; X at position 8 is I, A, or V; X at position 9 is T, A, D, E, G, H, I, K, L, M, N, Q, R, S, V, W, or Y; X at position 10 is N, A, M, or S; X at position 11 is I, F, G, H, K, L, M, N, Q, R, S, T, V, W, or Y; X at position 13 is E, A, D, G, H, K, L, M, N, P, Q, R, S, T, V, W, or Y;

(c) HVR-H3 comprises the amino acid sequence of RXDXXXXXY (SEQ ID NO: 203), wherein X at position 2 is S, A, F, G, I, L, M, N, R, T, V, W, or Y; X at position 4 is G, or W; X at position 5 is T, D, E, F, H, I, K, L, M, N, Q, V, W, or Y; X at position 6 is Y, D, F, H, N, R, or W; X at position 7 is E, D, G, H, K, M, N, Q, R, V, or Y; X at position 8 is G, K, R, S, or T.

4. The antibody of any one of clauses 1-3, wherein: (a) HVR-H1 comprises an amino acid sequence selected from SEQ ID NOs: 41, 73-106; (b) HVR-H2 comprises an amino acid sequence selected from SEQ ID NOs: 42, 108-202; (c) HVR-H3 comprises an amino acid sequence selected from SEQ ID NOs: 43, 204-249.

5. The antibody of any one of clauses 1-4, wherein: (a) HVR-L1 comprises the amino acid sequence of SEQ ID NO: 13; (b) HVR-L2 comprises the amino acid sequence of SEQ ID NO: 14; (c) HVR-L3 comprises the amino acid sequence of SEQ ID NO: 15; (d) HVR-H1 comprises an amino acid sequence selected from SEQ ID NOs: 41, 73-106; (e) HVR-H2 comprises an amino acid sequence selected from SEQ ID NOs: 42, 108-202; (f) HVR-H3 comprises an amino acid sequence selected from SEQ ID NOs: 43, 204-249.

6. The antibody of any one of clauses 1-5, wherein: (a) HVR-L1 comprises the amino acid sequence of SEQ ID NO: 13; (b) HVR-L2 comprises the amino acid sequence of SEQ ID NO: 14; (c) HVR-L3 comprises the amino acid sequence of SEQ ID NO: 15; (d) HVR-H1 comprises an amino acid sequence selected from SEQ ID NOs: 41, 83, 91, 92, 94, 95, 102; (e) HVR-H2 comprises an amino acid sequence selected from SEQ ID NOs: 42, 108, 112, 113, 116, 118, 122, 125, 138, 178, 181, 190, 197; (f) HVR-H3 comprises an amino acid sequence selected from SEQ ID NOs: 43, 208, 219, 221, 223, 227.

7. The antibody of any one of clauses 1-6, wherein: (a) HVR-L1 comprises the amino acid sequence of SEQ ID NO: 13; (b) HVR-L2 comprises the amino acid sequence of SEQ ID NO: 14; (c) HVR-L3 comprises the amino acid sequence of SEQ ID NO: 15; (d) HVR-H1 comprises an amino acid sequence selected from SEQ ID NOs: 41, or 95; (e) HVR-H2 comprises an amino acid sequence selected from SEQ ID NOs: 42, 108, 112, 113, 190, or 197; (f) HVR-H3 comprises an amino acid sequence selected from SEQ ID NOs: 43, 221, or 227.

8. The antibody of clause 1, wherein:

(a) HVR-L1 comprises the amino acid sequence of RASQXIXXNXH (SEQ ID NO: 308), wherein X at position 5 is D, A, E, G, H, K, N, P, Q, S, or T; X at position 7 is Y, or F; X at position 8 is R, K, or Q; X at position 10 is L, I, M, or V;

(b) HVR-L2 comprises the amino acid sequence of HAXXXXS (SEQ ID NO: 325), wherein X at position 3 is S, or E; X at position 4 is D, E, K, or Q; X at position 5 is S, H, L, R, or V; X at position 6 is I, or V;

(c) HVR-L3 comprises the amino acid sequence of XQGYXMPXT (SEQ ID NO: 335), wherein X at position 1 is L, G, M, or Q; X at position 5 is S, A, E, Q, or V; X at position 8 is Y, or F.

9. The antibody of any one of clauses 1 or 8, wherein: (a) HVR-L1 comprises an amino acid sequence selected from SEQ ID NOs: 37, 309-324; (b) HVR-L2 comprises an amino acid sequence selected from SEQ ID NOs: 38, 326-334; (c) HVR-L3 comprises an amino acid sequence selected from SEQ ID NOs: 39, 336-343.

10. The antibody of any one of clauses 1, or 8-9, wherein:

(a) HVR-H1 comprises the amino acid sequence of or XXXGXS (SEQ ID NO: 344), wherein X at position 1 is T, A, D, E, G, H, K, M, N, Q, R, or S; X at position 2 is T, D, E, G, H, N, Q, or S; X at position 3 is Y, F, M, or Q; X at position 5 is M, I, L, or V;

(b) HVR-H2 comprises the amino acid sequence of WIN-TXXGVPTYAD (SEQ ID NO: 369), wherein X at position 5 is D, or E; X at position 6 is S, or T;

(c) HVR-H3 comprises the amino acid sequence of XIYYGWGXFDY (SEQ ID NO: 372), wherein X at position 1 is N, or M; X at position 8 is N, F, H, or Y.

11. The antibody of any one of clauses 1, 8-10, wherein: (a) HVR-H1 comprises an amino acid sequence selected from SEQ ID NOs: 65, 345-368; (b) HVR-H2 comprises an amino acid sequence selected from SEQ ID NOs: 66, 370-371; (c) HVR-H3 comprises an amino acid sequence selected from SEQ ID NOs: 67, 373-376.

12. The antibody of any one of clauses 1, 8-11, wherein: (a) HVR-L1 comprises the amino acid sequence of SEQ ID NO: 37, 309-324; (b) HVR-L2 comprises the amino acid sequence of SEQ ID NO: 38, 326-334; (c) HVR-L3 comprises the amino acid sequence of SEQ ID NO: 39, 336-343; (d) HVR-H1 comprises an amino acid sequence selected from SEQ ID NOs: 65, 345-368; (e) HVR-H2 comprises an amino acid sequence selected from SEQ ID NOs: 66, 370-371; (f) HVR-H3 comprises an amino acid sequence selected from SEQ ID NOs: 67, 373-376.

13. The antibody of any one of clauses 1-12, wherein the antibody comprises: a first light chain framework region (FR-L1) comprising an amino acid sequence of SEQ ID NO: 276; a second light chain framework region (FR-L2) comprising an amino acid sequence of SEQ ID NO: 277; a third light chain framework region (FR-L3) comprising an amino acid sequence of SEQ ID NO: 278; and a fourth light chain framework region (FR-L4) comprising an amino acid sequence of SEQ ID NO: 279.

14. The antibody of any one of clauses 1-13, wherein the antibody comprises: a first heavy chain framework region (FR-H1) comprising an amino acid sequence of SEQ ID NO: 292; a second heavy chain framework region (FR-H2) comprising an amino acid sequence of SEQ ID NO: 293; a third heavy chain framework region (FR-H3) comprising an amino acid sequence of SEQ ID NO: 294; and a fourth heavy chain framework region (FR-H4) comprising an amino acid sequence of SEQ ID NO: 295.

15. The antibody of any one of clauses 1-12, wherein the antibody comprises: a first light chain framework region (FR-L1) comprising an amino acid sequence of SEQ ID NO: 280; a second light chain framework region (FR-L2) comprising an amino acid sequence of SEQ ID NO: 281; a third light chain framework region (FR-L3) comprising an amino acid sequence of SEQ ID NO: 282; and a fourth light chain framework region (FR-L4) comprising an amino acid sequence of SEQ ID NO: 283;

16. The antibody of any one of clauses 1-12, or 15 wherein the antibody comprises: a first heavy chain framework region (FR-H1) comprising an amino acid sequence of SEQ ID NO: 300; a second heavy chain framework region (FR-H2) comprising an amino acid sequence of SEQ ID NO: 301; a third heavy chain framework region (FR-H3) comprising an amino acid sequence of SEQ ID NO: 302; and a fourth heavy chain framework region (FR-H4) comprising an amino acid of SEQ ID NO: 303.

17. The antibody of any one of clauses 1-12, wherein the antibody comprises: a first light chain framework region (FR-L1) comprising an amino acid sequence of SEQ ID NO: 284; a second light chain framework region (FR-L2) comprising an amino acid sequence of SEQ ID NO: 285; a third light chain framework region (FR-L3) comprising an amino acid sequence of SEQ ID NO: 286; and a fourth light chain framework region (FR-L4) comprising an amino acid sequence of SEQ ID NO: 287.

18. The antibody of any one of clauses 1-12, or 17 wherein the antibody comprises: a first heavy chain framework region (FR-H1) comprising an amino acid sequence of SEQ ID NO: 296; a second heavy chain framework region (FR-H2) comprising an amino acid sequence of SEQ ID NO: 297; a third heavy chain framework region (FR-H3) comprising an amino acid sequence of SEQ ID NO: 298; and a fourth heavy chain framework region (FR-H4) comprising an amino acid sequence of SEQ ID NO: 299.

19. The antibody of any one of clauses 1-12, wherein the antibody comprises: a first light chain framework region (FR-L1) comprising an amino acid sequence of SEQ ID NO: 288; a second light chain framework region (FR-L2) comprising an amino acid sequence of SEQ ID NO: 289; a third light chain framework region (FR-L3) comprising an amino acid sequence of SEQ ID NO: 290; and a fourth light chain framework region (FR-L4) comprising an amino acid sequence of SEQ ID NO: 291;

20. The antibody of any one of clauses 1-12, or 19 wherein the antibody comprises: a first heavy chain framework region (FR-H1) comprising an amino acid sequence of SEQ ID NO: 304; a second heavy chain framework region (FR-H2) comprising an amino acid sequence of SEQ ID NO: 305; a third heavy chain framework region (FR-H3) comprising an amino acid sequence of SEQ ID NO: 306; and a fourth heavy chain framework region (FR-H4) comprising an amino acid of SEQ ID NO: 307.

21. The antibody of any one of clauses 1-20, wherein the antibody comprises a light chain variable domain ($V_L$) amino acid sequence having at least 90% identity to a sequence selected from SEQ ID NO: 12, 16, 20, 24, 28, 32, or 36; and/or a heavy chain variable domain ($V_H$) amino acid sequence having at least 90% identity to a sequence selected from SEQ ID NO: 40, 44, 48, 52, 56, 60, or 64.

22. The antibody of clause 21, wherein the antibody comprises a light chain variable domain ($V_L$) amino acid sequence having at least 90% identity to SEQ ID NO: 12, and/or a heavy chain variable domain ($V_H$) amino acid sequence having at least 90% identity to SEQ ID NO: 40.

23. The antibody of clause 21, wherein the antibody comprises a light chain variable domain ($V_L$) amino acid sequence having at least 90% identity to SEQ ID NO: 36, and/or a heavy chain variable domain ($V_H$) amino acid sequence having at least 90% identity to SEQ ID NO: 64.

24. The antibody of any one of clauses 1-20, wherein the antibody comprises a light chain (LC) amino acid sequence having at least 90% identity to a sequence selected from SEQ ID NO: 440, 441, 442, 443, 444, 445, or 446; and/or a heavy chain (HC) amino acid sequence having at least 90% identity to a sequence selected from SEQ ID NO: 447, 448, 449, 450, 451, 452, 453, 484, 485, 486, 487, 488, 489, or 490.

25. The antibody of clause 24, wherein the antibody comprises a light chain (LC) amino acid sequence having at least 90% identity to SEQ ID NO: 440; and/or a heavy chain (HC) amino acid sequence having at least 90% identity to SEQ ID NO: 447, or 484.

26. The antibody of clause 24, wherein the antibody comprises a light chain (LC) amino acid sequence having at least 90% identity to SEQ ID NO: 446; and/or a heavy chain (HC) amino acid sequence having at least 90% identity to SEQ ID NO: 453, or 490.

27. The antibody of any one of clauses 1-6, wherein the antibody comprises a light chain variable domain ($V_L$) amino acid sequence having at least 90% identity to SEQ ID NO: 68, and/or a heavy chain variable domain ($V_H$) amino acid sequence having at least 90% identity to a sequence selected from SEQ ID NO: 69, 250, 251, 252, 253, 254, 255, 256, 257, 258, 259, 260, 261, 262, 263, 264, 265, 266, 267, 268, 269, 270, 271, 272, 273, 274, 275, 460, 461, 462, 463, or 464.

28. The antibody of clause 27, wherein the antibody comprises a light chain variable domain ($V_L$) amino acid sequence of SEQ ID NO: 68.

29. The antibody of any one of clauses 27 or 28, wherein the antibody comprises a heavy chain variable domain ($V_H$) amino acid sequence selected from SEQ ID NO: 69, 250, 251, 252, 253, 254, 255, 256, 257, 258, 259, 260, 261, 262, 263, 264, 265, 266, 267, 268, 269, 270, 271, 272, 273, 274, or 275.

30. The antibody of clause 27, wherein the antibody comprises:

the light chain variable domain ($V_L$) amino acid sequence of SEQ ID NO: 68, and the heavy chain variable domain ($V_H$) amino acid sequence of SEQ ID NO: 69;

the light chain variable domain ($V_L$) amino acid sequence of SEQ ID NO: 68, and the heavy chain variable domain ($V_H$) amino acid sequence of SEQ ID NO: 250;

the light chain variable domain ($V_L$) amino acid sequence of SEQ ID NO: 68, and the heavy chain variable domain ($V_H$) amino acid sequence of SEQ ID NO: 251;

the light chain variable domain ($V_L$) amino acid sequence of SEQ ID NO: 68, and the heavy chain variable domain ($V_H$) amino acid sequence of SEQ ID NO: 252;

the light chain variable domain ($V_L$) amino acid sequence of SEQ ID NO: 68, and the heavy chain variable domain ($V_H$) amino acid sequence of SEQ ID NO: 253;

the light chain variable domain ($V_L$) amino acid sequence of SEQ ID NO: 68, and the heavy chain variable domain ($V_H$) amino acid sequence of SEQ ID NO: 254;

the light chain variable domain ($V_L$) amino acid sequence of SEQ ID NO: 68, and the heavy chain variable domain ($V_H$) amino acid sequence of SEQ ID NO: 255;

the light chain variable domain ($V_L$) amino acid sequence of SEQ ID NO: 68, and the heavy chain variable domain ($V_H$) amino acid sequence of SEQ ID NO: 256;

the light chain variable domain ($V_L$) amino acid sequence of SEQ ID NO: 68, and the heavy chain variable domain ($V_H$) amino acid sequence of SEQ ID NO: 257;

the light chain variable domain ($V_L$) amino acid sequence of SEQ ID NO: 68, and the heavy chain variable domain ($V_H$) amino acid sequence of SEQ ID NO: 258;

the light chain variable domain ($V_L$) amino acid sequence of SEQ ID NO: 68, and the heavy chain variable domain ($V_H$) amino acid sequence of SEQ ID NO: 259;

the light chain variable domain (V$_L$) amino acid sequence of SEQ ID NO: 68, and the heavy chain variable domain (V$_H$) amino acid sequence of SEQ ID NO: 260;

the light chain variable domain (V$_L$) amino acid sequence of SEQ ID NO: 68, and the heavy chain variable domain (V$_H$) amino acid sequence of SEQ ID NO: 261;

the light chain variable domain (V$_L$) amino acid sequence of SEQ ID NO: 68, and the heavy chain variable domain (V$_H$) amino acid sequence of SEQ ID NO: 262;

the light chain variable domain (V$_L$) amino acid sequence of SEQ ID NO: 68, and the heavy chain variable domain (V$_H$) amino acid sequence of SEQ ID NO: 263;

the light chain variable domain (V$_L$) amino acid sequence of SEQ ID NO: 68, and the heavy chain variable domain (V$_H$) amino acid sequence of SEQ ID NO: 264;

the light chain variable domain (V$_L$) amino acid sequence of SEQ ID NO: 68, and the heavy chain variable domain (V$_H$) amino acid sequence of SEQ ID NO: 265;

the light chain variable domain (V$_L$) amino acid sequence of SEQ ID NO: 68, and the heavy chain variable domain (V$_H$) amino acid sequence of SEQ ID NO: 266;

the light chain variable domain (V$_L$) amino acid sequence of SEQ ID NO: 68, and the heavy chain variable domain (V$_H$) amino acid sequence of SEQ ID NO: 267;

the light chain variable domain (V$_L$) amino acid sequence of SEQ ID NO: 68, and the heavy chain variable domain (V$_H$) amino acid sequence of SEQ ID NO: 268;

the light chain variable domain (V$_L$) amino acid sequence of SEQ ID NO: 68, and the heavy chain variable domain (V$_H$) amino acid sequence of SEQ ID NO: 269;

the light chain variable domain (V$_L$) amino acid sequence of SEQ ID NO: 68, and the heavy chain variable domain (V$_H$) amino acid sequence of SEQ ID NO: 270;

the light chain variable domain (V$_L$) amino acid sequence of SEQ ID NO: 68, and the heavy chain variable domain (V$_H$) amino acid sequence of SEQ ID NO: 271;

the light chain variable domain (V$_L$) amino acid sequence of SEQ ID NO: 68, and the heavy chain variable domain (V$_H$) amino acid sequence of SEQ ID NO: 272;

the light chain variable domain (V$_L$) amino acid sequence of SEQ ID NO: 68, and the heavy chain variable domain (V$_H$) amino acid sequence of SEQ ID NO: 273;

the light chain variable domain (V$_L$) amino acid sequence of SEQ ID NO: 68, and the heavy chain variable domain (V$_H$) amino acid sequence of SEQ ID NO: 274; or the light chain variable domain (V$_L$) amino acid sequence of SEQ ID NO: 68, and the heavy chain variable domain (V$_H$) amino acid sequence of SEQ ID NO: 275.

31. The antibody of any one of clauses 1-6, wherein the antibody comprises a light chain (LC) amino acid sequence having at least 90% identity to SEQ ID NO: 454, and/or a heavy chain (HC) amino acid sequence having at least 90% identity to a sequence selected from SEQ ID NO: 455, 456, 457, 458, 459, 465, 466, 467, 468, 469, 491, 492, 493, 494, 495, 496, 497, 498, 499, or 500.

32. The antibody of clause 31, wherein the antibody comprises:

the light chain (LC) amino acid sequence of SEQ ID NO: 454, and the heavy chain (HC) amino acid sequence of SEQ ID NO: 455;

the light chain (LC) amino acid sequence of SEQ ID NO: 454, and the heavy chain (HC) amino acid sequence of SEQ ID NO: 456;

the light chain (LC) amino acid sequence of SEQ ID NO: 454, and the heavy chain (HC) amino acid sequence of SEQ ID NO: 457;

the light chain (LC) amino acid sequence of SEQ ID NO: 454, and the heavy chain (HC) amino acid sequence of SEQ ID NO: 458;

the light chain (LC) amino acid sequence of SEQ ID NO: 454, and the heavy chain (HC) amino acid sequence of SEQ ID NO: 459;

the light chain (LC) amino acid sequence of SEQ ID NO: 454, and the heavy chain (HC) amino acid sequence of SEQ ID NO: 491;

the light chain (LC) amino acid sequence of SEQ ID NO: 454, and the heavy chain (HC) amino acid sequence of SEQ ID NO: 492;

the light chain (LC) amino acid sequence of SEQ ID NO: 454, and the heavy chain (HC) amino acid sequence of SEQ ID NO: 493;

the light chain (LC) amino acid sequence of SEQ ID NO: 454, and the heavy chain (HC) amino acid sequence of SEQ ID NO: 494; or the light chain (LC) amino acid sequence of SEQ ID NO: 454, and the heavy chain (HC) amino acid sequence of SEQ ID NO: 495.

33. The antibody of any one of clauses 1, 7-12, wherein the antibody comprises a light chain variable domain (V$_L$) amino acid sequence having at least 90% identity to a sequence selected from SEQ ID NO: 70, and 373-409; and/or a heavy chain variable domain (V$_H$) amino acid sequence having at least 90% identity to a sequence selected from SEQ ID NO: 71, and 410-439.

34. The antibody of clause 33, wherein the antibody comprises a light chain variable domain (V$_L$) amino acid sequence selected from SEQ ID NO: 70, and 377-409.

35. The antibody of any one of clauses 33 or 34, wherein the antibody comprises a heavy chain variable domain (V$_H$) amino acid sequence selected from SEQ ID NO: 71, and 410-439.

36. The antibody of any one of clauses 1, 7-12, wherein the antibody comprises a light chain (LC) amino acid sequence having at least 90% identity to SEQ ID NO: 470; and/or a heavy chain (HC) amino acid sequence having at least 90% identity to SEQ ID NO: 471 or 501.

37. The antibody of clause 36, wherein the antibody comprises: the light chain (LC) amino acid sequence of SEQ ID NO: 470, and the heavy chain (HC) amino acid sequence of SEQ ID NO: 471 or 501.

38. An anti-CD96 antibody comprising:

a first light chain hypervariable region (HVR-L1) of SEQ ID NO: 13, a second light chain hypervariable region (HVR-L2) of SEQ ID NO: 14, and a third light chain hypervariable region (HVR-L3) of SEQ ID NO: 15; and/or a first heavy chain hypervariable region (HVR-H1) of SEQ ID NO: 72, a second heavy chain hypervariable region (HVR-H2) of SEQ ID NO: 107, and a third heavy chain hypervariable region (HVR-H3) of SEQ ID NO: 203; or a first light chain hypervariable region (HVR-L1) of SEQ ID NO: 308, a second light chain hypervariable region (HVR-L2) of SEQ ID NO: 325, a third light chain hypervariable region (HVR-L3) of SEQ ID NO: 335, and/or a first heavy chain hypervariable region (HVR-H1) of SEQ ID NO: 344, a second heavy chain hypervariable region (HVR-H2) of SEQ ID NO: 369, and a third heavy chain hypervariable region (HVR-H3) of SEQ ID NO: 372.

39. An anti-CD96 antibody comprising:

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 43;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 42, and a third heavy chain hypervariable region (HVR-H3) of SEQ ID NO: 43;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 108, and a third heavy chain hypervariable region (HVR-H3) of SEQ ID NO: 43;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 112, and a third heavy chain hypervariable region (HVR-H3) of SEQ ID NO: 43;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 190, and a third heavy chain hypervariable region (HVR-H3) of SEQ ID NO: 43;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 197, and a third heavy chain hypervariable region (HVR-H3) of SEQ ID NO: 43;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 221;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 227;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 112, and a third heavy chain hypervariable region (HVR-H3) of SEQ ID NO: 221;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 112, and a third heavy chain hypervariable region (HVR-H3) of SEQ ID NO: 227;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 113, and a third heavy chain hypervariable region (HVR-H3) of SEQ ID NO: 221;

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 113, and a third heavy chain hypervariable region (HVR-H3) of SEQ ID NO: 227; or a first light chain hypervariable region (HVR-L1) of SEQ ID NO: 37, a second light chain hypervariable region (HVR-L2) of SEQ ID NO: 38, a third light chain hypervariable region (HVR-L3) of SEQ ID NO: 39; and/or a first heavy chain hypervariable region (HVR-H1) of SEQ ID NO: 65, a second heavy chain hypervariable region (HVR-H2) of SEQ ID NO: 66, and a third heavy chain hypervariable region (HVR-H3) of SEQ ID NO: 67.

40. An anti-CD96 antibody comprising:

a light chain variable domain ($V_L$) amino acid sequence of SEQ ID NO: 68; and/or a heavy chain variable domain ($V_H$) amino acid sequence of SEQ ID NO: 69;

a light chain variable domain ($V_L$) amino acid sequence of SEQ ID NO: 68; and/or a heavy chain variable domain ($V_H$) amino acid sequence of SEQ ID NO: 250;

a light chain variable domain ($V_L$) amino acid sequence of SEQ ID NO: 68; and/or a heavy chain variable domain ($V_H$) amino acid sequence of SEQ ID NO: 251;

a light chain variable domain ($V_L$) amino acid sequence of SEQ ID NO: 68; and/or a heavy chain variable domain ($V_H$) amino acid sequence of SEQ ID NO: 252;

a light chain variable domain ($V_L$) amino acid sequence of SEQ ID NO: 68; and/or a heavy chain variable domain ($V_H$) amino acid sequence of SEQ ID NO: 253;

a light chain variable domain ($V_L$) amino acid sequence of SEQ ID NO: 68; and/or a heavy chain variable domain ($V_H$) amino acid sequence of SEQ ID NO: 254;

a light chain variable domain ($V_L$) amino acid sequence of SEQ ID NO: 68; and/or a heavy chain variable domain ($V_H$) amino acid sequence of SEQ ID NO: 255;

a light chain variable domain ($V_L$) amino acid sequence of SEQ ID NO: 68; and/or a heavy chain variable domain ($V_H$) amino acid sequence of SEQ ID NO: 256;

a light chain variable domain ($V_L$) amino acid sequence of SEQ ID NO: 68; and/or a heavy chain variable domain ($V_H$) amino acid sequence of SEQ ID NO: 257;

a light chain variable domain ($V_L$) amino acid sequence of SEQ ID NO: 68; and/or a heavy chain variable domain ($V_H$) amino acid sequence of SEQ ID NO: 258;

a light chain variable domain ($V_L$) amino acid sequence of SEQ ID NO: 68; and/or a heavy chain variable domain ($V_H$) amino acid sequence of SEQ ID NO: 259;

a light chain variable domain ($V_L$) amino acid sequence of SEQ ID NO: 68; and/or a heavy chain variable domain ($V_H$) amino acid sequence of SEQ ID NO: 260;

a light chain variable domain ($V_L$) amino acid sequence of SEQ ID NO: 68; and/or a heavy chain variable domain ($V_H$) amino acid sequence of SEQ ID NO: 261;

a light chain variable domain ($V_L$) amino acid sequence of SEQ ID NO: 68; and/or a heavy chain variable domain ($V_H$) amino acid sequence of SEQ ID NO: 262;

a light chain variable domain ($V_L$) amino acid sequence of SEQ ID NO: 68; and/or a heavy chain variable domain ($V_H$) amino acid sequence of SEQ ID NO: 263;

a light chain variable domain ($V_L$) amino acid sequence of SEQ ID NO: 68; and/or a heavy chain variable domain ($V_H$) amino acid sequence of SEQ ID NO: 264;

a light chain variable domain ($V_L$) amino acid sequence of SEQ ID NO: 68; and/or a heavy chain variable domain ($V_H$) amino acid sequence of SEQ ID NO: 265;

a light chain variable domain ($V_L$) amino acid sequence of SEQ ID NO: 68; and/or a heavy chain variable domain ($V_H$) amino acid sequence of SEQ ID NO: 266;

a light chain variable domain ($V_L$) amino acid sequence of SEQ ID NO: 68; and/or a heavy chain variable domain ($V_H$) amino acid sequence of SEQ ID NO: 267;

a light chain variable domain ($V_L$) amino acid sequence of SEQ ID NO: 68; and/or a heavy chain variable domain ($V_H$) amino acid sequence of SEQ ID NO: 268;

a light chain variable domain ($V_L$) amino acid sequence of SEQ ID NO: 68; and/or a heavy chain variable domain ($V_H$) amino acid sequence of SEQ ID NO: 269;

a light chain variable domain ($V_L$) amino acid sequence of SEQ ID NO: 68; and/or a heavy chain variable domain ($V_H$) amino acid sequence of SEQ ID NO: 270;

a light chain variable domain ($V_L$) amino acid sequence of SEQ ID NO: 68; and/or a heavy chain variable domain ($V_H$) amino acid sequence of SEQ ID NO: 271;

a light chain variable domain ($V_L$) amino acid sequence of SEQ ID NO: 68; and/or a heavy chain variable domain ($V_H$) amino acid sequence of SEQ ID NO: 272;

a light chain variable domain ($V_L$) amino acid sequence of SEQ ID NO: 68; and/or a heavy chain variable domain ($V_H$) amino acid sequence of SEQ ID NO: 273;

a light chain variable domain ($V_L$) amino acid sequence of SEQ ID NO: 68; and/or a heavy chain variable domain ($V_H$) amino acid sequence of SEQ ID NO: 274;

a light chain variable domain ($V_L$) amino acid sequence of SEQ ID NO: 68; and/or a heavy chain variable domain ($V_H$) amino acid sequence of SEQ ID NO: 275;

a light chain variable domain ($V_L$) amino acid sequence of SEQ ID NO: 70; and/or a heavy chain variable domain ($V_H$) amino acid sequence of SEQ ID NO: 71.

41. An anti-CD96 antibody comprising:

a light chain (LC) amino acid sequence of SEQ ID NO: 440; and/or a heavy chain (HC) amino acid sequence of SEQ ID NO: 447;

a light chain (LC) amino acid sequence of SEQ ID NO: 441; and/or a heavy chain (HC) amino acid sequence of SEQ ID NO: 448;

a light chain (LC) amino acid sequence of SEQ ID NO: 442; and/or a heavy chain (HC) amino acid sequence of SEQ ID NO: 449;

a light chain (LC) amino acid sequence of SEQ ID NO: 443; and/or a heavy chain (HC) amino acid sequence of SEQ ID NO: 450;

a light chain (LC) amino acid sequence of SEQ ID NO: 444; and/or a heavy chain (HC) amino acid sequence of SEQ ID NO: 451;

a light chain (LC) amino acid sequence of SEQ ID NO: 445; and a heavy chain (HC) amino acid sequence of SEQ ID NO: 452;

a light chain (LC) amino acid sequence of SEQ ID NO: 446; and/or a heavy chain (HC) amino acid sequence of SEQ ID NO: 453;

a light chain (LC) amino acid sequence of SEQ ID NO: 454; and/or a heavy chain (HC) amino acid sequence of SEQ ID NO: 455;

a light chain (LC) amino acid sequence of SEQ ID NO: 454; and/or a heavy chain (HC) amino acid sequence of SEQ ID NO: 456;

a light chain (LC) amino acid sequence of SEQ ID NO: 454; and/or a heavy chain (HC) amino acid sequence of SEQ ID NO: 457;

a light chain (LC) amino acid sequence of SEQ ID NO: 454; and/or a heavy chain (HC) amino acid sequence of SEQ ID NO: 458;

a light chain (LC) amino acid sequence of SEQ ID NO: 454; and/or a heavy chain (HC) amino acid sequence of SEQ ID NO: 459;

a light chain (LC) amino acid sequence of SEQ ID NO: 470; and/or a heavy chain (HC) amino acid sequence of SEQ ID NO: 471;

a light chain (LC) amino acid sequence of SEQ ID NO: 454; and/or a heavy chain (HC) amino acid sequence of SEQ ID NO: 491;

a light chain (LC) amino acid sequence of SEQ ID NO: 454; and/or a heavy chain (HC) amino acid sequence of SEQ ID NO: 492;

a light chain (LC) amino acid sequence of SEQ ID NO: 454; and/or a heavy chain (HC) amino acid sequence of SEQ ID NO: 493;

a light chain (LC) amino acid sequence of SEQ ID NO: 454; and/or a heavy chain (HC) amino acid sequence of SEQ ID NO: 494;

a light chain (LC) amino acid sequence of SEQ ID NO: 454; and/or a heavy chain (HC) amino acid sequence of SEQ ID NO: 495; or a light chain (LC) amino acid sequence of SEQ ID NO: 470; and/or a heavy chain (HC) amino acid sequence of SEQ ID NO: 501.

42. The antibody of any one of clauses 1-41, wherein the antibody binds to human CD96 with a binding affinity of $1 \times 10^{-8}$ M or less, $1 \times 10^{-9}$ M or less, $1 \times 10^{-10}$ M or less, or $1 \times 10^{-11}$ M or less; optionally, wherein the binding affinity is measured by equilibrium dissociation constant ($K_D$) to a hu-CD96 polypeptide of SEQ ID NO: 4.

43. The antibody of any one of clauses 1-42, wherein the antibody binds to cynomolgus monkey CD96 with a binding affinity of $1 \times 10^{-8}$ M or less, $1 \times 10^{-9}$ M or less, $1 \times 10^{-10}$ M or less, or $1 \times 10^{-11}$ M or less; optionally, wherein the binding affinity is measured by equilibrium dissociation constant ($K_D$) to a cy-CD96 polypeptide of SEQ ID NO: 7.

44. The antibody of any one of clauses 1-43, wherein the antibody binds to human CD96 and to cynomolgus monkey CD96 with a binding affinity of $1 \times 10^{-8}$ M or less, $1 \times 10^{-9}$ M or less, $1 \times 10^{-10}$ M or less, or $1 \times 10^{-11}$ M or less; optionally, wherein the binding affinity is measured by equilibrium dissociation constant ($K_D$) to a hu-CD96 polypeptide of SEQ ID NO: 4 and a cy-CD96 polypeptide of SEQ ID NO: 7.

45. The antibody of any one of clauses 1-44, wherein the antibody binds to human CD96 isoform 1 expressed on a cell with an antibody $EC_{50}$ concentration of 5 nM or less, 1 nM or less, or 0.1 nM or less; optionally, wherein the cell is a HEK293T cell.

46. The antibody of any one of clauses 1-45, wherein the antibody binds to human CD96 isoform 2 expressed on a cell with an antibody $EC_{50}$ concentration of 5 nM or less, 1 nM or less, or 0.1 nM or less; optionally, wherein the cell is a CHO cell.

47. The antibody of any one of clauses 1-46, wherein the antibody binds to human PBMCs with an antibody $EC_{50}$ concentration of 5 nM or less, 1 nM or less, or 0.1 nM or less.

48. The antibody of any one of clauses 1-47, wherein the antibody binds to cynomolgus monkey PBMCs with an antibody $EC_{50}$ concentration of 5 nM or less, 1 nM or less, or 0.1 nM or less.

49. The antibody of any one of clauses 1-48, wherein the antibody decreases binding of human CD155 to human CD96 expressed on CHO cells by at least 90%, at least 95%, at least 99%, or 100%; optionally, wherein at a human CD155 concentration of 10 nM the antibody has an $IC_{50}$ of 5 nM or less, 1 nM or less, or 0.1 nM or less.

50. The antibody of any one of clauses 1-49, wherein the antibody increases IFNγ secretion from human PBMCs by at least 1.8-fold, at least 1.9-fold, at least 2-fold, at least 2.1 fold, or at least 2.20-fold; optionally, wherein the antibody has an $EC_{50}$ concentration of 0.3 nM or less, 0.2 nM or less, or 0.1 nM or less.

51. The antibody of any one of clauses 1-50, wherein the antibody increases IL-2 secretion from human PBMCs by at least 1.8-fold, at least 1.9-fold, at least 2-fold, at least 2.1 fold, or at least 2.20-fold; optionally, wherein the antibody has an $EC_{50}$ concentration of 0.3 nM or less, 0.2 nM or less, or 0.1 nM or less.

52. The antibody of any one of clauses 1-51, wherein the antibody binds to human and/or cynomolgus monkey CD226 expressed on cells, optionally HEK293 cells, with an antibody $EC_{50}$ concentration of 500 nM or less, 300 nM or less, 250 nM or less, 200 nM or less, 150 nM or less, 100 nM or less, or 50 nM or less.

53. The antibody of any one of clauses 1-52, wherein the antibody binds to human CD226 with a binding affinity of 1 µM or less, 900 nM or less, 800 nM or less, 700 nM or less, from 1 µM to 50 nM, or from 800 nM to 200 nM; optionally, wherein the binding affinity is measured by equilibrium dissociation constant ($K_D$) to a huCD226 polypeptide of SEQ ID NO: 482.

54. The antibody of any one of clauses 1-53, wherein the antibody binds to cynomolgus monkey CD226 with a binding affinity of 1 µM or less, 800 nM or less, 500 nM or less, 300 nM or less, 100 nM or less, from 1 µM to 50 nM, from 500 nM to 60 nM, or from 300 nM to 70 nM; optionally, wherein the binding affinity is measured by equilibrium dissociation constant ($K_D$) to a cyCD226 polypeptide of SEQ ID NO: 483.

55. The antibody of any one of clauses 1-54, wherein the antibody specifically binds to one or more amino acid residues within domain 1 of hu-CD96, wherein domain 1 comprises the amino acid sequence of SEQ ID NO: 5; optionally, wherein the one or more amino acid residues comprise T28 and V29 of SEQ ID NO: 5.

56. The antibody of any one of clauses 1-55, wherein the antibody does not bind to amino acid residues within domain 2 and/or domain 3 of human CD96.

57. The antibody of any one of clauses 1-55, wherein the antibody cross-reacts with a cynomolgus monkey CD96 polypeptide of SEQ ID NO: 7.

58. The antibody of any one of clauses 1-57, wherein the antibody is a monoclonal antibody.

59. The antibody of any one of clauses 1-58, wherein the antibody is a recombinant antibody.

60. The antibody of any one of clauses 1-59, wherein the antibody is a chimeric antibody.

61. The antibody of any one of clauses 1-60, wherein the antibody is a humanized or human antibody.

62. The antibody of any one of clauses 1-61, wherein the antibody is an antibody fragment, optionally selected from the group consisting of F(ab')$_2$, Fab', Fab, Fv, single domain antibody (VHH), single-arm antibody, and scFv.

63. The antibody of any one of clauses 1-61, wherein the antibody is a full-length antibody of class IgG; optionally, wherein the class IgG antibody has an isotype selected from IgG1, IgG2, IgG3, and IgG4.

64. The antibody of clause 63, wherein the antibody is an Fc region variant; optionally wherein the Fc region variant alters effector function or alters half-life.

65. The antibody of clause 64, wherein the Fc region variant decreases effector function and/or results in an effectorless antibody; optionally, wherein the Fc region variant comprises an amino acid substitution at position 297 resulting in effectorless function.

66. The antibody of any one of clauses 1-65, wherein the antibody is an immunoconjugate; optionally, wherein the immunoconjugate comprises a therapeutic agent for treatment of CD96-mediated condition or disease; optionally, wherein the therapeutic agent is a chemotherapeutic agent or cytotoxic agent for the treatment of cancer.

67. The antibody of any one of clauses 1-66, wherein the antibody is a multispecific antibody, optionally a bispecific antibody.

68. The antibody of clause 67, wherein the antibody is a bispecific antibody comprising a specificity for an antigen selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA; optionally, wherein the antigen is selected from PD1, TIGIT, LAG3, PVRIG, KIR, TIM-3, and CRTAM.

69. The antibody of any one of clauses 1-69, wherein the antibody is a synthetic antibody comprising the CDRs grafted onto a scaffold other than an immunoglobulin scaffold or immunoglobulin framework, optionally a scaffold selected from an alternative protein scaffold, and an artificial polymer scaffold.

70. An anti-CD96 antibody that specifically binds to the same epitope as the antibody of any one of clauses 1-69.

71. An anti-CD96 antibody, wherein the antibody specifically binds to one or more amino acid residues within domain 1 of human CD96, wherein domain 1 comprises the amino acid sequence of SEQ ID NO: 5; optionally, wherein the one or more amino acid residues within domain 1 of human CD96 comprise residues 28 and 29 of SEQ ID NO: 5 corresponding to residues 49 and 50 of human CD96 of SEQ ID NO: 2.

72. An isolated polynucleotide encoding the antibody of any one of clauses 1-71.

73. The polynucleotide of clause 72, further comprising a nucleotide sequence encoding a signal peptide (SP).

74. The polynucleotide of clause 72, wherein the polynucleotide encodes a light chain and a heavy chain.

75. The polynucleotide of clause 72, wherein the polynucleotide comprises a polynucleotide sequence comprising one or more codons selected for optimal expression of the antibody in a mammalian cell.

76. The polynucleotide of clause 72, wherein the polynucleotide sequence comprises one or more codons selected for optimal expression of the antibody in a Chinese Hamster Ovary (CHO) cell.

77. A vector comprising a polynucleotide of any one of clauses 72-76.

78. An isolated host cell comprising the vector of clause 77.

79. A host cell comprising a polynucleotide of any one of clauses 72-76.

80. An isolated host cell that expresses the antibody of any one of clauses 1-71.

81. The host cell of clause 80, wherein the host cell is selected from a Chinese hamster ovary (CHO) cell, a myeloma cell (e.g., Y0, NS0, Sp2/0), a monkey kidney cell (COS-7), a human embryonic kidney line (293), a baby hamster kidney cell (BHK), a mouse Sertoli cell (e.g., TM4), an African green monkey kidney cell (VERO-76), a human cervical carcinoma cell (HELA), a canine kidney cell, a human lung cell (W138), a human liver cell (Hep G2), a mouse mammary tumor cell, a TRI cell, an MRC 5 cell, and a FS4 cell.

82. A method of producing an antibody comprising culturing the host cell of any one of clauses 78-81 so that an antibody is produced.

83. A hybridoma that produces an antibody of any one of clauses 1-71.

84. A pharmaceutical composition comprising an anti-CD96 antibody of any one of clauses 1-71 and a pharmaceutically acceptable carrier.

85. The pharmaceutical composition of clause 84, wherein the anti-CD96 antibody is the sole active agent of the composition.

86. The pharmaceutical composition of clause 84, wherein the composition comprises an additional active agent.

87. The pharmaceutical composition of clause 86, wherein the additional active agent is a chemotherapeutic agent.

88. The pharmaceutical composition of clause 86, wherein the additional active agent is an antibody comprising a specificity for an immune checkpoint molecule.

89. The pharmaceutical composition of clause 88, wherein the immune checkpoint molecule is selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA; optionally, wherein the immune checkpoint molecule is selected from PD1, TIGIT, LAG3, PVRIG, KIR, TIM-3, and CRTAM.

90. The pharmaceutical composition of clause 86, wherein the additional active agent is an antibody comprising a specificity for PD1; optionally, wherein the antibody comprising a specificity for PD1 is selected from dostarlimab, pembrolizumab, nivolumab, and pidilizumab.

91. A method of treating a CD96 mediated disease in a subject, comprising administering to the subject a therapeutically effective amount of an antibody of any one of clauses 1-71, or administering to the subject a therapeutically effective amount of a pharmaceutical composition of any one of clauses 84-90.

92. A method of treating a disease mediated by binding to CD155 expressed on cells in a subject, the method comprising administering to the subject a therapeutically effective amount of an antibody of any one of clauses 1-71, or administering to the subject a therapeutically effective amount of a pharmaceutical composition of any one of clauses 84-90.

93. A method of treating a disease mediated by CD226 and/or TIGIT in a subject, the method comprising administering to the subject a therapeutically effective amount of an antibody of any one of clauses 1-71, or administering to the subject a therapeutically effective amount of a pharmaceutical composition of any one of clauses 84-90.

94. A method of treating cancer in a subject, the method comprising administering to the subject a therapeutically effective amount of an antibody of any one of clauses 1-71, or administering to the subject a therapeutically effective amount of a pharmaceutical composition of any one of clauses 84-90; optionally, wherein the cancer is selected from adrenal gland cancer, bladder cancer, brain cancer, breast cancer, cervical cancer, colorectal cancer, EGJ adenocarcinoma, esophageal cancer, gall bladder cancer, gastric cancer, head and neck cancer, heart cancer, hepatocellular carcinoma, kidney cancer, liver cancer, melanoma, mesothelioma, non-small cell lung cancer, ovarian cancer, pancreatic cancer, prostate cancer, spleen cancer, small cell lung cancer, testicular cancer, thyroid cancer, and uterine cancer.

95. The method of any one of clauses 91-94, wherein the antibody is a bispecific antibody comprising a specificity for an antigen selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA; optionally, wherein the antigen is selected from PD-1, TIGIT, LAG3, PVRIG, KIR, TIM-3, and CRTAM.

96. The method of any one of clauses 91-95, wherein the method comprises co-administering to the subject a therapeutically effective amount of an antibody comprising a specificity for PD1; optionally, wherein the antibody comprising a specificity for PD1 is selected from dostarlimab, pembrolizumab, nivolumab, and pidilizumab.

97. A method of treating a pathogenic infection in a subject, the method comprising administering to the subject a therapeutically amount of an antibody of any one of clauses 1-71, or administering to the subject a therapeutically effective amount of a pharmaceutical composition of any one of clauses 84-90; optionally, wherein the pathogenic infection is selected from: *Acinetobacter baumannii*, *Acinetobacter lwoffii*, *Acinetobacter* spp. (incl. MDR), *Actinomycetes*, Adenovirus, *Aeromonas* spp., *Alcaligenes faecalis*, *Alcaligenes* spp./*Achromobacter* spp., *Alcaligenes xylosoxidans* (incl. ESBL/MRGN), Arbovirus, *Aspergillus* spp., Astrovirus, *Bacillus anthracis*, *Bacillus cereus*, *Bacillus subtilis*, *Bacteroides fragilis*, *Bartonella quintana*, *Bordetella pertussis*, *Borrelia burgdorferi*, *Borrelia recurrentis*, *Brevundimonas diminuta*. *Brevundimonas vesicularis*. *Brucella* spp., *Burkholderia cepacia* (incl. MDR), *Burkholderia mallei*, *Burkholderia pseudomallei*, *Campylobacter jejuni/coli*, *Candida albicans*, *Candida krusei*, *Candida parapsilosis*, Chikungunya virus (CHIKV), *Chlamydia pneumoniae*, *Chlamydia psittaci*, *Chlamydia trachomatis*, *Citrobacter* spp., *Clostridium botulinum*, *Clostridium difficile*, *Clostridium perfringens*, *Clostridium tetani*, Coronavirus (incl. SARS- and MERS-CoV), *Corynebacterium diphtheriae*, *Corynebacterium pseudotuberculosis*, *Corynebacterium* spp., *Corynebacterium ulcerans*, *Coxiella burnetii*, Coxsackievirus, Crimean-Congo haemorrhagic fever virus, *Cryptococcus neoformans*. *Cryptosporidium hominis*, *Cryptosporidium parvum*, *Cyclospora cayetanensis*, Cytomegalovirus (CMV), Dengue virus, Ebola virus, Echovirus, *Entamoeba histolytica, Enterobacter aerogenes, Enterobacter cloacae* (incl. ESBL/MRGN), *Enterococcus faecalis* (incl. VRE), *Enterococcus faecium* (incl. VRE), *Enterococcus hirae, Epidermophyton* spp., Epstein-Barr virus (EBV), *Escherichia coli* (incl. EHEC, EPEC, ETEC, EIEC, EAEC. ESBL/MRGN, DAEC), Foot-and-mouth disease virus (FMDV), *Francisella tularensis, Giardia lamblia, Haemophilus influenzae*, Hantavirus, *Helicobacter pylori*, Helminths (Worms), Hepatitis A virus (HAV), Hepatitis B virus (HBV), Hepatitis C virus (HCV), Hepatitis D virus, Hepatitis E virus, Herpes simplex virus (HSV), *Histoplasma capsulatum*, Human enterovirus 71, Human herpesvirus 6 (HHV-6), Human herpesvirus 7 (HHV-7), Human herpesvirus 8 (HHV-8), Human immunodeficiency virus (HIV), Human metapneumovirus, Human papillomavirus (HPV), Influenza virus, *Klebsiella granulomatis, Klebsiella oxytoca* (incl. ESBL/MRGN), *Klebsiella pneumoniae* MDR (incl. ESBL/MRGN), Lassa virus, *Leclercia adecarboxylata, Legionella pneumophila, Leishmania* spp., *Leptospira interrogans, Leuconostoc pseudomesenteroides, Listeria monocytogenes*, Marburg virus, Measles virus, *Micrococcus luteus, Microsporum* spp., Molluscipoxvirus, *Morganella* spp., Mumps virus, *Mycobacterium* chimaera Myco, *Mycobacterium leprae* Myco, *Mycobacterium tuberculosis* (incl. MDR), *Mycoplasma genitalium, Mycoplasma pneumoniae, Neisseria meningitidis, Neisseria gonorrhoeae*, Norovirus, *Orientia tsutsugamushi, Pantoea agglomerans*, Parainfluenza virus, Parvovirus, *Pediculus humanus capitis, Pediculus humanus corporis, Plasmodium* spp., *Pneumocystis jiroveci*, Poliovirus, Polyomavirus, *Proteus mirabilis* (incl. ESBL/MRGN), *Proteus vulgaris, Providencia rettgeri, Providencia stuartii, Pseudomonas aeruginosa, Pseudomonas* spp., Rabies virus, *Ralstonia* spp., Respiratory syncytial virus (RSV), Rhinovirus, *Rickettsia prowazekii, Rickettsia typhi, Roseomonas gilardii*, Rotavirus, Rubella virus, *Salmonella enteritidis, Salmonella paratyphi, Salmonella* spp., *Salmonella typhimurium, Sarcoptes scabiei* (Itch mite), Sapovirus, *Serratia marcescens* (incl. ESBL/MRGN), *Shigella sonnei, Sphingomonas* species, *Staphylococcus aureus* (incl. MRSA, VRSA), *Staphylococcus capitis, Staphylococcus epidermidis* (incl. MRSE), *Staphylococcus haemolyticus, Staphylococcus hominis, Staphylococcus lugdunensis, Staphylococcus saprophyticus, Stenotrophomonas maltophilia. Streptococcus pneumoniae, Streptococcus pyogenes* (incl. PRSP), *Streptococcus* spp., TBE virus, *Toxoplasma gondii, Treponema pallidum, Trichinella spiralis, Trichomonas vaginalis, Trichophyton* spp., *Trichosporon* spp., *Trypanosoma brucei* gambiense, *Trypanosoma brucei* rhodesiense, *Trypanosoma cruzi*, Vaccinia virus, Varicella zoster virus (VSV), Variola virus, *Vibrio cholerae*, West Nile virus (WNV), Yellow fever virus, *Yersinia enterocolitica, Yersinia pestis, Yersinia pseudotuberculosis*, Zika virus, and the like.

98. A method of treating a viral infection in a subject, the method comprising administering to the subject a therapeutically amount of an antibody of any one of clauses 1-71, or administering to the subject a therapeutically effective amount of a pharmaceutical composition of any one of clauses 84-90; optionally, wherein the viral infection is selected from: Adenovirus, Arbovirus, Astrovirus, Chikungunya virus (CHIKV), Coronavirus (incl. SARS- and MERS-CoV), Crimean-Congo haemorrhagic fever virus, Cytomegalovirus (CMV), Dengue virus, Ebola virus, Echovirus, Epstein-Barr virus (EBV), Foot-and-mouth disease virus (FMDV), Hantavirus, Hepatitis A virus (HAV), Hepatitis B virus (HBV), Hepatitis C virus (HCV), Hepatitis D virus, Hepatitis E virus, Herpes simplex virus (HSV), Human enterovirus 71, Human herpesvirus 6 (HHV-6), Human herpesvirus 7 (HHV-7), Human herpesvirus 8 (HHV-8), Human immunodeficiency virus (HIV), Human metapneumovirus, Human papillomavirus (HPV), Influenza virus, Marburg virus, Measles virus, Mumps virus, Norovirus, Parainfluenza virus, Parvovirus, Poliovirus, Polyomavirus, Rabies virus, Respiratory syncytial virus (RSV), Rhinovirus, Rotavirus, Rubella virus, Sapovirus, TBE virus, Vaccinia virus, Varicella zoster virus (VSV), Variola virus, West Nile virus (WNV), Yellow fever virus, and Zika virus.

99. An anti-CD96 antibody that competes with antibody Nk92.39 for binding to an epitope of human CD96 and has a binding affinity of $1 \times 10^{-8}$ M or less; optionally, wherein the binding affinity to human CD96 is measured by equilibrium dissociation constant ($K_D$) to a hu-CD96 polypeptide of SEQ ID NO: 4; optionally, wherein the antibody binds to human and/or cynomolgus monkey CD226 with a binding affinity of 50 nM to 1 µM; optionally wherein the binding affinity to human and/or cynomolgus monkey CD226 is measured by $K_D$ to a hu-CD226 polypeptide of SEQ ID NO: 482 and/or a cy-CD226 polypeptide of SEQ ID NO:483.

100. The antibody of clause 99, wherein the antibody comprises:

a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 43;

a first light chain hypervariable region (HVR-L1) of SEQ ID NO: 17, a second light chain hypervariable region (HVR-L2) of SEQ ID NO: 18, a third light chain hypervariable region (HVR-L3) of SEQ ID NO: 19; and/or a first heavy chain hypervariable region (HVR-H1) of SEQ ID NO: 45, a second heavy chain hypervariable region (HVR-H2) of SEQ ID NO: 46, and a third heavy chain hypervariable region (HVR-H3) of SEQ ID NO: 47;

a first light chain hypervariable region (HVR-L1) of SEQ ID NO: 21, a second light chain hypervariable region (HVR-L2) of SEQ ID NO: 22, a third light chain hypervariable region (HVR-L3) of SEQ ID NO: 23; and/or a first heavy chain hypervariable region (HVR-H1) of SEQ ID NO: 49, a second heavy chain hypervariable region (HVR-H2) of SEQ ID NO: 50, and a third heavy chain hypervariable region (HVR-H3) of SEQ ID NO: 51;

a first light chain hypervariable region (HVR-L1) of SEQ ID NO: 25, a second light chain hypervariable region (HVR-L2) of SEQ ID NO: 26, a third light chain hypervariable region (HVR-L3) of SEQ ID NO: 27; and/or a first heavy chain hypervariable region (HVR-H1) of SEQ ID NO: 53, a second heavy chain hypervariable region (HVR-H2) of SEQ ID NO: 54, and a third heavy chain hypervariable region (HVR-H3) of SEQ ID NO: 55;

a first light chain hypervariable region (HVR-L1) of SEQ ID NO: 29, a second light chain hypervariable region (HVR-L2) of SEQ ID NO: 30, a third light chain hypervariable region (HVR-L3) of SEQ ID NO: 31; and/or a first heavy chain hypervariable region (HVR-H1) of SEQ ID NO: 57, a second heavy chain hypervariable region (HVR-H2) of SEQ ID NO: 58, and a third heavy chain hypervariable region (HVR-H3) of SEQ ID NO: 59; or a first light chain hypervariable region (HVR-L1) of SEQ ID NO: 37, a second light chain hypervariable region (HVR-L2) of SEQ ID NO: 38, a third light chain hypervariable region (HVR-L3) of SEQ ID NO: 39; and/or a first heavy chain hypervariable region (HVR-H1) of SEQ ID NO: 65, a second heavy chain hypervariable region (HVR- H2) of SEQ ID NO: 66, and a third heavy chain hypervariable region (HVR-H3) of SEQ ID NO: 67.

101. The antibody of any one of clauses 99-100, wherein the antibody comprises:

a light chain variable domain ($V_L$) amino acid sequence having at least 90% identity to SEQ ID NO: 12; and/or a heavy chain variable domain ($V_H$) amino acid sequence having at least 90% identity to SEQ ID NO: 40;

a light chain variable domain ($V_L$) amino acid sequence having at least 90% identity to SEQ ID NO: 16; and/or a heavy chain variable domain ($V_H$) amino acid sequence having at least 90% identity to SEQ ID NO: 44;

a light chain variable domain ($V_L$) amino acid sequence having at least 90% identity to SEQ ID NO: 20; and/or a heavy chain variable domain ($V_H$) amino acid sequence having at least 90% identity to SEQ ID NO: 48;

a light chain variable domain ($V_L$) amino acid sequence having at least 90% identity to SEQ ID NO: 24; and/or a heavy chain variable domain ($V_H$) amino acid sequence having at least 90% identity to SEQ ID NO: 52;

a light chain variable domain ($V_L$) amino acid sequence having at least 90% identity to SEQ ID NO: 28; and/or a heavy chain variable domain ($V_H$) amino acid sequence having at least 90% identity to SEQ ID NO: 56;

a light chain variable domain ($V_L$) amino acid sequence having at least 90% identity to SEQ ID NO: 36; and/or a heavy chain variable domain ($V_H$) amino acid sequence having at least 90% identity to SEQ ID NO: 64;

a light chain variable domain ($V_L$) amino acid sequence having at least 90% identity to SEQ ID NO: 68; and/or a heavy chain variable domain ($V_H$) amino acid sequence having at least 90% identity to an amino acid sequence selected from SEQ ID NO: 69, 250-275, or 460-464; or a light chain variable domain ($V_L$) amino acid sequence having at least 90% identity to SEQ ID NO: 70; and/or a heavy chain variable domain ($V_H$) amino acid sequence having at least 90% identity to SEQ ID NO: 71.

102. The antibody of any one of clauses 99-101, wherein the antibody comprises:

a light chain (LC) amino acid sequence of SEQ ID NO: 440; and/or a heavy chain (HC) amino acid sequence of SEQ ID NO: 447 or 484;

a light chain (LC) amino acid sequence of SEQ ID NO: 441; and/or a heavy chain (HC) amino acid sequence of SEQ ID NO: 448 or 485;

a light chain (LC) amino acid sequence of SEQ ID NO: 442; and/or a heavy chain (HC) amino acid sequence of SEQ ID NO: 449 or 486;

a light chain (LC) amino acid sequence of SEQ ID NO: 443; and/or a heavy chain (HC) amino acid sequence of SEQ ID NO: 450 or 487;

a light chain (LC) amino acid sequence of SEQ ID NO: 444; and/or a heavy chain (HC) amino acid sequence of SEQ ID NO: 451 or 488;

a light chain (LC) amino acid sequence of SEQ ID NO: 446; and/or a heavy chain (HC) amino acid sequence of SEQ ID NO: 453 or 490;

a light chain (LC) amino acid sequence of SEQ ID NO: 454; and/or a heavy chain (HC) amino acid sequence selected from SEQ ID NO: 455-459, and 491-495; or a light chain (LC) amino acid sequence of SEQ ID NO: 470; and/or a heavy chain (HC) amino acid sequence of SEQ ID NO: 471 or 501.

103. The antibody of any one of clauses 1-71 for use as a medicament; optionally, for use in the treatment of a cancer or a pathogenic infection.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

Bibliography

1. Foote et al., (1992) "Antibody framework residues affecting the conformation of the hypervariable loops" J. Mol. Biol. 224: 487-499
2. Hotzel et al., (2012) "A strategy for risk mitigation of antibodies with fast clearance" mAbs 4(6): 753-760
3. Brenner et al., (1992) "Encoded combinatorial chemistry" Proc. Natl. Acad. Sci. USA 89(12): 5381-5383
4. Kunkel et al., (1987) "Rapid and efficient site-specific mutagenesis without phenotypic selection" Methods Enzymol. 154: 367-382
5. Masella et al., (2012) "PANDAseq: paired-end assembler for illumina sequences" BMC Bioinformatics 13:31
6. Koenig et al., (2015) "Mutational landscape of antibody variable domains reveals a switch modulating the interdomain conformational dynamics and antigen binding" J. Biol. Chem. 290(36): 21773-21786
7. Meyer et al., (2009) "CD96 interaction with CD155 via its first Ig-like domain is modulated by alternative splicing or mutations in distal Ig-like domains." J. Biol. Chem. 284:2235-44
8. Fuchs et al., (2004) "Cutting edge: CD96 (tactile) promotes NK cell-target cell adhesion by interacting with the poliovirus receptor (CD155)." J. Immunol. 172:3994-8.

What is claimed is:

1. An anti-CD96 antibody comprising: (i) a first light chain hypervariable region (HVR-L1), a second light chain hypervariable region (HVR-L2), and a third light chain hypervariable region (HVR-L3), and (ii) a first heavy chain hypervariable region (HVR-H1), a second heavy chain hypervariable region (HVR-H2), and a third heavy chain hypervariable region (HVR-H3), wherein:

(a) HVR-L1 is SEQ ID NO: 13, HVR-L2 is SEQ ID NO: 14, HVR-L3 is SEQ ID NO: 15, HVR-H1 is SEQ ID NO: 41, HVR-H2 is SEQ ID NO: 42, and HVR-H3 is SEQ ID NO: 43;

(b) HVR-L1 is SEQ ID NO: 13, HVR-L2 is SEQ ID NO: 14, HVR-L3 is SEQ ID NO: 15, HVR-H1 is SEQ ID NO: 95, HVR-H2 is SEQ ID NO: 42, and HVR-H3 is SEQ ID NO: 43;

(c) HVR-L1 is SEQ ID NO: 13, HVR-L2 is SEQ ID NO: 14, HVR-L3 is SEQ ID NO: 15, HVR-H1 is SEQ ID NO: 41, HVR-H2 is SEQ ID NO: 112, and HVR-H3 is SEQ ID NO: 43;

(d) HVR-L1 is SEQ ID NO: 13, HVR-L2 is SEQ ID NO: 14, HVR-L3 is SEQ ID NO: 15, HVR-H1 is SEQ ID NO: 41, HVR-H2 is SEQ ID NO: 42, and HVR-H3 is SEQ ID NO: 221;

(e) HVR-L1 is SEQ ID NO: 37, HVR-L2 is SEQ ID NO: 38, HVR-L3 is SEQ ID NO: 39, HVR-H1 is SEQ ID NO: 65, HVR-H2 is SEQ ID NO: 66, and HVR-H3 is SEQ ID NO: 67; or (f) HVR-L1 is SEQ ID NO: 13, HVR-L2 is SEQ ID NO: 14, HVR-L3 is SEQ ID NO: 15, HVR-H1 is SEQ ID NO: 95, HVR-H2 is SEQ ID NO: 112, and HVR-H3 is SEQ ID NO: 221.

2. The antibody of claim 1, wherein the antibody comprises a light chain variable domain ($V_L$) amino acid sequence having at least 90% identity to SEQ ID NO: 68, and a heavy chain variable domain ($V_H$) amino acid sequence having at least 90% identity to SEQ ID NO: 272.

3. The antibody of claim 1, wherein the antibody comprises a light chain (LC) amino acid sequence having at least 90% identity to SEQ ID NO: 454, and a heavy chain (HC) amino acid sequence having at least 90% identity to SEQ ID NO: 492.

4. The antibody of claim 1, wherein:
the antibody binds to human CD96 with a binding affinity of $1\times10^{-8}$ M or less, $1\times10^{-9}$ M or less, $1\times10^{-10}$ M or less, or $1\times10^{-11}$ M or less;
the antibody binds to cynomolgus monkey CD96 with a binding affinity of $1\times10^{-8}$ M or less, $1\times10^{-9}$ M or less, $1\times10^{-10}$ M or less, or $1\times10^{-11}$ M or less;
the antibody binds to human CD96 isoform 1 expressed on a cell with an antibody $EC_{50}$ concentration of 5 nM or less, 1 nM or less, or 0.1 nM or less;
the antibody binds to human CD96 isoform 2 expressed on a cell with an antibody $EC_{50}$ concentration of 5 nM or less, 1 nM or less, or 0.1 nM or less;
the antibody binds to human PBMCs with an antibody $EC_{50}$ concentration of 5 nM or less, 1 nM or less, or 0.1 nM or less;
the antibody binds to cynomolgus monkey PBMCs with an antibody $EC_{50}$ concentration of 5 nM or less, 1 nM or less, or 0.1 nM or less;
the antibody decreases binding of human CD155 to human CD96 expressed on CHO cells by at least 90%, at least 95%, at least 99%, or 100%;
the antibody increases IFNγ secretion from human PBMCs by at least 1.8-fold, at least 1.9-fold, at least 2-fold, at least 2.1-fold, or at least 2.20-fold;
the antibody increases IL-2 secretion from human PBMCs by at least 1.8-fold, at least 1.9-fold, at least 2-fold, at least 2.1-fold, or at least 2.20-fold;
the antibody binds to human and/or cynomolgus monkey CD226 expressed on cells;
the antibody binds to human CD226 with a binding affinity of 1 μM or less, 900 nM or less, 800 nM or less, 700 nM or less, from 1 μM to 50 nM, or from 800 nM to 200 nM; and/or
the antibody binds to cynomolgus monkey CD226 with a binding affinity of 1 μM or less, 800 nM or less, 500 nM or less, 300 nM or less, 100 nM or less, from 1 μM to 50 nM, from 500 nM to 60 nM, or from 300 nM to 70 nM.

5. The antibody of claim 1, wherein the antibody specifically binds to one or more amino acid residues within domain 1 of hu-CD96, wherein domain 1 comprises the amino acid sequence of SEQ ID NO: 5.

6. An isolated polynucleotide or vector encoding the antibody of claim 1.

7. A pharmaceutical composition comprising an anti-CD96 antibody of claim 1 and a pharmaceutically acceptable carrier.

8. The antibody of claim 5, wherein the one or more amino acid residues comprise T28 and V29 of SEQ ID NO: 5.

9. An isolated host cell comprising the polynucleotide or vector of claim 6.

10. A method of producing an antibody comprising culturing the host cell of claim 9 so that an antibody is produced.

11. The composition of claim 7, wherein the composition further comprises a chemotherapeutic agent or an antibody comprising a specificity for an immune checkpoint molecule.

12. An anti-CD96 antibody comprising: (i) a first light chain hypervariable region (HVR-L1), a second light chain hypervariable region (HVR-L2), and a third light chain hypervariable region (HVR-L3), and (ii) a first heavy chain hypervariable region (HVR-H1), a second heavy chain hypervariable region (HVR-H2), and a third heavy chain hypervariable region (HVR-H3); wherein HVR-L1 is SEQ ID NO: 13, HVR-L2 is SEQ ID NO: 14, HVR-L3 is SEQ ID NO: 15, HVR-H1 is SEQ ID NO: 95, HVR-H2 is SEQ ID NO: 112, and HVR-H3 is SEQ ID NO: 221.

13. An anti-CD96 antibody comprising a light chain variable domain ($V_L$) amino acid sequence of SEQ ID NO: 68, and a heavy chain variable domain ($V_H$) amino acid sequence having SEQ ID NO: 272.

14. An anti-CD96 antibody comprising a light chain (LC) amino acid sequence of SEQ ID NO: 454, and a heavy chain (HC) amino acid sequence of SEQ ID NO: 492.

15. The antibody of claim 2, wherein the antibody comprises the light chain variable domain ($V_L$) amino acid sequence of SEQ ID NO: 68, and the heavy chain variable domain ($V_H$) amino acid sequence of SEQ ID NO: 272.

16. The antibody of claim 3, wherein the antibody comprises the light chain (LC) amino acid sequence of SEQ ID NO: 454, and the heavy chain (HC) amino acid sequence of SEQ ID NO: 492.

17. The antibody of claim 4, wherein the antibody binds to human CD96 with a binding affinity of $1\times10^{-8}$ M or less, $1\times10^{-9}$ M or less, $1\times10^{-10}$ M or less, or $1\times10^{-11}$ M or less and wherein the binding affinity is measured by equilibrium dissociation constant ($K_D$) to a hu-CD96 polypeptide of SEQ ID NO: 4.

18. The antibody of claim 4, wherein the antibody binds to cynomolgus monkey CD96 with a binding affinity of $1\times10^{-8}$ M or less, $1\times10^{-9}$ M or less, $1\times10^{-10}$ M or less, or $1\times10^{-11}$ M or less and wherein the binding affinity is measured by equilibrium dissociation constant ($K_D$) to a cy-CD96 polypeptide of SEQ ID NO: 7.

19. The antibody of claim 4, wherein the antibody binds to human CD96 isoform 1 expressed on a cell with an antibody $EC_{50}$ concentration of 5 nM or less, 1 nM or less, or 0.1 nM or less and wherein the cell is a HEK293T cell.

20. The antibody of claim 4, wherein the antibody binds to human CD96 isoform 2 expressed on a cell with an antibody $EC_{50}$ concentration of 5 nM or less, 1 nM or less, or 0.1 nM or less and wherein the cell is a CHO cell.

21. The antibody of claim 4, wherein the antibody decreases binding of human CD155 to human CD96 expressed on CHO cells by at least 90%, at least 95%, at least 99%, or 100% and wherein at a human CD155 concentration of 10 nM the antibody has an $IC_{50}$ of 5 nM or less, 1 nM or less, or 0.1 nM or less.

22. The antibody of claim 4, wherein the antibody increases IFNγ secretion from human PBMCs by at least 1.8-fold, at least 1.9-fold, at least 2-fold, at least 2.1-fold, or at least 2.20-fold and wherein the antibody has an EC50 concentration of 0.3 nM or less, 0.2 nM or less, or 0.1 nM or less.

23. The antibody of claim 4, wherein the antibody increases IL-2 secretion from human PBMCs by at least 1.8-fold, at least 1.9-fold, at least 2-fold, at least 2.1-fold, or at least 2.20-fold and wherein the antibody has an $EC_{50}$ concentration of 0.3 nM or less, 0.2 nM or less, or 0.1 nM or less.

24. The antibody of claim 4, wherein the antibody binds to human and/or cynomolgus monkey CD226 expressed on HEK293 cells, with an antibody $EC_{50}$ concentration of 500 nM or less, 300 nM or less, 250 nM or less, 200 nM or less, 150 nM or less, 100 nM or less, or 50 nM or less.

25. The antibody of claim 4, wherein the antibody binds to human CD226 with a binding affinity of 1 μM or less, 900 nM or less, 800 nM or less, 700 nM or less, from 1 μM to 50 nM, or from 800 nM to 200 nM; and wherein the binding affinity is measured by equilibrium dissociation constant ($K_D$) to a hu-CD226 polypeptide of SEQ ID NO: 482.

26. The antibody of claim 4, wherein the antibody binds to cynomolgus monkey CD226 with a binding affinity of 1 μM or less, 800 nM or less, 500 nM or less, 300 nM or less, 100 nM or less, from 1 μM to 50 nM, from 500 nM to 60 nM, or from 300 nM to 70 nM; and wherein the binding affinity is measured by equilibrium dissociation constant ($K_D$) to a cyCD226 polypeptide of SEQ ID NO: 483.

27. The isolated host cell of claim 9, wherein the host cell is selected from a Chinese hamster ovary (CHO) cell, a myeloma cell (e.g. Y0, NS0, Sp2/0), a monkey kidney cell (COS-7), a human embryonic kidney line (293), a baby hamster kidney cell (BHK), a mouse Sertoli cell (e.g., TM4), an African green monkey kidney cell (VERO-76), a human cervical carcinoma cell (HELA), a canine kidney cell, a human lung cell (W138), a human liver cell (Hep G2), a mouse mammary tumor cell, a TR cell, a Medical Research Council 5 (MRC 5) cell, and a FS4 cell.

28. The composition of claim 7, wherein the anti-CD96 antibody is the sole active agent of the composition.

\* \* \* \* \*

SEQUENCE LISTING

<160> NUMBER OF SEQ ID NOS: 501

<210> SEQ ID NO 1
<211> LENGTH: 585
<212> TYPE: PRT
<213> ORGANISM: homo sapiens

```
<400> SEQUENCE: 1

Met Glu Lys Lys Trp Lys Tyr Cys Ala Val Tyr Tyr Ile Ile Gln Ile
1               5                   10                  15

His Phe Val Lys Gly Val Trp Glu Lys Thr Val Asn Thr Glu Glu Asn
            20                  25                  30

Val Tyr Ala Thr Leu Gly Ser Asp Val Asn Leu Thr Cys Gln Thr Gln
        35                  40                  45

Thr Val Gly Phe Phe Val Gln Met Gln Trp Ser Lys Val Thr Asn Lys
    50                  55                  60

Ile Asp Leu Ile Ala Val Tyr His Pro Gln Tyr Gly Phe Tyr Cys Ala
65                  70                  75                  80

Tyr Gly Arg Pro Cys Glu Ser Leu Val Thr Phe Thr Glu Thr Pro Glu
                85                  90                  95

Asn Gly Ser Lys Trp Thr Leu His Leu Arg Asn Met Ser Cys Ser Val
            100                 105                 110

Ser Gly Arg Tyr Glu Cys Met Leu Val Leu Tyr Pro Glu Gly Ile Gln
        115                 120                 125

Thr Lys Ile Tyr Asn Leu Leu Ile Gln Thr His Val Thr Ala Asp Glu
    130                 135                 140

Trp Asn Ser Asn His Thr Ile Glu Ile Glu Ile Asn Gln Thr Leu Glu
145                 150                 155                 160

Ile Pro Cys Phe Gln Asn Ser Ser Lys Ile Ser Ser Glu Phe Thr
                165                 170                 175

Tyr Ala Trp Ser Val Glu Asn Ser Ser Thr Asp Ser Trp Val Leu Leu
            180                 185                 190

Ser Lys Gly Ile Lys Glu Asp Asn Gly Thr Gln Glu Thr Leu Ile Ser
        195                 200                 205

Gln Asn His Leu Ile Ser Asn Ser Thr Leu Leu Lys Asp Arg Val Lys
    210                 215                 220

Leu Gly Thr Asp Tyr Arg Leu His Leu Ser Pro Val Gln Ile Phe Asp
225                 230                 235                 240

Asp Gly Arg Lys Phe Ser Cys His Ile Arg Val Gly Pro Asn Lys Ile
                245                 250                 255

Leu Arg Ser Ser Thr Thr Val Lys Val Phe Ala Lys Pro Glu Ile Pro
            260                 265                 270

Val Ile Val Glu Asn Asn Ser Thr Asp Val Leu Val Glu Arg Arg Phe
        275                 280                 285

Thr Cys Leu Leu Lys Asn Val Phe Pro Lys Ala Asn Ile Thr Trp Phe
    290                 295                 300

Ile Asp Gly Ser Phe Leu His Asp Glu Lys Glu Gly Ile Tyr Ile Thr
305                 310                 315                 320

Asn Glu Glu Arg Lys Gly Lys Asp Gly Phe Leu Glu Leu Lys Ser Val
                325                 330                 335

Leu Thr Arg Val His Ser Asn Lys Pro Ala Gln Ser Asp Asn Leu Thr
            340                 345                 350

Ile Trp Cys Met Ala Leu Ser Pro Val Pro Gly Asn Lys Val Trp Asn
        355                 360                 365

Ile Ser Ser Glu Lys Ile Thr Phe Leu Leu Gly Ser Glu Ile Ser Ser
    370                 375                 380

Thr Asp Pro Pro Leu Ser Val Thr Glu Ser Thr Leu Asp Thr Gln Pro
385                 390                 395                 400

Ser Pro Ala Ser Ser Val Ser Pro Ala Arg Tyr Pro Ala Thr Ser Ser
                405                 410                 415
```

-continued

```
Val Thr Leu Val Asp Val Ser Ala Leu Arg Pro Asn Thr Thr Pro Gln
            420                 425                 430

Pro Ser Asn Ser Ser Met Thr Thr Arg Gly Phe Asn Tyr Pro Trp Thr
        435                 440                 445

Ser Ser Gly Thr Asp Thr Lys Lys Ser Val Ser Arg Ile Pro Ser Glu
    450                 455                 460

Thr Tyr Ser Ser Pro Ser Gly Ala Gly Ser Thr Leu His Asp Asn
465                 470                 475                 480

Val Phe Thr Ser Thr Ala Arg Ala Phe Ser Glu Val Pro Thr Thr Ala
                485                 490                 495

Asn Gly Ser Thr Lys Thr Asn His Val His Ile Thr Gly Ile Val Val
            500                 505                 510

Asn Lys Pro Lys Asp Gly Met Ser Trp Pro Val Ile Val Ala Ala Leu
        515                 520                 525

Leu Phe Cys Cys Met Ile Leu Phe Gly Leu Gly Val Arg Lys Trp Cys
    530                 535                 540

Gln Tyr Gln Lys Glu Ile Met Glu Arg Pro Pro Pro Phe Lys Pro Pro
545                 550                 555                 560

Pro Pro Pro Ile Lys Tyr Thr Cys Ile Gln Glu Pro Asn Glu Ser Asp
                565                 570                 575

Leu Pro Tyr His Glu Met Glu Thr Leu
            580                 585

<210> SEQ ID NO 2
<211> LENGTH: 569
<212> TYPE: PRT
<213> ORGANISM: homo sapiens

<400> SEQUENCE: 2

Met Glu Lys Lys Trp Lys Tyr Cys Ala Val Tyr Tyr Ile Ile Gln Ile
1               5                   10                  15

His Phe Val Lys Gly Val Trp Glu Lys Thr Val Asn Thr Glu Glu Asn
            20                  25                  30

Val Tyr Ala Thr Leu Gly Ser Asp Val Asn Leu Thr Cys Gln Thr Gln
        35                  40                  45

Thr Val Gly Phe Phe Val Gln Met Gln Trp Ser Lys Val Thr Asn Lys
    50                  55                  60

Ile Asp Leu Ile Ala Val Tyr His Pro Gln Tyr Gly Phe Tyr Cys Ala
65              70                  75                  80

Tyr Gly Arg Pro Cys Glu Ser Leu Val Thr Phe Thr Glu Thr Pro Glu
                85                  90                  95

Asn Gly Ser Lys Trp Thr Leu His Leu Arg Asn Met Ser Cys Ser Val
            100                 105                 110

Ser Gly Arg Tyr Glu Cys Met Leu Val Leu Tyr Pro Glu Gly Ile Gln
        115                 120                 125

Thr Lys Ile Tyr Asn Leu Leu Ile Gln Thr His Val Thr Ala Asp Glu
    130                 135                 140

Trp Asn Ser Asn His Thr Ile Glu Ile Glu Ile Asn Gln Thr Leu Glu
145                 150                 155                 160

Ile Pro Cys Phe Gln Asn Ser Ser Lys Ile Ser Ser Glu Phe Thr
                165                 170                 175

Tyr Ala Trp Ser Val Glu Asp Asn Gly Thr Gln Glu Thr Leu Ile Ser
            180                 185                 190

Gln Asn His Leu Ile Ser Asn Ser Thr Leu Leu Lys Asp Arg Val Lys
```

```
                195                 200                 205
Leu Gly Thr Asp Tyr Arg Leu His Leu Ser Pro Val Gln Ile Phe Asp
210                 215                 220
Asp Gly Arg Lys Phe Ser Cys His Ile Arg Val Gly Pro Asn Lys Ile
225                 230                 235                 240
Leu Arg Ser Ser Thr Thr Val Lys Val Phe Ala Lys Pro Glu Ile Pro
                245                 250                 255
Val Ile Val Glu Asn Asn Ser Thr Asp Val Leu Val Glu Arg Arg Phe
                260                 265                 270
Thr Cys Leu Leu Lys Asn Val Phe Pro Lys Ala Asn Ile Thr Trp Phe
                275                 280                 285
Ile Asp Gly Ser Phe Leu His Asp Glu Lys Glu Gly Ile Tyr Ile Thr
            290                 295                 300
Asn Glu Glu Arg Lys Gly Lys Asp Gly Phe Leu Glu Leu Lys Ser Val
305                 310                 315                 320
Leu Thr Arg Val His Ser Asn Lys Pro Ala Gln Ser Asp Asn Leu Thr
                325                 330                 335
Ile Trp Cys Met Ala Leu Ser Pro Val Pro Gly Asn Lys Val Trp Asn
                340                 345                 350
Ile Ser Ser Glu Lys Ile Thr Phe Leu Leu Gly Ser Glu Ile Ser Ser
            355                 360                 365
Thr Asp Pro Pro Leu Ser Val Thr Glu Ser Thr Leu Asp Thr Gln Pro
        370                 375                 380
Ser Pro Ala Ser Ser Val Ser Pro Ala Arg Tyr Pro Ala Thr Ser Ser
385                 390                 395                 400
Val Thr Leu Val Asp Val Ser Ala Leu Arg Pro Asn Thr Thr Pro Gln
                405                 410                 415
Pro Ser Asn Ser Ser Met Thr Thr Arg Gly Phe Asn Tyr Pro Trp Thr
                420                 425                 430
Ser Ser Gly Thr Asp Thr Lys Lys Ser Val Ser Arg Ile Pro Ser Glu
            435                 440                 445
Thr Tyr Ser Ser Ser Pro Ser Gly Ala Gly Ser Thr Leu His Asp Asn
        450                 455                 460
Val Phe Thr Ser Thr Ala Arg Ala Phe Ser Glu Val Pro Thr Thr Ala
465                 470                 475                 480
Asn Gly Ser Thr Lys Thr Asn His Val His Ile Thr Gly Ile Val Val
                485                 490                 495
Asn Lys Pro Lys Asp Gly Met Ser Trp Pro Val Ile Val Ala Ala Leu
                500                 505                 510
Leu Phe Cys Cys Met Ile Leu Phe Gly Leu Gly Val Arg Lys Trp Cys
            515                 520                 525
Gln Tyr Gln Lys Glu Ile Met Glu Arg Pro Pro Phe Lys Pro Pro Pro
        530                 535                 540
Pro Pro Pro Ile Lys Tyr Thr Cys Ile Gln Glu Pro Asn Glu Ser Asp
545                 550                 555                 560
Leu Pro Tyr His Glu Met Glu Thr Leu
                565

<210> SEQ ID NO 3
<211> LENGTH: 1710
<212> TYPE: DNA
<213> ORGANISM: homo sapiens

<400> SEQUENCE: 3
```

| | |
|---|---|
| atggagaaaa aatggaaata ctgtgctgtc tattacatca tccagataca ttttgtcaag | 60 |
| ggagtttggg aaaaaacagt caacacagaa gaaaatgttt atgctacact tggctctgat | 120 |
| gtcaacctga cctgccaaac acagacagta ggcttcttcg tgcagatgca atggtccaag | 180 |
| gtcaccaata agatagacct gattgctgtc tatcatcccc aatacggctt ctactgtgcc | 240 |
| tatgggagac cctgtgagtc acttgtgact ttcacagaaa ctcctgagaa tgggtcaaaa | 300 |
| tggactctgc acttaaggaa tatgtcttgt tcagtcagtg aaggtacga gtgtatgctt | 360 |
| gttctgtatc cagagggcat tcagactaaa atctacaacc ttctcattca gacacacgtt | 420 |
| acagcagatg aatggaacag caaccatacg atagaaatag agataaatca gactctggaa | 480 |
| ataccatgct ttcaaaatag ctcctcaaaa atttcatctg agttcaccta tgcatggtcg | 540 |
| gtggaggata atggaactca ggaaacactt atctcccaaa atcacctcat cagcaattcc | 600 |
| acattactta agatagagt caagcttggt acagactaca gactccacct ctctccagtc | 660 |
| caaatcttcg atgatgggcg gaagttctct tgccacatta gagtcggtcc taacaaaatc | 720 |
| ttgaggagct ccaccacagt caaggttttt gctaaaccag aaatccctgt gattgtggaa | 780 |
| aataactcca cggatgtctt ggtagagaga agattacct gcttactaaa gaatgtattt | 840 |
| cccaaagcaa atatcacatg gtttatagat ggaagttttc ttcatgatga aaagaagga | 900 |
| atatatatta ctaatgaaga gagaaaaggc aaagatggat ttttggaact gaagtctgtt | 960 |
| ttaacaaggg tacatagtaa taaaccagcc caatcagaca acttgaccat ttggtgtatg | 1020 |
| gctctgtctc cagtcccagg aaataaagtg tggaacatct catcagaaaa gatcactttt | 1080 |
| ctcttaggtt ctgaaatttc ctcaacagac cctccactga gtgttacaga atctaccctt | 1140 |
| gacacccaac cttctccagc cagcagtgta tctcctgcaa gatatccagc tacatcttca | 1200 |
| gtgacccttg tagatgtgag tgccttgagg ccaaacacca ctcctcaacc cagcaattcc | 1260 |
| agtatgacta cccgaggctt caactatccc tggacctcca gtgggacaga taccaaaaaa | 1320 |
| tcagtttcac ggatacctag tgaaacatac agttcatccc cctcaggtgc aggctcaaca | 1380 |
| cttcatgaca atgtctttac cagcacagcc agagcatttt cagaagtccc cacaactgcc | 1440 |
| aatggatcta cgaaaactaa tcacgtccat atcactggta ttgtggtcaa taagcccaaa | 1500 |
| gatggaatgt cctggccagt gattgtagca gctttactct tttgctgcat gatattgttt | 1560 |
| ggtcttggag tgagaaaatg gtgtcagtac caaaaagaaa taatgaaag acctccacct | 1620 |
| ttcaagccac caccacctcc catcaagtac acttgcattc aagagcccaa cgaaagtgat | 1680 |
| ctgccttatc atgagatgga gaccctctag | 1710 |

<210> SEQ ID NO 4
<211> LENGTH: 479
<212> TYPE: PRT
<213> ORGANISM: artificial
<220> FEATURE:
<223> OTHER INFORMATION: Synthetic polypeptide

<400> SEQUENCE: 4

Val Trp Glu Lys Thr Val Asn Thr Glu Glu Asn Val Tyr Ala Thr Leu
1               5                   10                  15

Gly Ser Asp Val Asn Leu Thr Cys Gln Thr Gln Thr Val Gly Phe Phe
            20                  25                  30

Val Gln Met Gln Trp Ser Lys Val Thr Asn Lys Ile Asp Leu Ile Ala
        35                  40                  45

Val Tyr His Pro Gln Tyr Gly Phe Tyr Cys Ala Tyr Gly Arg Pro Cys
    50                  55                  60

```
Glu Ser Leu Val Thr Phe Thr Glu Thr Pro Glu Asn Gly Ser Lys Trp
 65                  70                  75                  80

Thr Leu His Leu Arg Asn Met Ser Cys Ser Val Ser Gly Arg Tyr Glu
                 85                  90                  95

Cys Met Leu Val Leu Tyr Pro Glu Gly Ile Gln Thr Lys Ile Tyr Asn
                100                 105                 110

Leu Leu Ile Gln Thr His Val Thr Ala Asp Glu Trp Asn Ser Asn His
            115                 120                 125

Thr Ile Glu Ile Glu Ile Asn Gln Thr Leu Glu Ile Pro Cys Phe Gln
130                 135                 140

Asn Ser Ser Lys Ile Ser Ser Glu Phe Thr Tyr Ala Trp Ser Val
145                 150                 155                 160

Glu Asp Asn Gly Thr Gln Glu Thr Leu Ile Ser Gln Asn His Leu Ile
                165                 170                 175

Ser Asn Ser Thr Leu Leu Lys Asp Arg Val Lys Leu Gly Thr Asp Tyr
                180                 185                 190

Arg Leu His Leu Ser Pro Val Gln Ile Phe Asp Asp Gly Arg Lys Phe
            195                 200                 205

Ser Cys His Ile Arg Val Gly Pro Asn Lys Ile Leu Arg Ser Ser Thr
210                 215                 220

Thr Val Lys Val Phe Ala Lys Pro Glu Ile Pro Val Ile Val Glu Asn
225                 230                 235                 240

Asn Ser Thr Asp Val Leu Val Glu Arg Arg Phe Thr Cys Leu Leu Lys
                245                 250                 255

Asn Val Phe Pro Lys Ala Asn Ile Thr Trp Phe Ile Asp Gly Ser Phe
                260                 265                 270

Leu His Asp Glu Lys Glu Gly Ile Tyr Ile Thr Asn Glu Glu Arg Lys
            275                 280                 285

Gly Lys Asp Gly Phe Leu Glu Leu Lys Ser Val Leu Thr Arg Val His
290                 295                 300

Ser Asn Lys Pro Ala Gln Ser Asp Asn Leu Thr Ile Trp Cys Met Ala
305                 310                 315                 320

Leu Ser Pro Val Pro Gly Asn Lys Val Trp Asn Ile Ser Ser Glu Lys
                325                 330                 335

Ile Thr Phe Leu Leu Gly Ser Glu Ile Ser Ser Thr Asp Pro Pro Leu
                340                 345                 350

Ser Val Thr Glu Ser Thr Leu Asp Thr Gln Pro Ser Pro Ala Ser Ser
            355                 360                 365

Val Ser Pro Ala Arg Tyr Pro Ala Thr Ser Ser Val Thr Leu Val Asp
        370                 375                 380

Val Ser Ala Leu Arg Pro Asn Thr Thr Pro Gln Pro Ser Asn Ser Ser
385                 390                 395                 400

Met Thr Thr Arg Gly Phe Asn Tyr Pro Trp Thr Ser Ser Gly Thr Asp
                405                 410                 415

Thr Lys Lys Ser Val Ser Arg Ile Pro Ser Glu Thr Tyr Ser Ser Ser
                420                 425                 430

Pro Ser Gly Ala Gly Ser Thr Leu His Asp Asn Val Phe Thr Ser Thr
            435                 440                 445

Ala Arg Ala Phe Ser Glu Val Pro Thr Thr Ala Asn Gly Ser Thr Lys
        450                 455                 460

Thr Asn His Val His Ile Thr Gly Ile Val Val Asn Lys Pro Lys
465                 470                 475
```

-continued

```
<210> SEQ ID NO 5
<211> LENGTH: 116
<212> TYPE: PRT
<213> ORGANISM: artificial
<220> FEATURE:
<223> OTHER INFORMATION: Synthetic polypeptide

<400> SEQUENCE: 5

Val Trp Glu Lys Thr Val Asn Thr Glu Glu Asn Val Tyr Ala Thr Leu
1               5                   10                  15

Gly Ser Asp Val Asn Leu Thr Cys Gln Thr Gln Thr Val Gly Phe Phe
            20                  25                  30

Val Gln Met Gln Trp Ser Lys Val Thr Asn Lys Ile Asp Leu Ile Ala
        35                  40                  45

Val Tyr His Pro Gln Tyr Gly Phe Tyr Cys Ala Tyr Gly Arg Pro Cys
    50                  55                  60

Glu Ser Leu Val Thr Phe Thr Glu Thr Pro Glu Asn Gly Ser Lys Trp
65                  70                  75                  80

Thr Leu His Leu Arg Asn Met Ser Cys Ser Val Ser Gly Arg Tyr Glu
                85                  90                  95

Cys Met Leu Val Leu Tyr Pro Glu Gly Ile Gln Thr Lys Ile Tyr Asn
            100                 105                 110

Leu Leu Ile Gln
        115

<210> SEQ ID NO 6
<211> LENGTH: 338
<212> TYPE: PRT
<213> ORGANISM: artificial
<220> FEATURE:
<223> OTHER INFORMATION: Synthetic polypeptide

<400> SEQUENCE: 6

Val Trp Glu Lys Thr Val Asn Thr Glu Glu Asn Val Tyr Ala Thr Leu
1               5                   10                  15

Gly Ser Asp Val Asn Leu Thr Cys Gln Thr Gln Thr Val Gly Phe Phe
            20                  25                  30

Val Gln Met Gln Trp Ser Lys Val Thr Asn Lys Ile Asp Leu Ile Ala
        35                  40                  45

Val Tyr His Pro Gln Tyr Gly Phe Tyr Cys Ala Tyr Gly Arg Pro Cys
    50                  55                  60

Glu Ser Leu Val Thr Phe Thr Glu Thr Pro Glu Asn Gly Ser Lys Trp
65                  70                  75                  80

Thr Leu His Leu Arg Asn Met Ser Cys Ser Val Ser Gly Arg Tyr Glu
                85                  90                  95

Cys Met Leu Val Leu Tyr Pro Glu Gly Ile Gln Thr Lys Ile Tyr Asn
            100                 105                 110

Leu Leu Ile Gln Thr His Val Thr Ala Asp Glu Trp Asn Ser Asn His
        115                 120                 125

Thr Ile Glu Ile Glu Ile Asn Gln Thr Leu Glu Ile Pro Cys Phe Gln
    130                 135                 140

Asn Ser Ser Ser Lys Ile Ser Ser Glu Phe Thr Tyr Ala Trp Ser Val
145                 150                 155                 160

Glu Asp Asn Gly Thr Gln Glu Thr Leu Ile Ser Gln Asn His Leu Ile
                165                 170                 175

Ser Asn Ser Thr Leu Leu Lys Asp Arg Val Lys Leu Gly Thr Asp Tyr
            180                 185                 190
```

```
Arg Leu His Leu Ser Pro Val Gln Ile Phe Asp Asp Gly Arg Lys Phe
            195                 200                 205

Ser Cys His Ile Arg Val Gly Pro Asn Lys Ile Leu Arg Ser Ser Thr
210                 215                 220

Thr Val Lys Val Phe Ala Lys Pro Glu Ile Pro Val Ile Val Glu Asn
225                 230                 235                 240

Asn Ser Thr Asp Val Leu Val Glu Arg Arg Phe Thr Cys Leu Leu Lys
            245                 250                 255

Asn Val Phe Pro Lys Ala Asn Ile Thr Trp Phe Ile Asp Gly Ser Phe
            260                 265                 270

Leu His Asp Glu Lys Glu Gly Ile Tyr Ile Thr Asn Glu Glu Arg Lys
            275                 280                 285

Gly Lys Asp Gly Phe Leu Glu Leu Lys Ser Val Leu Thr Arg Val His
            290                 295                 300

Ser Asn Lys Pro Ala Gln Ser Asp Asn Leu Thr Ile Trp Cys Met Ala
305                 310                 315                 320

Leu Ser Pro Val Pro Gly Asn Lys Val Trp Asn Ile Ser Ser Glu Lys
            325                 330                 335

Ile Thr

<210> SEQ ID NO 7
<211> LENGTH: 479
<212> TYPE: PRT
<213> ORGANISM: artificial
<220> FEATURE:
<223> OTHER INFORMATION: Synthetic polypeptide

<400> SEQUENCE: 7

Val Trp Gly Lys Pro Phe Asn Thr Glu Glu Asn Ile Tyr Ala Thr Leu
1               5                   10                  15

Gly Ser Asp Val Asn Leu Thr Cys Gln Thr Gln Ala Lys Gly Phe Leu
            20                  25                  30

Val Gln Met Gln Trp Ser Lys Val Thr Asp Lys Ala Asp Leu Ile Ala
            35                  40                  45

Leu Tyr His Pro Gln Tyr Gly Phe His Cys Ala Tyr Gly Ser Pro Cys
        50                  55                  60

Glu Ser Leu Val Thr Phe Thr Gln Thr Pro Glu Asn Gly Ser Lys Trp
65                  70                  75                  80

Thr Leu His Leu Arg Asn Met Ser Ser Ser Val Ser Gly Arg Tyr Glu
                85                  90                  95

Cys Met Leu Thr Leu Tyr Pro Glu Gly Met Gln Thr Lys Ile Tyr Asn
            100                 105                 110

Leu Leu Ile Gln Thr His Val Thr Pro Asp Glu Trp Lys Ser Asn His
            115                 120                 125

Thr Ile Glu Ile Glu Ile Asn Gln Thr Leu Glu Ile Pro Cys Phe Gln
130                 135                 140

Asn Ser Ser Ser Glu Ile Ser Ser Glu Phe Thr Tyr Ala Trp Leu Val
145                 150                 155                 160

Glu Asp Asn Gly Thr Gln Gln Thr Leu Ile Ser Gln Asp His Leu Ile
                165                 170                 175

Ser Ser Ser Thr Leu Leu Lys Asp Arg Val Lys Val Gly Ile Asp Tyr
            180                 185                 190

Arg Leu His Leu Ser Pro Val Gln Ile Phe Asp Asp Gly Arg Lys Phe
            195                 200                 205
```

```
Ser Cys His Ile Arg Val Gly Pro Asp Lys Ile Leu Arg Ser Ser Thr
    210                 215                 220
Thr Ile Lys Val Phe Ala Lys Pro Glu Ile Pro Met Ile Val Glu Asn
225                 230                 235                 240
Asn Ser Thr Asp Val Leu Val Glu Arg Thr Phe Thr Cys Leu Leu Lys
                245                 250                 255
Asn Val Phe Pro Lys Ala Asn Ile Ile Trp Phe Ile Asp Gly Ser Phe
                260                 265                 270
Leu His Asp Glu Lys Glu Gly Ile Tyr Ile Thr Asn Glu Glu Arg Lys
            275                 280                 285
Gly Lys Asp Gly Phe Leu Glu Leu Lys Ser Val Leu Thr Arg Val His
        290                 295                 300
Ser Asp Lys Pro Ala Gln Ser Asp Asn Leu Thr Ile Trp Cys Met Ala
305                 310                 315                 320
Leu Ser Pro Val Pro Gly Asn Lys Val Trp Asn Ile Ser Ser Glu Lys
                325                 330                 335
Ile Thr Phe Leu Leu Gly Ser Glu Met Ser Thr Thr Asp Leu Pro Pro
                340                 345                 350
Ser Val Thr Glu Ser Thr Leu Asp Thr Gln Pro Ser Pro Ala Ser Ser
                355                 360                 365
Val Ser Pro Thr Arg Tyr Pro Ala Thr Ser Ser Val Thr Leu Ala Asp
370                 375                 380
Val Ser Ala Leu Arg Pro Asn Thr Thr Pro Gln Ser Ser Ser Ser Ser
385                 390                 395                 400
Val Thr Thr Gln Asp Phe Asn Tyr Pro Trp Thr Ser Ser Gly Thr Asp
                405                 410                 415
Ala Lys Lys Ser Phe Ser Gln Ile Pro Ser Glu Thr Tyr Ser Ser Ser
            420                 425                 430
Pro Ser Gly Ala Gly Ser Thr Leu His Asp Asn Val Phe Thr Ser Thr
        435                 440                 445
Thr Arg Ala Leu Ser Glu Val Pro Thr Thr Ala Asn Gly Ser Thr Lys
    450                 455                 460
Thr Asn His Val His Ile Thr Gly Ile Val Val Ser Lys Pro Lys
465                 470                 475
```

<210> SEQ ID NO 8
<211> LENGTH: 338
<212> TYPE: PRT
<213> ORGANISM: artificial
<220> FEATURE:
<223> OTHER INFORMATION: Synthetic polypeptide

<400> SEQUENCE: 8

```
Val Trp Gly Lys Pro Phe Asn Thr Glu Glu Asn Ile Tyr Ala Thr Leu
1               5                   10                  15
Gly Ser Asp Val Asn Leu Thr Cys Gln Thr Gln Ala Lys Gly Phe Leu
                20                  25                  30
Val Gln Met Gln Trp Ser Lys Val Thr Asp Lys Ala Asp Leu Ile Ala
            35                  40                  45
Leu Tyr His Pro Gln Tyr Gly Phe His Cys Ala Tyr Gly Ser Pro Cys
        50                  55                  60
Glu Ser Leu Val Thr Phe Thr Gln Thr Pro Glu Asn Gly Ser Lys Trp
65                  70                  75                  80
Thr Leu His Leu Arg Asn Met Ser Ser Ser Val Ser Gly Arg Tyr Glu
                85                  90                  95
```

```
Cys Met Leu Thr Leu Tyr Pro Glu Gly Met Gln Thr Lys Ile Tyr Asn
                100                 105                 110

Leu Leu Ile Gln Thr His Val Thr Pro Asp Glu Trp Lys Ser Asn His
            115                 120                 125

Thr Ile Glu Ile Glu Ile Asn Gln Thr Leu Glu Ile Pro Cys Phe Gln
130                 135                 140

Asn Ser Ser Glu Ile Ser Ser Glu Phe Thr Tyr Ala Trp Leu Val
145                 150                 155                 160

Glu Asp Asn Gly Thr Gln Gln Thr Leu Ile Ser Gln Asp His Leu Ile
                165                 170                 175

Ser Ser Ser Thr Leu Leu Lys Asp Arg Val Lys Val Gly Ile Asp Tyr
            180                 185                 190

Arg Leu His Leu Ser Pro Val Gln Ile Phe Asp Asp Gly Arg Lys Phe
            195                 200                 205

Ser Cys His Ile Arg Val Gly Pro Asp Lys Ile Leu Arg Ser Ser Thr
210                 215                 220

Thr Ile Lys Val Phe Ala Lys Pro Glu Ile Pro Met Ile Val Glu Asn
225                 230                 235                 240

Asn Ser Thr Asp Val Leu Val Glu Arg Thr Phe Thr Cys Leu Leu Lys
                245                 250                 255

Asn Val Phe Pro Lys Ala Asn Ile Ile Trp Phe Ile Asp Gly Ser Phe
            260                 265                 270

Leu His Asp Glu Lys Glu Gly Ile Tyr Ile Thr Asn Glu Glu Arg Lys
            275                 280                 285

Gly Lys Asp Gly Phe Leu Glu Leu Lys Ser Val Leu Thr Arg Val His
290                 295                 300

Ser Asp Lys Pro Ala Gln Ser Asp Asn Leu Thr Ile Trp Cys Met Ala
305                 310                 315                 320

Leu Ser Pro Val Pro Gly Asn Lys Val Trp Asn Ile Ser Ser Glu Lys
                325                 330                 335

Ile Thr

<210> SEQ ID NO 9
<211> LENGTH: 338
<212> TYPE: PRT
<213> ORGANISM: artificial
<220> FEATURE:
<223> OTHER INFORMATION: Synthetic polypeptide

<400> SEQUENCE: 9

Val Trp Gly Lys Pro Leu Asn Thr Glu Glu Asn Ile Tyr Ala Thr Leu
1               5                   10                  15

Gly Ser Asp Val Asn Leu Thr Cys Gln Thr Gln Ala Lys Gly Phe Leu
                20                  25                  30

Val Gln Met Gln Trp Ser Lys Val Thr Asp Lys Ala Asp Leu Ile Ala
            35                  40                  45

Leu Tyr His Pro Gln Tyr Gly Phe His Cys Ala Tyr Gly Ser Pro Cys
        50                  55                  60

Glu Ser Leu Val Thr Phe Thr Gln Thr Pro Glu Asn Gly Ser Lys Trp
65                  70                  75                  80

Thr Leu His Leu Arg Asn Met Ser Ser Ser Val Ser Gly Arg Tyr Glu
                85                  90                  95

Cys Met Leu Thr Leu Tyr Pro Glu Gly Met Gln Thr Lys Ile Tyr Asn
                100                 105                 110

Leu Leu Ile Gln Thr His Val Thr Pro Asp Glu Trp Lys Ser Asn His
            115                 120                 125
```

```
                    115                 120                 125
Thr Ile Glu Ile Glu Ile Asn Gln Thr Leu Glu Ile Pro Cys Phe Gln
130                 135                 140

Asn Ser Ser Ser Glu Ile Ser Ser Glu Phe Thr Tyr Ala Trp Leu Val
145                 150                 155                 160

Glu Asp Asn Gly Thr Gln Gln Thr Leu Ile Ser Gln Asp His Leu Ile
                165                 170                 175

Ser Ser Ser Thr Leu Leu Lys Asp Arg Val Lys Val Gly Thr Asp Tyr
            180                 185                 190

Arg Leu His Leu Ser Pro Val Gln Ile Phe Asp Asp Gly Arg Lys Phe
                195                 200                 205

Ser Cys His Ile Arg Val Gly Pro Asp Lys Ile Leu Arg Ser Ser Thr
            210                 215                 220

Thr Ile Lys Val Phe Ala Lys Pro Glu Ile Pro Met Ile Val Glu Asn
225                 230                 235                 240

Asn Ser Thr Asp Val Leu Val Glu Arg Ile Phe Thr Cys Leu Leu Thr
                245                 250                 255

Asn Val Phe Pro Lys Ala Asn Ile Ile Trp Phe Ile Asp Gly Ser Phe
                260                 265                 270

Leu His Asp Glu Lys Glu Gly Ile Tyr Ile Thr Asn Glu Glu Arg Lys
            275                 280                 285

Gly Lys Asp Gly Phe Leu Glu Leu Lys Ser Val Leu Thr Arg Val His
            290                 295                 300

Ser Asp Lys Pro Ala Gln Ser Asp Asn Leu Thr Ile Trp Cys Met Ala
305                 310                 315                 320

Leu Ser Pro Val Pro Gly Asn Lys Val Trp Asn Ile Ser Ser Glu Lys
                325                 330                 335

Ile Thr

<210> SEQ ID NO 10
<211> LENGTH: 323
<212> TYPE: PRT
<213> ORGANISM: artificial
<220> FEATURE:
<223> OTHER INFORMATION: Synthetic polypeptide

<400> SEQUENCE: 10

Trp Pro Pro Pro Gly Thr Gly Asp Val Val Gln Ala Pro Thr Gln
1               5                   10                  15

Val Pro Gly Phe Leu Gly Asp Ser Val Thr Leu Pro Cys Tyr Leu Gln
                20                  25                  30

Val Pro Asn Met Glu Val Thr His Val Ser Gln Leu Thr Trp Ala Arg
            35                  40                  45

His Gly Glu Ser Gly Ser Met Ala Val Phe His Gln Thr Gln Gly Pro
        50                  55                  60

Ser Tyr Ser Glu Ser Lys Arg Leu Glu Phe Val Ala Ala Arg Leu Gly
65                  70                  75                  80

Ala Glu Leu Arg Asn Ala Ser Leu Arg Met Phe Gly Leu Arg Val Glu
                85                  90                  95

Asp Glu Gly Asn Tyr Thr Cys Leu Phe Val Thr Phe Pro Gln Gly Ser
            100                 105                 110

Arg Ser Val Asp Ile Trp Leu Arg Val Leu Ala Lys Pro Gln Asn Thr
            115                 120                 125

Ala Glu Val Gln Lys Val Gln Leu Thr Gly Glu Pro Val Pro Met Ala
130                 135                 140
```

```
Arg Cys Val Ser Thr Gly Gly Arg Pro Ala Gln Ile Thr Trp His
145                 150                 155                 160

Ser Asp Leu Gly Gly Met Pro Asn Thr Ser Gln Val Pro Gly Phe Leu
                165                 170                 175

Ser Gly Thr Val Thr Val Thr Ser Leu Trp Ile Leu Val Pro Ser Ser
            180                 185                 190

Gln Val Asp Gly Lys Asn Val Thr Cys Lys Val Glu His Glu Ser Phe
            195                 200                 205

Glu Lys Pro Gln Leu Leu Thr Val Asn Leu Thr Val Tyr Tyr Pro Pro
        210                 215                 220

Glu Val Ser Ile Ser Gly Tyr Asp Asn Asn Trp Tyr Leu Gly Gln Asn
225                 230                 235                 240

Glu Ala Thr Leu Thr Cys Asp Ala Arg Ser Asn Pro Glu Pro Thr Gly
                245                 250                 255

Tyr Asn Trp Ser Thr Thr Met Gly Pro Leu Pro Pro Phe Ala Val Ala
            260                 265                 270

Gln Gly Ala Gln Leu Leu Ile Arg Pro Val Asp Lys Pro Ile Asn Thr
        275                 280                 285

Thr Leu Ile Cys Asn Val Thr Asn Ala Leu Gly Ala Arg Gln Ala Glu
        290                 295                 300

Leu Thr Val Gln Val Lys Glu Gly Pro Pro Ser Glu His Ser Gly Met
305                 310                 315                 320

Ser Arg Asn

<210> SEQ ID NO 11
<211> LENGTH: 317
<212> TYPE: PRT
<213> ORGANISM: artificial
<220> FEATURE:
<223> OTHER INFORMATION: Synthetic polypeptide

<400> SEQUENCE: 11

Asp Ile Arg Val Leu Val Pro Tyr Asn Ser Thr Gly Val Leu Gly Gly
1               5                   10                  15

Ser Thr Thr Leu His Cys Ser Leu Thr Ser Asn Glu Asn Val Thr Ile
                20                  25                  30

Thr Gln Ile Thr Trp Met Lys Lys Asp Ser Gly Gly Ser His Ala Leu
            35                  40                  45

Val Ala Val Phe His Pro Lys Lys Gly Pro Asn Ile Lys Glu Pro Glu
        50                  55                  60

Arg Val Lys Phe Leu Ala Ala Gln Gln Asp Leu Arg Asn Ala Ser Leu
65                  70                  75                  80

Ala Ile Ser Asn Leu Ser Val Glu Asp Glu Gly Ile Tyr Glu Cys Gln
                85                  90                  95

Ile Ala Thr Phe Pro Arg Gly Ser Arg Ser Thr Asn Ala Trp Leu Lys
            100                 105                 110

Val Gln Ala Arg Pro Lys Asn Thr Ala Glu Ala Leu Glu Pro Ser Pro
        115                 120                 125

Thr Leu Ile Leu Gln Asp Val Ala Lys Cys Ile Ser Ala Asn Gly His
    130                 135                 140

Pro Pro Gly Arg Ile Ser Trp Pro Ser Asn Val Asn Gly Ser His Arg
145                 150                 155                 160

Glu Met Lys Glu Pro Gly Ser Gln Pro Gly Thr Thr Thr Val Thr Ser
                165                 170                 175
```

```
Tyr Leu Ser Met Val Pro Ser Arg Gln Ala Asp Gly Lys Asn Ile Thr
            180                 185                 190

Cys Thr Val Glu His Glu Ser Leu Gln Glu Leu Asp Gln Leu Leu Val
            195                 200                 205

Thr Leu Ser Gln Pro Tyr Pro Pro Glu Asn Val Ser Ile Ser Gly Tyr
            210                 215                 220

Asp Gly Asn Trp Tyr Val Gly Leu Thr Asn Leu Thr Leu Thr Cys Glu
225                 230                 235                 240

Ala His Ser Lys Pro Ala Pro Asp Met Ala Gly Tyr Asn Trp Ser Thr
            245                 250                 255

Thr Thr Gly Asp Phe Pro Asn Ser Val Lys Arg Gln Gly Asn Met Leu
            260                 265                 270

Leu Ile Ser Thr Val Glu Asp Gly Leu Asn Asn Thr Val Ile Val Cys
            275                 280                 285

Glu Val Thr Asn Ala Leu Gly Ser Gly Gln Gly Gln Val His Ile Ile
            290                 295                 300

Val Lys Glu Lys Pro Glu Asn Met Gln Gln Asn Thr Arg
305                 310                 315

<210> SEQ ID NO 12
<211> LENGTH: 107
<212> TYPE: PRT
<213> ORGANISM: artificial
<220> FEATURE:
<223> OTHER INFORMATION: Synthetic polypeptide

<400> SEQUENCE: 12

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Ala
            20                  25                  30

Ile Val Trp Tyr Gln Lys Lys Pro Gly Gln Ser Pro Lys Thr Leu Ile
            35                  40                  45

Tyr Ser Ala Ser Thr Arg Tyr Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Ser Ser Ser Pro Leu
                85                  90                  95

Thr Phe Gly Ser Gly Thr Lys Leu Glu Ile Lys
            100                 105

<210> SEQ ID NO 13
<211> LENGTH: 11
<212> TYPE: PRT
<213> ORGANISM: artificial
<220> FEATURE:
<223> OTHER INFORMATION: Synthetic polypeptide

<400> SEQUENCE: 13

Lys Ala Ser Gln Asn Val Gly Thr Ala Ile Val
1               5                   10

<210> SEQ ID NO 14
<211> LENGTH: 7
<212> TYPE: PRT
<213> ORGANISM: artificial
<220> FEATURE:
<223> OTHER INFORMATION: Synthetic polypeptide
```

```
<400> SEQUENCE: 14

Ser Ala Ser Thr Arg Tyr Thr
1               5

<210> SEQ ID NO 15
<211> LENGTH: 9
<212> TYPE: PRT
<213> ORGANISM: artificial
<220> FEATURE:
<223> OTHER INFORMATION: Synthetic polypeptide

<400> SEQUENCE: 15

Gln Gln Tyr Ser Ser Ser Pro Leu Thr
1               5

<210> SEQ ID NO 16
<211> LENGTH: 112
<212> TYPE: PRT
<213> ORGANISM: artificial
<220> FEATURE:
<223> OTHER INFORMATION: Synthetic polypeptide

<400> SEQUENCE: 16

Asp Val Val Met Thr Gln Thr Pro Leu Thr Leu Ser Val Thr Leu Gly
1               5                   10                  15

His Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Glu Ser
        35                  40                  45

Pro Lys Leu Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ala
                85                  90                  95

Thr His Ser Pro Gln Thr Phe Gly Gly Gly Thr Lys Leu Glu Ile Lys
            100                 105                 110

<210> SEQ ID NO 17
<211> LENGTH: 16
<212> TYPE: PRT
<213> ORGANISM: artificial
<220> FEATURE:
<223> OTHER INFORMATION: Synthetic polypeptide

<400> SEQUENCE: 17

Lys Ser Ser Gln Ser Leu Leu Asp Ser Asp Gly Lys Thr Tyr Leu Asn
1               5                   10                  15

<210> SEQ ID NO 18
<211> LENGTH: 7
<212> TYPE: PRT
<213> ORGANISM: artificial
<220> FEATURE:
<223> OTHER INFORMATION: Synthetic polypeptide

<400> SEQUENCE: 18

Leu Val Ser Lys Leu Asp Ser
1               5

<210> SEQ ID NO 19
<211> LENGTH: 9
<212> TYPE: PRT
```

```
<213> ORGANISM: artificial
<220> FEATURE:
<223> OTHER INFORMATION: Synthetic polypeptide

<400> SEQUENCE: 19

Leu Gln Ala Thr His Ser Pro Gln Thr
1               5

<210> SEQ ID NO 20
<211> LENGTH: 107
<212> TYPE: PRT
<213> ORGANISM: artificial
<220> FEATURE:
<223> OTHER INFORMATION: Synthetic polypeptide

<400> SEQUENCE: 20

Asp Ile Gln Met Asn Gln Ser Pro Ser Ser Leu Ser Ala Ser Leu Gly
1               5                   10                  15

Asp Thr Ile Thr Ile Thr Cys Arg Val Ser Gln Asp Ile Ser Phe Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Ala Tyr Tyr Cys Leu Gln Ser Gln Ser Tyr Pro Tyr
                85                  90                  95

Thr Phe Gly Gly Gly Thr Lys Leu Glu Ile Lys
            100                 105

<210> SEQ ID NO 21
<211> LENGTH: 11
<212> TYPE: PRT
<213> ORGANISM: artificial
<220> FEATURE:
<223> OTHER INFORMATION: Synthetic polypeptide

<400> SEQUENCE: 21

Arg Val Ser Gln Asp Ile Ser Phe Trp Leu Ser
1               5                   10

<210> SEQ ID NO 22
<211> LENGTH: 7
<212> TYPE: PRT
<213> ORGANISM: artificial
<220> FEATURE:
<223> OTHER INFORMATION: Synthetic polypeptide

<400> SEQUENCE: 22

Lys Ala Ser Asn Leu His Thr
1               5

<210> SEQ ID NO 23
<211> LENGTH: 9
<212> TYPE: PRT
<213> ORGANISM: artificial
<220> FEATURE:
<223> OTHER INFORMATION: Synthetic polypeptide

<400> SEQUENCE: 23

Leu Gln Ser Gln Ser Tyr Pro Tyr Thr
1               5
```

```
<210> SEQ ID NO 24
<211> LENGTH: 106
<212> TYPE: PRT
<213> ORGANISM: artificial
<220> FEATURE:
<223> OTHER INFORMATION: Synthetic polypeptide

<400> SEQUENCE: 24

Glu Asn Val Leu Thr Gln Ser Pro Ala Ile Met Ser Ala Thr Leu Gly
1               5                   10                  15

Glu Lys Val Thr Met Asn Cys Arg Ala Ser Ser Asn Val Lys Tyr Met
            20                  25                  30

Tyr Trp Tyr Gln Gln Lys Ser Gly Val Ser Pro Lys Leu Trp Ile Tyr
        35                  40                  45

Tyr Thr Ser Asn Leu Ala Ser Gly Val Pro Thr Arg Phe Ser Gly Ser
    50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Phe Thr Ser Ser Pro Leu Thr
                85                  90                  95

Phe Gly Ala Gly Thr Lys Leu Glu Leu Lys
            100                 105

<210> SEQ ID NO 25
<211> LENGTH: 10
<212> TYPE: PRT
<213> ORGANISM: artificial
<220> FEATURE:
<223> OTHER INFORMATION: Synthetic polypeptide

<400> SEQUENCE: 25

Arg Ala Ser Ser Asn Val Lys Tyr Met Tyr
1               5                   10

<210> SEQ ID NO 26
<211> LENGTH: 7
<212> TYPE: PRT
<213> ORGANISM: artificial
<220> FEATURE:
<223> OTHER INFORMATION: Synthetic polypeptide

<400> SEQUENCE: 26

Tyr Thr Ser Asn Leu Ala Ser
1               5

<210> SEQ ID NO 27
<211> LENGTH: 9
<212> TYPE: PRT
<213> ORGANISM: artificial
<220> FEATURE:
<223> OTHER INFORMATION: Synthetic polypeptide

<400> SEQUENCE: 27

Gln Gln Phe Thr Ser Ser Pro Leu Thr
1               5

<210> SEQ ID NO 28
<211> LENGTH: 111
<212> TYPE: PRT
<213> ORGANISM: artificial
<220> FEATURE:
<223> OTHER INFORMATION: Synthetic polypeptide

<400> SEQUENCE: 28
```

```
Asp Ile Val Leu Thr Gln Ser Pro Ala Ser Leu Ala Val Ser Leu Gly
1               5                  10                  15

Gln Arg Ala Ile Ile Ser Cys Lys Ala Ser Gln Ser Val Thr Phe Ala
            20                  25                  30

Asp Thr Gly Leu Met His Trp Tyr Gln Gln Lys Pro Gly Gln Gln Pro
        35                  40                  45

Lys Leu Leu Ile Tyr Arg Ala Ser Asn Leu Glu Val Gly Val Pro Thr
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln Gln Ser Arg
                85                  90                  95

Glu Tyr Pro Trp Thr Phe Gly Gly Gly Thr Lys Leu Glu Ile Lys
            100                 105                 110
```

<210> SEQ ID NO 29
<211> LENGTH: 15
<212> TYPE: PRT
<213> ORGANISM: artificial
<220> FEATURE:
<223> OTHER INFORMATION: Synthetic polypeptide

<400> SEQUENCE: 29

```
Lys Ala Ser Gln Ser Val Thr Phe Ala Asp Thr Gly Leu Met His
1               5                  10                  15
```

<210> SEQ ID NO 30
<211> LENGTH: 7
<212> TYPE: PRT
<213> ORGANISM: artificial
<220> FEATURE:
<223> OTHER INFORMATION: Synthetic polypeptide

<400> SEQUENCE: 30

```
Arg Ala Ser Asn Leu Glu Val
1               5
```

<210> SEQ ID NO 31
<211> LENGTH: 9
<212> TYPE: PRT
<213> ORGANISM: artificial
<220> FEATURE:
<223> OTHER INFORMATION: Synthetic polypeptide

<400> SEQUENCE: 31

```
Gln Gln Ser Arg Glu Tyr Pro Trp Thr
1               5
```

<210> SEQ ID NO 32
<211> LENGTH: 109
<212> TYPE: PRT
<213> ORGANISM: artificial
<220> FEATURE:
<223> OTHER INFORMATION: Synthetic polypeptide

<400> SEQUENCE: 32

```
Gln Ala Val Val Thr Gln Glu Ser Ala Leu Thr Thr Ser Pro Gly Glu
1               5                  10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45
```

```
Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ser Leu Trp Tyr Gly Ser
                    85                  90                  95

His Trp Val Phe Gly Gly Gly Thr Lys Leu Thr Val Leu
                100                 105
```

<210> SEQ ID NO 33
<211> LENGTH: 14
<212> TYPE: PRT
<213> ORGANISM: artificial
<220> FEATURE:
<223> OTHER INFORMATION: Synthetic polypeptide

<400> SEQUENCE: 33

```
Arg Ser Ser Thr Gly Ala Val Thr Thr Ser Asn Tyr Ala Asn
 1               5                  10
```

<210> SEQ ID NO 34
<211> LENGTH: 7
<212> TYPE: PRT
<213> ORGANISM: artificial
<220> FEATURE:
<223> OTHER INFORMATION: Synthetic polypeptide

<400> SEQUENCE: 34

```
Gly Thr Asn Asn Arg Ala Pro
 1               5
```

<210> SEQ ID NO 35
<211> LENGTH: 9
<212> TYPE: PRT
<213> ORGANISM: artificial
<220> FEATURE:
<223> OTHER INFORMATION: Synthetic polypeptide

<400> SEQUENCE: 35

```
Ser Leu Trp Tyr Gly Ser His Trp Val
 1               5
```

<210> SEQ ID NO 36
<211> LENGTH: 107
<212> TYPE: PRT
<213> ORGANISM: artificial
<220> FEATURE:
<223> OTHER INFORMATION: Synthetic polypeptide

<400> SEQUENCE: 36

```
Asp Ile Leu Met Thr Gln Ser Pro Thr Thr Leu Ser Val Thr Pro Gly
 1               5                  10                  15

Glu Thr Val Ser Leu Ser Cys Arg Ala Ser Gln Asp Ile Tyr Arg Asn
                20                  25                  30

Leu His Trp Tyr Gln Gln Lys Ser Gln Gly Thr Pro Arg Leu Leu Ile
            35                  40                  45

Lys His Ala Ser Asp Ser Ile Ser Gly Ile Pro Ser Arg Phe Thr Gly
     50                  55                  60

Ser Gly Ser Gly Thr Asp Phe Thr Leu Ser Ile Asn Ser Val Lys Pro
 65                  70                  75                  80

Glu Asp Glu Gly Ile Tyr Tyr Cys Leu Gln Gly Tyr Ser Met Pro Tyr
                85                  90                  95
```

Thr Phe Gly Gly Gly Thr Lys Leu Glu Ile Lys
            100                 105

<210> SEQ ID NO 37
<211> LENGTH: 11
<212> TYPE: PRT
<213> ORGANISM: artificial
<220> FEATURE:
<223> OTHER INFORMATION: Synthetic polypeptide

<400> SEQUENCE: 37

Arg Ala Ser Gln Asp Ile Tyr Arg Asn Leu His
1               5                   10

<210> SEQ ID NO 38
<211> LENGTH: 7
<212> TYPE: PRT
<213> ORGANISM: artificial
<220> FEATURE:
<223> OTHER INFORMATION: Synthetic polypeptide

<400> SEQUENCE: 38

His Ala Ser Asp Ser Ile Ser
1               5

<210> SEQ ID NO 39
<211> LENGTH: 9
<212> TYPE: PRT
<213> ORGANISM: artificial
<220> FEATURE:
<223> OTHER INFORMATION: Synthetic polypeptide

<400> SEQUENCE: 39

Leu Gln Gly Tyr Ser Met Pro Tyr Thr
1               5

<210> SEQ ID NO 40
<211> LENGTH: 119
<212> TYPE: PRT
<213> ORGANISM: artificial
<220> FEATURE:
<223> OTHER INFORMATION: Synthetic polypeptide

<400> SEQUENCE: 40

Gln Val Gln Leu Gln Gln Pro Gly Ala Glu Leu Val Thr Pro Gly Ala
1               5                   10                  15

Ser Val Lys Leu Ser Cys Lys Ala Ser Gly Phe Thr Phe Thr Asn Asn
            20                  25                  30

Trp Met His Trp Val Lys Gln Arg Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Lys Ala Thr Val Thr Val Asp Lys Ser Ser Ser Thr Val Tyr
65                  70                  75                  80

Ile Gln Leu Ser Ser Leu Thr Ser Glu Asp Ser Ala Val Tyr Tyr Cys
                85                  90                  95

Arg Ser Asp Gly Thr Tyr Glu Tyr Phe Asp Tyr Trp Gly Gln Gly
            100                 105                 110

Thr Pro Leu Thr Val Ser Ser
        115

<210> SEQ ID NO 41

```
<211> LENGTH: 6
<212> TYPE: PRT
<213> ORGANISM: artificial
<220> FEATURE:
<223> OTHER INFORMATION: Synthetic polypeptide

<400> SEQUENCE: 41

Thr Asn Asn Trp Met His
1               5

<210> SEQ ID NO 42
<211> LENGTH: 13
<212> TYPE: PRT
<213> ORGANISM: artificial
<220> FEATURE:
<223> OTHER INFORMATION: Synthetic polypeptide

<400> SEQUENCE: 42

Met Ile His Pro Asn Ser Gly Ile Thr Asn Ile Asn Glu
1               5                   10

<210> SEQ ID NO 43
<211> LENGTH: 12
<212> TYPE: PRT
<213> ORGANISM: artificial
<220> FEATURE:
<223> OTHER INFORMATION: Synthetic polypeptide

<400> SEQUENCE: 43

Arg Ser Asp Gly Thr Tyr Glu Gly Tyr Phe Asp Tyr
1               5                   10

<210> SEQ ID NO 44
<211> LENGTH: 117
<212> TYPE: PRT
<213> ORGANISM: artificial
<220> FEATURE:
<223> OTHER INFORMATION: Synthetic polypeptide

<400> SEQUENCE: 44

Gln Val Gln Leu Gln Gln Ser Gly Ala Asp Leu Ala Arg Pro Gly Ala
1               5                   10                  15

Ser Ile Lys Leu Ser Cys Lys Ala Ser Gly Tyr Thr Phe Thr Gly Tyr
            20                  25                  30

Gly Val Thr Trp Val Lys Gln Ser Thr Gly Gln Gly Leu Asp Trp Ile
        35                  40                  45

Gly Glu Ile Tyr Pro Gly Thr Val Ile Thr Tyr Tyr Asn Ala Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Gly Leu Gly Arg Ala Met Asp Tyr Trp Gly Gln Gly Thr Ser
            100                 105                 110

Val Thr Val Ser Ser
        115

<210> SEQ ID NO 45
<211> LENGTH: 6
<212> TYPE: PRT
<213> ORGANISM: artificial
<220> FEATURE:
<223> OTHER INFORMATION: Synthetic polypeptide
```

```
<400> SEQUENCE: 45

Thr Gly Tyr Gly Val Thr
1               5

<210> SEQ ID NO 46
<211> LENGTH: 13
<212> TYPE: PRT
<213> ORGANISM: artificial
<220> FEATURE:
<223> OTHER INFORMATION: Synthetic polypeptide

<400> SEQUENCE: 46

Glu Ile Tyr Pro Gly Thr Val Ile Thr Tyr Tyr Asn Ala
1               5                   10

<210> SEQ ID NO 47
<211> LENGTH: 10
<212> TYPE: PRT
<213> ORGANISM: artificial
<220> FEATURE:
<223> OTHER INFORMATION: Synthetic polypeptide

<400> SEQUENCE: 47

Ala Arg Gly Leu Gly Arg Ala Met Asp Tyr
1               5                   10

<210> SEQ ID NO 48
<211> LENGTH: 121
<212> TYPE: PRT
<213> ORGANISM: artificial
<220> FEATURE:
<223> OTHER INFORMATION: Synthetic polypeptide

<400> SEQUENCE: 48

Gln Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Phe Pro Gly Thr Glu Gly Ile Tyr Tyr Asn Glu Lys Phe
    50                  55                  60

Lys Gly Lys Ala Thr Leu Thr Val Asp Lys Ser Ser Thr Thr Ala Tyr
65                  70                  75                  80

Met Leu Leu Ser Ser Leu Thr Ser Glu Asp Ser Ala Val Tyr Phe Cys
                85                  90                  95

Ala Arg Glu Gly Asp Tyr Arg Tyr Tyr Ser Pro Leu Gly Tyr Trp Gly
            100                 105                 110

Gln Gly Thr Leu Val Thr Val Ser Ala
        115                 120

<210> SEQ ID NO 49
<211> LENGTH: 6
<212> TYPE: PRT
<213> ORGANISM: artificial
<220> FEATURE:
<223> OTHER INFORMATION: Synthetic polypeptide

<400> SEQUENCE: 49

Thr Asp Tyr Tyr Ile Asn
1               5
```

```
<210> SEQ ID NO 50
<211> LENGTH: 13
<212> TYPE: PRT
<213> ORGANISM: artificial
<220> FEATURE:
<223> OTHER INFORMATION: Synthetic polypeptide

<400> SEQUENCE: 50

Trp Ile Phe Pro Gly Thr Glu Gly Ile Tyr Tyr Asn Glu
1               5                   10

<210> SEQ ID NO 51
<211> LENGTH: 14
<212> TYPE: PRT
<213> ORGANISM: artificial
<220> FEATURE:
<223> OTHER INFORMATION: Synthetic polypeptide

<400> SEQUENCE: 51

Ala Arg Glu Gly Asp Tyr Arg Tyr Tyr Ser Pro Leu Gly Tyr
1               5                   10

<210> SEQ ID NO 52
<211> LENGTH: 117
<212> TYPE: PRT
<213> ORGANISM: artificial
<220> FEATURE:
<223> OTHER INFORMATION: Synthetic polypeptide

<400> SEQUENCE: 52

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Asn Phe Asn Asp Tyr
                20                  25                  30

Tyr Ile Asn Trp Val Asn Gln Arg Pro Gly Gln Gly Leu Glu Trp Ile
            35                  40                  45

Gly Trp Ile Phe Pro Gly Arg Ile Ile Thr Tyr Tyr Asn Glu Lys Phe
        50                  55                  60

Lys Gly Lys Ala Thr Leu Thr Val Asp Thr Ser Ser Asn Thr Ala Tyr
65                  70                  75                  80

Met Leu Leu Ser Ser Leu Thr Ser Glu Asp Ser Ala Val Tyr Phe Cys
                85                  90                  95

Ala Arg Gly Val Gly Glu Gly Phe Asp Tyr Trp Gly Gln Gly Thr Thr
            100                 105                 110

Leu Thr Val Ser Ser
        115

<210> SEQ ID NO 53
<211> LENGTH: 6
<212> TYPE: PRT
<213> ORGANISM: artificial
<220> FEATURE:
<223> OTHER INFORMATION: Synthetic polypeptide

<400> SEQUENCE: 53

Asn Asp Tyr Tyr Ile Asn
1               5

<210> SEQ ID NO 54
<211> LENGTH: 13
<212> TYPE: PRT
<213> ORGANISM: artificial
<220> FEATURE:
<223> OTHER INFORMATION: Synthetic polypeptide
```

-continued

<400> SEQUENCE: 54

Trp Ile Phe Pro Gly Arg Ile Ile Thr Tyr Tyr Asn Glu
1               5                   10

<210> SEQ ID NO 55
<211> LENGTH: 10
<212> TYPE: PRT
<213> ORGANISM: artificial
<220> FEATURE:
<223> OTHER INFORMATION: Synthetic polypeptide

<400> SEQUENCE: 55

Ala Arg Gly Val Gly Glu Gly Phe Asp Tyr
1               5                   10

<210> SEQ ID NO 56
<211> LENGTH: 118
<212> TYPE: PRT
<213> ORGANISM: artificial
<220> FEATURE:
<223> OTHER INFORMATION: Synthetic polypeptide

<400> SEQUENCE: 56

Glu Val Gln Leu Leu Glu Thr Gly Gly Gly Leu Val Lys Ser Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Ala Ile Ser Asp Asp Gly Thr Tyr Thr Tyr Tyr Pro Asp Ser Val
    50                  55                  60

Lys Gly Arg Phe Thr Ile Ser Arg Asp Asn Ala Asn Asn Tyr Leu Tyr
65                  70                  75                  80

Leu Gln Met Ser Ser Leu Lys Ser Glu Asp Thr Ala Ile Tyr Tyr Cys
                85                  90                  95

Ala Lys Ala Gly Ser Tyr Asp Tyr Phe Asp Val Trp Gly Ala Gly Thr
            100                 105                 110

Thr Val Thr Val Ser Ser
        115

<210> SEQ ID NO 57
<211> LENGTH: 6
<212> TYPE: PRT
<213> ORGANISM: artificial
<220> FEATURE:
<223> OTHER INFORMATION: Synthetic polypeptide

<400> SEQUENCE: 57

Ser Asp Tyr Tyr Met Tyr
1               5

<210> SEQ ID NO 58
<211> LENGTH: 13
<212> TYPE: PRT
<213> ORGANISM: artificial
<220> FEATURE:
<223> OTHER INFORMATION: Synthetic polypeptide

<400> SEQUENCE: 58

Ala Ile Ser Asp Asp Gly Thr Tyr Thr Tyr Tyr Pro Asp
1               5                   10

```
<210> SEQ ID NO 59
<211> LENGTH: 11
<212> TYPE: PRT
<213> ORGANISM: artificial
<220> FEATURE:
<223> OTHER INFORMATION: Synthetic polypeptide

<400> SEQUENCE: 59

Ala Lys Ala Gly Ser Tyr Asp Tyr Phe Asp Val
1               5                   10

<210> SEQ ID NO 60
<211> LENGTH: 116
<212> TYPE: PRT
<213> ORGANISM: artificial
<220> FEATURE:
<223> OTHER INFORMATION: Synthetic polypeptide

<400> SEQUENCE: 60

Gln Val Gln Leu Lys Glu Ser Gly Pro Gly Leu Val Ala Pro Ser Gln
1               5                   10                  15

Ser Leu Ser Ile Ile Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Ile Ile Trp Ala Gly Gly Ser Thr Asn Tyr Asn Ser Ala Leu Met
    50                  55                  60

Ser Arg Leu Thr Ile Ser Lys Asp Asn Ser Lys Ser Gln Val Phe Leu
65                  70                  75                  80

Lys Met Asn Ser Leu Gln Thr Asn Asp Thr Ala Ile Tyr Tyr Cys Ala
                85                  90                  95

Arg Val Ser Met Met Gly Phe Ala Tyr Trp Gly Gln Gly Thr Leu Val
            100                 105                 110

Thr Val Ser Ala
        115

<210> SEQ ID NO 61
<211> LENGTH: 6
<212> TYPE: PRT
<213> ORGANISM: artificial
<220> FEATURE:
<223> OTHER INFORMATION: Synthetic polypeptide

<400> SEQUENCE: 61

Thr Asn Tyr Gly Ile His
1               5

<210> SEQ ID NO 62
<211> LENGTH: 12
<212> TYPE: PRT
<213> ORGANISM: artificial
<220> FEATURE:
<223> OTHER INFORMATION: Synthetic polypeptide

<400> SEQUENCE: 62

Ile Ile Trp Ala Gly Gly Ser Thr Asn Tyr Asn Ser
1               5                   10

<210> SEQ ID NO 63
<211> LENGTH: 10
<212> TYPE: PRT
<213> ORGANISM: artificial
<220> FEATURE:
```

<223> OTHER INFORMATION: Synthetic polypeptide

<400> SEQUENCE: 63

Ala Arg Val Ser Met Met Gly Phe Ala Tyr
1               5                   10

<210> SEQ ID NO 64
<211> LENGTH: 120
<212> TYPE: PRT
<213> ORGANISM: artificial
<220> FEATURE:
<223> OTHER INFORMATION: Synthetic polypeptide

<400> SEQUENCE: 64

Gln Ile Gln Leu Val Gln Ser Gly Pro Glu Leu Lys Pro Gly Glu
1               5                   10                  15

Thr Val Lys Ile Ser Cys Lys Ala Ser Gly Tyr Pro Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Asp Ser Gly Val Pro Thr Tyr Ala Asp Asp Phe
    50                  55                  60

Lys Gly Arg Phe Ala Phe Ser Leu Glu Thr Ser Ala Asn Thr Ala Tyr
65                  70                  75                  80

Leu Gln Ile Asn Ser Leu Lys Asn Glu Asp Ala Ala Thr Tyr Phe Cys
                85                  90                  95

Ala Arg Asn Ile Tyr Tyr Gly Trp Gly Asn Phe Asp Tyr Trp Gly Gln
            100                 105                 110

Gly Thr Ile Leu Thr Val Ser Ser
        115                 120

<210> SEQ ID NO 65
<211> LENGTH: 6
<212> TYPE: PRT
<213> ORGANISM: artificial
<220> FEATURE:
<223> OTHER INFORMATION: Synthetic polypeptide

<400> SEQUENCE: 65

Thr Thr Tyr Gly Met Ser
1               5

<210> SEQ ID NO 66
<211> LENGTH: 13
<212> TYPE: PRT
<213> ORGANISM: artificial
<220> FEATURE:
<223> OTHER INFORMATION: Synthetic polypeptide

<400> SEQUENCE: 66

Trp Ile Asn Thr Asp Ser Gly Val Pro Thr Tyr Ala Asp
1               5                   10

<210> SEQ ID NO 67
<211> LENGTH: 13
<212> TYPE: PRT
<213> ORGANISM: artificial
<220> FEATURE:
<223> OTHER INFORMATION: Synthetic polypeptide

<400> SEQUENCE: 67

Ala Arg Asn Ile Tyr Tyr Gly Trp Gly Asn Phe Asp Tyr
1               5                   10

<210> SEQ ID NO 68
<211> LENGTH: 107
<212> TYPE: PRT
<213> ORGANISM: artificial
<220> FEATURE:
<223> OTHER INFORMATION: Synthetic polypeptide

<400> SEQUENCE: 68

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Ile Val Trp Tyr Gln Gln Lys Pro Gly Lys Ala Pro Lys Val Leu Ile
        35                  40                  45

Tyr Ser Ala Ser Thr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Pro Leu
                85                  90                  95

Thr Phe Gly Gln Gly Thr Lys Val Glu Ile Lys
            100                 105

<210> SEQ ID NO 69
<211> LENGTH: 119
<212> TYPE: PRT
<213> ORGANISM: artificial
<220> FEATURE:
<223> OTHER INFORMATION: Synthetic polypeptide

<400> SEQUENCE: 69

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser
        115

<210> SEQ ID NO 70
<211> LENGTH: 107
<212> TYPE: PRT
<213> ORGANISM: artificial
<220> FEATURE:
<223> OTHER INFORMATION: Synthetic polypeptide

<400> SEQUENCE: 70

Glu Ile Val Met Thr Gln Ser Pro Asp Phe Gln Ser Val Thr Pro Lys
1               5                   10                  15

```
Glu Lys Val Thr Ile Thr Cys Arg Ala Ser Gln Asp Ile Tyr Arg Asn
                20                  25                  30

Leu His Trp Tyr Gln Gln Lys Pro Asp Gln Thr Pro Lys Leu Leu Ile
         35                  40                  45

Lys His Ala Ser Asp Ser Ile Ser Gly Ile Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys Leu Gln Gly Tyr Ser Met Pro Tyr
                 85                  90                  95

Thr Phe Gly Gly Gly Thr Lys Val Glu Ile Lys
            100                 105
```

<210> SEQ ID NO 71
<211> LENGTH: 120
<212> TYPE: PRT
<213> ORGANISM: artificial
<220> FEATURE:
<223> OTHER INFORMATION: Synthetic polypeptide

<400> SEQUENCE: 71

```
Glu Ile Gln Leu Val Gln Ser Gly Ser Glu Leu Lys Lys Pro Gly Ala
1               5                  10                  15

Ser Val Lys Val Ser Cys Lys Ala Ser Gly Tyr Pro Phe Thr Thr Tyr
                20                  25                  30

Gly Met Ser Trp Val Arg Gln Ala Pro Gly Gln Gly Leu Glu Trp Met
         35                  40                  45

Gly Trp Ile Asn Thr Asp Ser Gly Val Pro Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Ile Tyr Tyr Gly Trp Gly Asn Phe Asp Tyr Trp Gly Gln
                100                 105                 110

Gly Thr Leu Val Thr Val Ser Ser
            115                 120
```

<210> SEQ ID NO 72
<211> LENGTH: 6
<212> TYPE: PRT
<213> ORGANISM: artificial
<220> FEATURE:
<223> OTHER INFORMATION: Synthetic polypeptide
<220> FEATURE:
<221> NAME/KEY: VARIANT
<222> LOCATION: (1)..(1)
<223> OTHER INFORMATION: X at 1 is T, A, D, E, G, H, K, N, Q, R, S, V,
      W, or Y.
<220> FEATURE:
<221> NAME/KEY: VARIANT
<222> LOCATION: (3)..(3)
<223> OTHER INFORMATION: X at 3 is N, A, F, G, H, M, R, S, V, or Y.
<220> FEATURE:
<221> NAME/KEY: VARIANT
<222> LOCATION: (4)..(4)
<223> OTHER INFORMATION: X at 4 is W, or F.
<220> FEATURE:
<221> NAME/KEY: VARIANT
<222> LOCATION: (5)..(5)
<223> OTHER INFORMATION: X at 5 is M, A, D, E, F, G, L, N, Q, R, S, T,
      V, or W.

<400> SEQUENCE: 72

```
Xaa Asn Xaa Xaa Xaa His
1               5

<210> SEQ ID NO 73
<211> LENGTH: 6
<212> TYPE: PRT
<213> ORGANISM: artificial
<220> FEATURE:
<223> OTHER INFORMATION: Synthetic polypeptide

<400> SEQUENCE: 73

Ala Asn Asn Trp Met His
1               5

<210> SEQ ID NO 74
<211> LENGTH: 6
<212> TYPE: PRT
<213> ORGANISM: artificial
<220> FEATURE:
<223> OTHER INFORMATION: Synthetic polypeptide

<400> SEQUENCE: 74

Asp Asn Asn Trp Met His
1               5

<210> SEQ ID NO 75
<211> LENGTH: 6
<212> TYPE: PRT
<213> ORGANISM: artificial
<220> FEATURE:
<223> OTHER INFORMATION: Synthetic polypeptide

<400> SEQUENCE: 75

Glu Asn Asn Trp Met His
1               5

<210> SEQ ID NO 76
<211> LENGTH: 6
<212> TYPE: PRT
<213> ORGANISM: artificial
<220> FEATURE:
<223> OTHER INFORMATION: Synthetic polypeptide

<400> SEQUENCE: 76

Gly Asn Asn Trp Met His
1               5

<210> SEQ ID NO 77
<211> LENGTH: 6
<212> TYPE: PRT
<213> ORGANISM: artificial
<220> FEATURE:
<223> OTHER INFORMATION: Synthetic polypeptide

<400> SEQUENCE: 77

His Asn Asn Trp Met His
1               5

<210> SEQ ID NO 78
<211> LENGTH: 6
<212> TYPE: PRT
<213> ORGANISM: artificial
<220> FEATURE:
<223> OTHER INFORMATION: Synthetic polypeptide

<400> SEQUENCE: 78
```

Lys Asn Asn Trp Met His
1               5

<210> SEQ ID NO 79
<211> LENGTH: 6
<212> TYPE: PRT
<213> ORGANISM: artificial
<220> FEATURE:
<223> OTHER INFORMATION: Synthetic polypeptide

<400> SEQUENCE: 79

Asn Asn Asn Trp Met His
1               5

<210> SEQ ID NO 80
<211> LENGTH: 6
<212> TYPE: PRT
<213> ORGANISM: artificial
<220> FEATURE:
<223> OTHER INFORMATION: Synthetic polypeptide

<400> SEQUENCE: 80

Gln Asn Asn Trp Met His
1               5

<210> SEQ ID NO 81
<211> LENGTH: 6
<212> TYPE: PRT
<213> ORGANISM: artificial
<220> FEATURE:
<223> OTHER INFORMATION: Synthetic polypeptide

<400> SEQUENCE: 81

Arg Asn Asn Trp Met His
1               5

<210> SEQ ID NO 82
<211> LENGTH: 6
<212> TYPE: PRT
<213> ORGANISM: artificial
<220> FEATURE:
<223> OTHER INFORMATION: Synthetic polypeptide

<400> SEQUENCE: 82

Ser Asn Asn Trp Met His
1               5

<210> SEQ ID NO 83
<211> LENGTH: 6
<212> TYPE: PRT
<213> ORGANISM: artificial
<220> FEATURE:
<223> OTHER INFORMATION: Synthetic polypeptide

<400> SEQUENCE: 83

Val Asn Asn Trp Met His
1               5

<210> SEQ ID NO 84
<211> LENGTH: 6
<212> TYPE: PRT
<213> ORGANISM: artificial
<220> FEATURE:
<223> OTHER INFORMATION: Synthetic polypeptide

<400> SEQUENCE: 84

Trp Asn Asn Trp Met His

```
1               5

<210> SEQ ID NO 85
<211> LENGTH: 6
<212> TYPE: PRT
<213> ORGANISM: artificial
<220> FEATURE:
<223> OTHER INFORMATION: Synthetic polypeptide

<400> SEQUENCE: 85

Tyr Asn Asn Trp Met His
1               5

<210> SEQ ID NO 86
<211> LENGTH: 6
<212> TYPE: PRT
<213> ORGANISM: artificial
<220> FEATURE:
<223> OTHER INFORMATION: Synthetic polypeptide

<400> SEQUENCE: 86

Thr Asn Ala Trp Met His
1               5

<210> SEQ ID NO 87
<211> LENGTH: 6
<212> TYPE: PRT
<213> ORGANISM: artificial
<220> FEATURE:
<223> OTHER INFORMATION: Synthetic polypeptide

<400> SEQUENCE: 87

Thr Asn Phe Trp Met His
1               5

<210> SEQ ID NO 88
<211> LENGTH: 6
<212> TYPE: PRT
<213> ORGANISM: artificial
<220> FEATURE:
<223> OTHER INFORMATION: Synthetic polypeptide

<400> SEQUENCE: 88

Thr Asn Gly Trp Met His
1               5

<210> SEQ ID NO 89
<211> LENGTH: 6
<212> TYPE: PRT
<213> ORGANISM: artificial
<220> FEATURE:
<223> OTHER INFORMATION: Synthetic polypeptide

<400> SEQUENCE: 89

Thr Asn His Trp Met His
1               5

<210> SEQ ID NO 90
<211> LENGTH: 6
<212> TYPE: PRT
<213> ORGANISM: artificial
<220> FEATURE:
<223> OTHER INFORMATION: Synthetic polypeptide

<400> SEQUENCE: 90

Thr Asn Met Trp Met His
1               5
```

```
<210> SEQ ID NO 91
<211> LENGTH: 6
<212> TYPE: PRT
<213> ORGANISM: artificial
<220> FEATURE:
<223> OTHER INFORMATION: Synthetic polypeptide

<400> SEQUENCE: 91

Thr Asn Arg Trp Met His
1               5

<210> SEQ ID NO 92
<211> LENGTH: 6
<212> TYPE: PRT
<213> ORGANISM: artificial
<220> FEATURE:
<223> OTHER INFORMATION: Synthetic polypeptide

<400> SEQUENCE: 92

Thr Asn Ser Trp Met His
1               5

<210> SEQ ID NO 93
<211> LENGTH: 6
<212> TYPE: PRT
<213> ORGANISM: artificial
<220> FEATURE:
<223> OTHER INFORMATION: Synthetic polypeptide

<400> SEQUENCE: 93

Thr Asn Val Trp Met His
1               5

<210> SEQ ID NO 94
<211> LENGTH: 6
<212> TYPE: PRT
<213> ORGANISM: artificial
<220> FEATURE:
<223> OTHER INFORMATION: Synthetic polypeptide

<400> SEQUENCE: 94

Thr Asn Tyr Trp Met His
1               5

<210> SEQ ID NO 95
<211> LENGTH: 6
<212> TYPE: PRT
<213> ORGANISM: artificial
<220> FEATURE:
<223> OTHER INFORMATION: Synthetic polypeptide

<400> SEQUENCE: 95

Thr Asn Asn Phe Met His
1               5

<210> SEQ ID NO 96
<211> LENGTH: 6
<212> TYPE: PRT
<213> ORGANISM: artificial
<220> FEATURE:
<223> OTHER INFORMATION: Synthetic polypeptide

<400> SEQUENCE: 96

Thr Asn Asn Trp Ala His
1               5
```

<210> SEQ ID NO 97
<211> LENGTH: 6
<212> TYPE: PRT
<213> ORGANISM: artificial
<220> FEATURE:
<223> OTHER INFORMATION: Synthetic polypeptide

<400> SEQUENCE: 97

Thr Asn Asn Trp Glu His
1               5

<210> SEQ ID NO 98
<211> LENGTH: 6
<212> TYPE: PRT
<213> ORGANISM: artificial
<220> FEATURE:
<223> OTHER INFORMATION: Synthetic polypeptide

<400> SEQUENCE: 98

Thr Asn Asn Trp Phe His
1               5

<210> SEQ ID NO 99
<211> LENGTH: 6
<212> TYPE: PRT
<213> ORGANISM: artificial
<220> FEATURE:
<223> OTHER INFORMATION: Synthetic polypeptide

<400> SEQUENCE: 99

Thr Asn Asn Trp Leu His
1               5

<210> SEQ ID NO 100
<211> LENGTH: 6
<212> TYPE: PRT
<213> ORGANISM: artificial
<220> FEATURE:
<223> OTHER INFORMATION: Synthetic polypeptide

<400> SEQUENCE: 100

Thr Asn Asn Trp Asn His
1               5

<210> SEQ ID NO 101
<211> LENGTH: 6
<212> TYPE: PRT
<213> ORGANISM: artificial
<220> FEATURE:
<223> OTHER INFORMATION: Synthetic polypeptide

<400> SEQUENCE: 101

Thr Asn Asn Trp Gln His
1               5

<210> SEQ ID NO 102
<211> LENGTH: 6
<212> TYPE: PRT
<213> ORGANISM: artificial
<220> FEATURE:
<223> OTHER INFORMATION: Synthetic polypeptide

<400> SEQUENCE: 102

Thr Asn Asn Trp Arg His
1               5

-continued

```
<210> SEQ ID NO 103
<211> LENGTH: 6
<212> TYPE: PRT
<213> ORGANISM: artificial
<220> FEATURE:
<223> OTHER INFORMATION: Synthetic polypeptide

<400> SEQUENCE: 103

Thr Asn Asn Trp Ser His
1               5

<210> SEQ ID NO 104
<211> LENGTH: 6
<212> TYPE: PRT
<213> ORGANISM: artificial
<220> FEATURE:
<223> OTHER INFORMATION: Synthetic polypeptide

<400> SEQUENCE: 104

Thr Asn Asn Trp Thr His
1               5

<210> SEQ ID NO 105
<211> LENGTH: 6
<212> TYPE: PRT
<213> ORGANISM: artificial
<220> FEATURE:
<223> OTHER INFORMATION: Synthetic polypeptide

<400> SEQUENCE: 105

Thr Asn Asn Trp Val His
1               5

<210> SEQ ID NO 106
<211> LENGTH: 6
<212> TYPE: PRT
<213> ORGANISM: artificial
<220> FEATURE:
<223> OTHER INFORMATION: Synthetic polypeptide

<400> SEQUENCE: 106

Thr Asn Asn Trp Trp His
1               5

<210> SEQ ID NO 107
<211> LENGTH: 13
<212> TYPE: PRT
<213> ORGANISM: artificial
<220> FEATURE:
<223> OTHER INFORMATION: Synthetic polypeptide
<220> FEATURE:
<221> NAME/KEY: VARIANT
<222> LOCATION: (1)..(1)
<223> OTHER INFORMATION: X at 1 is M or F.
<220> FEATURE:
<221> NAME/KEY: VARIANT
<222> LOCATION: (2)..(2)
<223> OTHER INFORMATION: X at 2 is I, L, M, or V.
<220> FEATURE:
<221> NAME/KEY: VARIANT
<222> LOCATION: (4)..(4)
<223> OTHER INFORMATION: X at 4 is P, A, D, E, F, G, H, I, K, L, M, N,
     Q, R, S, T, V, or W.
<220> FEATURE:
<221> NAME/KEY: VARIANT
<222> LOCATION: (5)..(5)
<223> OTHER INFORMATION: X at 5 is N, A, D, E, F, G, H, I, K, L, M, Q,
     R, S, T, V, W, or Y.
<220> FEATURE:
<221> NAME/KEY: VARIANT
<222> LOCATION: (6)..(6)
```

```
<223> OTHER INFORMATION: X at 6 is S, A, G, T, or V.
<220> FEATURE:
<221> NAME/KEY: VARIANT
<222> LOCATION: (7)..(7)
<223> OTHER INFORMATION: X at 7 is G, A, or S.
<220> FEATURE:
<221> NAME/KEY: VARIANT
<222> LOCATION: (8)..(8)
<223> OTHER INFORMATION: X at 8 is I, A, or V.
<220> FEATURE:
<221> NAME/KEY: VARIANT
<222> LOCATION: (9)..(9)
<223> OTHER INFORMATION: X at 9 is T, A, D, E, G, H, I, K, L, M, N, Q,
      R, S, V, W, or Y.
<220> FEATURE:
<221> NAME/KEY: VARIANT
<222> LOCATION: (10)..(10)
<223> OTHER INFORMATION: X at 10 is N, A, M, or S.
<220> FEATURE:
<221> NAME/KEY: VARIANT
<222> LOCATION: (11)..(11)
<223> OTHER INFORMATION: X at 11 is I, F, G, H, K, L, M, N, Q, R, S, T,
      V, W, or Y.
<220> FEATURE:
<221> NAME/KEY: VARIANT
<222> LOCATION: (13)..(13)
<223> OTHER INFORMATION: X at 13 is E, A, D, G, H, K, L, M, N, P, Q, R,
      S, T, V, W, or Y.

<400> SEQUENCE: 107

Xaa Xaa His Xaa Xaa Xaa Xaa Xaa Xaa Xaa Xaa Asn Xaa
1               5                   10

<210> SEQ ID NO 108
<211> LENGTH: 13
<212> TYPE: PRT
<213> ORGANISM: artificial
<220> FEATURE:
<223> OTHER INFORMATION: Synthetic polypeptide

<400> SEQUENCE: 108

Phe Ile His Pro Asn Ser Gly Ile Thr Asn Ile Asn Glu
1               5                   10

<210> SEQ ID NO 109
<211> LENGTH: 13
<212> TYPE: PRT
<213> ORGANISM: artificial
<220> FEATURE:
<223> OTHER INFORMATION: Synthetic polypeptide

<400> SEQUENCE: 109

Met Leu His Pro Asn Ser Gly Ile Thr Asn Ile Asn Glu
1               5                   10

<210> SEQ ID NO 110
<211> LENGTH: 13
<212> TYPE: PRT
<213> ORGANISM: artificial
<220> FEATURE:
<223> OTHER INFORMATION: Synthetic polypeptide

<400> SEQUENCE: 110

Met Met His Pro Asn Ser Gly Ile Thr Asn Ile Asn Glu
1               5                   10

<210> SEQ ID NO 111
<211> LENGTH: 13
<212> TYPE: PRT
<213> ORGANISM: artificial
<220> FEATURE:
```

<223> OTHER INFORMATION: Synthetic polypeptide

<400> SEQUENCE: 111

Met Val His Pro Asn Ser Gly Ile Thr Asn Ile Asn Glu
1               5                   10

<210> SEQ ID NO 112
<211> LENGTH: 13
<212> TYPE: PRT
<213> ORGANISM: artificial
<220> FEATURE:
<223> OTHER INFORMATION: Synthetic polypeptide

<400> SEQUENCE: 112

Met Ile His Ala Asn Ser Gly Ile Thr Asn Ile Asn Glu
1               5                   10

<210> SEQ ID NO 113
<211> LENGTH: 13
<212> TYPE: PRT
<213> ORGANISM: artificial
<220> FEATURE:
<223> OTHER INFORMATION: Synthetic polypeptide

<400> SEQUENCE: 113

Phe Ile His Ala Asn Ser Gly Ile Thr Asn Ile Asn Glu
1               5                   10

<210> SEQ ID NO 114
<211> LENGTH: 13
<212> TYPE: PRT
<213> ORGANISM: artificial
<220> FEATURE:
<223> OTHER INFORMATION: Synthetic polypeptide

<400> SEQUENCE: 114

Met Ile His Asp Asn Ser Gly Ile Thr Asn Ile Asn Glu
1               5                   10

<210> SEQ ID NO 115
<211> LENGTH: 13
<212> TYPE: PRT
<213> ORGANISM: artificial
<220> FEATURE:
<223> OTHER INFORMATION: Synthetic polypeptide

<400> SEQUENCE: 115

Met Ile His Glu Asn Ser Gly Ile Thr Asn Ile Asn Glu
1               5                   10

<210> SEQ ID NO 116
<211> LENGTH: 13
<212> TYPE: PRT
<213> ORGANISM: artificial
<220> FEATURE:
<223> OTHER INFORMATION: Synthetic polypeptide

<400> SEQUENCE: 116

Met Ile His Phe Asn Ser Gly Ile Thr Asn Ile Asn Glu
1               5                   10

<210> SEQ ID NO 117
<211> LENGTH: 13
<212> TYPE: PRT
<213> ORGANISM: artificial
<220> FEATURE:
<223> OTHER INFORMATION: Synthetic polypeptide

<400> SEQUENCE: 117

Met Ile His Gly Asn Ser Gly Ile Thr Asn Ile Asn Glu
1               5                   10

<210> SEQ ID NO 118
<211> LENGTH: 13
<212> TYPE: PRT
<213> ORGANISM: artificial
<220> FEATURE:
<223> OTHER INFORMATION: Synthetic polypeptide

<400> SEQUENCE: 118

Met Ile His His Asn Ser Gly Ile Thr Asn Ile Asn Glu
1               5                   10

<210> SEQ ID NO 119
<211> LENGTH: 13
<212> TYPE: PRT
<213> ORGANISM: artificial
<220> FEATURE:
<223> OTHER INFORMATION: Synthetic polypeptide

<400> SEQUENCE: 119

Met Ile His Ile Asn Ser Gly Ile Thr Asn Ile Asn Glu
1               5                   10

<210> SEQ ID NO 120
<211> LENGTH: 13
<212> TYPE: PRT
<213> ORGANISM: artificial
<220> FEATURE:
<223> OTHER INFORMATION: Synthetic polypeptide

<400> SEQUENCE: 120

Met Ile His Lys Asn Ser Gly Ile Thr Asn Ile Asn Glu
1               5                   10

<210> SEQ ID NO 121
<211> LENGTH: 13
<212> TYPE: PRT
<213> ORGANISM: artificial
<220> FEATURE:
<223> OTHER INFORMATION: Synthetic polypeptide

<400> SEQUENCE: 121

Met Ile His Leu Asn Ser Gly Ile Thr Asn Ile Asn Glu
1               5                   10

<210> SEQ ID NO 122
<211> LENGTH: 13
<212> TYPE: PRT
<213> ORGANISM: artificial
<220> FEATURE:
<223> OTHER INFORMATION: Synthetic polypeptide

<400> SEQUENCE: 122

Met Ile His Met Asn Ser Gly Ile Thr Asn Ile Asn Glu
1               5                   10

<210> SEQ ID NO 123
<211> LENGTH: 13
<212> TYPE: PRT
<213> ORGANISM: artificial
<220> FEATURE:
<223> OTHER INFORMATION: Synthetic polypeptide

<400> SEQUENCE: 123

Met Ile His Asn Asn Ser Gly Ile Thr Asn Ile Asn Glu
1               5                   10

<210> SEQ ID NO 124
<211> LENGTH: 13
<212> TYPE: PRT
<213> ORGANISM: artificial
<220> FEATURE:
<223> OTHER INFORMATION: Synthetic polypeptide

<400> SEQUENCE: 124

Met Ile His Gln Asn Ser Gly Ile Thr Asn Ile Asn Glu
1               5                   10

<210> SEQ ID NO 125
<211> LENGTH: 13
<212> TYPE: PRT
<213> ORGANISM: artificial
<220> FEATURE:
<223> OTHER INFORMATION: Synthetic polypeptide

<400> SEQUENCE: 125

Met Ile His Arg Asn Ser Gly Ile Thr Asn Ile Asn Glu
1               5                   10

<210> SEQ ID NO 126
<211> LENGTH: 13
<212> TYPE: PRT
<213> ORGANISM: artificial
<220> FEATURE:
<223> OTHER INFORMATION: Synthetic polypeptide

<400> SEQUENCE: 126

Met Ile His Ser Asn Ser Gly Ile Thr Asn Ile Asn Glu
1               5                   10

<210> SEQ ID NO 127
<211> LENGTH: 13
<212> TYPE: PRT
<213> ORGANISM: artificial
<220> FEATURE:
<223> OTHER INFORMATION: Synthetic polypeptide

<400> SEQUENCE: 127

Met Ile His Thr Asn Ser Gly Ile Thr Asn Ile Asn Glu
1               5                   10

<210> SEQ ID NO 128
<211> LENGTH: 13
<212> TYPE: PRT
<213> ORGANISM: artificial
<220> FEATURE:
<223> OTHER INFORMATION: Synthetic polypeptide

<400> SEQUENCE: 128

Met Ile His Val Asn Ser Gly Ile Thr Asn Ile Asn Glu
1               5                   10

<210> SEQ ID NO 129
<211> LENGTH: 13
<212> TYPE: PRT
<213> ORGANISM: artificial
<220> FEATURE:
<223> OTHER INFORMATION: Synthetic polypeptide

<400> SEQUENCE: 129

Met Ile His Trp Asn Ser Gly Ile Thr Asn Ile Asn Glu
1               5                   10

<210> SEQ ID NO 130
<211> LENGTH: 13
<212> TYPE: PRT
<213> ORGANISM: artificial
<220> FEATURE:
<223> OTHER INFORMATION: Synthetic polypeptide

<400> SEQUENCE: 130

Met Ile His Pro Ala Ser Gly Ile Thr Asn Ile Asn Glu
1               5                   10

<210> SEQ ID NO 131
<211> LENGTH: 13
<212> TYPE: PRT
<213> ORGANISM: artificial
<220> FEATURE:
<223> OTHER INFORMATION: Synthetic polypeptide

<400> SEQUENCE: 131

Met Ile His Pro Asp Ser Gly Ile Thr Asn Ile Asn Glu
1               5                   10

<210> SEQ ID NO 132
<211> LENGTH: 13
<212> TYPE: PRT
<213> ORGANISM: artificial
<220> FEATURE:
<223> OTHER INFORMATION: Synthetic polypeptide

<400> SEQUENCE: 132

Met Ile His Pro Glu Ser Gly Ile Thr Asn Ile Asn Glu
1               5                   10

<210> SEQ ID NO 133
<211> LENGTH: 13
<212> TYPE: PRT
<213> ORGANISM: artificial
<220> FEATURE:
<223> OTHER INFORMATION: Synthetic polypeptide

<400> SEQUENCE: 133

Met Ile His Pro Phe Ser Gly Ile Thr Asn Ile Asn Glu
1               5                   10

<210> SEQ ID NO 134
<211> LENGTH: 13
<212> TYPE: PRT
<213> ORGANISM: artificial
<220> FEATURE:
<223> OTHER INFORMATION: Synthetic polypeptide

<400> SEQUENCE: 134

Met Ile His Pro Gly Ser Gly Ile Thr Asn Ile Asn Glu
1               5                   10

<210> SEQ ID NO 135
<211> LENGTH: 13
<212> TYPE: PRT
<213> ORGANISM: artificial
<220> FEATURE:
<223> OTHER INFORMATION: Synthetic polypeptide

<400> SEQUENCE: 135

Met Ile His Pro His Ser Gly Ile Thr Asn Ile Asn Glu
1               5                   10

<210> SEQ ID NO 136
<211> LENGTH: 13
<212> TYPE: PRT
<213> ORGANISM: artificial
<220> FEATURE:
<223> OTHER INFORMATION: Synthetic polypeptide

<400> SEQUENCE: 136

Met Ile His Pro Ile Ser Gly Ile Thr Asn Ile Asn Glu
1               5                   10

<210> SEQ ID NO 137
<211> LENGTH: 13
<212> TYPE: PRT
<213> ORGANISM: artificial
<220> FEATURE:
<223> OTHER INFORMATION: Synthetic polypeptide

<400> SEQUENCE: 137

Met Ile His Pro Lys Ser Gly Ile Thr Asn Ile Asn Glu
1               5                   10

<210> SEQ ID NO 138
<211> LENGTH: 13
<212> TYPE: PRT
<213> ORGANISM: artificial
<220> FEATURE:
<223> OTHER INFORMATION: Synthetic polypeptide

<400> SEQUENCE: 138

Met Ile His Pro Leu Ser Gly Ile Thr Asn Ile Asn Glu
1               5                   10

<210> SEQ ID NO 139
<211> LENGTH: 13
<212> TYPE: PRT
<213> ORGANISM: artificial
<220> FEATURE:
<223> OTHER INFORMATION: Synthetic polypeptide

<400> SEQUENCE: 139

Met Ile His Pro Met Ser Gly Ile Thr Asn Ile Asn Glu
1               5                   10

<210> SEQ ID NO 140
<211> LENGTH: 13
<212> TYPE: PRT
<213> ORGANISM: artificial
<220> FEATURE:
<223> OTHER INFORMATION: Synthetic polypeptide

<400> SEQUENCE: 140

Met Ile His Pro Gln Ser Gly Ile Thr Asn Ile Asn Glu
1               5                   10

<210> SEQ ID NO 141
<211> LENGTH: 13
<212> TYPE: PRT
<213> ORGANISM: artificial
<220> FEATURE:
<223> OTHER INFORMATION: Synthetic polypeptide

<400> SEQUENCE: 141

Met Ile His Pro Arg Ser Gly Ile Thr Asn Ile Asn Glu

```
1               5                  10
```

<210> SEQ ID NO 142
<211> LENGTH: 13
<212> TYPE: PRT
<213> ORGANISM: artificial
<220> FEATURE:
<223> OTHER INFORMATION: Synthetic polypeptide

<400> SEQUENCE: 142

```
Met Ile His Pro Ser Ser Gly Ile Thr Asn Ile Asn Glu
1               5                  10
```

<210> SEQ ID NO 143
<211> LENGTH: 13
<212> TYPE: PRT
<213> ORGANISM: artificial
<220> FEATURE:
<223> OTHER INFORMATION: Synthetic polypeptide

<400> SEQUENCE: 143

```
Met Ile His Pro Thr Ser Gly Ile Thr Asn Ile Asn Glu
1               5                  10
```

<210> SEQ ID NO 144
<211> LENGTH: 13
<212> TYPE: PRT
<213> ORGANISM: artificial
<220> FEATURE:
<223> OTHER INFORMATION: Synthetic polypeptide

<400> SEQUENCE: 144

```
Met Ile His Pro Val Ser Gly Ile Thr Asn Ile Asn Glu
1               5                  10
```

<210> SEQ ID NO 145
<211> LENGTH: 13
<212> TYPE: PRT
<213> ORGANISM: artificial
<220> FEATURE:
<223> OTHER INFORMATION: Synthetic polypeptide

<400> SEQUENCE: 145

```
Met Ile His Pro Trp Ser Gly Ile Thr Asn Ile Asn Glu
1               5                  10
```

<210> SEQ ID NO 146
<211> LENGTH: 13
<212> TYPE: PRT
<213> ORGANISM: artificial
<220> FEATURE:
<223> OTHER INFORMATION: Synthetic polypeptide

<400> SEQUENCE: 146

```
Met Ile His Pro Tyr Ser Gly Ile Thr Asn Ile Asn Glu
1               5                  10
```

<210> SEQ ID NO 147
<211> LENGTH: 13
<212> TYPE: PRT
<213> ORGANISM: artificial
<220> FEATURE:
<223> OTHER INFORMATION: Synthetic polypeptide

<400> SEQUENCE: 147

```
Met Ile His Pro Asn Ala Gly Ile Thr Asn Ile Asn Glu
1               5                  10
```

```
<210> SEQ ID NO 148
<211> LENGTH: 13
<212> TYPE: PRT
<213> ORGANISM: artificial
<220> FEATURE:
<223> OTHER INFORMATION: Synthetic polypeptide

<400> SEQUENCE: 148

Met Ile His Pro Asn Gly Gly Ile Thr Asn Ile Asn Glu
1               5                   10

<210> SEQ ID NO 149
<211> LENGTH: 13
<212> TYPE: PRT
<213> ORGANISM: artificial
<220> FEATURE:
<223> OTHER INFORMATION: Synthetic polypeptide

<400> SEQUENCE: 149

Met Ile His Pro Asn Thr Gly Ile Thr Asn Ile Asn Glu
1               5                   10

<210> SEQ ID NO 150
<211> LENGTH: 13
<212> TYPE: PRT
<213> ORGANISM: artificial
<220> FEATURE:
<223> OTHER INFORMATION: Synthetic polypeptide

<400> SEQUENCE: 150

Met Ile His Pro Asn Val Gly Ile Thr Asn Ile Asn Glu
1               5                   10

<210> SEQ ID NO 151
<211> LENGTH: 13
<212> TYPE: PRT
<213> ORGANISM: artificial
<220> FEATURE:
<223> OTHER INFORMATION: Synthetic polypeptide

<400> SEQUENCE: 151

Met Ile His Pro Asn Ser Ala Ile Thr Asn Ile Asn Glu
1               5                   10

<210> SEQ ID NO 152
<211> LENGTH: 13
<212> TYPE: PRT
<213> ORGANISM: artificial
<220> FEATURE:
<223> OTHER INFORMATION: Synthetic polypeptide

<400> SEQUENCE: 152

Met Ile His Pro Asn Ser Ser Ile Thr Asn Ile Asn Glu
1               5                   10

<210> SEQ ID NO 153
<211> LENGTH: 13
<212> TYPE: PRT
<213> ORGANISM: artificial
<220> FEATURE:
<223> OTHER INFORMATION: Synthetic polypeptide

<400> SEQUENCE: 153

Met Ile His Pro Asn Ser Gly Ala Thr Asn Ile Asn Glu
1               5                   10
```

```
<210> SEQ ID NO 154
<211> LENGTH: 13
<212> TYPE: PRT
<213> ORGANISM: artificial
<220> FEATURE:
<223> OTHER INFORMATION: Synthetic polypeptide

<400> SEQUENCE: 154

Met Ile His Pro Asn Ser Gly Val Thr Asn Ile Asn Glu
1               5                   10

<210> SEQ ID NO 155
<211> LENGTH: 13
<212> TYPE: PRT
<213> ORGANISM: artificial
<220> FEATURE:
<223> OTHER INFORMATION: Synthetic polypeptide

<400> SEQUENCE: 155

Met Ile His Pro Asn Ser Gly Ile Ala Asn Ile Asn Glu
1               5                   10

<210> SEQ ID NO 156
<211> LENGTH: 13
<212> TYPE: PRT
<213> ORGANISM: artificial
<220> FEATURE:
<223> OTHER INFORMATION: Synthetic polypeptide

<400> SEQUENCE: 156

Met Ile His Pro Asn Ser Gly Ile Asp Asn Ile Asn Glu
1               5                   10

<210> SEQ ID NO 157
<211> LENGTH: 13
<212> TYPE: PRT
<213> ORGANISM: artificial
<220> FEATURE:
<223> OTHER INFORMATION: Synthetic polypeptide

<400> SEQUENCE: 157

Met Ile His Pro Asn Ser Gly Ile Glu Asn Ile Asn Glu
1               5                   10

<210> SEQ ID NO 158
<211> LENGTH: 13
<212> TYPE: PRT
<213> ORGANISM: artificial
<220> FEATURE:
<223> OTHER INFORMATION: Synthetic polypeptide

<400> SEQUENCE: 158

Met Ile His Pro Asn Ser Gly Ile Gly Asn Ile Asn Glu
1               5                   10

<210> SEQ ID NO 159
<211> LENGTH: 13
<212> TYPE: PRT
<213> ORGANISM: artificial
<220> FEATURE:
<223> OTHER INFORMATION: Synthetic polypeptide

<400> SEQUENCE: 159

Met Ile His Pro Asn Ser Gly Ile His Asn Ile Asn Glu
1               5                   10
```

```
<210> SEQ ID NO 160
<211> LENGTH: 13
<212> TYPE: PRT
<213> ORGANISM: artificial
<220> FEATURE:
<223> OTHER INFORMATION: Synthetic polypeptide

<400> SEQUENCE: 160

Met Ile His Pro Asn Ser Gly Ile Ile Asn Ile Asn Glu
1               5                   10

<210> SEQ ID NO 161
<211> LENGTH: 13
<212> TYPE: PRT
<213> ORGANISM: artificial
<220> FEATURE:
<223> OTHER INFORMATION: Synthetic polypeptide

<400> SEQUENCE: 161

Met Ile His Pro Asn Ser Gly Ile Lys Asn Ile Asn Glu
1               5                   10

<210> SEQ ID NO 162
<211> LENGTH: 13
<212> TYPE: PRT
<213> ORGANISM: artificial
<220> FEATURE:
<223> OTHER INFORMATION: Synthetic polypeptide

<400> SEQUENCE: 162

Met Ile His Pro Asn Ser Gly Ile Leu Asn Ile Asn Glu
1               5                   10

<210> SEQ ID NO 163
<211> LENGTH: 13
<212> TYPE: PRT
<213> ORGANISM: artificial
<220> FEATURE:
<223> OTHER INFORMATION: Synthetic polypeptide

<400> SEQUENCE: 163

Met Ile His Pro Asn Ser Gly Ile Met Asn Ile Asn Glu
1               5                   10

<210> SEQ ID NO 164
<211> LENGTH: 13
<212> TYPE: PRT
<213> ORGANISM: artificial
<220> FEATURE:
<223> OTHER INFORMATION: Synthetic polypeptide

<400> SEQUENCE: 164

Met Ile His Pro Asn Ser Gly Ile Asn Asn Ile Asn Glu
1               5                   10

<210> SEQ ID NO 165
<211> LENGTH: 13
<212> TYPE: PRT
<213> ORGANISM: artificial
<220> FEATURE:
<223> OTHER INFORMATION: Synthetic polypeptide

<400> SEQUENCE: 165

Met Ile His Pro Asn Ser Gly Ile Gln Asn Ile Asn Glu
1               5                   10

<210> SEQ ID NO 166
```

```
<211> LENGTH: 13
<212> TYPE: PRT
<213> ORGANISM: artificial
<220> FEATURE:
<223> OTHER INFORMATION: Synthetic polypeptide

<400> SEQUENCE: 166

Met Ile His Pro Asn Ser Gly Ile Arg Asn Ile Asn Glu
1               5                   10

<210> SEQ ID NO 167
<211> LENGTH: 13
<212> TYPE: PRT
<213> ORGANISM: artificial
<220> FEATURE:
<223> OTHER INFORMATION: Synthetic polypeptide

<400> SEQUENCE: 167

Met Ile His Pro Asn Ser Gly Ile Ser Asn Ile Asn Glu
1               5                   10

<210> SEQ ID NO 168
<211> LENGTH: 13
<212> TYPE: PRT
<213> ORGANISM: artificial
<220> FEATURE:
<223> OTHER INFORMATION: Synthetic polypeptide

<400> SEQUENCE: 168

Met Ile His Pro Asn Ser Gly Ile Val Asn Ile Asn Glu
1               5                   10

<210> SEQ ID NO 169
<211> LENGTH: 13
<212> TYPE: PRT
<213> ORGANISM: artificial
<220> FEATURE:
<223> OTHER INFORMATION: Synthetic polypeptide

<400> SEQUENCE: 169

Met Ile His Pro Asn Ser Gly Ile Trp Asn Ile Asn Glu
1               5                   10

<210> SEQ ID NO 170
<211> LENGTH: 13
<212> TYPE: PRT
<213> ORGANISM: artificial
<220> FEATURE:
<223> OTHER INFORMATION: Synthetic polypeptide

<400> SEQUENCE: 170

Met Ile His Pro Asn Ser Gly Ile Tyr Asn Ile Asn Glu
1               5                   10

<210> SEQ ID NO 171
<211> LENGTH: 13
<212> TYPE: PRT
<213> ORGANISM: artificial
<220> FEATURE:
<223> OTHER INFORMATION: Synthetic polypeptide

<400> SEQUENCE: 171

Met Ile His Pro Asn Ser Gly Ile Thr Met Ile Asn Glu
1               5                   10

<210> SEQ ID NO 172
<211> LENGTH: 13
```

<212> TYPE: PRT
<213> ORGANISM: artificial
<220> FEATURE:
<223> OTHER INFORMATION: Synthetic polypeptide

<400> SEQUENCE: 172

Met Ile His Pro Asn Ser Gly Ile Thr Ser Ile Asn Glu
1               5                   10

<210> SEQ ID NO 173
<211> LENGTH: 13
<212> TYPE: PRT
<213> ORGANISM: artificial
<220> FEATURE:
<223> OTHER INFORMATION: Synthetic polypeptide

<400> SEQUENCE: 173

Met Ile His Pro Asn Ser Gly Ile Thr Asn Phe Asn Glu
1               5                   10

<210> SEQ ID NO 174
<211> LENGTH: 13
<212> TYPE: PRT
<213> ORGANISM: artificial
<220> FEATURE:
<223> OTHER INFORMATION: Synthetic polypeptide

<400> SEQUENCE: 174

Met Ile His Pro Asn Ser Gly Ile Thr Asn Gly Asn Glu
1               5                   10

<210> SEQ ID NO 175
<211> LENGTH: 13
<212> TYPE: PRT
<213> ORGANISM: artificial
<220> FEATURE:
<223> OTHER INFORMATION: Synthetic polypeptide

<400> SEQUENCE: 175

Met Ile His Pro Asn Ser Gly Ile Thr Asn His Asn Glu
1               5                   10

<210> SEQ ID NO 176
<211> LENGTH: 13
<212> TYPE: PRT
<213> ORGANISM: artificial
<220> FEATURE:
<223> OTHER INFORMATION: Synthetic polypeptide

<400> SEQUENCE: 176

Met Ile His Pro Asn Ser Gly Ile Thr Asn Lys Asn Glu
1               5                   10

<210> SEQ ID NO 177
<211> LENGTH: 13
<212> TYPE: PRT
<213> ORGANISM: artificial
<220> FEATURE:
<223> OTHER INFORMATION: Synthetic polypeptide

<400> SEQUENCE: 177

Met Ile His Pro Asn Ser Gly Ile Thr Asn Leu Asn Glu
1               5                   10

<210> SEQ ID NO 178
<211> LENGTH: 13
<212> TYPE: PRT

<213> ORGANISM: artificial
<220> FEATURE:
<223> OTHER INFORMATION: Synthetic polypeptide

<400> SEQUENCE: 178

Met Ile His Pro Asn Ser Gly Ile Thr Asn Met Asn Glu
1               5                   10

<210> SEQ ID NO 179
<211> LENGTH: 13
<212> TYPE: PRT
<213> ORGANISM: artificial
<220> FEATURE:
<223> OTHER INFORMATION: Synthetic polypeptide

<400> SEQUENCE: 179

Met Ile His Pro Asn Ser Gly Ile Thr Asn Asn Asn Glu
1               5                   10

<210> SEQ ID NO 180
<211> LENGTH: 13
<212> TYPE: PRT
<213> ORGANISM: artificial
<220> FEATURE:
<223> OTHER INFORMATION: Synthetic polypeptide

<400> SEQUENCE: 180

Met Ile His Pro Asn Ser Gly Ile Thr Asn Gln Asn Glu
1               5                   10

<210> SEQ ID NO 181
<211> LENGTH: 13
<212> TYPE: PRT
<213> ORGANISM: artificial
<220> FEATURE:
<223> OTHER INFORMATION: Synthetic polypeptide

<400> SEQUENCE: 181

Met Ile His Pro Asn Ser Gly Ile Thr Asn Arg Asn Glu
1               5                   10

<210> SEQ ID NO 182
<211> LENGTH: 13
<212> TYPE: PRT
<213> ORGANISM: artificial
<220> FEATURE:
<223> OTHER INFORMATION: Synthetic polypeptide

<400> SEQUENCE: 182

Met Ile His Pro Asn Ser Gly Ile Thr Asn Ser Asn Glu
1               5                   10

<210> SEQ ID NO 183
<211> LENGTH: 13
<212> TYPE: PRT
<213> ORGANISM: artificial
<220> FEATURE:
<223> OTHER INFORMATION: Synthetic polypeptide

<400> SEQUENCE: 183

Met Ile His Pro Asn Ser Gly Ile Thr Asn Thr Asn Glu
1               5                   10

<210> SEQ ID NO 184
<211> LENGTH: 13
<212> TYPE: PRT
<213> ORGANISM: artificial

<220> FEATURE:
<223> OTHER INFORMATION: Synthetic polypeptide

<400> SEQUENCE: 184

Met Ile His Pro Asn Ser Gly Ile Thr Asn Val Asn Glu
1               5                   10

<210> SEQ ID NO 185
<211> LENGTH: 13
<212> TYPE: PRT
<213> ORGANISM: artificial
<220> FEATURE:
<223> OTHER INFORMATION: Synthetic polypeptide

<400> SEQUENCE: 185

Met Ile His Pro Asn Ser Gly Ile Thr Asn Trp Asn Glu
1               5                   10

<210> SEQ ID NO 186
<211> LENGTH: 13
<212> TYPE: PRT
<213> ORGANISM: artificial
<220> FEATURE:
<223> OTHER INFORMATION: Synthetic polypeptide

<400> SEQUENCE: 186

Met Ile His Pro Asn Ser Gly Ile Thr Asn Tyr Asn Glu
1               5                   10

<210> SEQ ID NO 187
<211> LENGTH: 13
<212> TYPE: PRT
<213> ORGANISM: artificial
<220> FEATURE:
<223> OTHER INFORMATION: Synthetic polypeptide

<400> SEQUENCE: 187

Met Ile His Pro Asn Ser Gly Ile Thr Asn Ile Asn Ala
1               5                   10

<210> SEQ ID NO 188
<211> LENGTH: 13
<212> TYPE: PRT
<213> ORGANISM: artificial
<220> FEATURE:
<223> OTHER INFORMATION: Synthetic polypeptide

<400> SEQUENCE: 188

Met Ile His Pro Asn Ser Gly Ile Thr Asn Ile Asn Asp
1               5                   10

<210> SEQ ID NO 189
<211> LENGTH: 13
<212> TYPE: PRT
<213> ORGANISM: artificial
<220> FEATURE:
<223> OTHER INFORMATION: Synthetic polypeptide

<400> SEQUENCE: 189

Met Ile His Pro Asn Ser Gly Ile Thr Asn Ile Asn Gly
1               5                   10

<210> SEQ ID NO 190
<211> LENGTH: 13
<212> TYPE: PRT
<213> ORGANISM: artificial
<220> FEATURE:

<223> OTHER INFORMATION: Synthetic polypeptide

<400> SEQUENCE: 190

Met Ile His Pro Asn Ser Gly Ile Thr Asn Ile Asn His
1               5                   10

<210> SEQ ID NO 191
<211> LENGTH: 13
<212> TYPE: PRT
<213> ORGANISM: artificial
<220> FEATURE:
<223> OTHER INFORMATION: Synthetic polypeptide

<400> SEQUENCE: 191

Met Ile His Pro Asn Ser Gly Ile Thr Asn Ile Asn Lys
1               5                   10

<210> SEQ ID NO 192
<211> LENGTH: 13
<212> TYPE: PRT
<213> ORGANISM: artificial
<220> FEATURE:
<223> OTHER INFORMATION: Synthetic polypeptide

<400> SEQUENCE: 192

Met Ile His Pro Asn Ser Gly Ile Thr Asn Ile Asn Leu
1               5                   10

<210> SEQ ID NO 193
<211> LENGTH: 13
<212> TYPE: PRT
<213> ORGANISM: artificial
<220> FEATURE:
<223> OTHER INFORMATION: Synthetic polypeptide

<400> SEQUENCE: 193

Met Ile His Pro Asn Ser Gly Ile Thr Asn Ile Asn Met
1               5                   10

<210> SEQ ID NO 194
<211> LENGTH: 13
<212> TYPE: PRT
<213> ORGANISM: artificial
<220> FEATURE:
<223> OTHER INFORMATION: Synthetic polypeptide

<400> SEQUENCE: 194

Met Ile His Pro Asn Ser Gly Ile Thr Asn Ile Asn Asn
1               5                   10

<210> SEQ ID NO 195
<211> LENGTH: 13
<212> TYPE: PRT
<213> ORGANISM: artificial
<220> FEATURE:
<223> OTHER INFORMATION: Synthetic polypeptide

<400> SEQUENCE: 195

Met Ile His Pro Asn Ser Gly Ile Thr Asn Ile Asn Pro
1               5                   10

<210> SEQ ID NO 196
<211> LENGTH: 13
<212> TYPE: PRT
<213> ORGANISM: artificial
<220> FEATURE:
<223> OTHER INFORMATION: Synthetic polypeptide

<400> SEQUENCE: 196

Met Ile His Pro Asn Ser Gly Ile Thr Asn Ile Asn Gln
1               5                   10

<210> SEQ ID NO 197
<211> LENGTH: 13
<212> TYPE: PRT
<213> ORGANISM: artificial
<220> FEATURE:
<223> OTHER INFORMATION: Synthetic polypeptide

<400> SEQUENCE: 197

Met Ile His Pro Asn Ser Gly Ile Thr Asn Ile Asn Arg
1               5                   10

<210> SEQ ID NO 198
<211> LENGTH: 13
<212> TYPE: PRT
<213> ORGANISM: artificial
<220> FEATURE:
<223> OTHER INFORMATION: Synthetic polypeptide

<400> SEQUENCE: 198

Met Ile His Pro Asn Ser Gly Ile Thr Asn Ile Asn Ser
1               5                   10

<210> SEQ ID NO 199
<211> LENGTH: 13
<212> TYPE: PRT
<213> ORGANISM: artificial
<220> FEATURE:
<223> OTHER INFORMATION: Synthetic polypeptide

<400> SEQUENCE: 199

Met Ile His Pro Asn Ser Gly Ile Thr Asn Ile Asn Thr
1               5                   10

<210> SEQ ID NO 200
<211> LENGTH: 13
<212> TYPE: PRT
<213> ORGANISM: artificial
<220> FEATURE:
<223> OTHER INFORMATION: Synthetic polypeptide

<400> SEQUENCE: 200

Met Ile His Pro Asn Ser Gly Ile Thr Asn Ile Asn Val
1               5                   10

<210> SEQ ID NO 201
<211> LENGTH: 13
<212> TYPE: PRT
<213> ORGANISM: artificial
<220> FEATURE:
<223> OTHER INFORMATION: Synthetic polypeptide

<400> SEQUENCE: 201

Met Ile His Pro Asn Ser Gly Ile Thr Asn Ile Asn Trp
1               5                   10

<210> SEQ ID NO 202
<211> LENGTH: 13
<212> TYPE: PRT
<213> ORGANISM: artificial
<220> FEATURE:
<223> OTHER INFORMATION: Synthetic polypeptide

```
<400> SEQUENCE: 202

Met Ile His Pro Asn Ser Gly Ile Thr Asn Ile Asn Tyr
1               5                   10

<210> SEQ ID NO 203
<211> LENGTH: 12
<212> TYPE: PRT
<213> ORGANISM: artificial
<220> FEATURE:
<223> OTHER INFORMATION: Synthetic polypeptide
<220> FEATURE:
<221> NAME/KEY: VARIANT
<222> LOCATION: (2)..(2)
<223> OTHER INFORMATION: X at 2 is S, A, F, G, I, L, M, N, R, T, V, W,
      or Y.
<220> FEATURE:
<221> NAME/KEY: VARIANT
<222> LOCATION: (4)..(4)
<223> OTHER INFORMATION: X at 4 is G or W.
<220> FEATURE:
<221> NAME/KEY: VARIANT
<222> LOCATION: (5)..(5)
<223> OTHER INFORMATION: X at 5 is T, D, E, F, H, I, K, L, M, N, Q, V,
      W, or Y.
<220> FEATURE:
<221> NAME/KEY: VARIANT
<222> LOCATION: (6)..(6)
<223> OTHER INFORMATION: X at 6 is Y, D, F, H, N, R, or W.
<220> FEATURE:
<221> NAME/KEY: VARIANT
<222> LOCATION: (7)..(7)
<223> OTHER INFORMATION: X at 7 is E, D, G, H, K, M, N, Q, R, V, or Y.
<220> FEATURE:
<221> NAME/KEY: VARIANT
<222> LOCATION: (8)..(8)
<223> OTHER INFORMATION: X at 8 is G, K, R, S, or T.

<400> SEQUENCE: 203

Arg Xaa Asp Xaa Xaa Xaa Xaa Xaa Tyr Phe Asp Tyr
1               5                   10

<210> SEQ ID NO 204
<211> LENGTH: 12
<212> TYPE: PRT
<213> ORGANISM: artificial
<220> FEATURE:
<223> OTHER INFORMATION: Synthetic polypeptide

<400> SEQUENCE: 204

Arg Ala Asp Gly Thr Tyr Glu Gly Tyr Phe Asp Tyr
1               5                   10

<210> SEQ ID NO 205
<211> LENGTH: 12
<212> TYPE: PRT
<213> ORGANISM: artificial
<220> FEATURE:
<223> OTHER INFORMATION: Synthetic polypeptide

<400> SEQUENCE: 205

Arg Phe Asp Gly Thr Tyr Glu Gly Tyr Phe Asp Tyr
1               5                   10

<210> SEQ ID NO 206
<211> LENGTH: 12
<212> TYPE: PRT
<213> ORGANISM: artificial
<220> FEATURE:
<223> OTHER INFORMATION: Synthetic polypeptide

<400> SEQUENCE: 206
```

Arg Gly Asp Gly Thr Tyr Glu Gly Tyr Phe Asp Tyr
1               5                   10

<210> SEQ ID NO 207
<211> LENGTH: 12
<212> TYPE: PRT
<213> ORGANISM: artificial
<220> FEATURE:
<223> OTHER INFORMATION: Synthetic polypeptide

<400> SEQUENCE: 207

Arg Ile Asp Gly Thr Tyr Glu Gly Tyr Phe Asp Tyr
1               5                   10

<210> SEQ ID NO 208
<211> LENGTH: 12
<212> TYPE: PRT
<213> ORGANISM: artificial
<220> FEATURE:
<223> OTHER INFORMATION: Synthetic polypeptide

<400> SEQUENCE: 208

Arg Leu Asp Gly Thr Tyr Glu Gly Tyr Phe Asp Tyr
1               5                   10

<210> SEQ ID NO 209
<211> LENGTH: 12
<212> TYPE: PRT
<213> ORGANISM: artificial
<220> FEATURE:
<223> OTHER INFORMATION: Synthetic polypeptide

<400> SEQUENCE: 209

Arg Met Asp Gly Thr Tyr Glu Gly Tyr Phe Asp Tyr
1               5                   10

<210> SEQ ID NO 210
<211> LENGTH: 12
<212> TYPE: PRT
<213> ORGANISM: artificial
<220> FEATURE:
<223> OTHER INFORMATION: Synthetic polypeptide

<400> SEQUENCE: 210

Arg Asn Asp Gly Thr Tyr Glu Gly Tyr Phe Asp Tyr
1               5                   10

<210> SEQ ID NO 211
<211> LENGTH: 12
<212> TYPE: PRT
<213> ORGANISM: artificial
<220> FEATURE:
<223> OTHER INFORMATION: Synthetic polypeptide

<400> SEQUENCE: 211

Arg Arg Asp Gly Thr Tyr Glu Gly Tyr Phe Asp Tyr
1               5                   10

<210> SEQ ID NO 212
<211> LENGTH: 12
<212> TYPE: PRT
<213> ORGANISM: artificial
<220> FEATURE:
<223> OTHER INFORMATION: Synthetic polypeptide

<400> SEQUENCE: 212

Arg Thr Asp Gly Thr Tyr Glu Gly Tyr Phe Asp Tyr
1               5                   10

<210> SEQ ID NO 213
<211> LENGTH: 12
<212> TYPE: PRT
<213> ORGANISM: artificial
<220> FEATURE:
<223> OTHER INFORMATION: Synthetic polypeptide

<400> SEQUENCE: 213

Arg Val Asp Gly Thr Tyr Glu Gly Tyr Phe Asp Tyr
1               5                   10

<210> SEQ ID NO 214
<211> LENGTH: 12
<212> TYPE: PRT
<213> ORGANISM: artificial
<220> FEATURE:
<223> OTHER INFORMATION: Synthetic polypeptide

<400> SEQUENCE: 214

Arg Trp Asp Gly Thr Tyr Glu Gly Tyr Phe Asp Tyr
1               5                   10

<210> SEQ ID NO 215
<211> LENGTH: 12
<212> TYPE: PRT
<213> ORGANISM: artificial
<220> FEATURE:
<223> OTHER INFORMATION: Synthetic polypeptide

<400> SEQUENCE: 215

Arg Tyr Asp Gly Thr Tyr Glu Gly Tyr Phe Asp Tyr
1               5                   10

<210> SEQ ID NO 216
<211> LENGTH: 12
<212> TYPE: PRT
<213> ORGANISM: artificial
<220> FEATURE:
<223> OTHER INFORMATION: Synthetic polypeptide

<400> SEQUENCE: 216

Arg Ser Asp Trp Thr Tyr Glu Gly Tyr Phe Asp Tyr
1               5                   10

<210> SEQ ID NO 217
<211> LENGTH: 12
<212> TYPE: PRT
<213> ORGANISM: artificial
<220> FEATURE:
<223> OTHER INFORMATION: Synthetic polypeptide

<400> SEQUENCE: 217

Arg Ser Asp Gly Asp Tyr Glu Gly Tyr Phe Asp Tyr
1               5                   10

<210> SEQ ID NO 218
<211> LENGTH: 12
<212> TYPE: PRT
<213> ORGANISM: artificial
<220> FEATURE:
<223> OTHER INFORMATION: Synthetic polypeptide

<400> SEQUENCE: 218

Arg Ser Asp Gly Glu Tyr Glu Gly Tyr Phe Asp Tyr

```
<210> SEQ ID NO 219
<211> LENGTH: 12
<212> TYPE: PRT
<213> ORGANISM: artificial
<220> FEATURE:
<223> OTHER INFORMATION: Synthetic polypeptide

<400> SEQUENCE: 219

Arg Ser Asp Gly Phe Tyr Glu Gly Tyr Phe Asp Tyr
1               5                   10

<210> SEQ ID NO 220
<211> LENGTH: 12
<212> TYPE: PRT
<213> ORGANISM: artificial
<220> FEATURE:
<223> OTHER INFORMATION: Synthetic polypeptide

<400> SEQUENCE: 220

Arg Ser Asp Gly His Tyr Glu Gly Tyr Phe Asp Tyr
1               5                   10

<210> SEQ ID NO 221
<211> LENGTH: 12
<212> TYPE: PRT
<213> ORGANISM: artificial
<220> FEATURE:
<223> OTHER INFORMATION: Synthetic polypeptide

<400> SEQUENCE: 221

Arg Ser Asp Gly Ile Tyr Glu Gly Tyr Phe Asp Tyr
1               5                   10

<210> SEQ ID NO 222
<211> LENGTH: 12
<212> TYPE: PRT
<213> ORGANISM: artificial
<220> FEATURE:
<223> OTHER INFORMATION: Synthetic polypeptide

<400> SEQUENCE: 222

Arg Ser Asp Gly Lys Tyr Glu Gly Tyr Phe Asp Tyr
1               5                   10

<210> SEQ ID NO 223
<211> LENGTH: 12
<212> TYPE: PRT
<213> ORGANISM: artificial
<220> FEATURE:
<223> OTHER INFORMATION: Synthetic polypeptide

<400> SEQUENCE: 223

Arg Ser Asp Gly Leu Tyr Glu Gly Tyr Phe Asp Tyr
1               5                   10

<210> SEQ ID NO 224
<211> LENGTH: 12
<212> TYPE: PRT
<213> ORGANISM: artificial
<220> FEATURE:
<223> OTHER INFORMATION: Synthetic polypeptide

<400> SEQUENCE: 224

Arg Ser Asp Gly Met Tyr Glu Gly Tyr Phe Asp Tyr
1               5                   10
```

<210> SEQ ID NO 225
<211> LENGTH: 12
<212> TYPE: PRT
<213> ORGANISM: artificial
<220> FEATURE:
<223> OTHER INFORMATION: Synthetic polypeptide

<400> SEQUENCE: 225

Arg Ser Asp Gly Asn Tyr Glu Gly Tyr Phe Asp Tyr
1               5                   10

<210> SEQ ID NO 226
<211> LENGTH: 12
<212> TYPE: PRT
<213> ORGANISM: artificial
<220> FEATURE:
<223> OTHER INFORMATION: Synthetic polypeptide

<400> SEQUENCE: 226

Arg Ser Asp Gly Gln Tyr Glu Gly Tyr Phe Asp Tyr
1               5                   10

<210> SEQ ID NO 227
<211> LENGTH: 12
<212> TYPE: PRT
<213> ORGANISM: artificial
<220> FEATURE:
<223> OTHER INFORMATION: Synthetic polypeptide

<400> SEQUENCE: 227

Arg Ser Asp Gly Val Tyr Glu Gly Tyr Phe Asp Tyr
1               5                   10

<210> SEQ ID NO 228
<211> LENGTH: 12
<212> TYPE: PRT
<213> ORGANISM: artificial
<220> FEATURE:
<223> OTHER INFORMATION: Synthetic polypeptide

<400> SEQUENCE: 228

Arg Ser Asp Gly Trp Tyr Glu Gly Tyr Phe Asp Tyr
1               5                   10

<210> SEQ ID NO 229
<211> LENGTH: 12
<212> TYPE: PRT
<213> ORGANISM: artificial
<220> FEATURE:
<223> OTHER INFORMATION: Synthetic polypeptide

<400> SEQUENCE: 229

Arg Ser Asp Gly Tyr Tyr Glu Gly Tyr Phe Asp Tyr
1               5                   10

<210> SEQ ID NO 230
<211> LENGTH: 12
<212> TYPE: PRT
<213> ORGANISM: artificial
<220> FEATURE:
<223> OTHER INFORMATION: Synthetic polypeptide

<400> SEQUENCE: 230

Arg Ser Asp Gly Thr Asp Glu Gly Tyr Phe Asp Tyr
1               5                   10

```
<210> SEQ ID NO 231
<211> LENGTH: 12
<212> TYPE: PRT
<213> ORGANISM: artificial
<220> FEATURE:
<223> OTHER INFORMATION: Synthetic polypeptide

<400> SEQUENCE: 231

Arg Ser Asp Gly Thr Phe Glu Gly Tyr Phe Asp Tyr
1               5                   10

<210> SEQ ID NO 232
<211> LENGTH: 12
<212> TYPE: PRT
<213> ORGANISM: artificial
<220> FEATURE:
<223> OTHER INFORMATION: Synthetic polypeptide

<400> SEQUENCE: 232

Arg Ser Asp Gly Thr His Glu Gly Tyr Phe Asp Tyr
1               5                   10

<210> SEQ ID NO 233
<211> LENGTH: 12
<212> TYPE: PRT
<213> ORGANISM: artificial
<220> FEATURE:
<223> OTHER INFORMATION: Synthetic polypeptide

<400> SEQUENCE: 233

Arg Ser Asp Gly Thr Asn Glu Gly Tyr Phe Asp Tyr
1               5                   10

<210> SEQ ID NO 234
<211> LENGTH: 12
<212> TYPE: PRT
<213> ORGANISM: artificial
<220> FEATURE:
<223> OTHER INFORMATION: Synthetic polypeptide

<400> SEQUENCE: 234

Arg Ser Asp Gly Thr Arg Glu Gly Tyr Phe Asp Tyr
1               5                   10

<210> SEQ ID NO 235
<211> LENGTH: 12
<212> TYPE: PRT
<213> ORGANISM: artificial
<220> FEATURE:
<223> OTHER INFORMATION: Synthetic polypeptide

<400> SEQUENCE: 235

Arg Ser Asp Gly Thr Trp Glu Gly Tyr Phe Asp Tyr
1               5                   10

<210> SEQ ID NO 236
<211> LENGTH: 12
<212> TYPE: PRT
<213> ORGANISM: artificial
<220> FEATURE:
<223> OTHER INFORMATION: Synthetic polypeptide

<400> SEQUENCE: 236

Arg Ser Asp Gly Thr Tyr Asp Gly Tyr Phe Asp Tyr
1               5                   10
```

```
<210> SEQ ID NO 237
<211> LENGTH: 12
<212> TYPE: PRT
<213> ORGANISM: artificial
<220> FEATURE:
<223> OTHER INFORMATION: Synthetic polypeptide

<400> SEQUENCE: 237

Arg Ser Asp Gly Thr Tyr Gly Gly Tyr Phe Asp Tyr
1               5                   10

<210> SEQ ID NO 238
<211> LENGTH: 12
<212> TYPE: PRT
<213> ORGANISM: artificial
<220> FEATURE:
<223> OTHER INFORMATION: Synthetic polypeptide

<400> SEQUENCE: 238

Arg Ser Asp Gly Thr Tyr His Gly Tyr Phe Asp Tyr
1               5                   10

<210> SEQ ID NO 239
<211> LENGTH: 12
<212> TYPE: PRT
<213> ORGANISM: artificial
<220> FEATURE:
<223> OTHER INFORMATION: Synthetic polypeptide

<400> SEQUENCE: 239

Arg Ser Asp Gly Thr Tyr Lys Gly Tyr Phe Asp Tyr
1               5                   10

<210> SEQ ID NO 240
<211> LENGTH: 12
<212> TYPE: PRT
<213> ORGANISM: artificial
<220> FEATURE:
<223> OTHER INFORMATION: Synthetic polypeptide

<400> SEQUENCE: 240

Arg Ser Asp Gly Thr Tyr Met Gly Tyr Phe Asp Tyr
1               5                   10

<210> SEQ ID NO 241
<211> LENGTH: 12
<212> TYPE: PRT
<213> ORGANISM: artificial
<220> FEATURE:
<223> OTHER INFORMATION: Synthetic polypeptide

<400> SEQUENCE: 241

Arg Ser Asp Gly Thr Tyr Asn Gly Tyr Phe Asp Tyr
1               5                   10

<210> SEQ ID NO 242
<211> LENGTH: 12
<212> TYPE: PRT
<213> ORGANISM: artificial
<220> FEATURE:
<223> OTHER INFORMATION: Synthetic polypeptide

<400> SEQUENCE: 242

Arg Ser Asp Gly Thr Tyr Gln Gly Tyr Phe Asp Tyr
1               5                   10

<210> SEQ ID NO 243
```

```
<211> LENGTH: 12
<212> TYPE: PRT
<213> ORGANISM: artificial
<220> FEATURE:
<223> OTHER INFORMATION: Synthetic polypeptide

<400> SEQUENCE: 243

Arg Ser Asp Gly Thr Tyr Arg Gly Tyr Phe Asp Tyr
1               5                   10

<210> SEQ ID NO 244
<211> LENGTH: 12
<212> TYPE: PRT
<213> ORGANISM: artificial
<220> FEATURE:
<223> OTHER INFORMATION: Synthetic polypeptide

<400> SEQUENCE: 244

Arg Ser Asp Gly Thr Tyr Val Gly Tyr Phe Asp Tyr
1               5                   10

<210> SEQ ID NO 245
<211> LENGTH: 12
<212> TYPE: PRT
<213> ORGANISM: artificial
<220> FEATURE:
<223> OTHER INFORMATION: Synthetic polypeptide

<400> SEQUENCE: 245

Arg Ser Asp Gly Thr Tyr Tyr Gly Tyr Phe Asp Tyr
1               5                   10

<210> SEQ ID NO 246
<211> LENGTH: 12
<212> TYPE: PRT
<213> ORGANISM: artificial
<220> FEATURE:
<223> OTHER INFORMATION: Synthetic polypeptide

<400> SEQUENCE: 246

Arg Ser Asp Gly Thr Tyr Glu Lys Tyr Phe Asp Tyr
1               5                   10

<210> SEQ ID NO 247
<211> LENGTH: 12
<212> TYPE: PRT
<213> ORGANISM: artificial
<220> FEATURE:
<223> OTHER INFORMATION: Synthetic polypeptide

<400> SEQUENCE: 247

Arg Ser Asp Gly Thr Tyr Glu Arg Tyr Phe Asp Tyr
1               5                   10

<210> SEQ ID NO 248
<211> LENGTH: 12
<212> TYPE: PRT
<213> ORGANISM: artificial
<220> FEATURE:
<223> OTHER INFORMATION: Synthetic polypeptide

<400> SEQUENCE: 248

Arg Ser Asp Gly Thr Tyr Glu Ser Tyr Phe Asp Tyr
1               5                   10

<210> SEQ ID NO 249
<211> LENGTH: 12
```

```
<212> TYPE: PRT
<213> ORGANISM: artificial
<220> FEATURE:
<223> OTHER INFORMATION: Synthetic polypeptide

<400> SEQUENCE: 249

Arg Ser Asp Gly Thr Tyr Glu Thr Tyr Phe Asp Tyr
1               5                   10

<210> SEQ ID NO 250
<211> LENGTH: 119
<212> TYPE: PRT
<213> ORGANISM: artificial
<220> FEATURE:
<223> OTHER INFORMATION: Synthetic polypeptide

<400> SEQUENCE: 250

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Arg His Trp Val Arg Gln Ala Pro Gly Gln Gly Leu Glu Trp Ile
        35                  40                  45

Gly Met Ile His Phe Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Gly Tyr Phe Asp Tyr Trp Gly Gln Gly
            100                 105                 110

Thr Leu Val Thr Val Ser Ser
        115

<210> SEQ ID NO 251
<211> LENGTH: 119
<212> TYPE: PRT
<213> ORGANISM: artificial
<220> FEATURE:
<223> OTHER INFORMATION: Synthetic polypeptide

<400> SEQUENCE: 251

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Arg
            20                  25                  30

Trp Met His Trp Val Arg Gln Ala Pro Gly Gln Gly Leu Glu Trp Ile
        35                  40                  45

Gly Met Ile His Val Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Leu Tyr Glu Gly Tyr Phe Asp Tyr Trp Gly Gln Gly
            100                 105                 110

Thr Leu Val Thr Val Ser Ser
        115
```

<210> SEQ ID NO 252
<211> LENGTH: 119
<212> TYPE: PRT
<213> ORGANISM: artificial
<220> FEATURE:
<223> OTHER INFORMATION: Synthetic polypeptide

<400> SEQUENCE: 252

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Asp His Trp Val Arg Gln Ala Pro Gly Gln Gly Leu Glu Trp Ile
        35                  40                  45

Gly Met Ile His Pro Leu Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Gly Tyr Phe Asp Tyr Trp Gly Gln Gly
            100                 105                 110

Thr Leu Val Thr Val Ser Ser
        115

<210> SEQ ID NO 253
<211> LENGTH: 119
<212> TYPE: PRT
<213> ORGANISM: artificial
<220> FEATURE:
<223> OTHER INFORMATION: Synthetic polypeptide

<400> SEQUENCE: 253

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Arg His Trp Val Arg Gln Ala Pro Gly Gln Gly Leu Glu Trp Ile
        35                  40                  45

Gly Met Ile His Met Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Gly Tyr Phe Asp Tyr Trp Gly Gln Gly
            100                 105                 110

Thr Leu Val Thr Val Ser Ser
        115

<210> SEQ ID NO 254
<211> LENGTH: 119
<212> TYPE: PRT
<213> ORGANISM: artificial
<220> FEATURE:
<223> OTHER INFORMATION: Synthetic polypeptide

<400> SEQUENCE: 254

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
        20                  25                  30

Trp Arg His Trp Val Arg Gln Ala Pro Gly Gln Gly Leu Glu Trp Ile
        35                  40                  45

Gly Met Ile His Pro Leu Ser Gly Ile Thr Asn Ile Asn Glu Lys Phe
50                      55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Gly Tyr Phe Asp Tyr Trp Gly Gln Gly
                100                 105                 110

Thr Leu Val Thr Val Ser Ser
            115

<210> SEQ ID NO 255
<211> LENGTH: 119
<212> TYPE: PRT
<213> ORGANISM: artificial
<220> FEATURE:
<223> OTHER INFORMATION: Synthetic polypeptide

<400> SEQUENCE: 255

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Val Asn Asn
        20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Thr Asn Glu Lys Phe
50                      55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Ile Tyr Glu Gly Tyr Phe Asp Tyr Trp Gly Gln Gly
                100                 105                 110

Thr Leu Val Thr Val Ser Ser
            115

<210> SEQ ID NO 256
<211> LENGTH: 119
<212> TYPE: PRT
<213> ORGANISM: artificial
<220> FEATURE:
<223> OTHER INFORMATION: Synthetic polypeptide

<400> SEQUENCE: 256

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
        20                  25                  30

Trp Asp His Trp Val Arg Gln Ala Pro Gly Gln Gly Leu Glu Trp Ile
        35                  40                  45

Gly Met Ile His Pro Met Ser Gly Ile Thr Asn Ile Asn Glu Lys Phe
50                      55                  60

Lys Asn Arg Val Thr Met Thr Thr Asp Thr Ser Thr Ser Thr Ala Tyr

```
                65                  70                  75                  80
Met Glu Leu Arg Ser Leu Arg Ser Glu Asp Thr Ala Val Tyr Tyr Cys
                    85                  90                  95

Arg Ser Asp Gly Phe Tyr Glu Gly Tyr Phe Asp Tyr Trp Gly Gln Gly
                100                 105                 110

Thr Leu Val Thr Val Ser Ser
        115

<210> SEQ ID NO 257
<211> LENGTH: 119
<212> TYPE: PRT
<213> ORGANISM: artificial
<220> FEATURE:
<223> OTHER INFORMATION: Synthetic polypeptide

<400> SEQUENCE: 257

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
                20                  25                  30

Trp Arg His Trp Val Arg Gln Ala Pro Gly Gln Gly Leu Glu Trp Ile
            35                  40                  45

Gly Met Ile His Pro Asn Ser Gly Ile Thr Asn Ile Asn Glu Lys Phe
        50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                    85                  90                  95

Arg Ser Asp Gly Val Tyr Glu Gly Tyr Phe Asp Tyr Trp Gly Gln Gly
                100                 105                 110

Thr Leu Val Thr Val Ser Ser
        115

<210> SEQ ID NO 258
<211> LENGTH: 119
<212> TYPE: PRT
<213> ORGANISM: artificial
<220> FEATURE:
<223> OTHER INFORMATION: Synthetic polypeptide

<400> SEQUENCE: 258

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Ser
                20                  25                  30

Trp Met His Trp Val Arg Gln Ala Pro Gly Gln Gly Leu Glu Trp Ile
            35                  40                  45

Gly Met Ile His Pro Asn Ser Gly Ile Thr Asn Arg Asn Glu Lys Phe
        50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                    85                  90                  95

Arg Ser Asp Gly Ile Tyr Glu Gly Tyr Phe Asp Tyr Trp Gly Gln Gly
                100                 105                 110

Thr Leu Val Thr Val Ser Ser
        115
```

<210> SEQ ID NO 259
<211> LENGTH: 119
<212> TYPE: PRT
<213> ORGANISM: artificial
<220> FEATURE:
<223> OTHER INFORMATION: Synthetic polypeptide

<400> SEQUENCE: 259

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Tyr
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Met Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Tyr Phe Asp Tyr Trp Gly Gln Gly
            100                 105                 110

Thr Leu Val Thr Val Ser Ser
        115

<210> SEQ ID NO 260
<211> LENGTH: 119
<212> TYPE: PRT
<213> ORGANISM: artificial
<220> FEATURE:
<223> OTHER INFORMATION: Synthetic polypeptide

<400> SEQUENCE: 260

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Gly His Trp Val Arg Gln Ala Pro Gly Gln Gly Leu Glu Trp Ile
        35                  40                  45

Gly Met Ile His Arg Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Ile Tyr Glu Gly Tyr Phe Asp Tyr Trp Gly Gln Gly
            100                 105                 110

Thr Leu Val Thr Val Ser Ser
        115

<210> SEQ ID NO 261
<211> LENGTH: 119
<212> TYPE: PRT
<213> ORGANISM: artificial
<220> FEATURE:
<223> OTHER INFORMATION: Synthetic polypeptide

<400> SEQUENCE: 261

Glu Val Gln Leu Val Gln Ser Gly Ala Glu Val Lys Lys Pro Gly Ala

```
                1               5                  10                  15
            Ser Val Lys Val Ser Cys Lys Ala Ser Gly Phe Thr Phe Thr Asn Arg
                            20                  25                  30

Trp Met His Trp Val Arg Gln Ala Pro Gly Gln Gly Leu Glu Trp Ile
                        35                  40                  45

Gly Met Ile His His Asn Ser Gly Ile Thr Asn Ile Asn Glu Lys Phe
                    50                  55                  60

Lys Asn Arg Val Thr Met Thr Thr Asp Thr Ser Thr Ser Thr Ala Tyr
             65                  70                  75                  80

Met Glu Leu Arg Ser Leu Arg Ser Glu Asp Thr Ala Val Tyr Tyr Cys
                            85                  90                  95

Arg Ser Asp Gly Val Tyr Glu Gly Tyr Phe Asp Tyr Trp Gly Gln Gly
                            100                 105                 110

Thr Leu Val Thr Val Ser Ser
                        115

<210> SEQ ID NO 262
<211> LENGTH: 119
<212> TYPE: PRT
<213> ORGANISM: artificial
<220> FEATURE:
<223> OTHER INFORMATION: Synthetic polypeptide

<400> SEQUENCE: 262

Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Asn Asn
                20                  25                  30

Trp Ser His Trp Val Arg Gln Ala Pro Gly Gln Gly Leu Glu Trp Ile
            35                  40                  45

Gly Met Ile His Arg Asn Ser Gly Ile Thr Asn Ile Asn Glu Lys Phe
        50                  55                  60

Lys Asn Arg Val Thr Met Thr Thr Asp Thr Ser Thr Ser Thr Ala Tyr
 65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Gly Tyr Phe Asp Tyr Trp Gly Gln Gly
                100                 105                 110

Thr Leu Val Thr Val Ser Ser
            115

<210> SEQ ID NO 263
<211> LENGTH: 119
<212> TYPE: PRT
<213> ORGANISM: artificial
<220> FEATURE:
<223> OTHER INFORMATION: Synthetic polypeptide

<400> SEQUENCE: 263

Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Asn Asn
                20                  25                  30

Trp Asn His Trp Val Arg Gln Ala Pro Gly Gln Gly Leu Glu Trp Ile
            35                  40                  45

Gly Met Ile His Pro Asn Ser Gly Ile Thr Ala Ile Asn Glu Lys Phe
        50                  55                  60
```

```
Lys Asn Arg Val Thr Met Thr Thr Asp Thr Ser Ser Thr Ala Tyr
 65                  70                  75                  80

Met Glu Leu Arg Ser Leu Arg Ser Glu Asp Thr Ala Val Tyr Tyr Cys
                 85                  90                  95

Arg Leu Asp Gly Thr Tyr Glu Gly Tyr Phe Asp Tyr Trp Gly Gln Gly
            100                 105                 110

Thr Leu Val Thr Val Ser Ser
            115

<210> SEQ ID NO 264
<211> LENGTH: 119
<212> TYPE: PRT
<213> ORGANISM: artificial
<220> FEATURE:
<223> OTHER INFORMATION: Synthetic polypeptide

<400> SEQUENCE: 264

Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Asn Arg
                 20                  25                  30

Trp Met His Trp Val Arg Gln Ala Pro Gly Gln Gly Leu Glu Trp Ile
             35                  40                  45

Gly Met Ile His Ala Asn Ser Gly Ile Thr Asn Ile Asn Glu Lys Phe
         50                  55                  60

Lys Asn Arg Val Thr Met Thr Thr Asp Thr Ser Thr Ser Thr Ala Tyr
 65                  70                  75                  80

Met Glu Leu Arg Ser Leu Arg Ser Glu Asp Thr Ala Val Tyr Tyr Cys
                 85                  90                  95

Arg Ser Asp Gly Val Tyr Glu Gly Tyr Phe Asp Tyr Trp Gly Gln Gly
            100                 105                 110

Thr Leu Val Thr Val Ser Ser
            115

<210> SEQ ID NO 265
<211> LENGTH: 119
<212> TYPE: PRT
<213> ORGANISM: artificial
<220> FEATURE:
<223> OTHER INFORMATION: Synthetic polypeptide

<400> SEQUENCE: 265

Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Asn Asn
                 20                  25                  30

Phe Met His Trp Val Arg Gln Ala Pro Gly Gln Gly Leu Glu Trp Ile
             35                  40                  45

Gly Met Ile His Pro Asn Ser Gly Ile Thr Asn Ile Asn Glu Lys Phe
         50                  55                  60

Lys Asn Arg Val Thr Met Thr Thr Asp Thr Ser Thr Ser Thr Ala Tyr
 65                  70                  75                  80

Met Glu Leu Arg Ser Leu Arg Ser Glu Asp Thr Ala Val Tyr Tyr Cys
                 85                  90                  95

Arg Ser Asp Gly Thr Tyr Glu Gly Tyr Phe Asp Tyr Trp Gly Gln Gly
            100                 105                 110

Thr Leu Val Thr Val Ser Ser
            115
```

<210> SEQ ID NO 266
<211> LENGTH: 119
<212> TYPE: PRT
<213> ORGANISM: artificial
<220> FEATURE:
<223> OTHER INFORMATION: Synthetic polypeptide

<400> SEQUENCE: 266

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
                20                  25                  30

Trp Met His Trp Val Arg Gln Ala Pro Gly Gln Gly Leu Glu Trp Ile
            35                  40                  45

Gly Phe Ile His Pro Asn Ser Gly Ile Thr Asn Ile Asn Glu Lys Phe
        50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
                100                 105                 110

Thr Leu Val Thr Val Ser Ser
            115

<210> SEQ ID NO 267
<211> LENGTH: 119
<212> TYPE: PRT
<213> ORGANISM: artificial
<220> FEATURE:
<223> OTHER INFORMATION: Synthetic polypeptide

<400> SEQUENCE: 267

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
                20                  25                  30

Trp Met His Trp Val Arg Gln Ala Pro Gly Gln Gly Leu Glu Trp Ile
            35                  40                  45

Gly Met Ile His Ala Asn Ser Gly Ile Thr Asn Ile Asn Glu Lys Phe
        50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
                100                 105                 110

Thr Leu Val Thr Val Ser Ser
            115

<210> SEQ ID NO 268
<211> LENGTH: 119
<212> TYPE: PRT
<213> ORGANISM: artificial
<220> FEATURE:
<223> OTHER INFORMATION: Synthetic polypeptide

<400> SEQUENCE: 268

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Ile Asn His Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
                100                 105                 110

Thr Leu Val Thr Val Ser Ser
            115

<210> SEQ ID NO 269
<211> LENGTH: 119
<212> TYPE: PRT
<213> ORGANISM: artificial
<220> FEATURE:
<223> OTHER INFORMATION: Synthetic polypeptide

<400> SEQUENCE: 269

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Ile Asn Arg Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
                100                 105                 110

Thr Leu Val Thr Val Ser Ser
            115

<210> SEQ ID NO 270
<211> LENGTH: 119
<212> TYPE: PRT
<213> ORGANISM: artificial
<220> FEATURE:
<223> OTHER INFORMATION: Synthetic polypeptide

<400> SEQUENCE: 270

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Ile Asn Glu Lys Phe
    50                  55                  60

```
Lys Asn Arg Val Thr Met Thr Thr Asp Thr Ser Ser Thr Ala Tyr
 65                  70                  75                  80

Met Glu Leu Arg Ser Leu Arg Ser Glu Asp Thr Ala Val Tyr Tyr Cys
                 85                  90                  95

Arg Ser Asp Gly Ile Tyr Glu Gly Tyr Phe Asp Tyr Trp Gly Gln Gly
                100                 105                 110

Thr Leu Val Thr Val Ser Ser
        115
```

<210> SEQ ID NO 271
<211> LENGTH: 119
<212> TYPE: PRT
<213> ORGANISM: artificial
<220> FEATURE:
<223> OTHER INFORMATION: Synthetic polypeptide

<400> SEQUENCE: 271

```
Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Asn Asn
                 20                  25                  30

Trp Met His Trp Val Arg Gln Ala Pro Gly Gln Gly Leu Glu Trp Ile
             35                  40                  45

Gly Met Ile His Pro Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
 65                  70                  75                  80

Met Glu Leu Arg Ser Leu Arg Ser Glu Asp Thr Ala Val Tyr Tyr Cys
                 85                  90                  95

Arg Ser Asp Gly Val Tyr Glu Gly Tyr Phe Asp Tyr Trp Gly Gln Gly
                100                 105                 110

Thr Leu Val Thr Val Ser Ser
        115
```

<210> SEQ ID NO 272
<211> LENGTH: 119
<212> TYPE: PRT
<213> ORGANISM: artificial
<220> FEATURE:
<223> OTHER INFORMATION: Synthetic polypeptide

<400> SEQUENCE: 272

```
Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Asn Asn
                 20                  25                  30

Phe Met His Trp Val Arg Gln Ala Pro Gly Gln Gly Leu Glu Trp Ile
             35                  40                  45

Gly Met Ile His Ala Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
 65                  70                  75                  80

Met Glu Leu Arg Ser Leu Arg Ser Glu Asp Thr Ala Val Tyr Tyr Cys
                 85                  90                  95

Arg Ser Asp Gly Ile Tyr Glu Gly Tyr Phe Asp Tyr Trp Gly Gln Gly
                100                 105                 110

Thr Leu Val Thr Val Ser Ser
```

115

<210> SEQ ID NO 273
<211> LENGTH: 119
<212> TYPE: PRT
<213> ORGANISM: artificial
<220> FEATURE:
<223> OTHER INFORMATION: Synthetic polypeptide

<400> SEQUENCE: 273

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Phe Met His Trp Val Arg Gln Ala Pro Gly Gln Gly Leu Glu Trp Ile
        35                  40                  45

Gly Met Ile His Ala Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Gly Tyr Phe Asp Tyr Trp Gly Gln Gly
            100                 105                 110

Thr Leu Val Thr Val Ser Ser
            115

<210> SEQ ID NO 274
<211> LENGTH: 119
<212> TYPE: PRT
<213> ORGANISM: artificial
<220> FEATURE:
<223> OTHER INFORMATION: Synthetic polypeptide

<400> SEQUENCE: 274

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Phe Met His Trp Val Arg Gln Ala Pro Gly Gln Gly Leu Glu Trp Ile
        35                  40                  45

Gly Phe Ile His Ala Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Ile Tyr Glu Gly Tyr Phe Asp Tyr Trp Gly Gln Gly
            100                 105                 110

Thr Leu Val Thr Val Ser Ser
            115

<210> SEQ ID NO 275
<211> LENGTH: 119
<212> TYPE: PRT
<213> ORGANISM: artificial
<220> FEATURE:
<223> OTHER INFORMATION: Synthetic polypeptide

<400> SEQUENCE: 275

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Phe Met His Trp Val Arg Gln Ala Pro Gly Gln Gly Leu Glu Trp Ile
        35                  40                  45

Gly Phe Ile His Ala Asn Ser Gly Ile Thr Asn Ile Asn Glu Lys Phe
    50                  55                  60

Lys Asn Arg Val Thr Met Thr Thr Asp Thr Ser Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Gly Tyr Phe Asp Tyr Trp Gly Gln Gly
            100                 105                 110

Thr Leu Val Thr Val Ser Ser
        115

<210> SEQ ID NO 276
<211> LENGTH: 23
<212> TYPE: PRT
<213> ORGANISM: artificial
<220> FEATURE:
<223> OTHER INFORMATION: Synthetic polypeptide

<400> SEQUENCE: 276

Asp Ile Val Met Thr Gln Ser Gln Lys Phe Met Ser Thr Ser Val Gly
1               5                   10                  15

Asp Arg Val Ser Val Thr Cys
            20

<210> SEQ ID NO 277
<211> LENGTH: 15
<212> TYPE: PRT
<213> ORGANISM: artificial
<220> FEATURE:
<223> OTHER INFORMATION: Synthetic polypeptide

<400> SEQUENCE: 277

Trp Tyr Gln Lys Lys Pro Gly Gln Ser Pro Lys Thr Leu Ile Tyr
1               5                   10                  15

<210> SEQ ID NO 278
<211> LENGTH: 32
<212> TYPE: PRT
<213> ORGANISM: artificial
<220> FEATURE:
<223> OTHER INFORMATION: Synthetic polypeptide

<400> SEQUENCE: 278

Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Glu Tyr Phe Cys
            20                  25                  30

<210> SEQ ID NO 279
<211> LENGTH: 10
<212> TYPE: PRT
<213> ORGANISM: artificial
<220> FEATURE:
<223> OTHER INFORMATION: Synthetic polypeptide

<400> SEQUENCE: 279

Phe Gly Ser Gly Thr Lys Leu Glu Ile Lys
1               5                   10

<210> SEQ ID NO 280
<211> LENGTH: 23
<212> TYPE: PRT
<213> ORGANISM: artificial
<220> FEATURE:
<223> OTHER INFORMATION: Synthetic polypeptide

<400> SEQUENCE: 280

Asp Ile Gln Leu Thr Gln Ser Pro Ser Leu Ser Ala Ser Val Gly
1               5                   10                  15

Asp Arg Val Thr Ile Thr Cys
            20

<210> SEQ ID NO 281
<211> LENGTH: 15
<212> TYPE: PRT
<213> ORGANISM: artificial
<220> FEATURE:
<223> OTHER INFORMATION: Synthetic polypeptide

<400> SEQUENCE: 281

Trp Tyr Gln Gln Lys Pro Gly Lys Ala Pro Lys Val Leu Ile Tyr
1               5                   10                  15

<210> SEQ ID NO 282
<211> LENGTH: 32
<212> TYPE: PRT
<213> ORGANISM: artificial
<220> FEATURE:
<223> OTHER INFORMATION: Synthetic polypeptide

<400> SEQUENCE: 282

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 283
<211> LENGTH: 10
<212> TYPE: PRT
<213> ORGANISM: artificial
<220> FEATURE:
<223> OTHER INFORMATION: Synthetic polypeptide

<400> SEQUENCE: 283

Phe Gly Gln Gly Thr Lys Val Glu Ile Lys
1               5                   10

<210> SEQ ID NO 284
<211> LENGTH: 23
<212> TYPE: PRT
<213> ORGANISM: artificial
<220> FEATURE:
<223> OTHER INFORMATION: Synthetic polypeptide

<400> SEQUENCE: 284

Asp Ile Leu Met Thr Gln Ser Pro Thr Thr Leu Ser Val Thr Pro Gly
1               5                   10                  15

Glu Thr Val Ser Leu Ser Cys
            20

```
<210> SEQ ID NO 285
<211> LENGTH: 15
<212> TYPE: PRT
<213> ORGANISM: artificial
<220> FEATURE:
<223> OTHER INFORMATION: Synthetic polypeptide

<400> SEQUENCE: 285

Trp Tyr Gln Gln Lys Ser Gln Gly Thr Pro Arg Leu Leu Ile Lys
1               5                   10                  15

<210> SEQ ID NO 286
<211> LENGTH: 32
<212> TYPE: PRT
<213> ORGANISM: artificial
<220> FEATURE:
<223> OTHER INFORMATION: Synthetic polypeptide

<400> SEQUENCE: 286

Gly Ile Pro Ser Arg Phe Thr Gly Ser Gly Ser Gly Thr Asp Phe Thr
1               5                   10                  15

Leu Ser Ile Asn Ser Val Lys Pro Glu Asp Glu Gly Ile Tyr Tyr Cys
            20                  25                  30

<210> SEQ ID NO 287
<211> LENGTH: 10
<212> TYPE: PRT
<213> ORGANISM: artificial
<220> FEATURE:
<223> OTHER INFORMATION: Synthetic polypeptide

<400> SEQUENCE: 287

Phe Gly Gly Gly Thr Lys Leu Glu Ile Lys
1               5                   10

<210> SEQ ID NO 288
<211> LENGTH: 23
<212> TYPE: PRT
<213> ORGANISM: artificial
<220> FEATURE:
<223> OTHER INFORMATION: Synthetic polypeptide

<400> SEQUENCE: 288

Glu Ile Val Met Thr Gln Ser Pro Asp Phe Gln Ser Val Thr Pro Lys
1               5                   10                  15

Glu Lys Val Thr Ile Thr Cys
            20

<210> SEQ ID NO 289
<211> LENGTH: 15
<212> TYPE: PRT
<213> ORGANISM: artificial
<220> FEATURE:
<223> OTHER INFORMATION: Synthetic polypeptide

<400> SEQUENCE: 289

Trp Tyr Gln Gln Lys Pro Asp Gln Thr Pro Lys Leu Leu Ile Lys
1               5                   10                  15

<210> SEQ ID NO 290
<211> LENGTH: 32
<212> TYPE: PRT
<213> ORGANISM: artificial
<220> FEATURE:
<223> OTHER INFORMATION: Synthetic polypeptide

<400> SEQUENCE: 290
```

```
Gly Ile Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Ala Tyr Tyr Cys
            20                  25                  30
```

<210> SEQ ID NO 291
<211> LENGTH: 10
<212> TYPE: PRT
<213> ORGANISM: artificial
<220> FEATURE:
<223> OTHER INFORMATION: Synthetic polypeptide

<400> SEQUENCE: 291

```
Phe Gly Gly Gly Thr Lys Val Glu Ile Lys
1               5                   10
```

<210> SEQ ID NO 292
<211> LENGTH: 29
<212> TYPE: PRT
<213> ORGANISM: artificial
<220> FEATURE:
<223> OTHER INFORMATION: Synthetic polypeptide

<400> SEQUENCE: 292

```
Gln Val Gln Leu Gln Gln Pro Gly Ala Glu Leu Val Thr Pro Gly Ala
1               5                   10                  15

Ser Val Lys Leu Ser Cys Lys Ala Ser Gly Phe Thr Phe
            20                  25
```

<210> SEQ ID NO 293
<211> LENGTH: 14
<212> TYPE: PRT
<213> ORGANISM: artificial
<220> FEATURE:
<223> OTHER INFORMATION: Synthetic polypeptide

<400> SEQUENCE: 293

```
Trp Val Lys Gln Arg Pro Gly Gln Gly Leu Glu Trp Ile Gly
1               5                   10
```

<210> SEQ ID NO 294
<211> LENGTH: 34
<212> TYPE: PRT
<213> ORGANISM: artificial
<220> FEATURE:
<223> OTHER INFORMATION: Synthetic polypeptide

<400> SEQUENCE: 294

```
Lys Phe Lys Asn Lys Ala Thr Val Thr Val Asp Lys Ser Ser Ser Thr
1               5                   10                  15

Val Tyr Ile Gln Leu Ser Ser Leu Thr Ser Glu Asp Ser Ala Val Tyr
            20                  25                  30

Tyr Cys
```

<210> SEQ ID NO 295
<211> LENGTH: 11
<212> TYPE: PRT
<213> ORGANISM: artificial
<220> FEATURE:
<223> OTHER INFORMATION: Synthetic polypeptide

<400> SEQUENCE: 295

```
Trp Gly Gln Gly Thr Pro Leu Thr Val Ser Ser
1               5                   10
```

<210> SEQ ID NO 296
<211> LENGTH: 29
<212> TYPE: PRT
<213> ORGANISM: artificial
<220> FEATURE:
<223> OTHER INFORMATION: Synthetic polypeptide

<400> SEQUENCE: 296

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Pro Phe
            20                  25

<210> SEQ ID NO 297
<211> LENGTH: 14
<212> TYPE: PRT
<213> ORGANISM: artificial
<220> FEATURE:
<223> OTHER INFORMATION: Synthetic polypeptide

<400> SEQUENCE: 297

Trp Val Lys Gln Ala Pro Gly Lys Gly Leu Lys Trp Met Gly
1               5                   10

<210> SEQ ID NO 298
<211> LENGTH: 34
<212> TYPE: PRT
<213> ORGANISM: artificial
<220> FEATURE:
<223> OTHER INFORMATION: Synthetic polypeptide

<400> SEQUENCE: 298

Asp Phe Lys Gly Arg Phe Ala Phe Ser Leu Glu Thr Ser Ala Asn Thr
1               5                   10                  15

Ala Tyr Leu Gln Ile Asn Ser Leu Lys Asn Glu Asp Ala Ala Thr Tyr
            20                  25                  30

Phe Cys

<210> SEQ ID NO 299
<211> LENGTH: 11
<212> TYPE: PRT
<213> ORGANISM: artificial
<220> FEATURE:
<223> OTHER INFORMATION: Synthetic polypeptide

<400> SEQUENCE: 299

Trp Gly Gln Gly Thr Ile Leu Thr Val Ser Ser
1               5                   10

<210> SEQ ID NO 300
<211> LENGTH: 29
<212> TYPE: PRT
<213> ORGANISM: artificial
<220> FEATURE:
<223> OTHER INFORMATION: Synthetic polypeptide

<400> SEQUENCE: 300

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe
            20                  25

<210> SEQ ID NO 301

```
<211> LENGTH: 14
<212> TYPE: PRT
<213> ORGANISM: artificial
<220> FEATURE:
<223> OTHER INFORMATION: Synthetic polypeptide

<400> SEQUENCE: 301

Trp Val Arg Gln Ala Pro Gly Gln Gly Leu Glu Trp Ile Gly
1               5                   10

<210> SEQ ID NO 302
<211> LENGTH: 34
<212> TYPE: PRT
<213> ORGANISM: artificial
<220> FEATURE:
<223> OTHER INFORMATION: Synthetic polypeptide

<400> SEQUENCE: 302

Lys Phe Lys Asn Arg Val Thr Met Thr Thr Asp Thr Ser Thr Ser Thr
1               5                   10                  15

Ala Tyr Met Glu Leu Arg Ser Leu Arg Ser Glu Asp Thr Ala Val Tyr
            20                  25                  30

Tyr Cys

<210> SEQ ID NO 303
<211> LENGTH: 11
<212> TYPE: PRT
<213> ORGANISM: artificial
<220> FEATURE:
<223> OTHER INFORMATION: Synthetic polypeptide

<400> SEQUENCE: 303

Trp Gly Gln Gly Thr Leu Val Thr Val Ser Ser
1               5                   10

<210> SEQ ID NO 304
<211> LENGTH: 29
<212> TYPE: PRT
<213> ORGANISM: artificial
<220> FEATURE:
<223> OTHER INFORMATION: Synthetic polypeptide

<400> SEQUENCE: 304

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe
            20                  25

<210> SEQ ID NO 305
<211> LENGTH: 14
<212> TYPE: PRT
<213> ORGANISM: artificial
<220> FEATURE:
<223> OTHER INFORMATION: Synthetic polypeptide

<400> SEQUENCE: 305

Trp Val Arg Gln Ala Pro Gly Gln Gly Leu Glu Trp Met Gly
1               5                   10

<210> SEQ ID NO 306
<211> LENGTH: 34
<212> TYPE: PRT
<213> ORGANISM: artificial
<220> FEATURE:
<223> OTHER INFORMATION: Synthetic polypeptide
```

<400> SEQUENCE: 306

Asp Phe Lys Gly Arg Phe Val Phe Ser Leu Asp Thr Ser Val Ser Thr
1               5                   10                  15

Ala Tyr Leu Gln Ile Ser Ser Leu Lys Ala Glu Asp Thr Ala Val Tyr
            20                  25                  30

Phe Cys

<210> SEQ ID NO 307
<211> LENGTH: 11
<212> TYPE: PRT
<213> ORGANISM: artificial
<220> FEATURE:
<223> OTHER INFORMATION: Synthetic polypeptide

<400> SEQUENCE: 307

Trp Gly Gln Gly Thr Leu Val Thr Val Ser Ser
1               5                   10

<210> SEQ ID NO 308
<211> LENGTH: 11
<212> TYPE: PRT
<213> ORGANISM: artificial
<220> FEATURE:
<223> OTHER INFORMATION: Synthetic polypeptide
<220> FEATURE:
<221> NAME/KEY: VARIANT
<222> LOCATION: (5)..(5)
<223> OTHER INFORMATION: X at 5 is D, A, E, G, H, K, N, P, Q, S, or T.
<220> FEATURE:
<221> NAME/KEY: VARIANT
<222> LOCATION: (7)..(7)
<223> OTHER INFORMATION: X at 7 is Y or F.
<220> FEATURE:
<221> NAME/KEY: VARIANT
<222> LOCATION: (8)..(8)
<223> OTHER INFORMATION: X at 8 is R, K, or Q.
<220> FEATURE:
<221> NAME/KEY: VARIANT
<222> LOCATION: (10)..(10)
<223> OTHER INFORMATION: X at 10 is L, I, M, or V.

<400> SEQUENCE: 308

Arg Ala Ser Gln Xaa Ile Xaa Xaa Asn Xaa His
1               5                   10

<210> SEQ ID NO 309
<211> LENGTH: 11
<212> TYPE: PRT
<213> ORGANISM: artificial
<220> FEATURE:
<223> OTHER INFORMATION: Synthetic polypeptide

<400> SEQUENCE: 309

Arg Ala Ser Gln Ala Ile Tyr Arg Asn Leu His
1               5                   10

<210> SEQ ID NO 310
<211> LENGTH: 11
<212> TYPE: PRT
<213> ORGANISM: artificial
<220> FEATURE:
<223> OTHER INFORMATION: Synthetic polypeptide

<400> SEQUENCE: 310

Arg Ala Ser Gln Glu Ile Tyr Arg Asn Leu His
1               5                   10

```
<210> SEQ ID NO 311
<211> LENGTH: 11
<212> TYPE: PRT
<213> ORGANISM: artificial
<220> FEATURE:
<223> OTHER INFORMATION: Synthetic polypeptide

<400> SEQUENCE: 311

Arg Ala Ser Gln Gly Ile Tyr Arg Asn Leu His
1               5                   10

<210> SEQ ID NO 312
<211> LENGTH: 11
<212> TYPE: PRT
<213> ORGANISM: artificial
<220> FEATURE:
<223> OTHER INFORMATION: Synthetic polypeptide

<400> SEQUENCE: 312

Arg Ala Ser Gln His Ile Tyr Arg Asn Leu His
1               5                   10

<210> SEQ ID NO 313
<211> LENGTH: 11
<212> TYPE: PRT
<213> ORGANISM: artificial
<220> FEATURE:
<223> OTHER INFORMATION: Synthetic polypeptide

<400> SEQUENCE: 313

Arg Ala Ser Gln Lys Ile Tyr Arg Asn Leu His
1               5                   10

<210> SEQ ID NO 314
<211> LENGTH: 11
<212> TYPE: PRT
<213> ORGANISM: artificial
<220> FEATURE:
<223> OTHER INFORMATION: Synthetic polypeptide

<400> SEQUENCE: 314

Arg Ala Ser Gln Asn Ile Tyr Arg Asn Leu His
1               5                   10

<210> SEQ ID NO 315
<211> LENGTH: 11
<212> TYPE: PRT
<213> ORGANISM: artificial
<220> FEATURE:
<223> OTHER INFORMATION: Synthetic polypeptide

<400> SEQUENCE: 315

Arg Ala Ser Gln Pro Ile Tyr Arg Asn Leu His
1               5                   10

<210> SEQ ID NO 316
<211> LENGTH: 11
<212> TYPE: PRT
<213> ORGANISM: artificial
<220> FEATURE:
<223> OTHER INFORMATION: Synthetic polypeptide

<400> SEQUENCE: 316

Arg Ala Ser Gln Gln Ile Tyr Arg Asn Leu His
1               5                   10

<210> SEQ ID NO 317
```

```
<211> LENGTH: 11
<212> TYPE: PRT
<213> ORGANISM: artificial
<220> FEATURE:
<223> OTHER INFORMATION: Synthetic polypeptide

<400> SEQUENCE: 317

Arg Ala Ser Gln Ser Ile Tyr Arg Asn Leu His
1               5                   10

<210> SEQ ID NO 318
<211> LENGTH: 11
<212> TYPE: PRT
<213> ORGANISM: artificial
<220> FEATURE:
<223> OTHER INFORMATION: Synthetic polypeptide

<400> SEQUENCE: 318

Arg Ala Ser Gln Thr Ile Tyr Arg Asn Leu His
1               5                   10

<210> SEQ ID NO 319
<211> LENGTH: 11
<212> TYPE: PRT
<213> ORGANISM: artificial
<220> FEATURE:
<223> OTHER INFORMATION: Synthetic polypeptide

<400> SEQUENCE: 319

Arg Ala Ser Gln Asp Ile Phe Arg Asn Leu His
1               5                   10

<210> SEQ ID NO 320
<211> LENGTH: 11
<212> TYPE: PRT
<213> ORGANISM: artificial
<220> FEATURE:
<223> OTHER INFORMATION: Synthetic polypeptide

<400> SEQUENCE: 320

Arg Ala Ser Gln Asp Ile Tyr Lys Asn Leu His
1               5                   10

<210> SEQ ID NO 321
<211> LENGTH: 11
<212> TYPE: PRT
<213> ORGANISM: artificial
<220> FEATURE:
<223> OTHER INFORMATION: Synthetic polypeptide

<400> SEQUENCE: 321

Arg Ala Ser Gln Asp Ile Tyr Gln Asn Leu His
1               5                   10

<210> SEQ ID NO 322
<211> LENGTH: 11
<212> TYPE: PRT
<213> ORGANISM: artificial
<220> FEATURE:
<223> OTHER INFORMATION: Synthetic polypeptide

<400> SEQUENCE: 322

Arg Ala Ser Gln Asp Ile Tyr Arg Asn Ile His
1               5                   10

<210> SEQ ID NO 323
<211> LENGTH: 11
```

```
<212> TYPE: PRT
<213> ORGANISM: artificial
<220> FEATURE:
<223> OTHER INFORMATION: Synthetic polypeptide

<400> SEQUENCE: 323

Arg Ala Ser Gln Asp Ile Tyr Arg Asn Met His
1               5                   10

<210> SEQ ID NO 324
<211> LENGTH: 11
<212> TYPE: PRT
<213> ORGANISM: artificial
<220> FEATURE:
<223> OTHER INFORMATION: Synthetic polypeptide

<400> SEQUENCE: 324

Arg Ala Ser Gln Asp Ile Tyr Arg Asn Val His
1               5                   10

<210> SEQ ID NO 325
<211> LENGTH: 7
<212> TYPE: PRT
<213> ORGANISM: artificial
<220> FEATURE:
<223> OTHER INFORMATION: Synthetic polypeptide
<220> FEATURE:
<221> NAME/KEY: VARIANT
<222> LOCATION: (3)..(3)
<223> OTHER INFORMATION: X at 3 is S or E.
<220> FEATURE:
<221> NAME/KEY: VARIANT
<222> LOCATION: (4)..(4)
<223> OTHER INFORMATION: X at 4 is D, E, K, or Q.
<220> FEATURE:
<221> NAME/KEY: VARIANT
<222> LOCATION: (5)..(5)
<223> OTHER INFORMATION: X at 5 is S, H, L, R, or V.
<220> FEATURE:
<221> NAME/KEY: VARIANT
<222> LOCATION: (6)..(6)
<223> OTHER INFORMATION: X at 6 is I or V.

<400> SEQUENCE: 325

His Ala Xaa Xaa Xaa Xaa Ser
1               5

<210> SEQ ID NO 326
<211> LENGTH: 7
<212> TYPE: PRT
<213> ORGANISM: artificial
<220> FEATURE:
<223> OTHER INFORMATION: Synthetic polypeptide

<400> SEQUENCE: 326

His Ala Glu Asp Ser Ile Ser
1               5

<210> SEQ ID NO 327
<211> LENGTH: 7
<212> TYPE: PRT
<213> ORGANISM: artificial
<220> FEATURE:
<223> OTHER INFORMATION: Synthetic polypeptide

<400> SEQUENCE: 327

His Ala Ser Glu Ser Ile Ser
1               5
```

```
<210> SEQ ID NO 328
<211> LENGTH: 7
<212> TYPE: PRT
<213> ORGANISM: artificial
<220> FEATURE:
<223> OTHER INFORMATION: Synthetic polypeptide

<400> SEQUENCE: 328

His Ala Ser Lys Ser Ile Ser
1               5

<210> SEQ ID NO 329
<211> LENGTH: 7
<212> TYPE: PRT
<213> ORGANISM: artificial
<220> FEATURE:
<223> OTHER INFORMATION: Synthetic polypeptide

<400> SEQUENCE: 329

His Ala Ser Gln Ser Ile Ser
1               5

<210> SEQ ID NO 330
<211> LENGTH: 7
<212> TYPE: PRT
<213> ORGANISM: artificial
<220> FEATURE:
<223> OTHER INFORMATION: Synthetic polypeptide

<400> SEQUENCE: 330

His Ala Ser Asp His Ile Ser
1               5

<210> SEQ ID NO 331
<211> LENGTH: 7
<212> TYPE: PRT
<213> ORGANISM: artificial
<220> FEATURE:
<223> OTHER INFORMATION: Synthetic polypeptide

<400> SEQUENCE: 331

His Ala Ser Asp Leu Ile Ser
1               5

<210> SEQ ID NO 332
<211> LENGTH: 7
<212> TYPE: PRT
<213> ORGANISM: artificial
<220> FEATURE:
<223> OTHER INFORMATION: Synthetic polypeptide

<400> SEQUENCE: 332

His Ala Ser Asp Arg Ile Ser
1               5

<210> SEQ ID NO 333
<211> LENGTH: 7
<212> TYPE: PRT
<213> ORGANISM: artificial
<220> FEATURE:
<223> OTHER INFORMATION: Synthetic polypeptide

<400> SEQUENCE: 333

His Ala Ser Asp Val Ile Ser
1               5

<210> SEQ ID NO 334
```

```
<211> LENGTH: 7
<212> TYPE: PRT
<213> ORGANISM: artificial
<220> FEATURE:
<223> OTHER INFORMATION: Synthetic polypeptide

<400> SEQUENCE: 334

His Ala Ser Asp Ser Val Ser
1               5

<210> SEQ ID NO 335
<211> LENGTH: 9
<212> TYPE: PRT
<213> ORGANISM: artificial
<220> FEATURE:
<223> OTHER INFORMATION: Synthetic polypeptide
<220> FEATURE:
<221> NAME/KEY: VARIANT
<222> LOCATION: (1)..(1)
<223> OTHER INFORMATION: X at 1 is L, G, M, or Q.
<220> FEATURE:
<221> NAME/KEY: VARIANT
<222> LOCATION: (5)..(5)
<223> OTHER INFORMATION: X at 5 is S, A, E, Q, or V.
<220> FEATURE:
<221> NAME/KEY: VARIANT
<222> LOCATION: (8)..(8)
<223> OTHER INFORMATION: X at 8 is Y or F.

<400> SEQUENCE: 335

Xaa Gln Gly Tyr Xaa Met Pro Xaa Thr
1               5

<210> SEQ ID NO 336
<211> LENGTH: 9
<212> TYPE: PRT
<213> ORGANISM: artificial
<220> FEATURE:
<223> OTHER INFORMATION: Synthetic polypeptide

<400> SEQUENCE: 336

Gly Gln Gly Tyr Ser Met Pro Tyr Thr
1               5

<210> SEQ ID NO 337
<211> LENGTH: 9
<212> TYPE: PRT
<213> ORGANISM: artificial
<220> FEATURE:
<223> OTHER INFORMATION: Synthetic polypeptide

<400> SEQUENCE: 337

Met Gln Gly Tyr Ser Met Pro Tyr Thr
1               5

<210> SEQ ID NO 338
<211> LENGTH: 9
<212> TYPE: PRT
<213> ORGANISM: artificial
<220> FEATURE:
<223> OTHER INFORMATION: Synthetic polypeptide

<400> SEQUENCE: 338

Gln Gln Gly Tyr Ser Met Pro Tyr Thr
1               5

<210> SEQ ID NO 339
<211> LENGTH: 9
<212> TYPE: PRT
```

-continued

```
<213> ORGANISM: artificial
<220> FEATURE:
<223> OTHER INFORMATION: Synthetic polypeptide

<400> SEQUENCE: 339

Leu Gln Gly Tyr Ala Met Pro Tyr Thr
1               5

<210> SEQ ID NO 340
<211> LENGTH: 9
<212> TYPE: PRT
<213> ORGANISM: artificial
<220> FEATURE:
<223> OTHER INFORMATION: Synthetic polypeptide

<400> SEQUENCE: 340

Leu Gln Gly Tyr Glu Met Pro Tyr Thr
1               5

<210> SEQ ID NO 341
<211> LENGTH: 9
<212> TYPE: PRT
<213> ORGANISM: artificial
<220> FEATURE:
<223> OTHER INFORMATION: Synthetic polypeptide

<400> SEQUENCE: 341

Leu Gln Gly Tyr Gln Met Pro Tyr Thr
1               5

<210> SEQ ID NO 342
<211> LENGTH: 9
<212> TYPE: PRT
<213> ORGANISM: artificial
<220> FEATURE:
<223> OTHER INFORMATION: Synthetic polypeptide

<400> SEQUENCE: 342

Leu Gln Gly Tyr Val Met Pro Tyr Thr
1               5

<210> SEQ ID NO 343
<211> LENGTH: 9
<212> TYPE: PRT
<213> ORGANISM: artificial
<220> FEATURE:
<223> OTHER INFORMATION: Synthetic polypeptide

<400> SEQUENCE: 343

Leu Gln Gly Tyr Ser Met Pro Phe Thr
1               5

<210> SEQ ID NO 344
<211> LENGTH: 6
<212> TYPE: PRT
<213> ORGANISM: artificial
<220> FEATURE:
<223> OTHER INFORMATION: Synthetic polypeptide
<220> FEATURE:
<221> NAME/KEY: VARIANT
<222> LOCATION: (1)..(1)
<223> OTHER INFORMATION: X at 1 is T, A, D, E, G, H, K, M, N, Q, R, or
      S.
<220> FEATURE:
<221> NAME/KEY: VARIANT
<222> LOCATION: (2)..(2)
<223> OTHER INFORMATION: X at 2 is T, D, E, G, H, N, Q, or S.
<220> FEATURE:
<221> NAME/KEY: VARIANT
```

```
<222> LOCATION: (3)..(3)
<223> OTHER INFORMATION: X at 3 is Y, F, M, or Q.
<220> FEATURE:
<221> NAME/KEY: VARIANT
<222> LOCATION: (5)..(5)
<223> OTHER INFORMATION: X at 5 is M,I, L, or V.

<400> SEQUENCE: 344

Xaa Xaa Xaa Gly Xaa Ser
1               5

<210> SEQ ID NO 345
<211> LENGTH: 6
<212> TYPE: PRT
<213> ORGANISM: artificial
<220> FEATURE:
<223> OTHER INFORMATION: Synthetic polypeptide

<400> SEQUENCE: 345

Ala Thr Tyr Gly Met Ser
1               5

<210> SEQ ID NO 346
<211> LENGTH: 6
<212> TYPE: PRT
<213> ORGANISM: artificial
<220> FEATURE:
<223> OTHER INFORMATION: Synthetic polypeptide

<400> SEQUENCE: 346

Asp Thr Tyr Gly Met Ser
1               5

<210> SEQ ID NO 347
<211> LENGTH: 6
<212> TYPE: PRT
<213> ORGANISM: artificial
<220> FEATURE:
<223> OTHER INFORMATION: Synthetic polypeptide

<400> SEQUENCE: 347

Glu Thr Tyr Gly Met Ser
1               5

<210> SEQ ID NO 348
<211> LENGTH: 6
<212> TYPE: PRT
<213> ORGANISM: artificial
<220> FEATURE:
<223> OTHER INFORMATION: Synthetic polypeptide

<400> SEQUENCE: 348

Gly Thr Tyr Gly Met Ser
1               5

<210> SEQ ID NO 349
<211> LENGTH: 6
<212> TYPE: PRT
<213> ORGANISM: artificial
<220> FEATURE:
<223> OTHER INFORMATION: Synthetic polypeptide

<400> SEQUENCE: 349

His Thr Tyr Gly Met Ser
1               5

<210> SEQ ID NO 350
```

```
<211> LENGTH: 6
<212> TYPE: PRT
<213> ORGANISM: artificial
<220> FEATURE:
<223> OTHER INFORMATION: Synthetic polypeptide

<400> SEQUENCE: 350

Lys Thr Tyr Gly Met Ser
1               5

<210> SEQ ID NO 351
<211> LENGTH: 6
<212> TYPE: PRT
<213> ORGANISM: artificial
<220> FEATURE:
<223> OTHER INFORMATION: Synthetic polypeptide

<400> SEQUENCE: 351

Met Thr Tyr Gly Met Ser
1               5

<210> SEQ ID NO 352
<211> LENGTH: 6
<212> TYPE: PRT
<213> ORGANISM: artificial
<220> FEATURE:
<223> OTHER INFORMATION: Synthetic polypeptide

<400> SEQUENCE: 352

Asn Thr Tyr Gly Met Ser
1               5

<210> SEQ ID NO 353
<211> LENGTH: 6
<212> TYPE: PRT
<213> ORGANISM: artificial
<220> FEATURE:
<223> OTHER INFORMATION: Synthetic polypeptide

<400> SEQUENCE: 353

Gln Thr Tyr Gly Met Ser
1               5

<210> SEQ ID NO 354
<211> LENGTH: 6
<212> TYPE: PRT
<213> ORGANISM: artificial
<220> FEATURE:
<223> OTHER INFORMATION: Synthetic polypeptide

<400> SEQUENCE: 354

Arg Thr Tyr Gly Met Ser
1               5

<210> SEQ ID NO 355
<211> LENGTH: 6
<212> TYPE: PRT
<213> ORGANISM: artificial
<220> FEATURE:
<223> OTHER INFORMATION: Synthetic polypeptide

<400> SEQUENCE: 355

Ser Thr Tyr Gly Met Ser
1               5

<210> SEQ ID NO 356
<211> LENGTH: 6
```

```
<212> TYPE: PRT
<213> ORGANISM: artificial
<220> FEATURE:
<223> OTHER INFORMATION: Synthetic polypeptide

<400> SEQUENCE: 356

Thr Asp Tyr Gly Met Ser
1               5

<210> SEQ ID NO 357
<211> LENGTH: 6
<212> TYPE: PRT
<213> ORGANISM: artificial
<220> FEATURE:
<223> OTHER INFORMATION: Synthetic polypeptide

<400> SEQUENCE: 357

Thr Glu Tyr Gly Met Ser
1               5

<210> SEQ ID NO 358
<211> LENGTH: 6
<212> TYPE: PRT
<213> ORGANISM: artificial
<220> FEATURE:
<223> OTHER INFORMATION: Synthetic polypeptide

<400> SEQUENCE: 358

Thr Gly Tyr Gly Met Ser
1               5

<210> SEQ ID NO 359
<211> LENGTH: 6
<212> TYPE: PRT
<213> ORGANISM: artificial
<220> FEATURE:
<223> OTHER INFORMATION: Synthetic polypeptide

<400> SEQUENCE: 359

Thr His Tyr Gly Met Ser
1               5

<210> SEQ ID NO 360
<211> LENGTH: 6
<212> TYPE: PRT
<213> ORGANISM: artificial
<220> FEATURE:
<223> OTHER INFORMATION: Synthetic polypeptide

<400> SEQUENCE: 360

Thr Asn Tyr Gly Met Ser
1               5

<210> SEQ ID NO 361
<211> LENGTH: 6
<212> TYPE: PRT
<213> ORGANISM: artificial
<220> FEATURE:
<223> OTHER INFORMATION: Synthetic polypeptide

<400> SEQUENCE: 361

Thr Gln Tyr Gly Met Ser
1               5

<210> SEQ ID NO 362
<211> LENGTH: 6
<212> TYPE: PRT
```

<213> ORGANISM: artificial
<220> FEATURE:
<223> OTHER INFORMATION: Synthetic polypeptide

<400> SEQUENCE: 362

Thr Ser Tyr Gly Met Ser
1               5

<210> SEQ ID NO 363
<211> LENGTH: 6
<212> TYPE: PRT
<213> ORGANISM: artificial
<220> FEATURE:
<223> OTHER INFORMATION: Synthetic polypeptide

<400> SEQUENCE: 363

Thr Thr Phe Gly Met Ser
1               5

<210> SEQ ID NO 364
<211> LENGTH: 6
<212> TYPE: PRT
<213> ORGANISM: artificial
<220> FEATURE:
<223> OTHER INFORMATION: Synthetic polypeptide

<400> SEQUENCE: 364

Thr Thr Met Gly Met Ser
1               5

<210> SEQ ID NO 365
<211> LENGTH: 6
<212> TYPE: PRT
<213> ORGANISM: artificial
<220> FEATURE:
<223> OTHER INFORMATION: Synthetic polypeptide

<400> SEQUENCE: 365

Thr Thr Gln Gly Met Ser
1               5

<210> SEQ ID NO 366
<211> LENGTH: 6
<212> TYPE: PRT
<213> ORGANISM: artificial
<220> FEATURE:
<223> OTHER INFORMATION: Synthetic polypeptide

<400> SEQUENCE: 366

Thr Thr Tyr Gly Ile Ser
1               5

<210> SEQ ID NO 367
<211> LENGTH: 6
<212> TYPE: PRT
<213> ORGANISM: artificial
<220> FEATURE:
<223> OTHER INFORMATION: Synthetic polypeptide

<400> SEQUENCE: 367

Thr Thr Tyr Gly Leu Ser
1               5

<210> SEQ ID NO 368
<211> LENGTH: 6
<212> TYPE: PRT
<213> ORGANISM: artificial

```
<220> FEATURE:
<223> OTHER INFORMATION: Synthetic polypeptide

<400> SEQUENCE: 368

Thr Thr Tyr Gly Val Ser
1               5

<210> SEQ ID NO 369
<211> LENGTH: 13
<212> TYPE: PRT
<213> ORGANISM: artificial
<220> FEATURE:
<223> OTHER INFORMATION: Synthetic polypeptide
<220> FEATURE:
<221> NAME/KEY: VARIANT
<222> LOCATION: (5)..(5)
<223> OTHER INFORMATION: X at 5 is D or E.
<220> FEATURE:
<221> NAME/KEY: VARIANT
<222> LOCATION: (6)..(6)
<223> OTHER INFORMATION: X at 6 is S or T.

<400> SEQUENCE: 369

Trp Ile Asn Thr Xaa Xaa Gly Val Pro Thr Tyr Ala Asp
1               5                   10

<210> SEQ ID NO 370
<211> LENGTH: 13
<212> TYPE: PRT
<213> ORGANISM: artificial
<220> FEATURE:
<223> OTHER INFORMATION: Synthetic polypeptide

<400> SEQUENCE: 370

Trp Ile Asn Thr Glu Ser Gly Val Pro Thr Tyr Ala Asp
1               5                   10

<210> SEQ ID NO 371
<211> LENGTH: 13
<212> TYPE: PRT
<213> ORGANISM: artificial
<220> FEATURE:
<223> OTHER INFORMATION: Synthetic polypeptide

<400> SEQUENCE: 371

Trp Ile Asn Thr Asp Thr Gly Val Pro Thr Tyr Ala Asp
1               5                   10

<210> SEQ ID NO 372
<211> LENGTH: 13
<212> TYPE: PRT
<213> ORGANISM: artificial
<220> FEATURE:
<223> OTHER INFORMATION: Synthetic polypeptide
<220> FEATURE:
<221> NAME/KEY: VARIANT
<222> LOCATION: (3)..(3)
<223> OTHER INFORMATION: X at 3 is N or M.
<220> FEATURE:
<221> NAME/KEY: VARIANT
<222> LOCATION: (10)..(10)
<223> OTHER INFORMATION: X at 10 is N, F, H, or Y.

<400> SEQUENCE: 372

Ala Arg Xaa Ile Tyr Tyr Gly Trp Gly Xaa Phe Asp Tyr
1               5                   10

<210> SEQ ID NO 373
<211> LENGTH: 13
```

```
<212> TYPE: PRT
<213> ORGANISM: artificial
<220> FEATURE:
<223> OTHER INFORMATION: Synthetic polypeptide

<400> SEQUENCE: 373

Ala Arg Met Ile Tyr Tyr Gly Trp Gly Asn Phe Asp Tyr
1               5                   10

<210> SEQ ID NO 374
<211> LENGTH: 13
<212> TYPE: PRT
<213> ORGANISM: artificial
<220> FEATURE:
<223> OTHER INFORMATION: Synthetic polypeptide

<400> SEQUENCE: 374

Ala Arg Asn Ile Tyr Tyr Gly Trp Gly Phe Phe Asp Tyr
1               5                   10

<210> SEQ ID NO 375
<211> LENGTH: 13
<212> TYPE: PRT
<213> ORGANISM: artificial
<220> FEATURE:
<223> OTHER INFORMATION: Synthetic polypeptide

<400> SEQUENCE: 375

Ala Arg Asn Ile Tyr Tyr Gly Trp Gly His Phe Asp Tyr
1               5                   10

<210> SEQ ID NO 376
<211> LENGTH: 13
<212> TYPE: PRT
<213> ORGANISM: artificial
<220> FEATURE:
<223> OTHER INFORMATION: Synthetic polypeptide

<400> SEQUENCE: 376

Ala Arg Asn Ile Tyr Tyr Gly Trp Gly Tyr Phe Asp Tyr
1               5                   10

<210> SEQ ID NO 377
<211> LENGTH: 107
<212> TYPE: PRT
<213> ORGANISM: artificial
<220> FEATURE:
<223> OTHER INFORMATION: Synthetic polypeptide

<400> SEQUENCE: 377

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Ala Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
                100                 105
```

<210> SEQ ID NO 378
<211> LENGTH: 107
<212> TYPE: PRT
<213> ORGANISM: artificial
<220> FEATURE:
<223> OTHER INFORMATION: Synthetic polypeptide

<400> SEQUENCE: 378

```
Glu Ile Val Met Thr Gln Ser Pro Asp Phe Gln Ser Val Thr Pro Lys
1               5                   10                  15

Glu Lys Val Thr Ile Thr Cys Arg Ala Ser Gln Glu Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105
```

<210> SEQ ID NO 379
<211> LENGTH: 107
<212> TYPE: PRT
<213> ORGANISM: artificial
<220> FEATURE:
<223> OTHER INFORMATION: Synthetic polypeptide

<400> SEQUENCE: 379

```
Glu Ile Val Met Thr Gln Ser Pro Asp Phe Gln Ser Val Thr Pro Lys
1               5                   10                  15

Glu Lys Val Thr Ile Thr Cys Arg Ala Ser Gln Gly Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105
```

<210> SEQ ID NO 380
<211> LENGTH: 107
<212> TYPE: PRT
<213> ORGANISM: artificial
<220> FEATURE:
<223> OTHER INFORMATION: Synthetic polypeptide

<400> SEQUENCE: 380

```
Glu Ile Val Met Thr Gln Ser Pro Asp Phe Gln Ser Val Thr Pro Lys
1               5                   10                  15

Glu Lys Val Thr Ile Thr Cys Arg Ala Ser Gln His Ile Tyr Arg Asn
            20                  25                  30
```

```
Leu His Trp Tyr Gln Gln Lys Pro Asp Gln Thr Pro Lys Leu Leu Ile
            35                  40                  45

Lys His Ala Ser Asp Ser Ile Ser Gly Ile Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys Leu Gln Gly Tyr Ser Met Pro Tyr
                 85                  90                  95

Thr Phe Gly Gly Gly Thr Lys Val Glu Ile Lys
            100                 105
```

<210> SEQ ID NO 381
<211> LENGTH: 107
<212> TYPE: PRT
<213> ORGANISM: artificial
<220> FEATURE:
<223> OTHER INFORMATION: Synthetic polypeptide

<400> SEQUENCE: 381

```
Glu Ile Val Met Thr Gln Ser Pro Asp Phe Gln Ser Val Thr Pro Lys
 1               5                  10                  15

Glu Lys Val Thr Ile Thr Cys Arg Ala Ser Gln Lys Ile Tyr Arg Asn
            20                  25                  30

Leu His Trp Tyr Gln Gln Lys Pro Asp Gln Thr Pro Lys Leu Leu Ile
            35                  40                  45

Lys His Ala Ser Asp Ser Ile Ser Gly Ile Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys Leu Gln Gly Tyr Ser Met Pro Tyr
                 85                  90                  95

Thr Phe Gly Gly Gly Thr Lys Val Glu Ile Lys
            100                 105
```

<210> SEQ ID NO 382
<211> LENGTH: 107
<212> TYPE: PRT
<213> ORGANISM: artificial
<220> FEATURE:
<223> OTHER INFORMATION: Synthetic polypeptide

<400> SEQUENCE: 382

```
Glu Ile Val Met Thr Gln Ser Pro Asp Phe Gln Ser Val Thr Pro Lys
 1               5                  10                  15

Glu Lys Val Thr Ile Thr Cys Arg Ala Ser Gln Asn Ile Tyr Arg Asn
            20                  25                  30

Leu His Trp Tyr Gln Gln Lys Pro Asp Gln Thr Pro Lys Leu Leu Ile
            35                  40                  45

Lys His Ala Ser Asp Ser Ile Ser Gly Ile Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys Leu Gln Gly Tyr Ser Met Pro Tyr
                 85                  90                  95

Thr Phe Gly Gly Gly Thr Lys Val Glu Ile Lys
            100                 105
```

<210> SEQ ID NO 383

```
<211> LENGTH: 107
<212> TYPE: PRT
<213> ORGANISM: artificial
<220> FEATURE:
<223> OTHER INFORMATION: Synthetic polypeptide

<400> SEQUENCE: 383

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Pro Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 384
<211> LENGTH: 107
<212> TYPE: PRT
<213> ORGANISM: artificial
<220> FEATURE:
<223> OTHER INFORMATION: Synthetic polypeptide

<400> SEQUENCE: 384

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Gln Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 385
<211> LENGTH: 107
<212> TYPE: PRT
<213> ORGANISM: artificial
<220> FEATURE:
<223> OTHER INFORMATION: Synthetic polypeptide

<400> SEQUENCE: 385

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Ser Ile Tyr Arg Asn
            20                  25                  30

Leu His Trp Tyr Gln Gln Lys Pro Asp Gln Thr Pro Lys Leu Leu Ile
        35                  40                  45
```

```
Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 386
<211> LENGTH: 107
<212> TYPE: PRT
<213> ORGANISM: artificial
<220> FEATURE:
<223> OTHER INFORMATION: Synthetic polypeptide

<400> SEQUENCE: 386

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Thr Ile Tyr Arg Asn
                20                  25                  30

Leu His Trp Tyr Gln Gln Lys Pro Asp Gln Thr Pro Lys Leu Leu Ile
            35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 387
<211> LENGTH: 107
<212> TYPE: PRT
<213> ORGANISM: artificial
<220> FEATURE:
<223> OTHER INFORMATION: Synthetic polypeptide

<400> SEQUENCE: 387

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Phe Arg Asn
                20                  25                  30

Leu His Trp Tyr Gln Gln Lys Pro Asp Gln Thr Pro Lys Leu Leu Ile
            35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 388
<211> LENGTH: 107
<212> TYPE: PRT
<213> ORGANISM: artificial
```

<220> FEATURE:
<223> OTHER INFORMATION: Synthetic polypeptide

<400> SEQUENCE: 388

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Lys Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 389
<211> LENGTH: 107
<212> TYPE: PRT
<213> ORGANISM: artificial
<220> FEATURE:
<223> OTHER INFORMATION: Synthetic polypeptide

<400> SEQUENCE: 389

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Gln Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 390
<211> LENGTH: 107
<212> TYPE: PRT
<213> ORGANISM: artificial
<220> FEATURE:
<223> OTHER INFORMATION: Synthetic polypeptide

<400> SEQUENCE: 390

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Ile His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys Leu Gln Gly Tyr Ser Met Pro Tyr
                 85                  90                  95

Thr Phe Gly Gly Gly Thr Lys Val Glu Ile Lys
            100                 105

<210> SEQ ID NO 391
<211> LENGTH: 107
<212> TYPE: PRT
<213> ORGANISM: artificial
<220> FEATURE:
<223> OTHER INFORMATION: Synthetic polypeptide

<400> SEQUENCE: 391

Glu Ile Val Met Thr Gln Ser Pro Asp Phe Gln Ser Val Thr Pro Lys
 1               5                  10                  15

Glu Lys Val Thr Ile Thr Cys Arg Ala Ser Gln Asp Ile Tyr Arg Asn
                 20                  25                  30

Met His Trp Tyr Gln Gln Lys Pro Asp Gln Thr Pro Lys Leu Leu Ile
             35                  40                  45

Lys His Ala Ser Asp Ser Ile Ser Gly Ile Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys Leu Gln Gly Tyr Ser Met Pro Tyr
                 85                  90                  95

Thr Phe Gly Gly Gly Thr Lys Val Glu Ile Lys
            100                 105

<210> SEQ ID NO 392
<211> LENGTH: 107
<212> TYPE: PRT
<213> ORGANISM: artificial
<220> FEATURE:
<223> OTHER INFORMATION: Synthetic polypeptide

<400> SEQUENCE: 392

Glu Ile Val Met Thr Gln Ser Pro Asp Phe Gln Ser Val Thr Pro Lys
 1               5                  10                  15

Glu Lys Val Thr Ile Thr Cys Arg Ala Ser Gln Asp Ile Tyr Arg Asn
                 20                  25                  30

Val His Trp Tyr Gln Gln Lys Pro Asp Gln Thr Pro Lys Leu Leu Ile
             35                  40                  45

Lys His Ala Ser Asp Ser Ile Ser Gly Ile Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys Leu Gln Gly Tyr Ser Met Pro Tyr
                 85                  90                  95

Thr Phe Gly Gly Gly Thr Lys Val Glu Ile Lys
            100                 105

<210> SEQ ID NO 393
<211> LENGTH: 107
<212> TYPE: PRT
<213> ORGANISM: artificial
<220> FEATURE:
<223> OTHER INFORMATION: Synthetic polypeptide -continued

<400> SEQUENCE: 393

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Glu Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 394
<211> LENGTH: 107
<212> TYPE: PRT
<213> ORGANISM: artificial
<220> FEATURE:
<223> OTHER INFORMATION: Synthetic polypeptide

<400> SEQUENCE: 394

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 395
<211> LENGTH: 107
<212> TYPE: PRT
<213> ORGANISM: artificial
<220> FEATURE:
<223> OTHER INFORMATION: Synthetic polypeptide

<400> SEQUENCE: 395

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Lys Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
            85                  90                  95

Thr Phe Gly Gly Gly Thr Lys Val Glu Ile Lys
            100                 105

<210> SEQ ID NO 396
<211> LENGTH: 107
<212> TYPE: PRT
<213> ORGANISM: artificial
<220> FEATURE:
<223> OTHER INFORMATION: Synthetic polypeptide

<400> SEQUENCE: 396

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
            35                  40                  45

Lys His Ala Ser Gln Ser Ile Ser Gly Ile Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
            85                  90                  95

Thr Phe Gly Gly Gly Thr Lys Val Glu Ile Lys
            100                 105

<210> SEQ ID NO 397
<211> LENGTH: 107
<212> TYPE: PRT
<213> ORGANISM: artificial
<220> FEATURE:
<223> OTHER INFORMATION: Synthetic polypeptide

<400> SEQUENCE: 397

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
            35                  40                  45

Lys His Ala Ser Asp His Ile Ser Gly Ile Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
            85                  90                  95

Thr Phe Gly Gly Gly Thr Lys Val Glu Ile Lys
            100                 105

<210> SEQ ID NO 398
<211> LENGTH: 107
<212> TYPE: PRT
<213> ORGANISM: artificial
<220> FEATURE:
<223> OTHER INFORMATION: Synthetic polypeptide

<400> SEQUENCE: 398

Glu Ile Val Met Thr Gln Ser Pro Asp Phe Gln Ser Val Thr Pro Lys

```
                1               5                  10                  15
Glu Lys Val Thr Ile Thr Cys Arg Ala Ser Gln Asp Ile Tyr Arg Asn
                20                  25                  30

Leu His Trp Tyr Gln Gln Lys Pro Asp Gln Thr Pro Lys Leu Leu Ile
            35                  40                  45

Lys His Ala Ser Asp Leu Ile Ser Gly Ile Pro Ser Arg Phe Ser Gly
        50                  55                  60

Ser Gly Ser Gly Thr Asp Phe Thr Leu Thr Ile Asn Ser Leu Glu Ala
 65                 70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105
```

<210> SEQ ID NO 399
<211> LENGTH: 107
<212> TYPE: PRT
<213> ORGANISM: artificial
<220> FEATURE:
<223> OTHER INFORMATION: Synthetic polypeptide

<400> SEQUENCE: 399

```
Glu Ile Val Met Thr Gln Ser Pro Asp Phe Gln Ser Val Thr Pro Lys
 1               5                  10                  15

Glu Lys Val Thr Ile Thr Cys Arg Ala Ser Gln Asp Ile Tyr Arg Asn
                20                  25                  30

Leu His Trp Tyr Gln Gln Lys Pro Asp Gln Thr Pro Lys Leu Leu Ile
            35                  40                  45

Lys His Ala Ser Asp Arg Ile Ser Gly Ile Pro Ser Arg Phe Ser Gly
        50                  55                  60

Ser Gly Ser Gly Thr Asp Phe Thr Leu Thr Ile Asn Ser Leu Glu Ala
 65                 70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105
```

<210> SEQ ID NO 400
<211> LENGTH: 107
<212> TYPE: PRT
<213> ORGANISM: artificial
<220> FEATURE:
<223> OTHER INFORMATION: Synthetic polypeptide

<400> SEQUENCE: 400

```
Glu Ile Val Met Thr Gln Ser Pro Asp Phe Gln Ser Val Thr Pro Lys
 1               5                  10                  15

Glu Lys Val Thr Ile Thr Cys Arg Ala Ser Gln Asp Ile Tyr Arg Asn
                20                  25                  30

Leu His Trp Tyr Gln Gln Lys Pro Asp Gln Thr Pro Lys Leu Leu Ile
            35                  40                  45

Lys His Ala Ser Asp Val Ile Ser Gly Ile Pro Ser Arg Phe Ser Gly
        50                  55                  60

Ser Gly Ser Gly Thr Asp Phe Thr Leu Thr Ile Asn Ser Leu Glu Ala
 65                 70                  75                  80

Glu Asp Ala Ala Ala Tyr Tyr Cys Leu Gln Gly Tyr Ser Met Pro Tyr
                85                  90                  95
```

Thr Phe Gly Gly Gly Thr Lys Val Glu Ile Lys
            100                 105

<210> SEQ ID NO 401
<211> LENGTH: 107
<212> TYPE: PRT
<213> ORGANISM: artificial
<220> FEATURE:
<223> OTHER INFORMATION: Synthetic polypeptide

<400> SEQUENCE: 401

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Val Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys
            100                 105

<210> SEQ ID NO 402
<211> LENGTH: 107
<212> TYPE: PRT
<213> ORGANISM: artificial
<220> FEATURE:
<223> OTHER INFORMATION: Synthetic polypeptide

<400> SEQUENCE: 402

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Gly Gln Gly Tyr Ser Met Pro Tyr
                85                  90                  95

Thr Phe Gly Gly Gly Thr Lys Val Glu Ile Lys
            100                 105

<210> SEQ ID NO 403
<211> LENGTH: 107
<212> TYPE: PRT
<213> ORGANISM: artificial
<220> FEATURE:
<223> OTHER INFORMATION: Synthetic polypeptide

<400> SEQUENCE: 403

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn

```
                    20                  25                  30

Leu His Trp Tyr Gln Gln Lys Pro Asp Gln Thr Pro Lys Leu Leu Ile
            35                  40                  45

Lys His Ala Ser Asp Ser Ile Ser Gly Ile Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Met Gln Gly Tyr Ser Met Pro Tyr
                85                  90                  95

Thr Phe Gly Gly Gly Thr Lys Val Glu Ile Lys
                100                 105
```

<210> SEQ ID NO 404
<211> LENGTH: 107
<212> TYPE: PRT
<213> ORGANISM: artificial
<220> FEATURE:
<223> OTHER INFORMATION: Synthetic polypeptide

<400> SEQUENCE: 404

```
Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Gln Gln Gly Tyr Ser Met Pro Tyr
                85                  90                  95

Thr Phe Gly Gly Gly Thr Lys Val Glu Ile Lys
                100                 105
```

<210> SEQ ID NO 405
<211> LENGTH: 107
<212> TYPE: PRT
<213> ORGANISM: artificial
<220> FEATURE:
<223> OTHER INFORMATION: Synthetic polypeptide

<400> SEQUENCE: 405

```
Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ala Met Pro Tyr
                85                  90                  95

Thr Phe Gly Gly Gly Thr Lys Val Glu Ile Lys
                100                 105
```

<210> SEQ ID NO 406
<211> LENGTH: 107
<212> TYPE: PRT
<213> ORGANISM: artificial
<220> FEATURE:
<223> OTHER INFORMATION: Synthetic polypeptide

<400> SEQUENCE: 406

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Glu Met Pro Tyr
                85                  90                  95

Thr Phe Gly Gly Gly Thr Lys Val Glu Ile Lys
            100                 105

<210> SEQ ID NO 407
<211> LENGTH: 107
<212> TYPE: PRT
<213> ORGANISM: artificial
<220> FEATURE:
<223> OTHER INFORMATION: Synthetic polypeptide

<400> SEQUENCE: 407

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Gln Met Pro Tyr
                85                  90                  95

Thr Phe Gly Gly Gly Thr Lys Val Glu Ile Lys
            100                 105

<210> SEQ ID NO 408
<211> LENGTH: 107
<212> TYPE: PRT
<213> ORGANISM: artificial
<220> FEATURE:
<223> OTHER INFORMATION: Synthetic polypeptide

<400> SEQUENCE: 408

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile

```
              35                  40                  45
Lys His Ala Ser Asp Ser Ile Ser Gly Ile Pro Ser Arg Phe Ser Gly
        50                  55                  60
Ser Gly Ser Gly Thr Asp Phe Thr Leu Thr Ile Asn Ser Leu Glu Ala
65                  70                  75                  80
Glu Asp Ala Ala Ala Tyr Tyr Cys Leu Gln Gly Tyr Val Met Pro Tyr
                85                  90                  95
Thr Phe Gly Gly Gly Thr Lys Val Glu Ile Lys
            100                 105

<210> SEQ ID NO 409
<211> LENGTH: 107
<212> TYPE: PRT
<213> ORGANISM: artificial
<220> FEATURE:
<223> OTHER INFORMATION: Synthetic polypeptide

<400> SEQUENCE: 409

Glu Ile Val Met Thr Gln Ser Pro Asp Phe Gln Ser Val Thr Pro Lys
1               5                   10                  15
Glu Lys Val Thr Ile Thr Cys Arg Ala Ser Gln Asp Ile Tyr Arg Asn
            20                  25                  30
Leu His Trp Tyr Gln Gln Lys Pro Asp Gln Thr Pro Lys Leu Leu Ile
        35                  40                  45
Lys His Ala Ser Asp Ser Ile Ser Gly Ile Pro Ser Arg Phe Ser Gly
    50                  55                  60
Ser Gly Ser Gly Thr Asp Phe Thr Leu Thr Ile Asn Ser Leu Glu Ala
65                  70                  75                  80
Glu Asp Ala Ala Ala Tyr Tyr Cys Leu Gln Gly Tyr Ser Met Pro Phe
                85                  90                  95
Thr Phe Gly Gly Gly Thr Lys Val Glu Ile Lys
            100                 105

<210> SEQ ID NO 410
<211> LENGTH: 120
<212> TYPE: PRT
<213> ORGANISM: artificial
<220> FEATURE:
<223> OTHER INFORMATION: Synthetic polypeptide

<400> SEQUENCE: 410

Glu Ile Gln Leu Val Gln Ser Gly Ser Glu Leu Lys Lys Pro Gly Ala
1               5                   10                  15
Ser Val Lys Val Ser Cys Lys Ala Ser Gly Tyr Pro Phe Ala Thr Tyr
            20                  25                  30
Gly Met Ser Trp Val Arg Gln Ala Pro Gly Gln Gly Leu Glu Trp Met
        35                  40                  45
Gly Trp Ile Asn Thr Asp Ser Gly Val Pro Thr Tyr Ala Asp Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Phe Cys
                85                  90                  95
Ala Arg Asn Ile Tyr Tyr Gly Trp Gly Asn Phe Asp Tyr Trp Gly Gln
            100                 105                 110
Gly Thr Leu Val Thr Val Ser Ser
            115                 120
```

<210> SEQ ID NO 411
<211> LENGTH: 120
<212> TYPE: PRT
<213> ORGANISM: artificial
<220> FEATURE:
<223> OTHER INFORMATION: Synthetic polypeptide

<400> SEQUENCE: 411

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Asp Thr Tyr
                20                  25                  30

Gly Met Ser Trp Val Arg Gln Ala Pro Gly Gln Gly Leu Glu Trp Met
            35                  40                  45

Gly Trp Ile Asn Thr Asp Ser Gly Val Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
                100                 105                 110

Gly Thr Leu Val Thr Val Ser Ser
        115                 120

<210> SEQ ID NO 412
<211> LENGTH: 120
<212> TYPE: PRT
<213> ORGANISM: artificial
<220> FEATURE:
<223> OTHER INFORMATION: Synthetic polypeptide

<400> SEQUENCE: 412

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Glu Thr Tyr
                20                  25                  30

Gly Met Ser Trp Val Arg Gln Ala Pro Gly Gln Gly Leu Glu Trp Met
            35                  40                  45

Gly Trp Ile Asn Thr Asp Ser Gly Val Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
                100                 105                 110

Gly Thr Leu Val Thr Val Ser Ser
        115                 120

<210> SEQ ID NO 413
<211> LENGTH: 120
<212> TYPE: PRT
<213> ORGANISM: artificial
<220> FEATURE:
<223> OTHER INFORMATION: Synthetic polypeptide

<400> SEQUENCE: 413

Glu Ile Gln Leu Val Gln Ser Gly Ser Glu Leu Lys Lys Pro Gly Ala

```
1               5                   10                  15
Ser Val Lys Val Ser Cys Lys Ala Ser Gly Tyr Pro Phe Gly Thr Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
            115                 120

<210> SEQ ID NO 414
<211> LENGTH: 120
<212> TYPE: PRT
<213> ORGANISM: artificial
<220> FEATURE:
<223> OTHER INFORMATION: Synthetic polypeptide

<400> SEQUENCE: 414

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe His Thr Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
            115                 120

<210> SEQ ID NO 415
<211> LENGTH: 120
<212> TYPE: PRT
<213> ORGANISM: artificial
<220> FEATURE:
<223> OTHER INFORMATION: Synthetic polypeptide

<400> SEQUENCE: 415

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Lys Thr Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60
```

-continued

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 416
<211> LENGTH: 120
<212> TYPE: PRT
<213> ORGANISM: artificial
<220> FEATURE:
<223> OTHER INFORMATION: Synthetic polypeptide

<400> SEQUENCE: 416

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Met Thr Tyr
                20                  25                  30

Gly Met Ser Trp Val Arg Gln Ala Pro Gly Gln Gly Leu Glu Trp Met
            35                  40                  45

Gly Trp Ile Asn Thr Asp Ser Gly Val Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 417
<211> LENGTH: 120
<212> TYPE: PRT
<213> ORGANISM: artificial
<220> FEATURE:
<223> OTHER INFORMATION: Synthetic polypeptide

<400> SEQUENCE: 417

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Asn Thr Tyr
                20                  25                  30

Gly Met Ser Trp Val Arg Gln Ala Pro Gly Gln Gly Leu Glu Trp Met
            35                  40                  45

Gly Trp Ile Asn Thr Asp Ser Gly Val Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 418
<211> LENGTH: 120
<212> TYPE: PRT
<213> ORGANISM: artificial
<220> FEATURE:
<223> OTHER INFORMATION: Synthetic polypeptide

<400> SEQUENCE: 418

```
Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Gln Thr Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120
```

<210> SEQ ID NO 419
<211> LENGTH: 120
<212> TYPE: PRT
<213> ORGANISM: artificial
<220> FEATURE:
<223> OTHER INFORMATION: Synthetic polypeptide

<400> SEQUENCE: 419

```
Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Arg Thr Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120
```

<210> SEQ ID NO 420
<211> LENGTH: 120
<212> TYPE: PRT
<213> ORGANISM: artificial
<220> FEATURE:
<223> OTHER INFORMATION: Synthetic polypeptide

<400> SEQUENCE: 420

```
Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Ser Thr Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
                100                 105                 110

Gly Thr Leu Val Thr Val Ser Ser
            115                 120
```

<210> SEQ ID NO 421
<211> LENGTH: 120
<212> TYPE: PRT
<213> ORGANISM: artificial
<220> FEATURE:
<223> OTHER INFORMATION: Synthetic polypeptide

<400> SEQUENCE: 421

```
Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Asp Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
                100                 105                 110

Gly Thr Leu Val Thr Val Ser Ser
            115                 120
```

<210> SEQ ID NO 422
<211> LENGTH: 120
<212> TYPE: PRT
<213> ORGANISM: artificial
<220> FEATURE:
<223> OTHER INFORMATION: Synthetic polypeptide

<400> SEQUENCE: 422

```
Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Glu Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60
```

```
Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 423
<211> LENGTH: 120
<212> TYPE: PRT
<213> ORGANISM: artificial
<220> FEATURE:
<223> OTHER INFORMATION: Synthetic polypeptide

<400> SEQUENCE: 423

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Gly Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 424
<211> LENGTH: 120
<212> TYPE: PRT
<213> ORGANISM: artificial
<220> FEATURE:
<223> OTHER INFORMATION: Synthetic polypeptide

<400> SEQUENCE: 424

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr His Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
```

115                 120

<210> SEQ ID NO 425
<211> LENGTH: 120
<212> TYPE: PRT
<213> ORGANISM: artificial
<220> FEATURE:
<223> OTHER INFORMATION: Synthetic polypeptide

<400> SEQUENCE: 425

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Asn Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
            115                 120

<210> SEQ ID NO 426
<211> LENGTH: 120
<212> TYPE: PRT
<213> ORGANISM: artificial
<220> FEATURE:
<223> OTHER INFORMATION: Synthetic polypeptide

<400> SEQUENCE: 426

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Gln Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
            115                 120

<210> SEQ ID NO 427
<211> LENGTH: 120
<212> TYPE: PRT
<213> ORGANISM: artificial
<220> FEATURE:
<223> OTHER INFORMATION: Synthetic polypeptide

<400> SEQUENCE: 427

-continued

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Ser Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 428
<211> LENGTH: 120
<212> TYPE: PRT
<213> ORGANISM: artificial
<220> FEATURE:
<223> OTHER INFORMATION: Synthetic polypeptide

<400> SEQUENCE: 428

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Thr Phe
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 429
<211> LENGTH: 120
<212> TYPE: PRT
<213> ORGANISM: artificial
<220> FEATURE:
<223> OTHER INFORMATION: Synthetic polypeptide

<400> SEQUENCE: 429

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Thr Met
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe

```
                    50                  55                  60
Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 430
<211> LENGTH: 120
<212> TYPE: PRT
<213> ORGANISM: artificial
<220> FEATURE:
<223> OTHER INFORMATION: Synthetic polypeptide

<400> SEQUENCE: 430

Glu Ile Gln Leu Val Gln Ser Gly Ser Glu Leu Lys Lys Pro Gly Ala
  1               5                  10                  15

Ser Val Lys Val Ser Cys Lys Ala Ser Gly Tyr Pro Phe Thr Thr Gln
                 20                  25                  30

Gly Met Ser Trp Val Arg Gln Ala Pro Gly Gln Gly Leu Glu Trp Met
             35                  40                  45

Gly Trp Ile Asn Thr Asp Ser Gly Val Pro Thr Tyr Ala Asp Asp Phe
         50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 431
<211> LENGTH: 120
<212> TYPE: PRT
<213> ORGANISM: artificial
<220> FEATURE:
<223> OTHER INFORMATION: Synthetic polypeptide

<400> SEQUENCE: 431

Glu Ile Gln Leu Val Gln Ser Gly Ser Glu Leu Lys Lys Pro Gly Ala
  1               5                  10                  15

Ser Val Lys Val Ser Cys Lys Ala Ser Gly Tyr Pro Phe Thr Thr Tyr
                 20                  25                  30

Gly Ile Ser Trp Val Arg Gln Ala Pro Gly Gln Gly Leu Glu Trp Met
             35                  40                  45

Gly Trp Ile Asn Thr Asp Ser Gly Val Pro Thr Tyr Ala Asp Asp Phe
         50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Ile Tyr Tyr Gly Trp Gly Asn Phe Asp Tyr Trp Gly Gln
            100                 105                 110
```

Gly Thr Leu Val Thr Val Ser Ser
        115                 120

<210> SEQ ID NO 432
<211> LENGTH: 120
<212> TYPE: PRT
<213> ORGANISM: artificial
<220> FEATURE:
<223> OTHER INFORMATION: Synthetic polypeptide

<400> SEQUENCE: 432

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Thr Tyr
            20                  25                  30

Gly Leu Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 433
<211> LENGTH: 120
<212> TYPE: PRT
<213> ORGANISM: artificial
<220> FEATURE:
<223> OTHER INFORMATION: Synthetic polypeptide

<400> SEQUENCE: 433

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Thr Tyr
            20                  25                  30

Gly Val Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 434
<211> LENGTH: 120
<212> TYPE: PRT
<213> ORGANISM: artificial
<220> FEATURE:
<223> OTHER INFORMATION: Synthetic polypeptide

<400> SEQUENCE: 434

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Glu Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 435
<211> LENGTH: 120
<212> TYPE: PRT
<213> ORGANISM: artificial
<220> FEATURE:
<223> OTHER INFORMATION: Synthetic polypeptide

<400> SEQUENCE: 435

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Asp Thr Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Asn Phe Asp Tyr Trp Gly Gln
            100                 105                 110

Gly Thr Leu Val Thr Val Ser Ser
        115                 120

<210> SEQ ID NO 436
<211> LENGTH: 120
<212> TYPE: PRT
<213> ORGANISM: artificial
<220> FEATURE:
<223> OTHER INFORMATION: Synthetic polypeptide

<400> SEQUENCE: 436

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Thr Tyr
            20                  25                  30

Gly Met Ser Trp Val Arg Gln Ala Pro Gly Gln Gly Leu Glu Trp Met
        35                  40                  45

```
Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Met Ile Tyr Tyr Gly Trp Gly Asn Phe Asp Tyr Trp Gly Gln
            100                 105                 110

Gly Thr Leu Val Thr Val Ser Ser
            115                 120

<210> SEQ ID NO 437
<211> LENGTH: 120
<212> TYPE: PRT
<213> ORGANISM: artificial
<220> FEATURE:
<223> OTHER INFORMATION: Synthetic polypeptide

<400> SEQUENCE: 437

Glu Ile Gln Leu Val Gln Ser Gly Ser Glu Leu Lys Lys Pro Gly Ala
  1               5                  10                  15

Ser Val Lys Val Ser Cys Lys Ala Ser Gly Tyr Pro Phe Thr Thr Tyr
                 20                  25                  30

Gly Met Ser Trp Val Arg Gln Ala Pro Gly Gln Gly Leu Glu Trp Met
             35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Ile Tyr Tyr Gly Trp Gly Phe Phe Asp Tyr Trp Gly Gln
            100                 105                 110

Gly Thr Leu Val Thr Val Ser Ser
            115                 120

<210> SEQ ID NO 438
<211> LENGTH: 120
<212> TYPE: PRT
<213> ORGANISM: artificial
<220> FEATURE:
<223> OTHER INFORMATION: Synthetic polypeptide

<400> SEQUENCE: 438

Glu Ile Gln Leu Val Gln Ser Gly Ser Glu Leu Lys Lys Pro Gly Ala
  1               5                  10                  15

Ser Val Lys Val Ser Cys Lys Ala Ser Gly Tyr Pro Phe Thr Thr Tyr
                 20                  25                  30

Gly Met Ser Trp Val Arg Gln Ala Pro Gly Gln Gly Leu Glu Trp Met
             35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asn Ile Tyr Tyr Gly Trp Gly His Phe Asp Tyr Trp Gly Gln
            100                 105                 110
```

Gly Thr Leu Val Thr Val Ser Ser
        115                 120

<210> SEQ ID NO 439
<211> LENGTH: 120
<212> TYPE: PRT
<213> ORGANISM: artificial
<220> FEATURE:
<223> OTHER INFORMATION: Synthetic polypeptide

<400> SEQUENCE: 439

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Asp Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Ile Tyr Tyr Gly Trp Gly Tyr Phe Asp Tyr Trp Gly Gln
            100                 105                 110

Gly Thr Leu Val Thr Val Ser Ser
        115                 120

<210> SEQ ID NO 440
<211> LENGTH: 213
<212> TYPE: PRT
<213> ORGANISM: artificial
<220> FEATURE:
<223> OTHER INFORMATION: Synthetic polypeptide

<400> SEQUENCE: 440

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Ala
            20                  25                  30

Ile Val Trp Tyr Gln Lys Lys Pro Gly Gln Ser Pro Lys Thr Leu Ile
        35                  40                  45

Tyr Ser Ala Ser Thr Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Ser Ser Ser Pro Leu
                85                  90                  95

Thr Phe Gly Ser Gly Thr Lys Leu Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser 165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 441
<211> LENGTH: 218
<212> TYPE: PRT
<213> ORGANISM: artificial
<220> FEATURE:
<223> OTHER INFORMATION: Synthetic polypeptide

<400> SEQUENCE: 441

Asp Val Val Met Thr Gln Thr Pro Leu Thr Leu Ser Val Thr Leu Gly
1               5                   10                  15

His Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Glu Ser
        35                  40                  45

Pro Lys Leu Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ala
                85                  90                  95

Thr His Ser Pro Gln Thr Phe Gly Gly Gly Thr Lys Leu Glu Ile Lys
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 442
<211> LENGTH: 213
<212> TYPE: PRT
<213> ORGANISM: artificial
<220> FEATURE:
<223> OTHER INFORMATION: Synthetic polypeptide

<400> SEQUENCE: 442

Asp Ile Gln Met Asn Gln Ser Pro Ser Ser Leu Ser Ala Ser Leu Gly
1               5                   10                  15

Asp Thr Ile Thr Ile Thr Cys Arg Val Ser Gln Asp Ile Ser Phe Trp
            20                  25                  30

Leu Ser Trp Tyr Gln Gln Lys Pro Gly Asn Ile Pro Lys Leu Leu Ile
            35                  40                  45

Tyr Lys Ala Ser Asn Leu His Thr Gly Val Pro Pro Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Ala Tyr Tyr Cys Leu Gln Ser Gln Ser Tyr Pro Tyr
                 85                  90                  95

Thr Phe Gly Gly Gly Thr Lys Leu Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
        210

<210> SEQ ID NO 443
<211> LENGTH: 212
<212> TYPE: PRT
<213> ORGANISM: artificial
<220> FEATURE:
<223> OTHER INFORMATION: Synthetic polypeptide

<400> SEQUENCE: 443

Glu Asn Val Leu Thr Gln Ser Pro Ala Ile Met Ser Ala Thr Leu Gly
1               5                   10                  15

Glu Lys Val Thr Met Asn Cys Arg Ala Ser Ser Asn Val Lys Tyr Met
            20                  25                  30

Tyr Trp Tyr Gln Gln Lys Ser Gly Val Ser Pro Lys Leu Trp Ile Tyr
        35                  40                  45

Tyr Thr Ser Asn Leu Ala Ser Gly Val Pro Thr Arg Phe Ser Gly Ser
 50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Phe Thr Ser Ser Pro Leu Thr
                 85                  90                  95

Phe Gly Ala Gly Thr Lys Leu Glu Leu Lys Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

```
Tyr Leu Ser Leu Thr Pro Glu Gln Trp Lys Ser His Lys Ser Tyr Ser
            180                 185                 190

Cys Gln Val Thr His Glu Gly Ser Thr Val Glu Lys Thr Val Ala Pro
            195                 200                 205

Thr Glu Cys Ser
    210

<210> SEQ ID NO 444
<211> LENGTH: 217
<212> TYPE: PRT
<213> ORGANISM: artificial
<220> FEATURE:
<223> OTHER INFORMATION: Synthetic polypeptide

<400> SEQUENCE: 444

Asp Ile Val Leu Thr Gln Ser Pro Ala Ser Leu Ala Val Ser Leu Gly
1               5                   10                  15

Gln Arg Ala Ile Ile Ser Cys Lys Ala Ser Gln Ser Val Thr Phe Ala
            20                  25                  30

Asp Thr Gly Leu Met His Trp Tyr Gln Gln Lys Pro Gly Gln Gln Pro
        35                  40                  45

Lys Leu Leu Ile Tyr Arg Ala Ser Asn Leu Glu Val Gly Val Pro Thr
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln Gln Ser Arg
                85                  90                  95

Glu Tyr Pro Trp Thr Phe Gly Gly Gly Thr Lys Leu Glu Ile Lys Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Lys Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 445
<211> LENGTH: 215
<212> TYPE: PRT
<213> ORGANISM: artificial
<220> FEATURE:
<223> OTHER INFORMATION: Synthetic polypeptide

<400> SEQUENCE: 445

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45
```

Leu Ile Gly Gly Thr Asn Asn Arg Ala Pro Gly Val Pro Ala Arg Phe
            50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ser Leu Trp Tyr Gly Ser
                 85                  90                  95

His Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Lys
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 446
<211> LENGTH: 213
<212> TYPE: PRT
<213> ORGANISM: artificial
<220> FEATURE:
<223> OTHER INFORMATION: Synthetic polypeptide

<400> SEQUENCE: 446

Asp Ile Leu Met Thr Gln Ser Pro Thr Thr Leu Ser Val Thr Pro Gly
 1               5                  10                  15

Glu Thr Val Ser Leu Ser Cys Arg Ala Ser Gln Asp Ile Tyr Arg Asn
             20                  25                  30

Leu His Trp Tyr Gln Gln Lys Ser Gln Gly Thr Pro Arg Leu Leu Ile
         35                  40                  45

Lys His Ala Ser Asp Ser Ile Ser Gly Ile Pro Ser Arg Phe Thr Gly
     50                  55                  60

Ser Gly Ser Gly Thr Asp Phe Thr Leu Ser Ile Asn Ser Val Lys Pro
 65                  70                  75                  80

Glu Asp Glu Gly Ile Tyr Tyr Cys Leu Gln Gly Tyr Ser Met Pro Tyr
                 85                  90                  95

Thr Phe Gly Gly Gly Thr Lys Leu Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 447
<211> LENGTH: 448
<212> TYPE: PRT
<213> ORGANISM: artificial
<220> FEATURE:
<223> OTHER INFORMATION: Synthetic polypeptide

<400> SEQUENCE: 447

Gln Val Gln Leu Gln Gln Pro Gly Ala Glu Leu Val Thr Pro Gly Ala
1               5                   10                  15

Ser Val Lys Leu Ser Cys Lys Ala Ser Gly Phe Thr Phe Thr Asn Asn
            20                  25                  30

Trp Met His Trp Val Lys Gln Arg Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Lys Ala Thr Val Thr Val Asp Lys Ser Ser Ser Thr Val Tyr
65                  70                  75                  80

Ile Gln Leu Ser Ser Leu Thr Ser Glu Asp Ser Ala Val Tyr Tyr Cys
            85                  90                  95

Arg Ser Asp Gly Thr Tyr Glu Gly Tyr Phe Asp Tyr Trp Gly Gln Gly
        100                 105                 110

Thr Pro Leu Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 448
<211> LENGTH: 446
<212> TYPE: PRT
<213> ORGANISM: artificial
<220> FEATURE:
<223> OTHER INFORMATION: Synthetic polypeptide

<400> SEQUENCE: 448

Gln Val Gln Leu Gln Gln Ser Gly Ala Asp Leu Ala Arg Pro Gly Ala
1               5                   10                  15

Ser Ile Lys Leu Ser Cys Lys Ala Ser Gly Tyr Thr Phe Thr Gly Tyr
            20                  25                  30

Gly Val Thr Trp Val Lys Gln Ser Thr Gly Gln Gly Leu Asp Trp Ile
            35                  40                  45

Gly Glu Ile Tyr Pro Gly Thr Val Ile Thr Tyr Tyr Asn Ala Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Gly Leu Gly Arg Ala Met Asp Tyr Trp Gly Gln Gly Thr Ser
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Gly Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 449
<211> LENGTH: 450
<212> TYPE: PRT
<213> ORGANISM: artificial
<220> FEATURE:
<223> OTHER INFORMATION: Synthetic polypeptide

<400> SEQUENCE: 449

Gln Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Gly Trp Ile Phe Pro Gly Thr Glu Gly Ile Tyr Tyr Asn Glu Lys Phe
        50                  55                  60

Lys Gly Lys Ala Thr Leu Thr Val Asp Lys Ser Ser Thr Thr Ala Tyr
65                  70                  75                  80

Met Leu Leu Ser Ser Leu Thr Ser Glu Asp Ser Ala Val Tyr Phe Cys
                85                  90                  95

Ala Arg Glu Gly Asp Tyr Arg Tyr Tyr Ser Pro Leu Gly Tyr Trp Gly
            100                 105                 110

Gln Gly Thr Leu Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gly Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly
    450

<210> SEQ ID NO 450
<211> LENGTH: 446
<212> TYPE: PRT
<213> ORGANISM: artificial
<220> FEATURE:
<223> OTHER INFORMATION: Synthetic polypeptide

<400> SEQUENCE: 450

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Asn Phe Asn Asp Tyr
                20                  25                  30

Tyr Ile Asn Trp Val Asn Gln Arg Pro Gly Gln Gly Leu Glu Trp Ile
            35                  40                  45

Gly Trp Ile Phe Pro Gly Arg Ile Ile Thr Tyr Tyr Asn Glu Lys Phe
        50                  55                  60

Lys Gly Lys Ala Thr Leu Thr Val Asp Thr Ser Ser Asn Thr Ala Tyr
65                  70                  75                  80
```

Met Leu Leu Ser Ser Leu Thr Ser Glu Asp Ser Ala Val Tyr Phe Cys
                85                  90                  95

Ala Arg Gly Val Gly Glu Gly Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Gly Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 451
<211> LENGTH: 447
<212> TYPE: PRT
<213> ORGANISM: artificial
<220> FEATURE:
<223> OTHER INFORMATION: Synthetic polypeptide

<400> SEQUENCE: 451

```
Glu Val Gln Leu Leu Glu Thr Gly Gly Gly Leu Val Lys Ser Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Ala Ile Ser Asp Asp Gly Thr Tyr Thr Tyr Tyr Pro Asp Ser Val
    50                  55                  60

Lys Gly Arg Phe Thr Ile Ser Arg Asp Asn Ala Asn Asn Tyr Leu Tyr
65                  70                  75                  80

Leu Gln Met Ser Ser Leu Lys Ser Glu Asp Thr Ala Ile Tyr Tyr Cys
                85                  90                  95

Ala Lys Ala Gly Ser Tyr Asp Tyr Phe Asp Val Trp Gly Ala Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 452
<211> LENGTH: 445
<212> TYPE: PRT
<213> ORGANISM: artificial
<220> FEATURE:
<223> OTHER INFORMATION: Synthetic polypeptide

<400> SEQUENCE: 452

Gln Val Gln Leu Lys Glu Ser Gly Pro Gly Leu Val Ala Pro Ser Gln
1               5                   10                  15

Ser Leu Ser Ile Ile Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Ile Ile Trp Ala Gly Gly Ser Thr Asn Tyr Asn Ser Ala Leu Met
    50                  55                  60

Ser Arg Leu Thr Ile Ser Lys Asp Asn Ser Lys Ser Gln Val Phe Leu
65                  70                  75                  80

Lys Met Asn Ser Leu Gln Thr Asn Asp Thr Ala Ile Tyr Tyr Cys Ala
                85                  90                  95

Arg Val Ser Met Met Gly Phe Ala Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gly Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

```
Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 453
<211> LENGTH: 449
<212> TYPE: PRT
<213> ORGANISM: artificial
<220> FEATURE:
<223> OTHER INFORMATION: Synthetic polypeptide

<400> SEQUENCE: 453

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Pro Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Asp Ser Gly Val Pro Thr Tyr Ala Asp Asp Phe
    50                  55                  60

Lys Gly Arg Phe Ala Phe Ser Leu Glu Thr Ser Ala Asn Thr Ala Tyr
65                  70                  75                  80

Leu Gln Ile Asn Ser Leu Lys Asn Glu Asp Ala Ala Thr Tyr Phe Cys
                85                  90                  95

Ala Arg Asn Ile Tyr Tyr Gly Trp Gly Asn Phe Asp Tyr Trp Gly Gln
            100                 105                 110

Gly Thr Ile Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gly Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 454
<211> LENGTH: 213
<212> TYPE: PRT
<213> ORGANISM: artificial
<220> FEATURE:
<223> OTHER INFORMATION: Synthetic polypeptide

<400> SEQUENCE: 454

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Ile Val Trp Tyr Gln Gln Lys Pro Gly Lys Ala Pro Lys Val Leu Ile
        35                  40                  45

Tyr Ser Ala Ser Thr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Ser Pro Leu
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
            130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
```

```
                    165                 170                 175
Ser Tyr Leu Ser Leu Thr Pro Glu Gln Trp Lys Ser His Lys Ser Tyr
                180                 185                 190

Ser Cys Gln Val Thr His Glu Gly Ser Thr Val Glu Lys Thr Val Ala
            195                 200                 205

Pro Thr Glu Cys Ser
        210

<210> SEQ ID NO 455
<211> LENGTH: 448
<212> TYPE: PRT
<213> ORGANISM: artificial
<220> FEATURE:
<223> OTHER INFORMATION: Synthetic polypeptide

<400> SEQUENCE: 455

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
```

```
305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 456
<211> LENGTH: 448
<212> TYPE: PRT
<213> ORGANISM: artificial
<220> FEATURE:
<223> OTHER INFORMATION: Synthetic polypeptide

<400> SEQUENCE: 456

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Phe Met His Trp Val Arg Gln Ala Pro Gly Gln Gly Leu Glu Trp Ile
        35                  40                  45

Gly Met Ile His Ala Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Ile Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

```
                    225                 230                 235                 240
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Gly Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 457
<211> LENGTH: 448
<212> TYPE: PRT
<213> ORGANISM: artificial
<220> FEATURE:
<223> OTHER INFORMATION: Synthetic polypeptide

<400> SEQUENCE: 457

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
                20                  25                  30

Phe Met His Trp Val Arg Gln Ala Pro Gly Gln Gly Leu Glu Trp Ile
            35                  40                  45

Gly Met Ile His Ala Asn Ser Gly Ile Thr Asn Ile Asn Glu Lys Phe
        50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

145                 150                 155                 160
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 458
<211> LENGTH: 448
<212> TYPE: PRT
<213> ORGANISM: artificial
<220> FEATURE:
<223> OTHER INFORMATION: Synthetic polypeptide

<400> SEQUENCE: 458

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Phe Met His Trp Val Arg Gln Ala Pro Gly Gln Gly Leu Glu Trp Ile
        35                  40                  45

Gly Phe Ile His Ala Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr

```
            65                  70                  75                  80
Met Glu Leu Arg Ser Leu Arg Ser Glu Asp Thr Ala Val Tyr Tyr Cys
                    85                  90                  95

Arg Ser Asp Gly Ile Tyr Glu Gly Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 459
<211> LENGTH: 448
<212> TYPE: PRT
<213> ORGANISM: artificial
<220> FEATURE:
<223> OTHER INFORMATION: Synthetic polypeptide
```

<400> SEQUENCE: 459

| | | | | | | | | | | | | | | |
|---|---|---|---|---|---|---|---|---|---|---|---|---|---|---|
|Glu|Val|Gln|Leu|Val|Gln|Ser|Gly|Ala|Glu|Val|Lys|Lys|Pro|Gly|Ala|
|1| | | |5| | | | |10| | | | |15| |
|Ser|Val|Lys|Val|Ser|Cys|Lys|Ala|Ser|Gly|Phe|Thr|Phe|Thr|Asn|Asn|
| | | |20| | | | |25| | | | |30| | |
|Phe|Met|His|Trp|Val|Arg|Gln|Ala|Pro|Gly|Gln|Gly|Leu|Glu|Trp|Ile|
| | |35| | | | |40| | | | |45| | | |
|Gly|Phe|Ile|His|Ala|Asn|Ser|Gly|Ile|Thr|Asn|Ile|Asn|Glu|Lys|Phe|
| |50| | | | |55| | | | |60| | | | |
|Lys|Asn|Arg|Val|Thr|Met|Thr|Thr|Asp|Thr|Ser|Thr|Ser|Thr|Ala|Tyr|
|65| | | | |70| | | | |75| | | | |80|
|Met|Glu|Leu|Arg|Ser|Leu|Arg|Ser|Glu|Asp|Thr|Ala|Val|Tyr|Tyr|Cys|
| | | | |85| | | | |90| | | | |95| |
|Arg|Ser|Asp|Gly|Val|Tyr|Glu|Gly|Tyr|Phe|Asp|Tyr|Trp|Gly|Gln|Gly|
| | | |100| | | | |105| | | | |110| | |
|Thr|Leu|Val|Thr|Val|Ser|Ser|Ala|Ser|Thr|Lys|Gly|Pro|Ser|Val|Phe|
| | |115| | | | |120| | | | |125| | | |
|Pro|Leu|Ala|Pro|Ser|Ser|Lys|Ser|Thr|Ser|Gly|Gly|Thr|Ala|Ala|Leu|
| |130| | | | |135| | | | |140| | | | |
|Gly|Cys|Leu|Val|Lys|Asp|Tyr|Phe|Pro|Glu|Pro|Val|Thr|Val|Ser|Trp|
|145| | | | |150| | | | |155| | | | |160|
|Asn|Ser|Gly|Ala|Leu|Thr|Ser|Gly|Val|His|Thr|Phe|Pro|Ala|Val|Leu|
| | | | |165| | | | |170| | | | |175| |
|Gln|Ser|Ser|Gly|Leu|Tyr|Ser|Leu|Ser|Ser|Val|Val|Thr|Val|Pro|Ser|
| | | |180| | | | |185| | | | |190| | |
|Ser|Ser|Leu|Gly|Thr|Gln|Thr|Tyr|Ile|Cys|Asn|Val|Asn|His|Lys|Pro|
| | |195| | | | |200| | | | |205| | | |
|Ser|Asn|Thr|Lys|Val|Asp|Lys|Lys|Val|Glu|Pro|Lys|Ser|Cys|Asp|Lys|
| |210| | | | |215| | | | |220| | | | |
|Thr|His|Thr|Cys|Pro|Pro|Cys|Pro|Ala|Pro|Glu|Leu|Leu|Gly|Gly|Pro|
|225| | | | |230| | | | |235| | | | |240|
|Ser|Val|Phe|Leu|Phe|Pro|Pro|Lys|Pro|Lys|Asp|Thr|Leu|Met|Ile|Ser|
| | | | |245| | | | |250| | | | |255| |
|Arg|Thr|Pro|Glu|Val|Thr|Cys|Val|Val|Val|Asp|Val|Ser|His|Glu|Asp|
| | | |260| | | | |265| | | | |270| | |
|Pro|Glu|Val|Lys|Phe|Asn|Trp|Tyr|Val|Asp|Gly|Val|Glu|Val|His|Asn|
| | |275| | | | |280| | | | |285| | | |
|Ala|Lys|Thr|Lys|Pro|Arg|Glu|Glu|Gln|Tyr|Gly|Ser|Thr|Tyr|Arg|Val|
| |290| | | | |295| | | | |300| | | | |
|Val|Ser|Val|Leu|Thr|Val|Leu|His|Gln|Asp|Trp|Leu|Asn|Gly|Lys|Glu|
|305| | | | |310| | | | |315| | | | |320|
|Tyr|Lys|Cys|Lys|Val|Ser|Asn|Lys|Ala|Leu|Pro|Ala|Pro|Ile|Glu|Lys|
| | | | |325| | | | |330| | | | |335| |
|Thr|Ile|Ser|Lys|Ala|Lys|Gly|Gln|Pro|Arg|Glu|Pro|Gln|Val|Tyr|Thr|
| | | |340| | | | |345| | | | |350| | |
|Leu|Pro|Pro|Ser|Arg|Asp|Glu|Leu|Thr|Lys|Asn|Gln|Val|Ser|Leu|Thr|
| | |355| | | | |360| | | | |365| | | |
|Cys|Leu|Val|Lys|Gly|Phe|Tyr|Pro|Ser|Asp|Ile|Ala|Val|Glu|Trp|Glu|
| |370| | | | |375| | | | |380| | | | |
|Ser|Asn|Gly|Gln|Pro|Glu|Asn|Asn|Tyr|Lys|Thr|Thr|Pro|Pro|Val|Leu|
|385| | | | |390| | | | |395| | | | |400|
|Asp|Ser|Asp|Gly|Ser|Phe|Phe|Leu|Tyr|Ser|Lys|Leu|Thr|Val|Asp|Lys|
| | | | |405| | | | |410| | | | |415| |

-continued

Ser Arg Trp Gln Gln Gly Asn Val Phe Ser Cys Ser Val Met His Glu
          420                 425                 430

Ala Leu His Asn His Tyr Thr Gln Lys Ser Leu Ser Leu Ser Pro Gly
        435                 440                 445

<210> SEQ ID NO 460
<211> LENGTH: 119
<212> TYPE: PRT
<213> ORGANISM: artificial
<220> FEATURE:
<223> OTHER INFORMATION: Synthetic polypeptide

<400> SEQUENCE: 460

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Arg Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Arg Ala Thr Val Thr Val Asp Lys Ser Ser Ser Thr Val Tyr
65                  70                  75                  80

Ile Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser
        115

<210> SEQ ID NO 461
<211> LENGTH: 119
<212> TYPE: PRT
<213> ORGANISM: artificial
<220> FEATURE:
<223> OTHER INFORMATION: Synthetic polypeptide

<400> SEQUENCE: 461

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Arg Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Arg Ala Thr Val Thr Val Asp Lys Ser Ser Ser Thr Val Tyr
65                  70                  75                  80

Ile Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser
        115

<210> SEQ ID NO 462
<211> LENGTH: 119
<212> TYPE: PRT

```
<213> ORGANISM: artificial
<220> FEATURE:
<223> OTHER INFORMATION: Synthetic polypeptide

<400> SEQUENCE: 462

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Val
        35                  40                  45

Gly Met Ile His Pro Asn Ser Gly Ile Thr Asn Ile Asn Glu Lys Phe
    50                  55                  60

Lys Asn Arg Val Thr Met Thr Val Asp Lys Ser Thr Ser Thr Val Tyr
65                  70                  75                  80

Met Glu Leu Arg Ser Leu Arg Ser Asp Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser
        115

<210> SEQ ID NO 463
<211> LENGTH: 119
<212> TYPE: PRT
<213> ORGANISM: artificial
<220> FEATURE:
<223> OTHER INFORMATION: Synthetic polypeptide

<400> SEQUENCE: 463

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser
        115

<210> SEQ ID NO 464
<211> LENGTH: 119
<212> TYPE: PRT
<213> ORGANISM: artificial
<220> FEATURE:
<223> OTHER INFORMATION: Synthetic polypeptide

<400> SEQUENCE: 464

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30
```

Trp Met His Trp Val Arg Gln Ala Pro Gly Gln Gly Leu Glu Trp Ile
            35                  40                  45

Gly Met Ile His Pro Asn Ser Gly Ile Thr Asn Ile Asn Glu Lys Phe
        50                  55                  60

Lys Asn Arg Val Thr Met Thr Val Asp Lys Ser Thr Ser Thr Val Tyr
65                  70                  75                  80

Met Glu Leu Arg Ser Leu Arg Ser Asp Thr Ala Val Tyr Tyr Cys
                85                  90                  95

Ala Arg Asp Gly Thr Tyr Glu Gly Tyr Phe Asp Tyr Trp Gly Gln Gly
            100                 105                 110

Thr Leu Val Thr Val Ser Ser
            115

<210> SEQ ID NO 465
<211> LENGTH: 448
<212> TYPE: PRT
<213> ORGANISM: artificial
<220> FEATURE:
<223> OTHER INFORMATION: Synthetic polypeptide

<400> SEQUENCE: 465

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Arg Pro Gly Gln Gly Leu Glu Trp Ile
            35                  40                  45

Gly Met Ile His Pro Asn Ser Gly Ile Thr Asn Ile Asn Glu Lys Phe
        50                  55                  60

Lys Asn Arg Ala Thr Val Thr Val Asp Lys Ser Ser Ser Thr Val Tyr
65                  70                  75                  80

Ile Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 466
<211> LENGTH: 448
<212> TYPE: PRT
<213> ORGANISM: artificial
<220> FEATURE:
<223> OTHER INFORMATION: Synthetic polypeptide

<400> SEQUENCE: 466

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Arg Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Arg Ala Thr Val Thr Val Asp Lys Ser Ser Ser Thr Val Tyr
65                  70                  75                  80

Ile Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 467
<211> LENGTH: 448
<212> TYPE: PRT
<213> ORGANISM: artificial
<220> FEATURE:
<223> OTHER INFORMATION: Synthetic polypeptide

<400> SEQUENCE: 467

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Val
        35                  40                  45

Gly Met Ile His Pro Asn Ser Gly Ile Thr Asn Ile Asn Glu Lys Phe
    50                  55                  60

Lys Asn Arg Val Thr Met Thr Val Asp Lys Ser Thr Ser Thr Val Tyr
65                  70                  75                  80

Met Glu Leu Arg Ser Leu Arg Ser Asp Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

```
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Gly Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445

<210> SEQ ID NO 468
<211> LENGTH: 448
<212> TYPE: PRT
<213> ORGANISM: artificial
<220> FEATURE:
<223> OTHER INFORMATION: Synthetic polypeptide

<400> SEQUENCE: 468

Gln Val Gln Leu Val Gln Ser Gly Ala Glu Val Lys Lys Pro Gly Ala
1               5                   10                  15
Ser Val Lys Val Ser Cys Lys Ala Ser Gly Phe Thr Phe Thr Asn Asn
            20                  25                  30
```

```
Trp Met His Trp Val Arg Gln Ala Pro Gly Gln Gly Leu Glu Trp Ile
        35                  40                  45
Gly Met Ile His Pro Asn Ser Gly Ile Thr Asn Ile Asn Glu Lys Phe
    50                  55                  60
Lys Asn Arg Val Thr Met Thr Thr Asp Thr Ser Thr Ser Thr Ala Tyr
65                  70                  75                  80
Met Glu Leu Arg Ser Leu Arg Ser Asp Thr Ala Val Tyr Tyr Cys
                85                  90                  95
Arg Ser Asp Gly Thr Tyr Glu Gly Tyr Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Gly Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

<210> SEQ ID NO 469
<211> LENGTH: 448
<212> TYPE: PRT
<213> ORGANISM: artificial
<220> FEATURE:
<223> OTHER INFORMATION: Synthetic polypeptide

<400> SEQUENCE: 469

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Arg Val Thr Met Thr Val Asp Lys Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Asp Gly Thr Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 470
<211> LENGTH: 213
<212> TYPE: PRT
<213> ORGANISM: artificial
<220> FEATURE:
<223> OTHER INFORMATION: Synthetic polypeptide

<400> SEQUENCE: 470

Glu Ile Val Met Thr Gln Ser Pro Asp Phe Gln Ser Val Thr Pro Lys
1               5                   10                  15

Glu Lys Val Thr Ile Thr Cys Arg Ala Ser Gln Asp Ile Tyr Arg Asn
            20                  25                  30

Leu His Trp Tyr Gln Gln Lys Pro Asp Gln Thr Pro Lys Leu Leu Ile
        35                  40                  45

Lys His Ala Ser Asp Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Gly Tyr Ser Met Pro Tyr
                85                  90                  95

Thr Phe Gly Gly Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 471
<211> LENGTH: 449
<212> TYPE: PRT
<213> ORGANISM: artificial
<220> FEATURE:
<223> OTHER INFORMATION: Synthetic polypeptide

<400> SEQUENCE: 471

Glu Ile Gln Leu Val Gln Ser Gly Ser Glu Leu Lys Lys Pro Gly Ala
1               5                   10                  15

```
Ser Val Lys Val Ser Cys Lys Ala Ser Gly Tyr Pro Phe Thr Thr Tyr
            20                  25                  30
Gly Met Ser Trp Val Arg Gln Ala Pro Gly Gln Gly Leu Glu Trp Met
            35                  40                  45
Gly Trp Ile Asn Thr Asp Ser Gly Val Pro Thr Tyr Ala Asp Asp Phe
50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Phe Cys
                85                  90                  95
Ala Arg Asn Ile Tyr Tyr Gly Trp Gly Asn Phe Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Gly Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
            435                 440                 445
Gly

<210> SEQ ID NO 472
<211> LENGTH: 6
<212> TYPE: PRT
<213> ORGANISM: artificial
<220> FEATURE:
<223> OTHER INFORMATION: Synthetic polypeptide

<400> SEQUENCE: 472

Thr Asn Asn Trp Asp His
1               5

<210> SEQ ID NO 473
<211> LENGTH: 6
<212> TYPE: PRT
<213> ORGANISM: artificial
<220> FEATURE:
<223> OTHER INFORMATION: Synthetic polypeptide

<400> SEQUENCE: 473

Thr Asn Asn Trp Gly His
1               5

<210> SEQ ID NO 474
<211> LENGTH: 17
<212> TYPE: PRT
<213> ORGANISM: artificial
<220> FEATURE:
<223> OTHER INFORMATION: Synthetic polypeptide

<400> SEQUENCE: 474

Met Ile His Pro Asn Ser Gly Ile Thr Ala Ile Asn Glu Lys Phe Lys
1               5                   10                  15
Asn

<210> SEQ ID NO 475
<211> LENGTH: 256
<212> TYPE: PRT
<213> ORGANISM: artificial
<220> FEATURE:
<223> OTHER INFORMATION: Synthetic polypeptide

<400> SEQUENCE: 475

Gly Gly Gly Gly Ser Glu Asn Leu Tyr Phe Gln Gly Gly Gly Gly Ser
1               5                   10                  15

Glu Pro Lys Ser Cys Asp Lys Thr His Thr Cys Pro Pro Cys Pro Ala
            20                  25                  30

Pro Glu Leu Leu Gly Gly Pro Ser Val Phe Leu Phe Pro Pro Lys Pro
        35                  40                  45

Lys Asp Thr Leu Met Ile Ser Arg Thr Pro Glu Val Thr Cys Val Val
    50                  55                  60

Val Asp Val Ser His Glu Asp Pro Glu Val Lys Phe Asn Trp Tyr Val
65                  70                  75                  80

Asp Gly Val Glu Val His Asn Ala Lys Thr Lys Pro Arg Glu Glu Gln
                85                  90                  95

Tyr Asn Ser Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Ala
        115                 120                 125
```

```
Leu Pro Ala Pro Ile Glu Lys Thr Ile Ser Lys Ala Lys Gly Gln Pro
    130                 135                 140

Arg Glu Pro Gln Val Tyr Thr Leu Pro Pro Ser Arg Asp Glu Leu Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
225                 230                 235                 240

Ser Leu Ser Leu Ser Pro Gly Lys Asp Tyr Lys Asp Asp Asp Lys
                245                 250                 255
```

<210> SEQ ID NO 476
<211> LENGTH: 28
<212> TYPE: DNA
<213> ORGANISM: artificial
<220> FEATURE:
<223> OTHER INFORMATION: Synthetic polypeptide

<400> SEQUENCE: 476
tcttgtccac cttggtgctg ctggccgg                                      28

<210> SEQ ID NO 477
<211> LENGTH: 28
<212> TYPE: DNA
<213> ORGANISM: artificial
<220> FEATURE:
<223> OTHER INFORMATION: Synthetic polypeptide

<400> SEQUENCE: 477
tttgtccacc gtggtgctgc tggctggt                                      28

<210> SEQ ID NO 478
<211> LENGTH: 25
<212> TYPE: DNA
<213> ORGANISM: artificial
<220> FEATURE:
<223> OTHER INFORMATION: Synthetic polypeptide

<400> SEQUENCE: 478
gatcagtcca actgttcagg acgcc                                         25

<210> SEQ ID NO 479
<211> LENGTH: 33
<212> TYPE: DNA
<213> ORGANISM: artificial
<220> FEATURE:
<223> OTHER INFORMATION: Synthetic polypeptide

<400> SEQUENCE: 479
acactcagca cgggacaaac tcttctccac agt                                33

<210> SEQ ID NO 480
<211> LENGTH: 33
<212> TYPE: DNA
<213> ORGANISM: artificial
<220> FEATURE:

<223> OTHER INFORMATION: Synthetic polypeptide

<400> SEQUENCE: 480
acactctgca ggagacagac tcttttccac agt                         33

<210> SEQ ID NO 481
<211> LENGTH: 33
<212> TYPE: DNA
<213> ORGANISM: artificial
<220> FEATURE:
<223> OTHER INFORMATION: Synthetic polypeptide

<400> SEQUENCE: 481
acactcagca cgggacaaac tcttctccac atg                         33

<210> SEQ ID NO 482
<211> LENGTH: 344
<212> TYPE: PRT
<213> ORGANISM: Homo sapiens

<400> SEQUENCE: 482

Met Asp Tyr Pro Thr Leu Leu Ala Leu Leu His Val Tyr Arg Ala
1               5                   10                  15

Leu Cys Glu Glu Val Leu Trp His Thr Ser Val Pro Phe Ala Asn
                20                  25                  30

Met Ser Leu Glu Cys Val Tyr Pro Ser Met Gly Ile Leu Thr Gln Val
            35                  40                  45

Glu Trp Phe Lys Ile Gly Thr Gln Gln Asp Ser Ile Ala Ile Phe Ser
        50                  55                  60

Pro Thr His Gly Met Val Ile Arg Lys Pro Tyr Ala Glu Arg Val Tyr
65                  70                  75                  80

Phe Leu Asn Ser Thr Met Ala Ser Asn Asn Met Thr Leu Phe Phe Arg
                85                  90                  95

Asn Ala Ser Glu Asp Asp Val Gly Tyr Tyr Ser Cys Ser Leu Tyr Thr
            100                 105                 110

Tyr Pro Gln Gly Thr Trp Gln Lys Val Ile Gln Val Val Gln Ser Asp
        115                 120                 125

Ser Phe Glu Ala Ala Val Pro Ser Asn Ser His Ile Val Ser Glu Pro
    130                 135                 140

Gly Lys Asn Val Thr Leu Thr Cys Gln Pro Gln Met Thr Trp Pro Val
145                 150                 155                 160

Gln Ala Val Arg Trp Glu Lys Ile Gln Pro Arg Gln Ile Asp Leu Leu
                165                 170                 175

Thr Tyr Cys Asn Leu Val His Gly Arg Asn Phe Thr Ser Lys Phe Pro
            180                 185                 190

Arg Gln Ile Val Ser Asn Cys Ser His Gly Arg Trp Ser Val Ile Val
        195                 200                 205

Ile Pro Asp Val Thr Val Ser Asp Ser Gly Leu Tyr Arg Cys Tyr Leu
    210                 215                 220

Gln Ala Ser Ala Gly Glu Asn Glu Thr Phe Val Met Arg Leu Thr Val
225                 230                 235                 240

Ala Glu Gly Lys Thr Asp Asn Gln Tyr Thr Leu Phe Val Ala Gly Gly
                245                 250                 255

Thr Val Leu Leu Leu Leu Phe Val Ile Ser Ile Thr Thr Ile Ile Val
            260                 265                 270

Ile Phe Leu Asn Arg Arg Arg Arg Glu Arg Arg Asp Leu Phe Thr
        275                 280                 285

```
Glu Ser Trp Asp Thr Gln Lys Ala Pro Asn Asn Tyr Arg Ser Pro Ile
    290                 295                 300

Ser Thr Ser Gln Pro Thr Asn Gln Ser Met Asp Asp Thr Arg Glu Asp
305                 310                 315                 320

Ile Tyr Val Asn Tyr Pro Thr Phe Ser Arg Arg Pro Lys Thr Arg Val
                325                 330                 335

Asp Tyr Lys Asp Asp Asp Asp Lys
            340
```

<210> SEQ ID NO 483
<211> LENGTH: 344
<212> TYPE: PRT
<213> ORGANISM: Macaca fascicularis

<400> SEQUENCE: 483

```
Met Asp Tyr Pro Thr Leu Leu Leu Ala Leu Leu His Val Tyr Arg Ala
1               5                   10                  15

Leu Cys Glu Glu Val Leu Trp His Thr Ser Val Pro Phe Ala Glu Asn
            20                  25                  30

Met Ser Leu Glu Cys Val Tyr Pro Ser Val Gly Ile Leu Thr Gln Val
        35                  40                  45

Glu Trp Phe Lys Ile Gly Thr Glu Lys Asp Ser Ile Ala Ile Phe Ser
50                  55                  60

Pro Thr His Gly Met Val Ile Arg Lys Pro Tyr Ala Glu Arg Val Tyr
65                  70                  75                  80

Phe Leu Asn Ser Thr Met Ala Ser Asn Asn Met Thr Leu Phe Phe Arg
                85                  90                  95

Asn Ala Ser Glu Asp Asp Val Gly Tyr Tyr Ser Cys Ser Leu Tyr Thr
            100                 105                 110

Tyr Pro Gln Gly Thr Trp Gln Lys Val Ile Gln Val Val Gln Ser Asp
        115                 120                 125

Gly Phe Glu Ala Ala Val Pro Pro Asn Ser His Ile Val Ser Glu Pro
130                 135                 140

Gly Lys Asn Ile Thr Leu Thr Cys Gln Pro Gln Met Thr Trp Pro Val
145                 150                 155                 160

Gln Glu Val Arg Trp Glu Lys Val Gln Pro His Gln Ile Asp Leu Leu
                165                 170                 175

Thr Tyr Cys Asp Leu Val His Gly Arg Asn Phe Thr Ser Lys Phe Pro
            180                 185                 190

Arg Gln Ile Val Ser Asn Cys Ser His Gly Ser Trp Ser Phe Ile Val
        195                 200                 205

Val Pro Asp Val Thr Ala Ser Asp Ser Gly Leu Tyr Arg Cys His Leu
210                 215                 220

Gln Ala Ser Ala Gly Glu Asn Glu Thr Phe Val Met Arg Leu Thr Val
225                 230                 235                 240

Ala Glu Gly Gln Thr Asp Asn Gln Tyr Thr Arg Phe Val Thr Gly Gly
                245                 250                 255

Thr Val Leu Leu Leu Leu Phe Val Ile Ser Ile Thr Thr Ile Ile Val
            260                 265                 270

Ile Phe Leu Asn Arg Arg Arg Arg Glu Arg Asn Asp Leu Tyr Thr
        275                 280                 285

Glu Ser Trp Asp Thr Gln Lys Ala Pro Lys Asn Tyr Arg Ser Pro Ile
290                 295                 300

Ser Ala Asn Gln Pro Thr Asn Gln Ser Met Asp Asp Thr Arg Glu Asp
```

```
                 305                 310                 315                 320
Ile Tyr Val Asn Tyr Pro Thr Phe Ser Arg Arg Pro Lys Thr Arg Val
                325                 330                 335

Asp Tyr Lys Asp Asp Asp Lys
            340

<210> SEQ ID NO 484
<211> LENGTH: 449
<212> TYPE: PRT
<213> ORGANISM: artificial
<220> FEATURE:
<223> OTHER INFORMATION: Synthetic polypeptide

<400> SEQUENCE: 484

Gln Val Gln Leu Gln Gln Pro Gly Ala Glu Leu Val Thr Pro Gly Ala
1               5                   10                  15

Ser Val Lys Leu Ser Cys Lys Ala Ser Gly Phe Thr Phe Thr Asn Asn
            20                  25                  30

Trp Met His Trp Val Lys Gln Arg Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Lys Ala Thr Val Thr Val Asp Lys Ser Ser Ser Thr Val Tyr
65                  70                  75                  80

Ile Gln Leu Ser Ser Leu Thr Ser Glu Asp Ser Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Pro Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys

<210> SEQ ID NO 485
<211> LENGTH: 447
<212> TYPE: PRT
<213> ORGANISM: artificial
<220> FEATURE:
<223> OTHER INFORMATION: Synthetic polypeptide

<400> SEQUENCE: 485

Gln Val Gln Leu Gln Gln Ser Gly Ala Asp Leu Ala Arg Pro Gly Ala
1               5                   10                  15
Ser Ile Lys Leu Ser Cys Lys Ala Ser Gly Tyr Thr Phe Thr Gly Tyr
            20                  25                  30
Gly Val Thr Trp Val Lys Gln Ser Thr Gly Gln Gly Leu Asp Trp Ile
        35                  40                  45
Gly Glu Ile Tyr Pro Gly Thr Val Ile Thr Tyr Tyr Asn Ala Lys Phe
    50                  55                  60
Lys Gly Lys Ala Thr Leu Thr Ala Asp Lys Ser Ser Ser Thr Ala Tyr
65                  70                  75                  80
Met Glu Leu Arg Ser Leu Thr Ser Glu Asp Ser Ala Val Tyr Phe Cys
                85                  90                  95
Ala Arg Gly Leu Gly Arg Ala Met Asp Tyr Trp Gly Gln Gly Thr Ser
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Gly Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 486
<211> LENGTH: 451
<212> TYPE: PRT
<213> ORGANISM: artificial
<220> FEATURE:
<223> OTHER INFORMATION: Synthetic polypeptide

<400> SEQUENCE: 486

Gln Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Phe Pro Gly Thr Glu Gly Ile Tyr Tyr Asn Glu Lys Phe
    50                  55                  60

Lys Gly Lys Ala Thr Leu Thr Val Asp Lys Ser Ser Thr Thr Ala Tyr
65                  70                  75                  80

Met Leu Leu Ser Ser Leu Thr Ser Glu Asp Ser Ala Val Tyr Phe Cys
                85                  90                  95

Ala Arg Glu Gly Asp Tyr Arg Tyr Tyr Ser Pro Leu Gly Tyr Trp Gly
            100                 105                 110

Gln Gly Thr Leu Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Gly Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
450

<210> SEQ ID NO 487
<211> LENGTH: 447
<212> TYPE: PRT
<213> ORGANISM: artificial
<220> FEATURE:
<223> OTHER INFORMATION: Synthetic polypeptide

<400> SEQUENCE: 487

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Asn Phe Asn Asp Tyr
            20                  25                  30

Tyr Ile Asn Trp Val Asn Gln Arg Pro Gly Gln Gly Leu Glu Trp Ile
            35                  40                  45

Gly Trp Ile Phe Pro Gly Arg Ile Ile Thr Tyr Tyr Asn Glu Lys Phe
        50                  55                  60
```

```
Lys Gly Lys Ala Thr Leu Thr Val Asp Thr Ser Ser Asn Thr Ala Tyr
 65                  70                  75                  80

Met Leu Leu Ser Ser Leu Thr Ser Glu Asp Ser Ala Val Tyr Phe Cys
                 85                  90                  95

Ala Arg Gly Val Gly Glu Gly Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Gly Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 488
<211> LENGTH: 448
<212> TYPE: PRT
<213> ORGANISM: artificial
<220> FEATURE:
```

<223> OTHER INFORMATION: Synthetic polypeptide

<400> SEQUENCE: 488

```
Glu Val Gln Leu Leu Glu Thr Gly Gly Gly Leu Val Lys Ser Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Ala Ile Ser Asp Asp Gly Thr Tyr Thr Tyr Pro Asp Ser Val
    50                  55                  60

Lys Gly Arg Phe Thr Ile Ser Arg Asp Asn Ala Asn Asn Tyr Leu Tyr
65                  70                  75                  80

Leu Gln Met Ser Ser Leu Lys Ser Glu Asp Thr Ala Ile Tyr Tyr Cys
                85                  90                  95

Ala Lys Ala Gly Ser Tyr Asp Tyr Phe Asp Val Trp Gly Ala Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

-continued

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 489
<211> LENGTH: 446
<212> TYPE: PRT
<213> ORGANISM: artificial
<220> FEATURE:
<223> OTHER INFORMATION: Synthetic polypeptide

<400> SEQUENCE: 489

Gln Val Gln Leu Lys Glu Ser Gly Pro Gly Leu Val Ala Pro Ser Gln
1               5                   10                  15

Ser Leu Ser Ile Ile Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Ile Ile Trp Ala Gly Gly Ser Thr Asn Tyr Asn Ser Ala Leu Met
    50                  55                  60

Ser Arg Leu Thr Ile Ser Lys Asp Asn Ser Lys Ser Gln Val Phe Leu
65                  70                  75                  80

Lys Met Asn Ser Leu Gln Thr Asn Asp Thr Ala Ile Tyr Tyr Cys Ala
                85                  90                  95

Arg Val Ser Met Met Gly Phe Ala Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gly Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

-continued

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 490
<211> LENGTH: 450
<212> TYPE: PRT
<213> ORGANISM: artificial
<220> FEATURE:
<223> OTHER INFORMATION: Synthetic polypeptide

<400> SEQUENCE: 490

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Pro Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Asp Ser Gly Val Pro Thr Tyr Ala Asp Asp Phe
    50                  55                  60

Lys Gly Arg Phe Ala Phe Ser Leu Glu Thr Ser Ala Asn Thr Ala Tyr
65                  70                  75                  80

Leu Gln Ile Asn Ser Leu Lys Asn Glu Asp Ala Ala Thr Tyr Phe Cys
                85                  90                  95

Ala Arg Asn Ile Tyr Tyr Gly Trp Gly Asn Phe Asp Tyr Trp Gly Gln
            100                 105                 110

Gly Thr Ile Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

```
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Gly Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 491
<211> LENGTH: 449
<212> TYPE: PRT
<213> ORGANISM: artificial
<220> FEATURE:
<223> OTHER INFORMATION: Synthetic polypeptide

<400> SEQUENCE: 491

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

-continued

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 492
<211> LENGTH: 449
<212> TYPE: PRT
<213> ORGANISM: artificial
<220> FEATURE:
<223> OTHER INFORMATION: Synthetic polypeptide

<400> SEQUENCE: 492

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
                20                  25                  30

Phe Met His Trp Val Arg Gln Ala Pro Gly Gln Gly Leu Glu Trp Ile
            35                  40                  45

Gly Met Ile His Ala Asn Ser Gly Ile Thr Asn Ile Asn Glu Lys Phe

```
                50                  55                  60
Lys Asn Arg Val Thr Met Thr Thr Asp Thr Ser Thr Ser Thr Ala Tyr
 65                  70                  75                  80

Met Glu Leu Arg Ser Leu Arg Ser Glu Asp Thr Ala Val Tyr Tyr Cys
                 85                  90                  95

Arg Ser Asp Gly Ile Tyr Glu Gly Tyr Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Gly Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 493
<211> LENGTH: 449

```
<212> TYPE: PRT
<213> ORGANISM: artificial
<220> FEATURE:
<223> OTHER INFORMATION: Synthetic polypeptide

<400> SEQUENCE: 493
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 |
| Ser | Val | Lys | Val | Ser | Cys | Lys | Ala | Ser | Gly | Phe | Thr | Phe | Thr | Asn | Asn |
| | | | 20 | | | | | 25 | | | | | 30 | | |
| Phe | Met | His | Trp | Val | Arg | Gln | Ala | Pro | Gly | Gln | Gly | Leu | Glu | Trp | Ile |
| | | 35 | | | | | 40 | | | | | 45 | | | |
| Gly | Met | Ile | His | Ala | Asn | Ser | Gly | Ile | Thr | Asn | Ile | Asn | Glu | Lys | Phe |
| 50 | | | | | 55 | | | | | 60 | | | | | |
| Lys | Asn | Arg | Val | Thr | Met | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Glu | Asp | Thr | Ala | Val | Tyr | Tyr | Cys |
| | | | | 85 | | | | | 90 | | | | | 95 | |
| Arg | Ser | Asp | Gly | Val | Tyr | Glu | Gly | Tyr | Phe | Asp | Tyr | Trp | Gly | Gln | Gly |
| | | | 100 | | | | | 105 | | | | | 110 | | |
| Thr | Leu | Val | Thr | Val | Ser | Ser | Ala | Ser | Thr | Lys | Gly | Pro | Ser | Val | Phe |
| | | 115 | | | | | 120 | | | | | 125 | | | |
| Pro | Leu | Ala | Pro | Ser | Ser | Lys | Ser | Thr | Ser | Gly | Gly | Thr | Ala | Ala | Leu |
| 130 | | | | | 135 | | | | | 140 | | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | 195 | | | | | 200 | | | | | 205 | | | |
| Ser | Asn | Thr | Lys | Val | Asp | Lys | Lys | Val | Glu | Pro | Lys | Ser | Cys | Asp | Lys |
| 210 | | | | | 215 | | | | | 220 | | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Tyr | Gly | Ser | Thr | Tyr | Arg | Val |
| 290 | | | | | 295 | | | | | 300 | | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Asp | Glu | Leu | Thr | Lys | Asn | Gln | Val | Ser | Leu | Thr |
| | | 355 | | | | | 360 | | | | | 365 | | | |
| Cys | Leu | Val | Lys | Gly | Phe | Tyr | Pro | Ser | Asp | Ile | Ala | Val | Glu | Trp | Glu |
| 370 | | | | | 375 | | | | | 380 | | | | | |

```
Ser Asn Gly Gln Pro Glu Asn Asn Tyr Lys Thr Thr Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 494
<211> LENGTH: 449
<212> TYPE: PRT
<213> ORGANISM: artificial
<220> FEATURE:
<223> OTHER INFORMATION: Synthetic polypeptide

<400> SEQUENCE: 494

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Phe Met His Trp Val Arg Gln Ala Pro Gly Gln Gly Leu Glu Trp Ile
        35                  40                  45

Gly Phe Ile His Ala Asn Ser Gly Ile Thr Asn Ile Asn Glu Lys Phe
    50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Ile Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
```

```
             290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 495
<211> LENGTH: 449
<212> TYPE: PRT
<213> ORGANISM: artificial
<220> FEATURE:
<223> OTHER INFORMATION: Synthetic polypeptide

<400> SEQUENCE: 495

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
                20                  25                  30

Phe Met His Trp Val Arg Gln Ala Pro Gly Gln Gly Leu Glu Trp Ile
            35                  40                  45

Gly Phe Ile His Ala Asn Ser Gly Ile Thr Asn Ile Asn Glu Lys Phe
        50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Arg Ser Asp Gly Val Tyr Glu Gly Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 496
<211> LENGTH: 449
<212> TYPE: PRT
<213> ORGANISM: artificial
<220> FEATURE:
<223> OTHER INFORMATION: Synthetic polypeptide

<400> SEQUENCE: 496

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Thr Asn Asn
            20                  25                  30

Trp Met His Trp Val Arg Gln Arg Pro Gly Gln Gly Leu Glu Trp Ile
            35                  40                  45

Gly Met Ile His Pro Asn Ser Gly Ile Thr Asn Ile Asn Glu Lys Phe
        50                  55                  60

Lys Asn Arg Ala Thr Val Thr Val Asp Lys Ser Ser Ser Thr Val Tyr
65                  70                  75                  80

Ile Glu Leu Arg Ser Leu Arg Ser Glu Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 497
<211> LENGTH: 449
<212> TYPE: PRT
<213> ORGANISM: artificial
<220> FEATURE:
<223> OTHER INFORMATION: Synthetic polypeptide

<400> SEQUENCE: 497

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
```

-continued

```
             20                  25                  30
Trp Met His Trp Val Arg Gln Arg Pro Gly Gln Gly Leu Glu Trp Ile
             35                  40                  45
Gly Met Ile His Pro Asn Ser Gly Ile Thr Asn Ile Asn Glu Lys Phe
     50                  55                  60
Lys Asn Arg Ala Thr Val Thr Val Asp Lys Ser Ser Thr Val Tyr
 65                  70                  75                  80
Ile Glu Leu Arg Ser Leu Arg Ser Glu Asp Thr Ala Val Tyr Tyr Cys
                 85                  90                  95
Arg Ser Asp Gly Thr Tyr Glu Gly Tyr Phe Asp Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Gly Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
```

Lys

<210> SEQ ID NO 498
<211> LENGTH: 449
<212> TYPE: PRT
<213> ORGANISM: artificial
<220> FEATURE:
<223> OTHER INFORMATION: Synthetic polypeptide

<400> SEQUENCE: 498

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Val
        35                  40                  45

Gly Met Ile His Pro Asn Ser Gly Ile Thr Asn Ile Asn Glu Lys Phe
    50                  55                  60

Lys Asn Arg Val Thr Met Thr Val Asp Lys Ser Thr Ser Thr Val Tyr
65                  70                  75                  80

Met Glu Leu Arg Ser Leu Arg Ser Asp Asp Thr Ala Val Tyr Tyr Cys
                85                  90                  95

Arg Ser Asp Gly Thr Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 499
<211> LENGTH: 449
<212> TYPE: PRT
<213> ORGANISM: artificial
<220> FEATURE:
<223> OTHER INFORMATION: Synthetic polypeptide

<400> SEQUENCE: 499

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
                20                  25                  30

Trp Met His Trp Val Arg Gln Ala Pro Gly Gln Gly Leu Glu Trp Ile
            35                  40                  45

Gly Met Ile His Pro Asn Ser Gly Ile Thr Asn Ile Asn Glu Lys Phe
        50                  55                  60

Lys Asn Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Arg Ser Asp Gly Thr Tyr Glu Gly Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
                  260                 265                 270
Pro Glu Val Lys Phe Asn Trp Tyr Asp Gly Val Glu Val His Asn
            275                 280                 285

Ala Lys Thr Lys Pro Arg Glu Glu Gln Tyr Gly Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 500
<211> LENGTH: 449
<212> TYPE: PRT
<213> ORGANISM: artificial
<220> FEATURE:
<223> OTHER INFORMATION: Synthetic polypeptide

<400> SEQUENCE: 500

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Asn
            20                  25                  30

Trp Met His Trp Val Arg Gln Ala Pro Gly Gln Gly Leu Glu Trp Ile
        35                  40                  45

Gly Met Ile His Pro Asn Ser Gly Ile Thr Asn Ile Asn Glu Lys Phe
    50                  55                  60

Lys Asn Arg Val Thr Met Thr Val Asp Lys Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Asp Gly Thr Tyr Glu Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 501
<211> LENGTH: 450
<212> TYPE: PRT
<213> ORGANISM: artificial
<220> FEATURE:
<223> OTHER INFORMATION: Synthetic polypeptide

<400> SEQUENCE: 501

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Pro Phe Thr Thr Tyr
                20                  25                  30

Gly Met Ser Trp Val Arg Gln Ala Pro Gly Gln Gly Leu Glu Trp Met
            35                  40                  45

Gly Trp Ile Asn Thr Asp Ser Gly Val Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80
```

```
Leu Gln Ile Ser Ser Leu Lys Ala Glu Asp Thr Ala Val Tyr Phe Cys
                85                  90                  95
Ala Arg Asn Ile Tyr Tyr Gly Trp Gly Asn Phe Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Gly Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
    450
```